(12) United States Patent
Daviet et al.

(10) Patent No.: US 11,130,972 B2
(45) Date of Patent: *Sep. 28, 2021

(54) METHOD FOR PRODUCING FRAGRANT ALCOHOLS

(71) Applicant: Firmenich SA, Satigny (CH)

(72) Inventors: Laurent Daviet, Geneva (CH); Letizia Rocci, Geneva (CH); Michel Schalk, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/738,563

(22) Filed: Jan. 9, 2020

(65) Prior Publication Data

US 2020/0172936 A1    Jun. 4, 2020

Related U.S. Application Data

(60) Continuation of application No. 15/877,183, filed on Jan. 22, 2018, now Pat. No. 10,570,420, which is a division of application No. 15/023,640, filed as application No. PCT/EP2014/070060 on Sep. 19, 2014, now Pat. No. 9,909,145.

(60) Provisional application No. 61/880,149, filed on Sep. 19, 2013.

(51) Int. Cl.
*C12P 5/00*     (2006.01)
*C12P 7/02*     (2006.01)
*C12N 9/02*     (2006.01)

(52) U.S. Cl.
CPC ............ *C12P 5/007* (2013.01); *C12N 9/0071* (2013.01); *C12N 9/0079* (2013.01); *C12P 7/02* (2013.01); *C12Y 114/13* (2013.01); *C12Y 114/14001* (2013.01)

(58) Field of Classification Search
CPC .......... C12P 7/02; C12P 5/007; C12N 9/0079; C12N 9/0071; C12Y 114/13; C12Y 114/14001
See application file for complete search history.

(56) References Cited

U.S. PATENT DOCUMENTS

| 9,909,145 B2 | 3/2018 | Davient et al. |
| 10,570,420 B2* | 2/2020 | Daviet ............. C12Y 114/13 |
| 2011/0008836 A1 | 1/2011 | Schalk et al. |
| 2011/0281257 A1 | 11/2011 | Schalk et al. |
| 2016/0108374 A1 | 4/2016 | Bohlmann et al. |

FOREIGN PATENT DOCUMENTS

| WO | 2003025193 A1 | 3/2003 |
| WO | 2009109597 A1 | 9/2009 |
| WO | 2010067309 A1 | 6/2010 |
| WO | 2013064411 A1 | 5/2013 |
| WO | 2014067007 A1 | 5/2014 |

OTHER PUBLICATIONS

Diaz-Chavez, M., et al_ "Biosynthesis of sandalwood oil: santalum album CYP76F Cytochromes P450 produce santalols and bergamotol," PLOS One, vol. 8, Issue 9, 2013.
Broun et al., Catalytic plasticity of fatty acid modification enzymes underlying chemical diversity of plant lipids. Science,1998, vol. 282: 1315-1317.
Devos et al., Practical limits of function prediction. Proteins: Structure, Function, and Genetics. 2000, vol. 41: 98-107.
Seffernick et al., Melamine deaminase and Atrazine chlorohydrolase: 98 percent identical but functionally different. J. Bacterial., 2001, vol. 183 (8): 2405-2410.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine_ Biochemistry, 1999, vol. 38: 11643-11650.
Altschul et al., J. Mol. Biol. 215,1990, p. 403-410.
Altschul, J. Mol. Biol. , 1991, 219, p. 555-65.
Barnes H.J, Method EnzymoL, 272,1996, p. 3-14.
Cankar et al, FEBS Letters, 2011, p. 178-182.
Gotoh O., J Biol Chem, 267(1), 1992, p. 83-90.
Halkier et al, Arch. Biochem. Biophys., 322,1995, p. 369-377.
Haudenschield et al, Arch. Biochem. Biophys., 379, 2000, p. 127-136.
Jensen et al., Phytochemistry, vol. 71, 2010, p. 132-141.
Maurer et al, Advanced Synthesis & Catalysis, 345, 2003, p. 802-810.
Seifert et al., Chembiochem, 2009, vol. 10, p. 853.
Takahashi, et al., "Metabolic Engineering of Sesquiterpene Metabolism in Yeast", J. Biotechnology and Bioengineenng, 2007, vol. 97(1), p. 170-181.
Tatusova et al., "BLAST 2 Sequences, a new tool for comaring protein and nucleotide sequences", FEMS Microbiology Letters, 1999, vol. 174, p. 247-250.
Teoh et al., "*Artemisia annua* L. (Asteraceae) trichome-specific cDNAs reveal CYP71AV1, a cytochrome P450 with a key role . . . ", FEBS Letters, 2006, vol. 580, p. 1411-1416.
Tresse et al., "Comparative evaluation of adhesion, surface properties, and surface protein composition of Listeria . . . ", Journal of Applied Microbiology, 2006, 101, p. 53-62.
Wu et al., "Redirection of cytosolic or plastidic isoprenoid precursors elevates terpene production in plants", Nat. Biotechnol., 2006, vol. 24(11), p. 1441-1447.
Martin et al., "Engineering a mevalonate pathway in *Escherichia coli* for production of terpenoids", Nat. Biotechnol., 2003, vol. 21, 796-802.
Meinhold et al., "Engineering Cytochrome P450 BM3 for Terminal Alkane Hydroxylation", Advanced Synthesis & catalysis, 2006, vol. 348, p. 763-772.

(Continued)

*Primary Examiner* — Ganapathirama Raghu
(74) *Attorney, Agent, or Firm* — Armstrong Teasdale LLP

(57) ABSTRACT

This invention relates generally to methods and compositions for producing a sesquiterpene alcohol comprising contacting a sesquiterpene with a P450 polypeptide with monooxygenase activity.

7 Claims, 31 Drawing Sheets

Figure 2A:
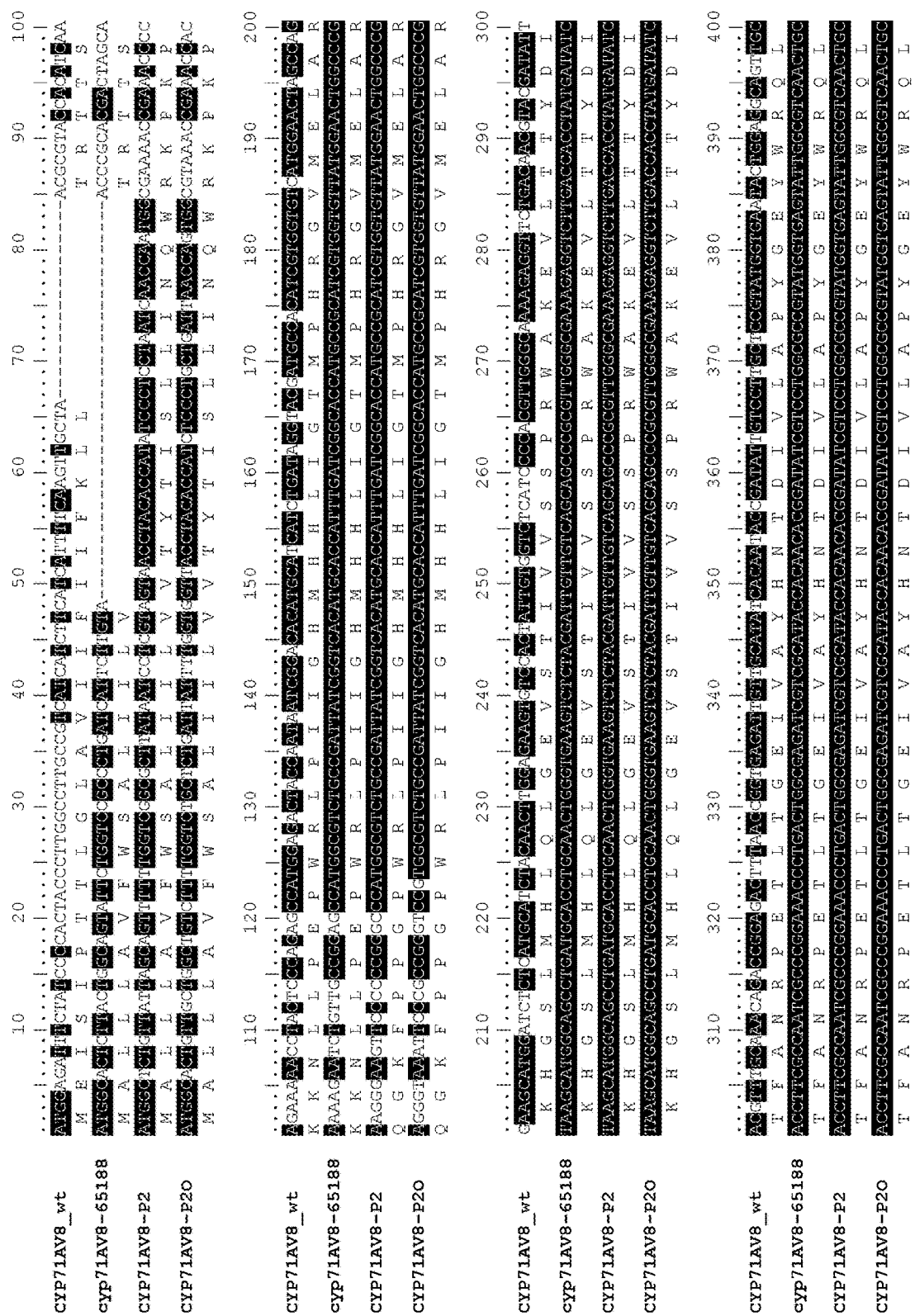

Specification includes a Sequence Listing.

(56) References Cited

OTHER PUBLICATIONS

Murashige et al., "A Revised Medium for Rapid Growth and Bio Assays with Tobacco Tissue Cultures", Physiologia Plantarum, 1962, vol. 15, p. 473-497.
International Search Report and Written Opinion of the International Searching Authority dated Mar. 10, 2015 for application No. PCT/EP2014/070060 filed Sep. 19, 2014.
International Preliminary Report on Patentability dated Mar. 22, 2016 for application No. PCT/EP2014/070060 filed Sep. 19, 2014.
Omura et al., "The Carbon Monoxide-binding Pigment of Liver Microsomes II.", J. Biol. Chem., Jul. 1964, vol. 239(7), p. 2379-2385.
Schalk et al., "Toward a Biosynthetic Route to Sclaeol and Amber Odorants", J. Am Chem. Soc., 2012, vol. 134, p. 18900-18903.
Schalk et al., "A single amino acid substitution (F363I) converts the regiochemistry of the spearmint (−)-limonene . . . ", Proc Natl Acad Sci USA, 2000, vol. 97(22), p. 11948-11953.
Schardl et al., "Design and construction of a versatile system for the expression of foreign genes in plants", Gene, 1987, vol. 61, p. 1-11.
Bohlmann, et al., XP2733709, Accession BBF82151, "Santalum album santalene synthase (SaSSY) polypeptide SEQ: 17", Jul. 3, 2014.
Han, et al., "Full=Cytochrome P450 CYP736AI2", XP002736380, UniProt Accession 1-12DH18, Mar. 21, 2012.
Cankar, et al., "Valencene oxidase [Cichorium intybus]", NCBI GenBank Accession No. ADM86719.1, Jan. 24, 2011.
Siminszky, et al., "CYP71D1Op [Glycine max]", GenBank Accession No. AAB94588.1, Mar. 2, 1999.
Martin, et al., E,E-alpha-farnesene synthase [Picea abiesr, GenBank Accession No. AAS47697.1, Aug. 29, 2004.
Picaud, et al., (E)-beta-farnesene synthase [Artemisia annua], GenBank Accession No. AAX39387.1, Jun. 1, 2005.
Ro, et al., "Amorpha-4,11-diene C-12 oxidase [Artemisia annual", GenBank Accession No. ABB82944.1, Apr. 13, 2006.
Kong, et al., "Cytochrome P450 reductase [Artemisia annual", GenBank Accession No. ABM88789.1, Jan. 28, 2007.
Rocci, et al., "Sesquisabinene B synthase [Santalum album]", GenBank Accession No. ADP37190.1, Nov. 7, 2010.
Rocci, et al., "Tps2-1 [Clausena lansium]", GenBank Accession No. ADR71055.1, Dec. 11, 2010.
Rocci, et al., "(−)-beta-bisabolene synthase [Santalum album]", GenBank Accession No. ADP37189.1, Nov. 7, 2010.
Rocci, et al., "Santalene bergamotene synthase 2 [Santalum album]", GenBank Accession No. ADP30867, Nov. 6, 2010.

* cited by examiner

Figure 1

```
                          10         20         30         40         50         60         70         80
                 ....|....|....|....|....|....|....|....|....|....|....|....|....|....|....|....|
CYP71AV8_wt      MEISIPTTLGLAVIFIFKL-------TRTTSKKNLLPEPWRLPIIGHMHHLIGTMPHRGVMELARKHGSLMHLQLGEV
CYP71AV8-65188   MALLAVFWSALIILV-------TRTTSKKNLLPEPWRLPIIGHMHHLIGTMPHRGVMELARKHGSLMHLQLGEV
CYP71AV8-P2      MALLAVFWSALIILVTYTISLLINQWRKPKPQGKFPPGPWRLPIIGHMHHLIGTMPHRGVMELARKHGSLMHLQLGEV
CYP71AV8-P2O     MALLAVFWSALIILVTYTISLLINQWRKPKPQGKFPPGPWRLPIIGHMHHLIGTMPHRGVMELARKHGSLMHLQLGEV
```

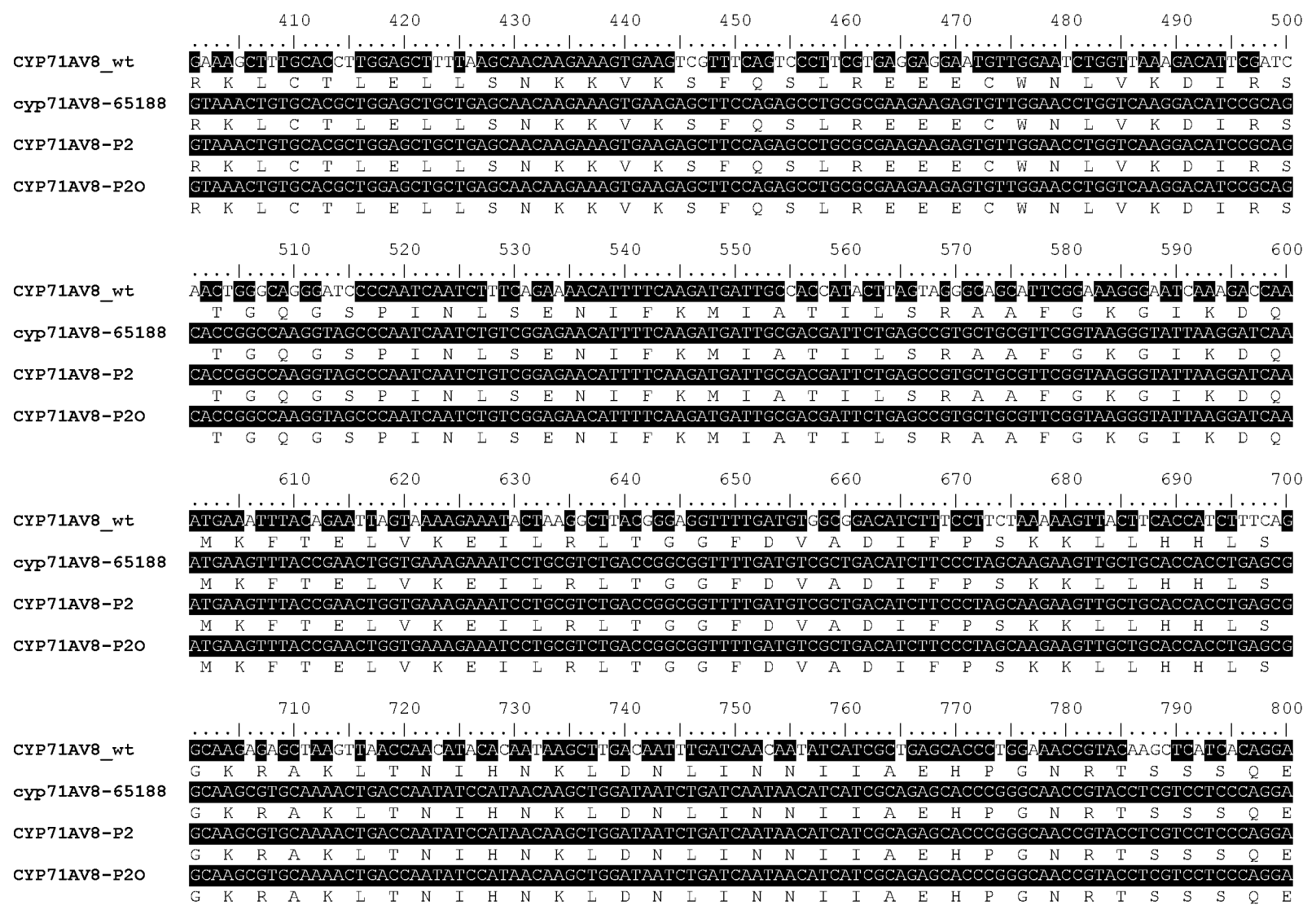

- Figure 3 -
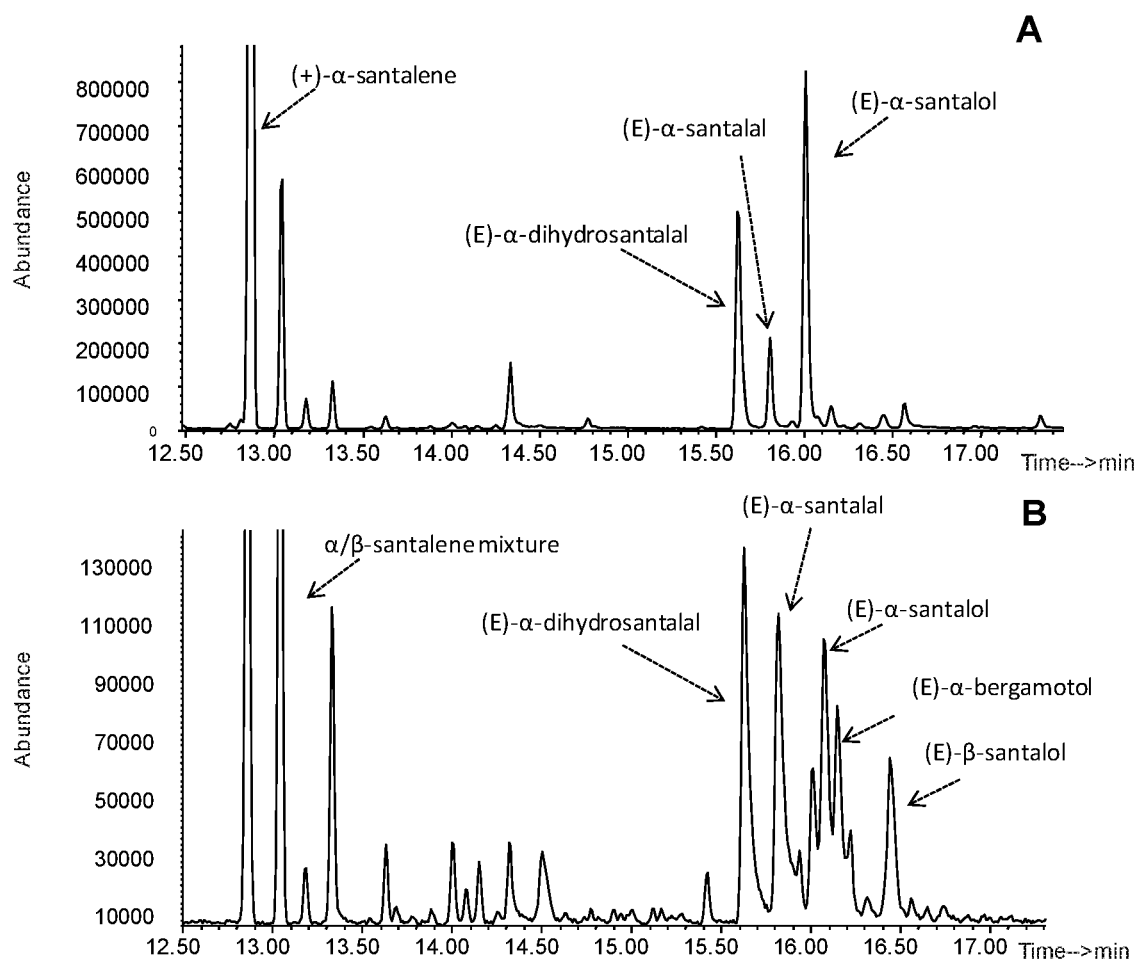

– Figure 4 –
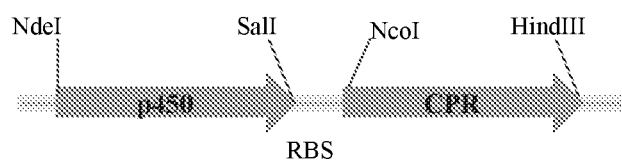

– Figure 5 –
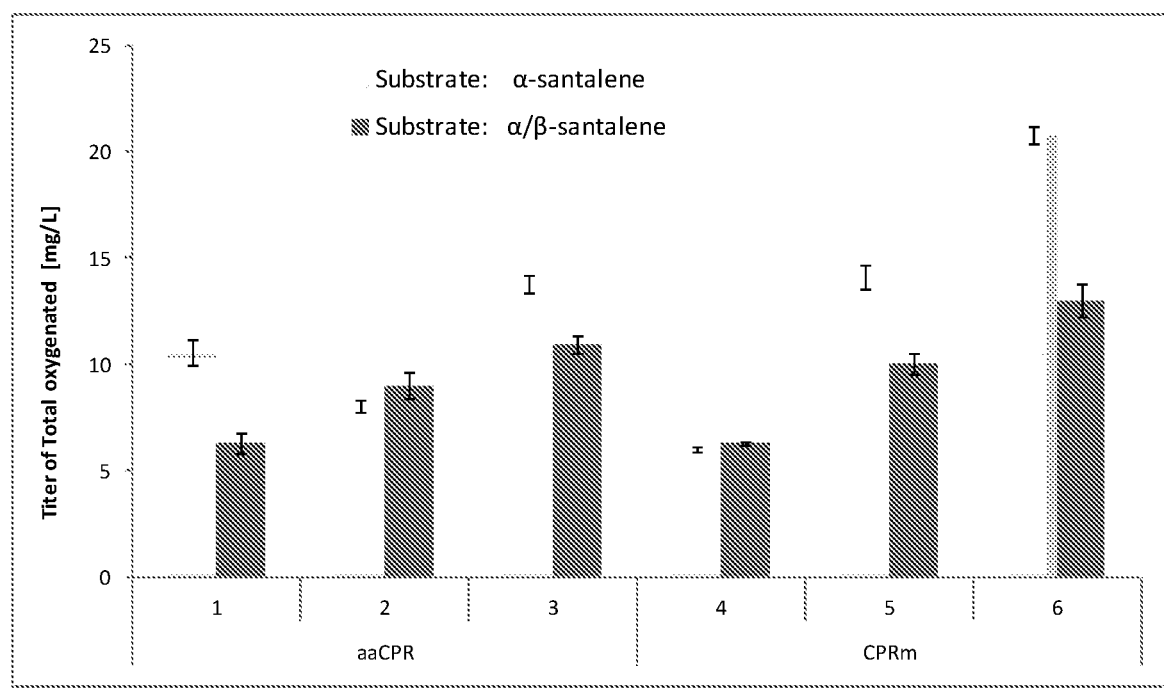

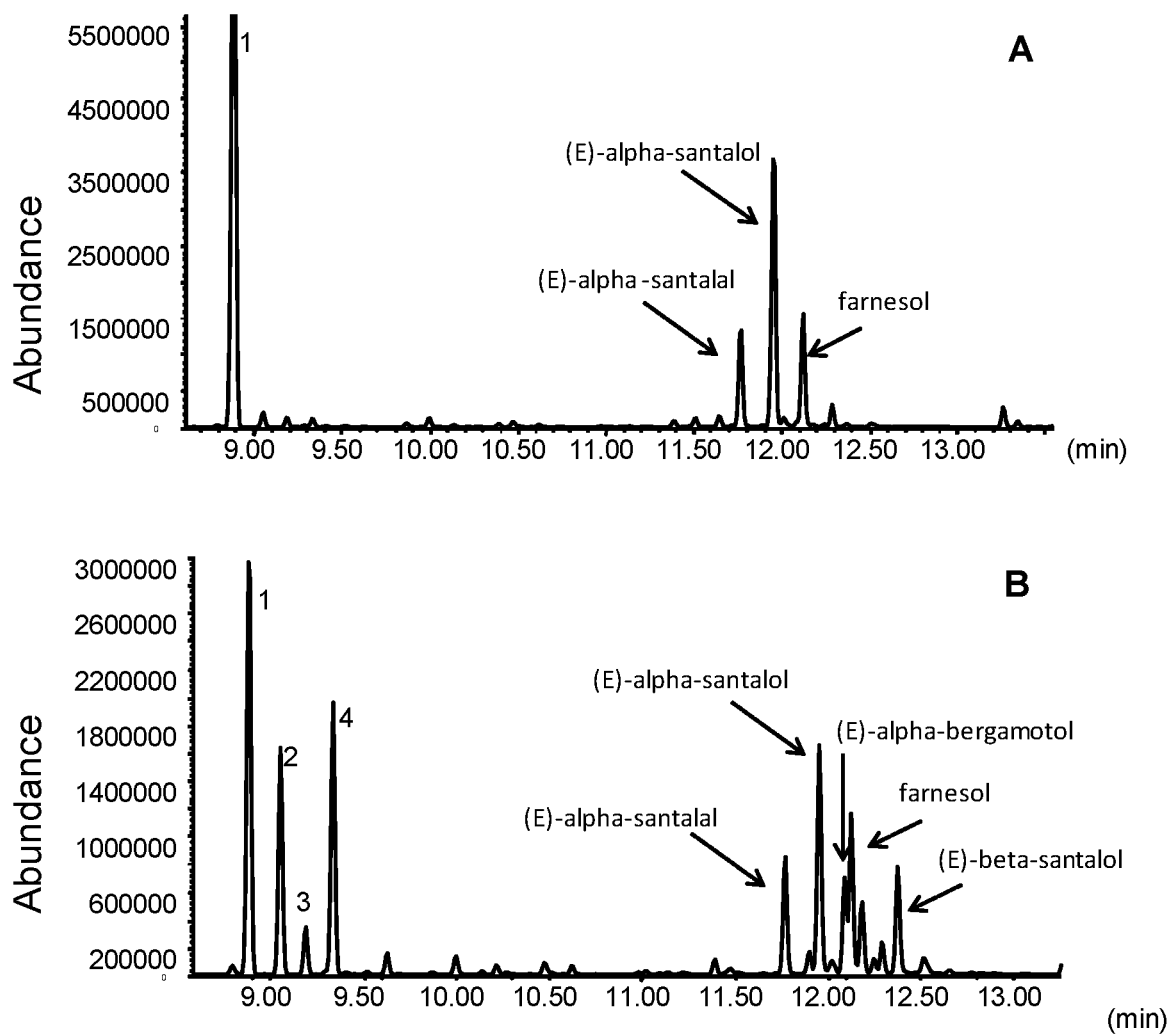
– Figure 6 –

-Figure 7 –
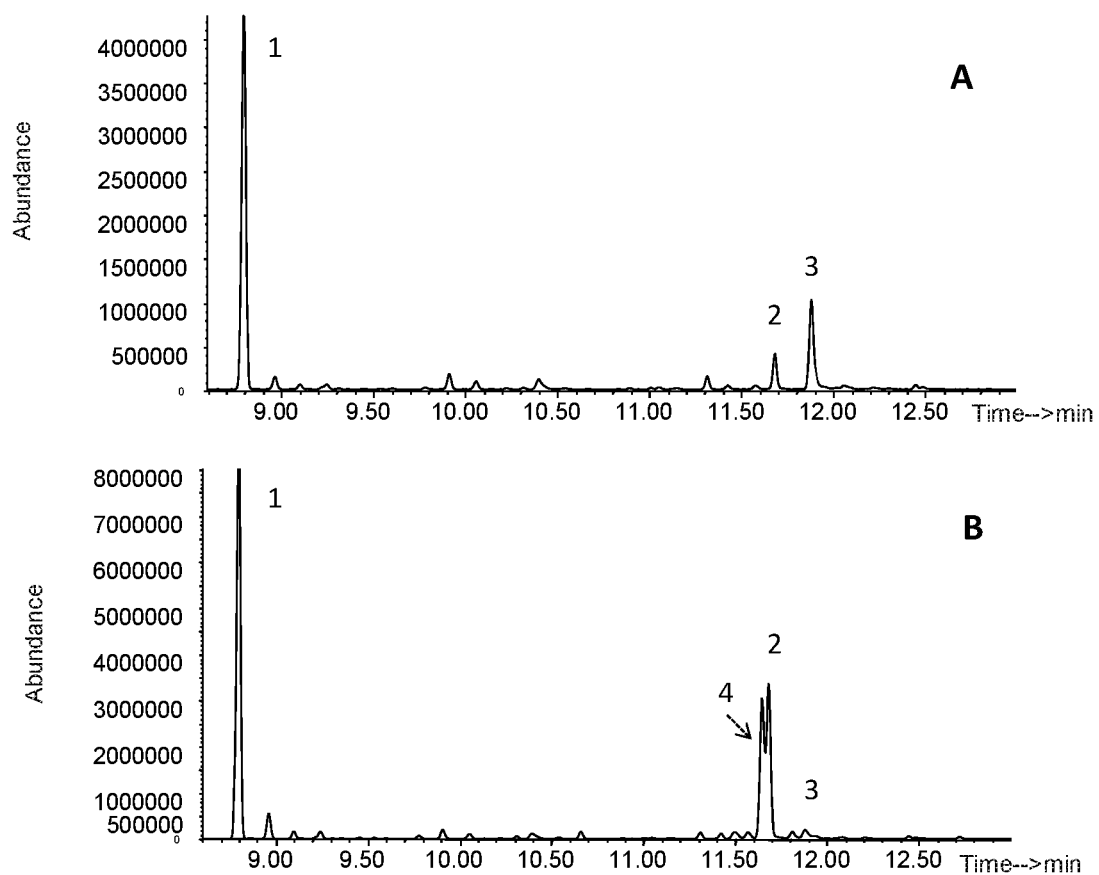

– Figure 8 –
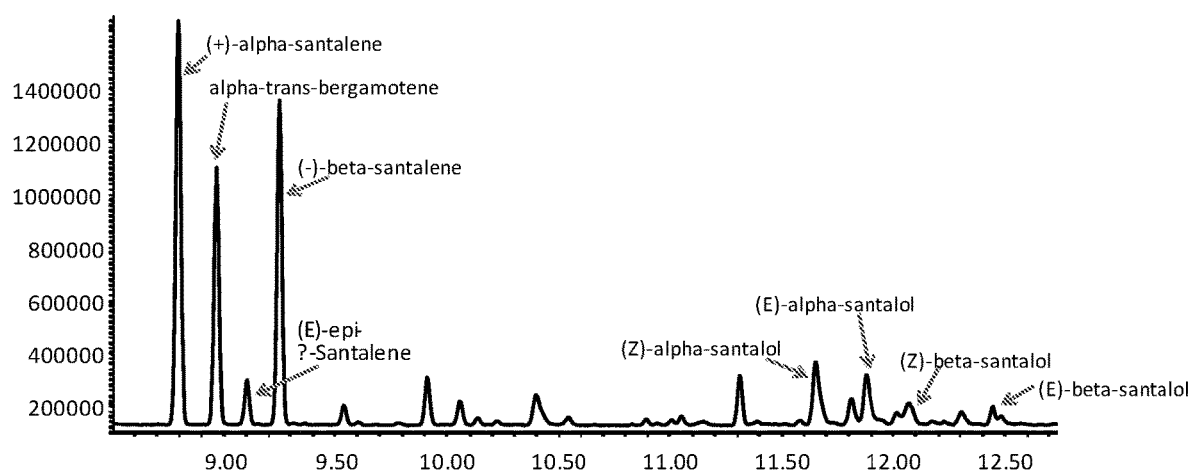

- Figure 9 -
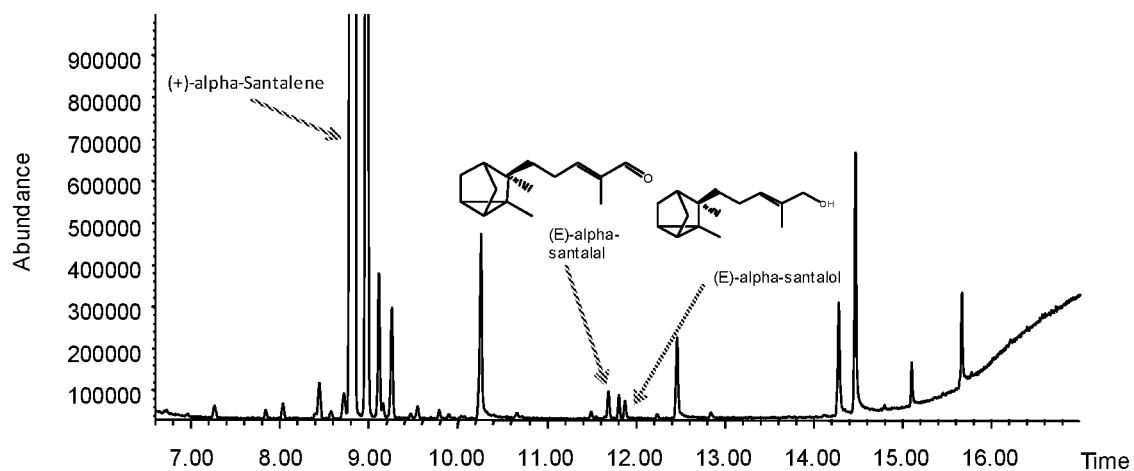

- Figure 10-
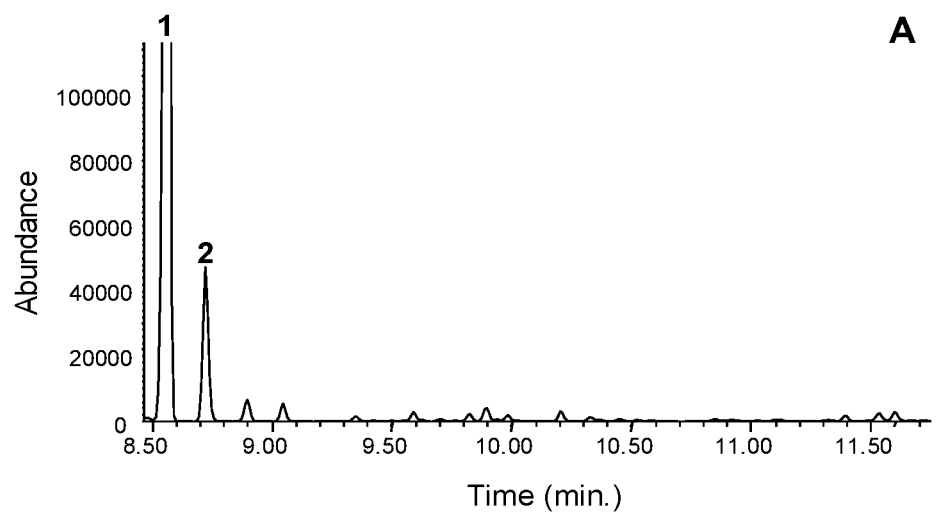
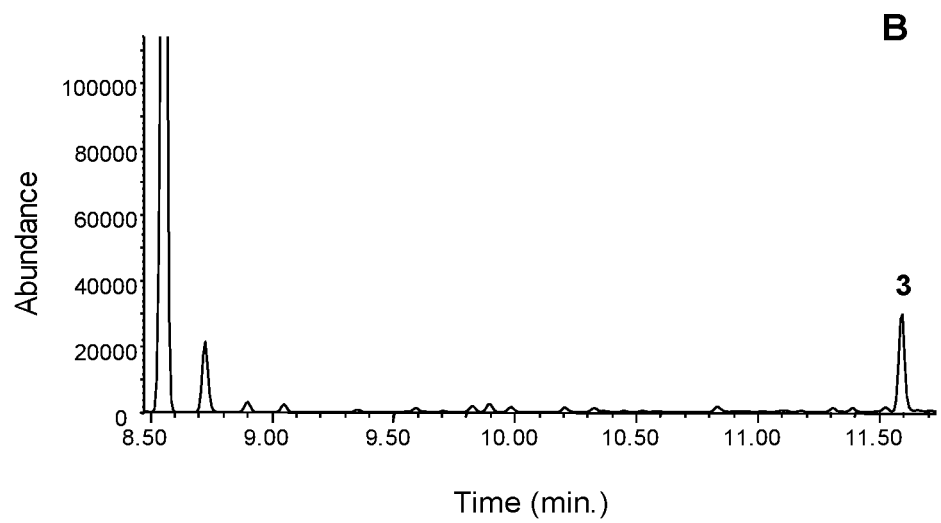

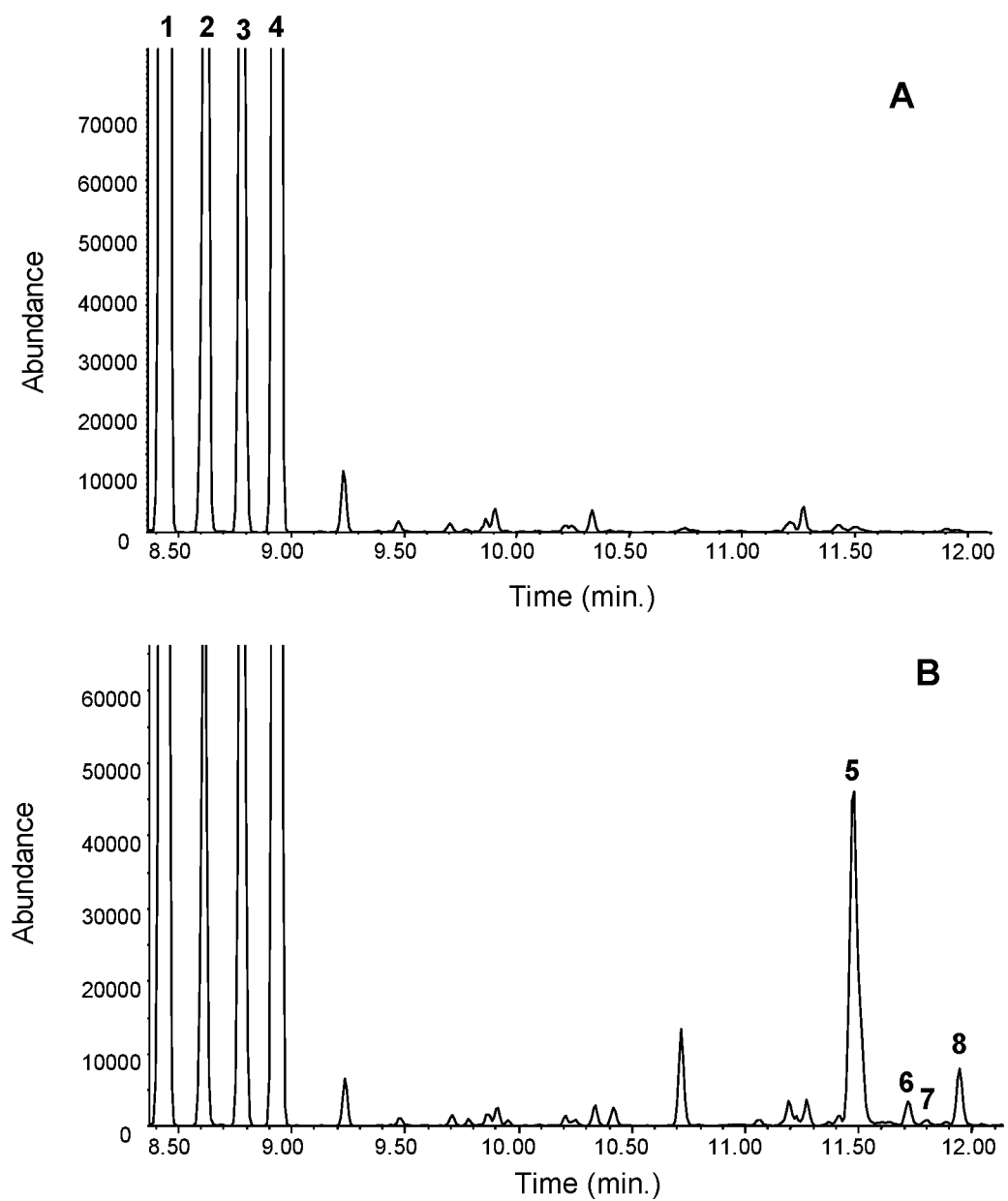
- Figure 11 -

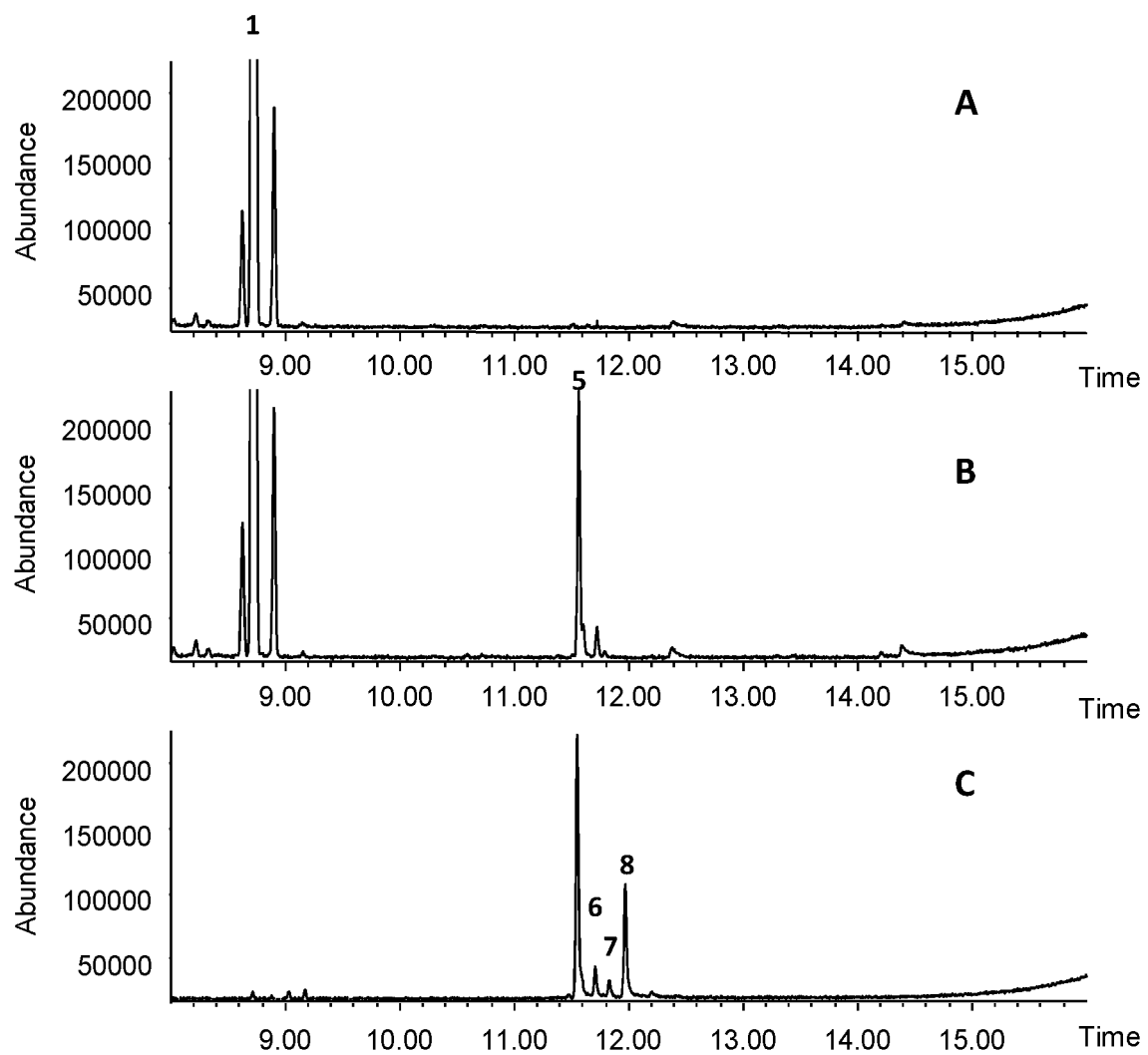
- Figure 12 -

- Figure 13 -
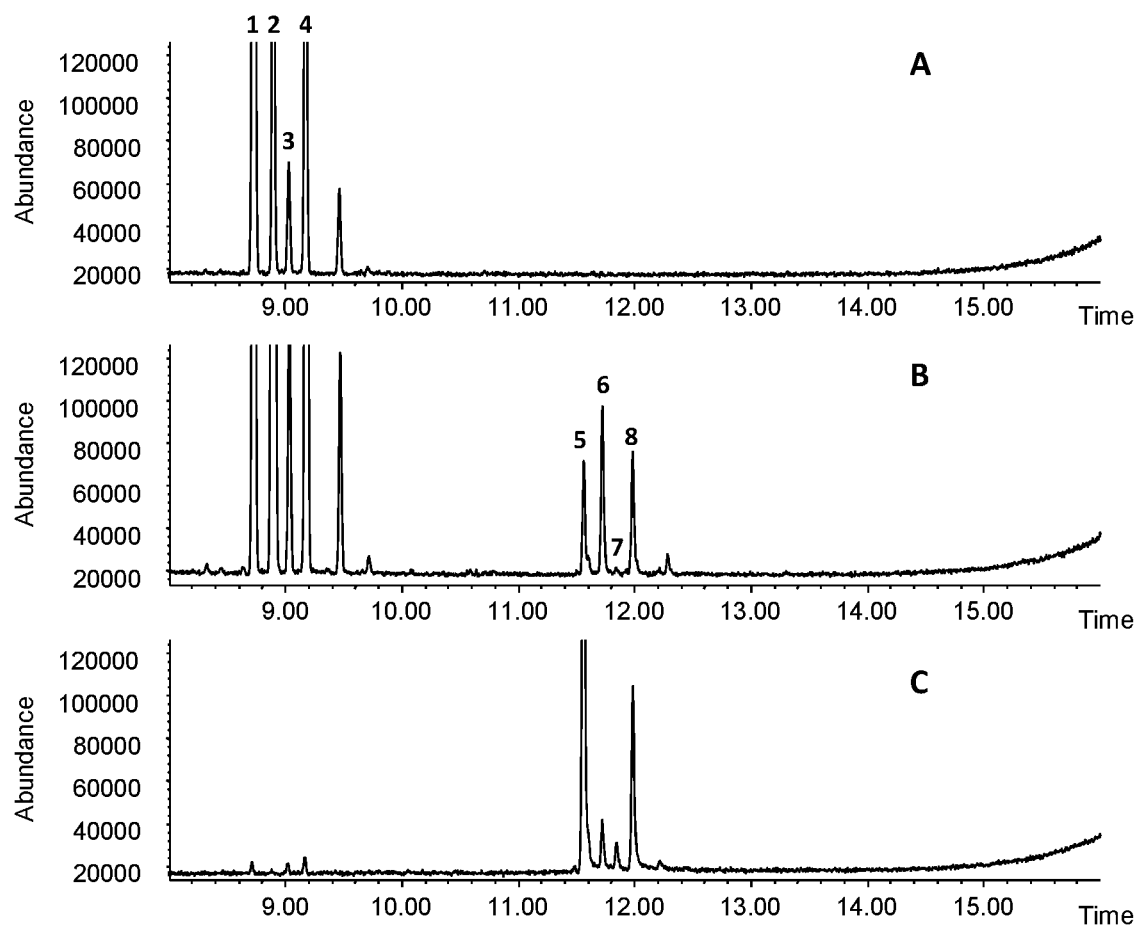

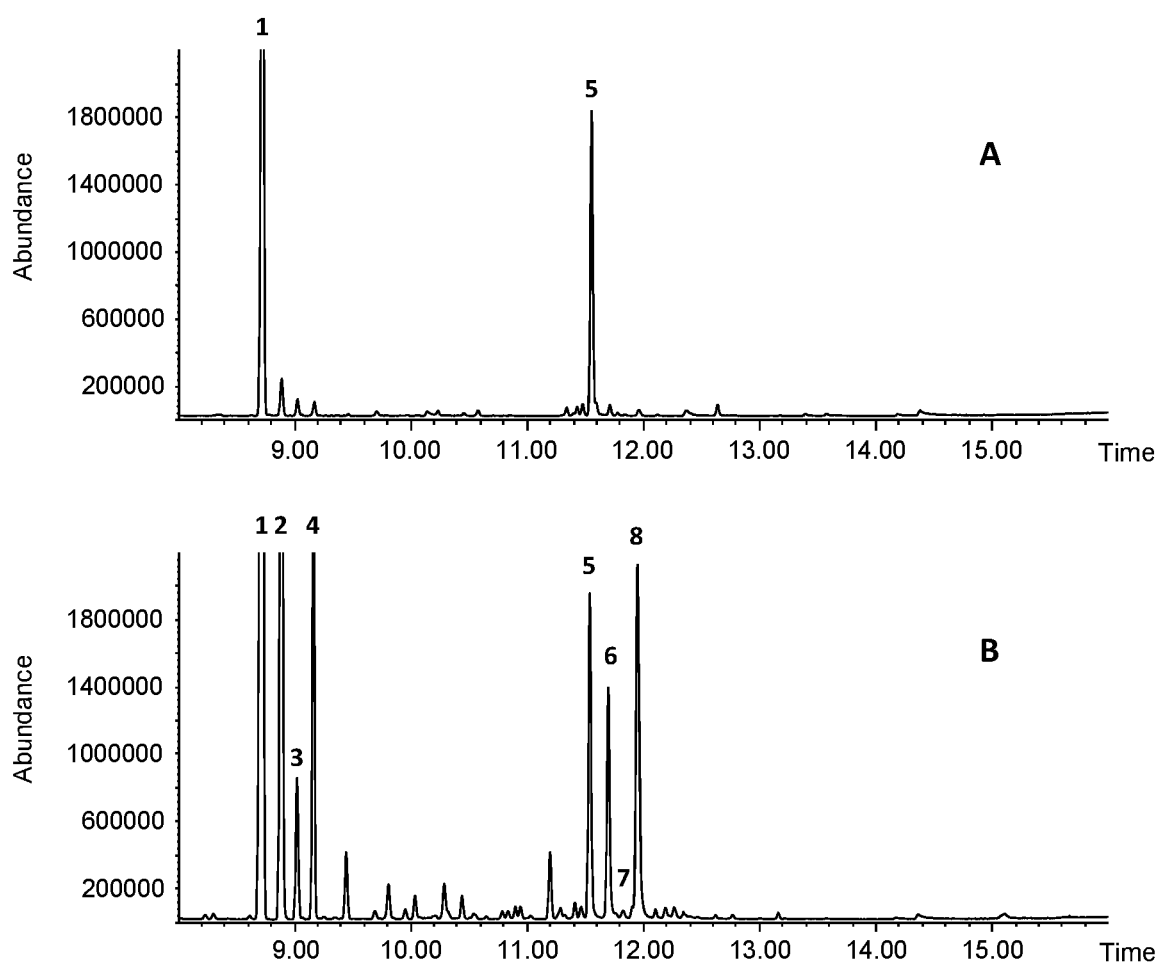
- Figure 14 -

– Figure 15 –
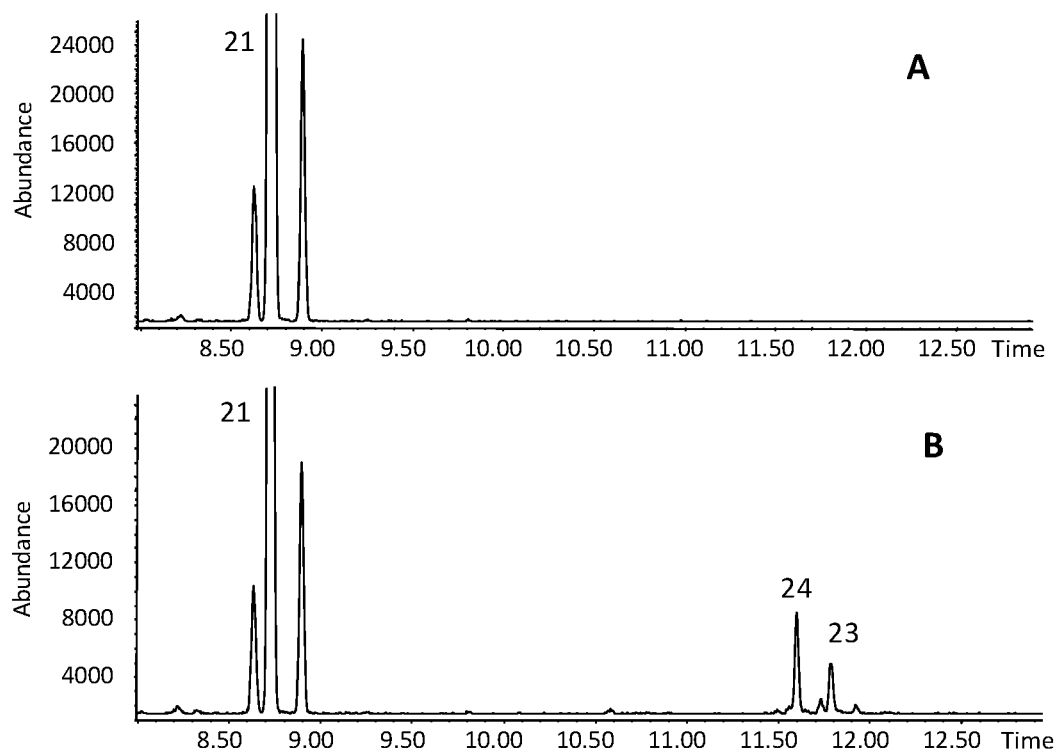

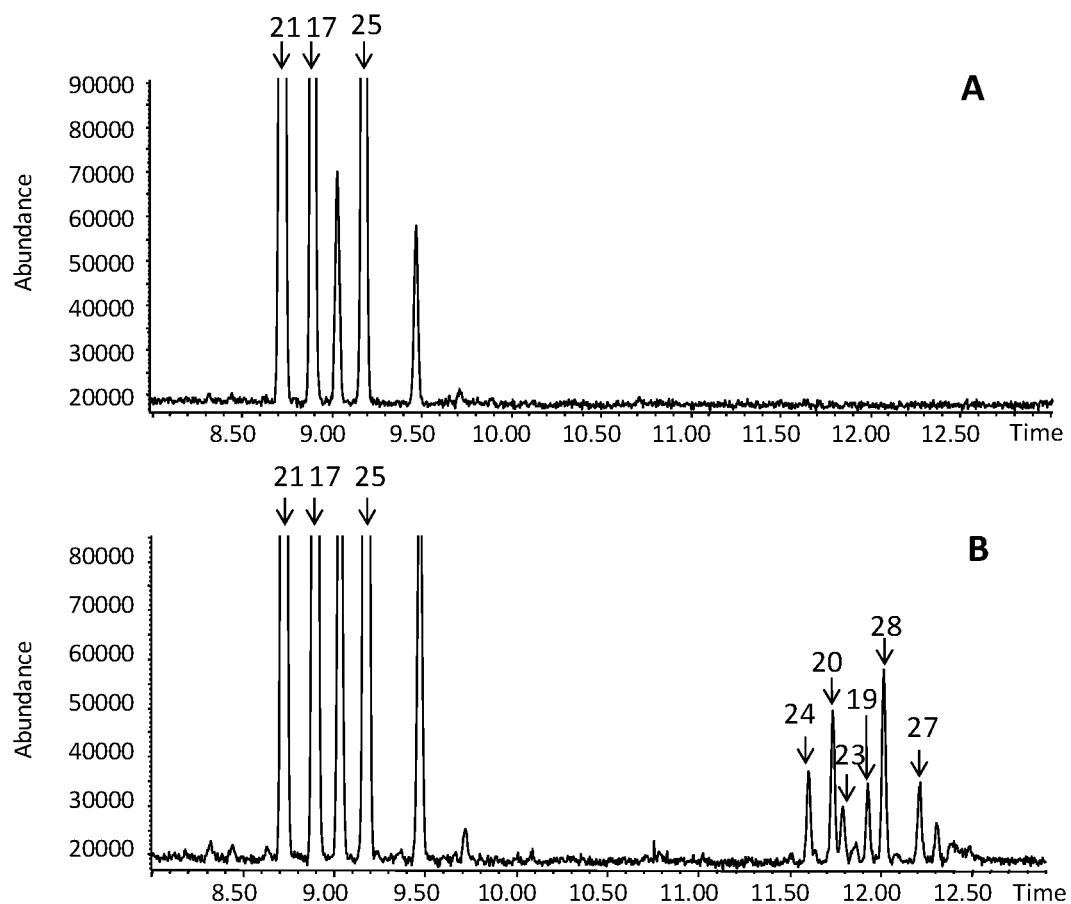
- Figure 16 -

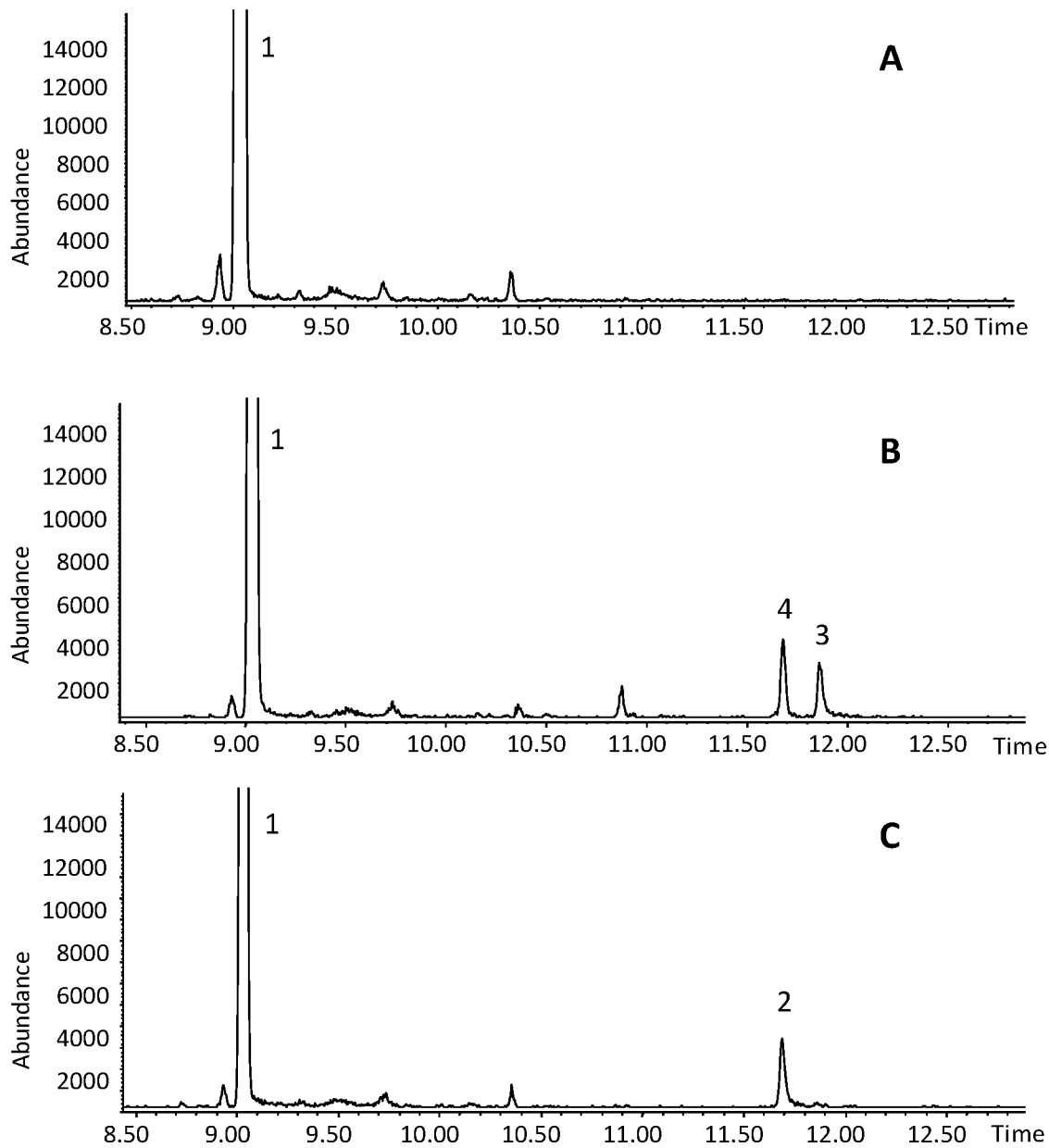
- Figure 17 -

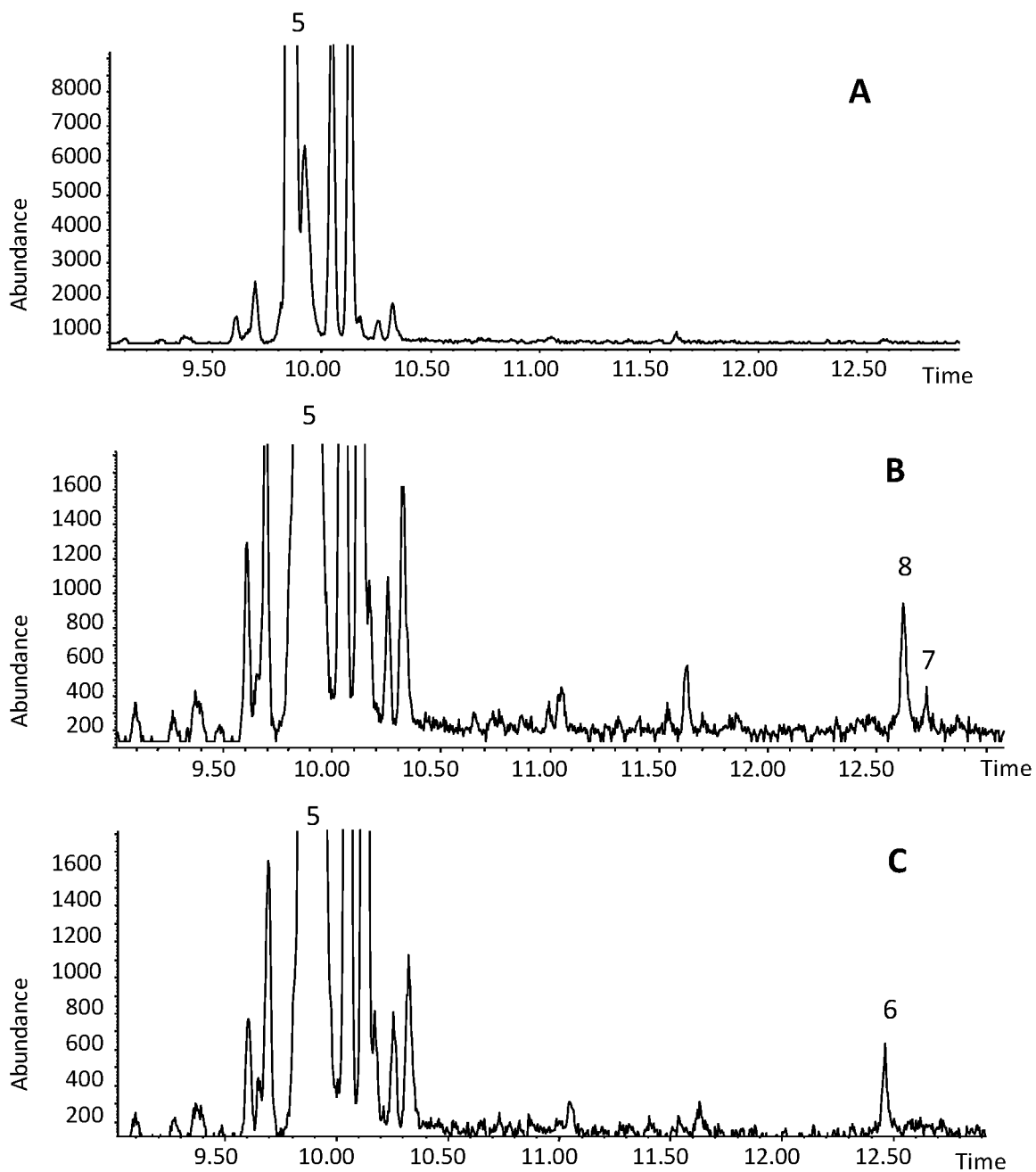
- Figure 18—

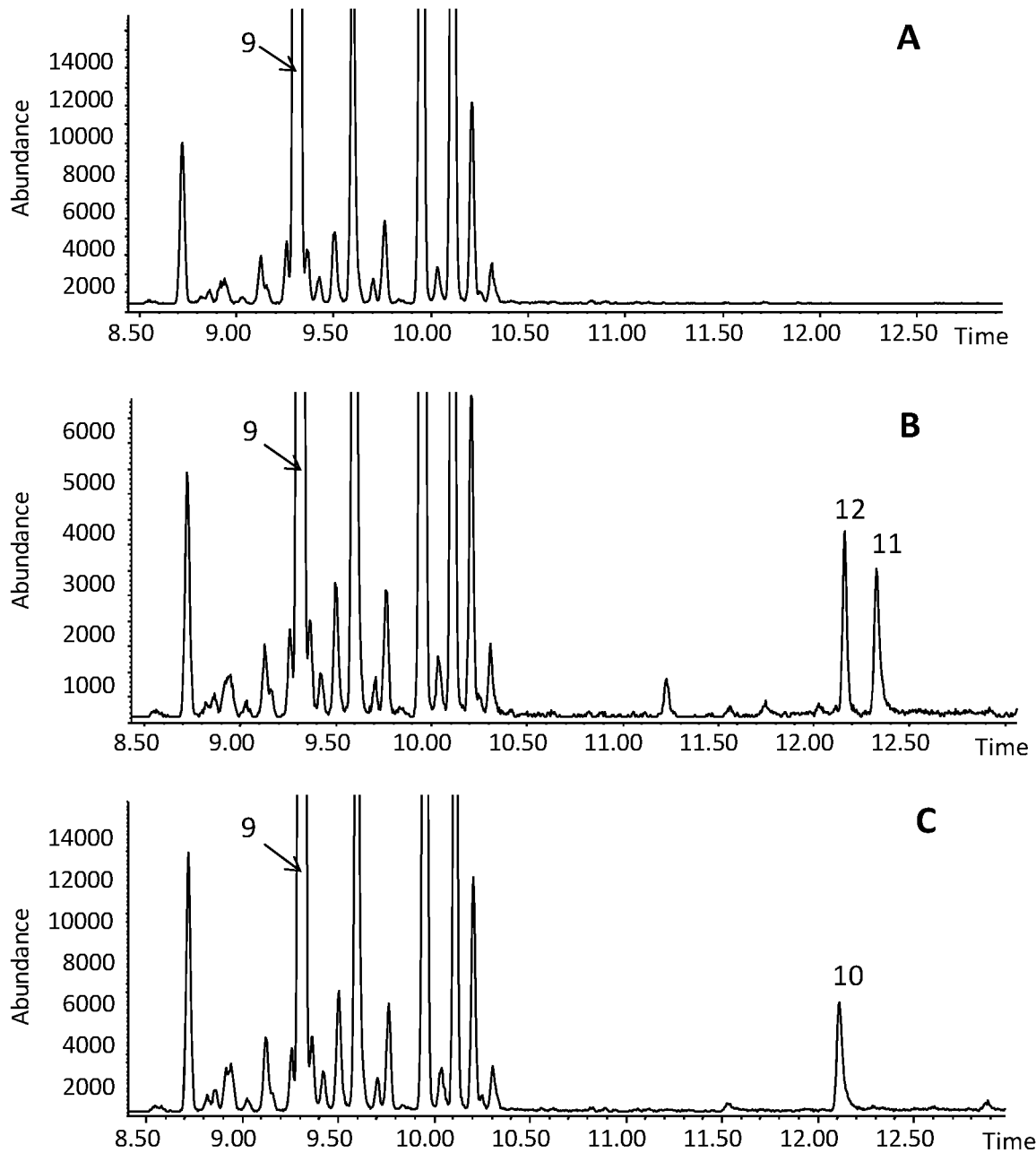
- Figure 19 -

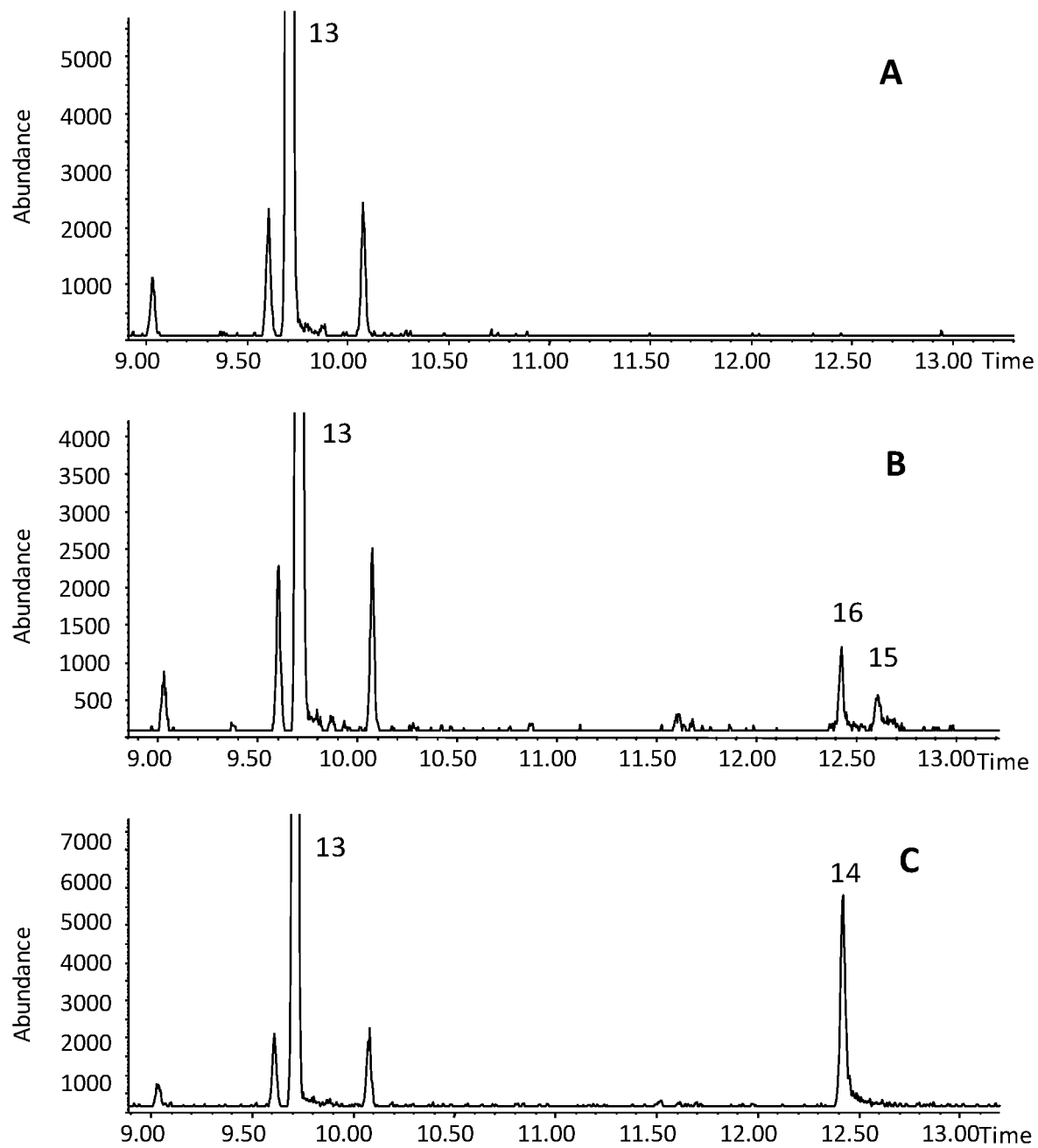
- Figure 20—

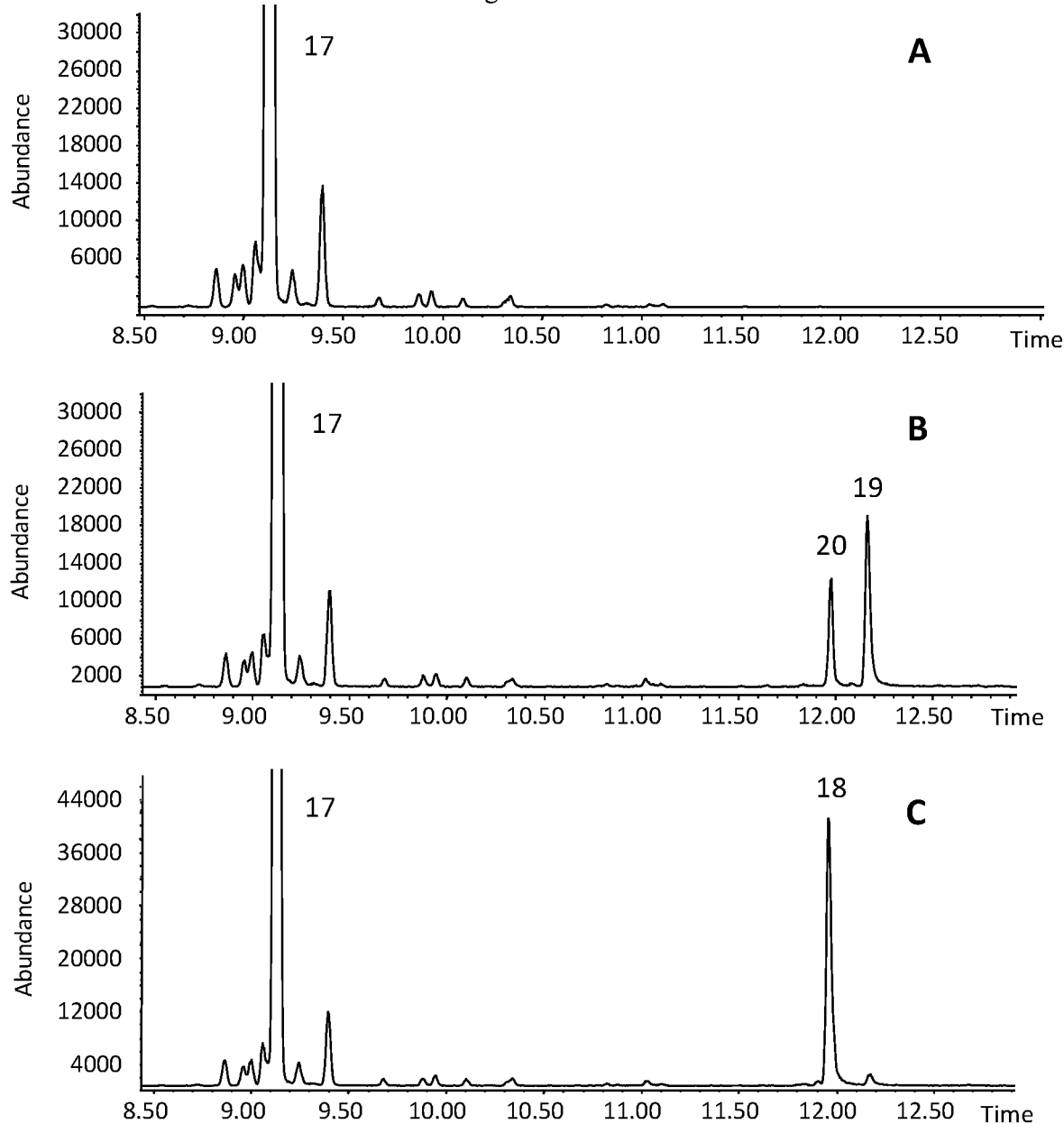
- Figure 21 -

- Figure 22 -
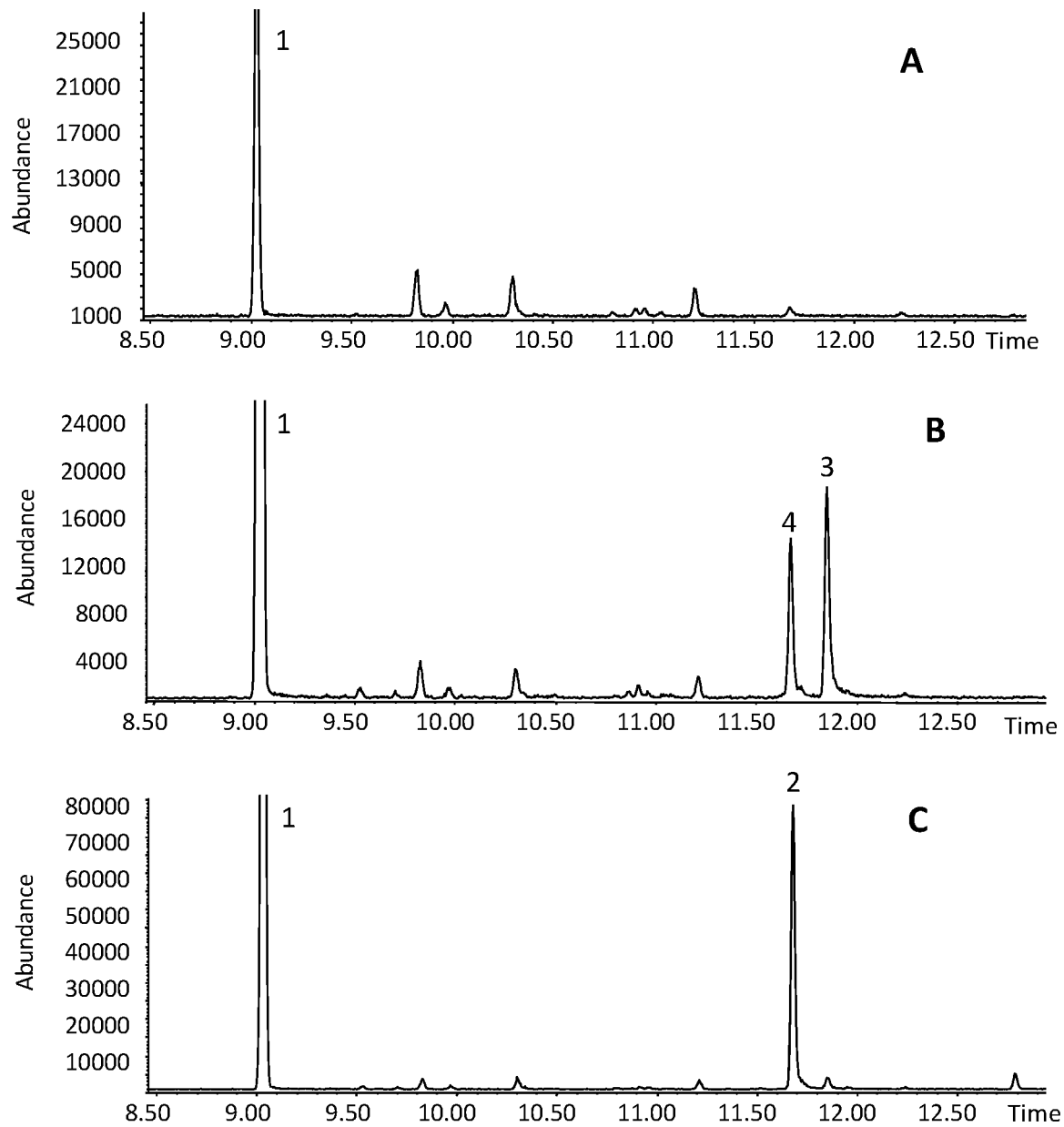

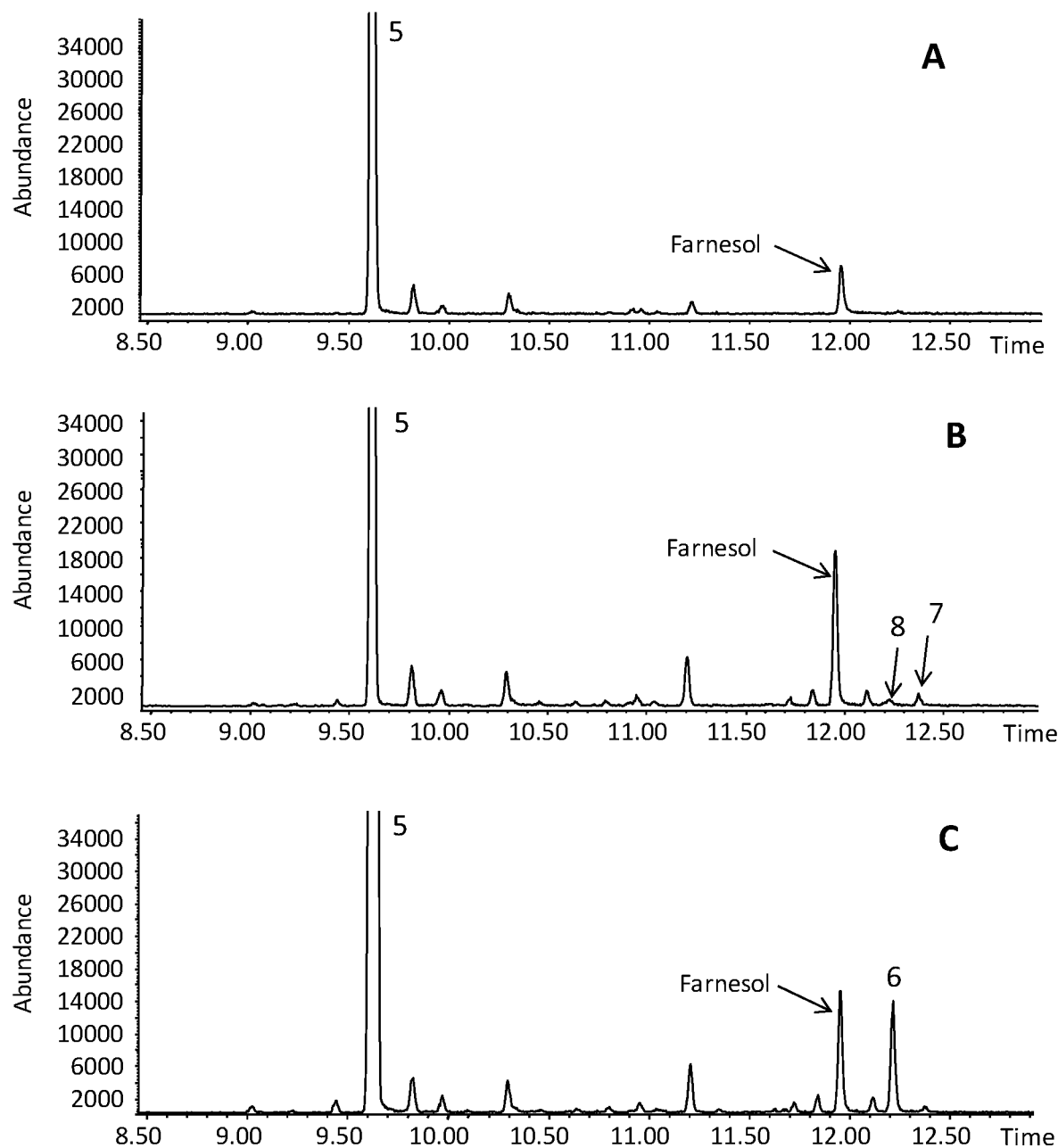
- Figure 23 -

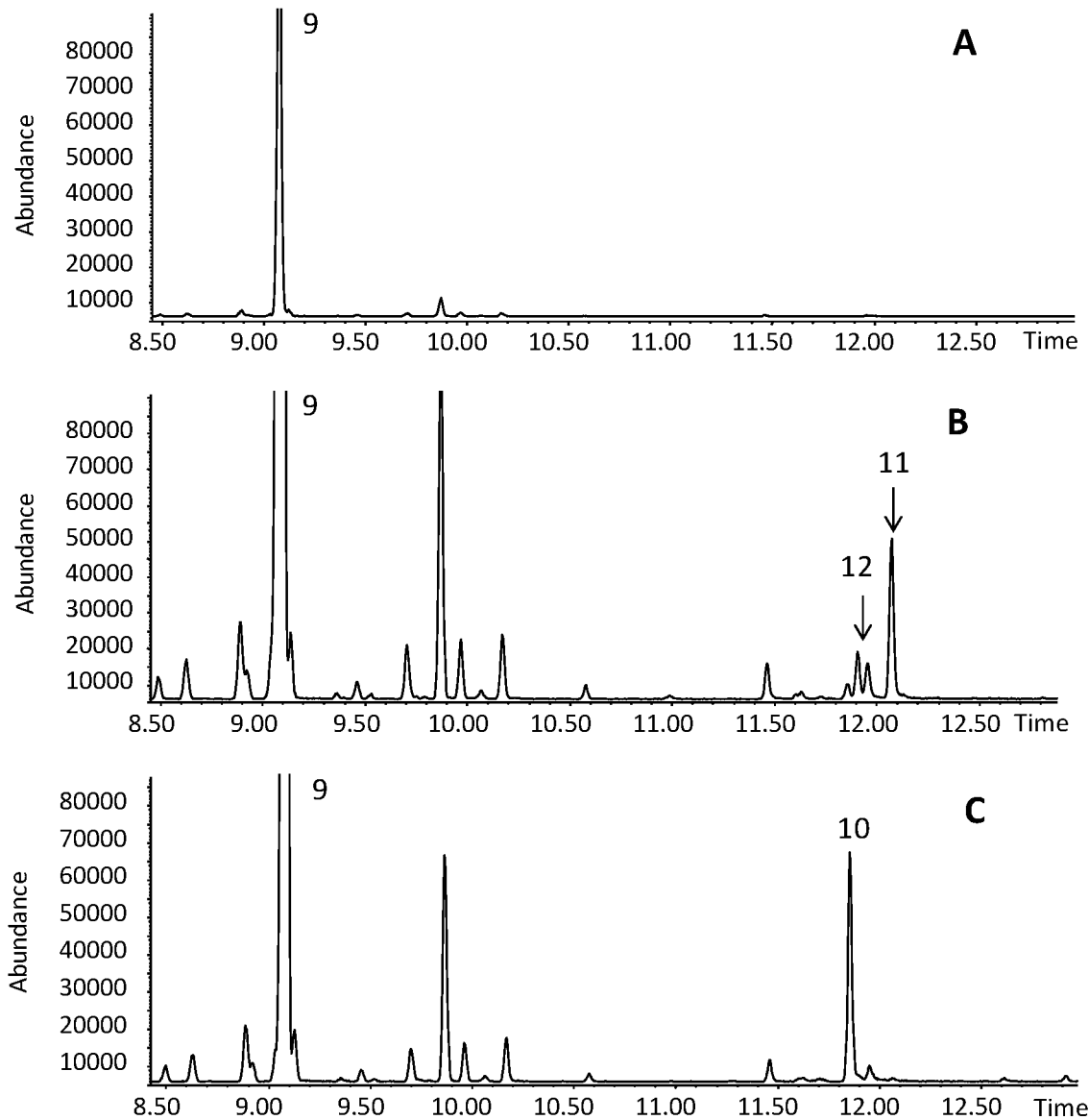
- Figure 24 -

- Figure 25 -
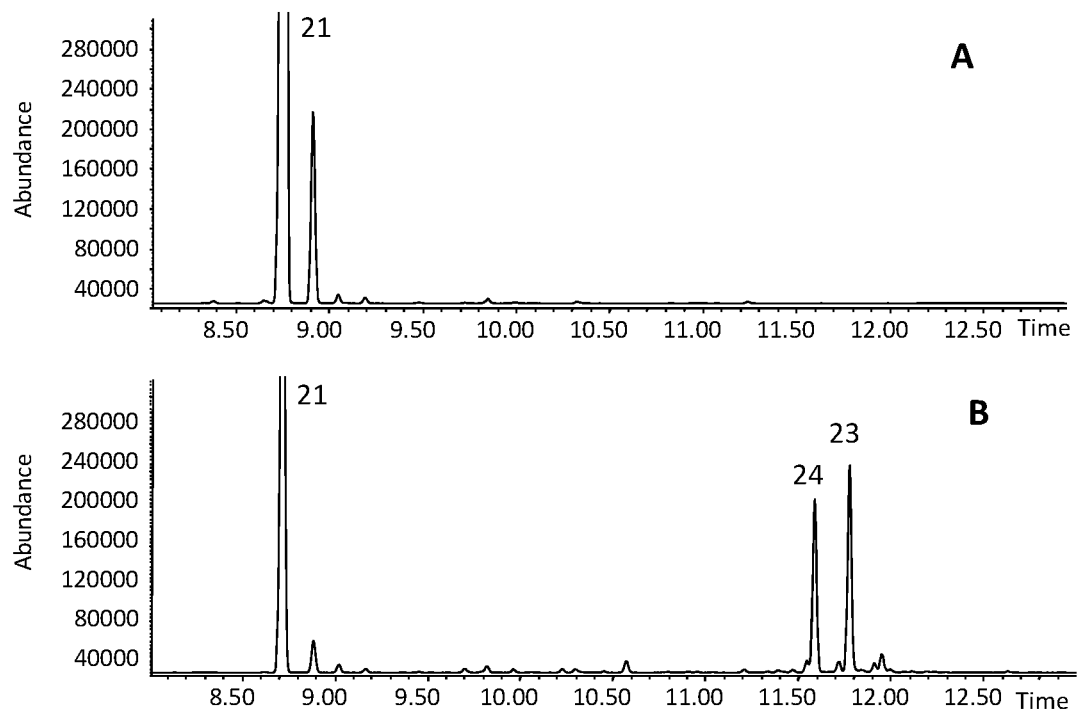

- Figure 26 -
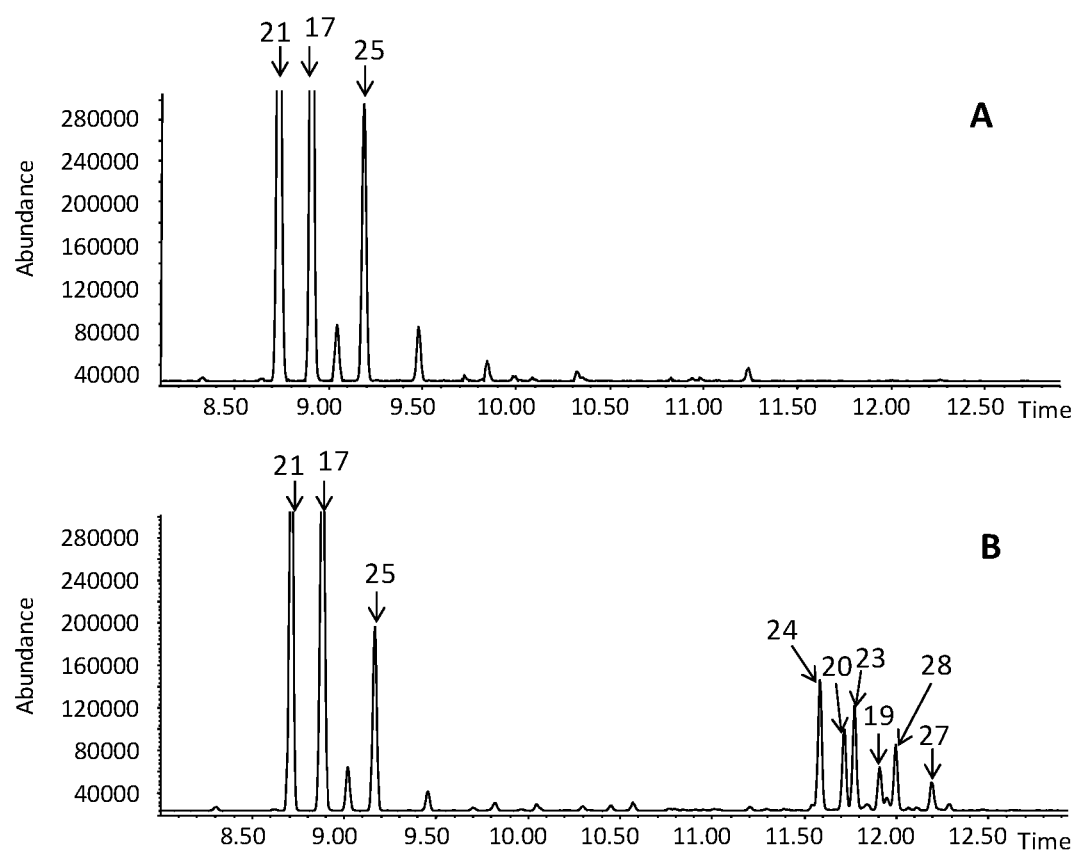

- Figure 27A –

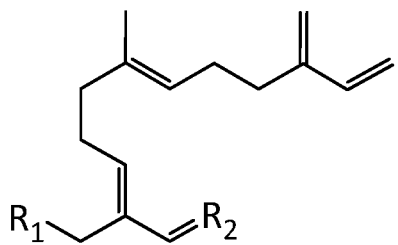

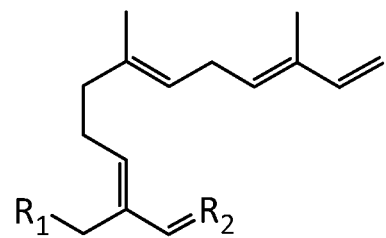

1. *trans-β*-farnesene;   $R_1$ = H, $R_2$ = H,H
2. *(2Z,6E)-* *β*-sinensol; $R_1$ = OH, $R_2$ = H,H
3. *(2E,6E)-* *β*-sinensol; $R_1$ = H, $R_2$ = OH,H
4. *(2E,6E)-* *β*-sinensal; $R_1$ = H, $R_2$ = O 5. *trans-α*-farnesene:   $R_1$ = H, $R_2$ = H,H
6. *(2Z,6E,9E)-α*-sinensol; $R_1$ = OH, $R_2$ = H,H
7. *(2E,6E,9E)-α*-sinensol; $R_1$ = H, $R_2$ = OH,H
8. *(2E,6E,9E)-α*-sinensal; $R_1$ = H, $R_2$ = O

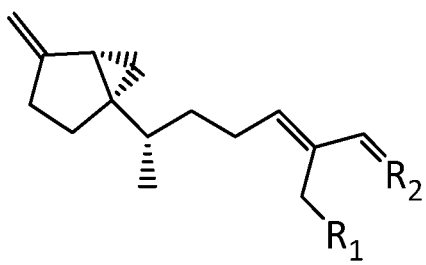

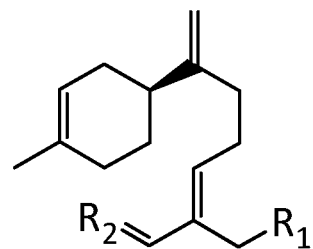

9. *(-)*-Sesquisabinene B; $R_1$ = H, $R_2$ = H,H
10. $R_1$ = OH, $R_2$ = H,H
11. $R_1$ = H, $R_2$ = OH,H
12. $R_1$ = H, $R_2$ = O 13. *(-)-β*-Bisabolene;   $R_1$ = H, $R_2$ = H,H
14. *(-)-(Z)*-lanceol;    $R_1$ = OH, $R_2$ = H,H
15. *(E)*-lanceol;  $R_1$ = H, $R_2$ = OH,H
16. *(E)*-lanceal   $R_1$ = H, $R_2$ = O

- Figure 27B -
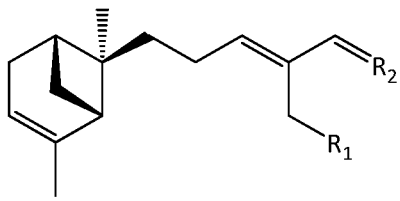
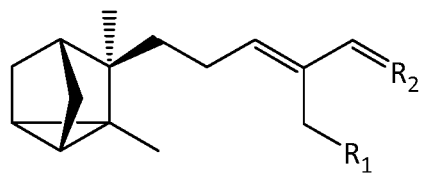
17. *(-)-trans-α-*Bergamotene; $R_1$ = H, $R_2$ = H,H
18. *(-)-(Z)-trans-α-*bergamotol; $R_1$ = OH, $R_2$ = H,H
19. *(-)-(E)-trans-α-*bergamotol; $R_1$ = H, $R_2$ = OH,H
20. *(E)-trans-α-*bergamotal; $R_1$ = H, $R_2$ = O
21. *(+)-α-*santalene; $R_1$ = H, $R_2$ = H,H
22. *(+)-(Z)-α-*santalol; $R_1$ = OH, $R_2$ = H,H
23. *(+)-(E)-α-*santalol; $R_1$ = H, $R_2$ = OH,H
24. *(E)-α-*santalal; $R_1$ = H, $R_2$ = O
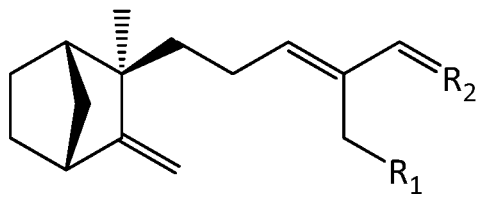
25. *(-)-β-*santalene; $R_1$ = H, $R_2$ = H,H
26. *(-)-(Z)- β-*santalol; $R_1$ = OH, $R_2$ = H,H
27. *(-)-(E)- β-*santalol; $R_1$ = H, $R_2$ = OH,H
28. *(-)-(E)- β-*santalal; $R_1$ = H, $R_2$ = O

SEQUENCE LISTING

```
<160> NUMBER OF SEQ ID NOS: 104

<210> SEQ ID NO 1
<211> LENGTH: 1500
<212> TYPE: DNA
<213> ORGANISM: Cichorium intybus

<400> SEQUENCE: 1
atggagattt ctatccccac tacccttggc cttgccgtca tcatcttcat cattttcaag      60
ttgctaacgc gtaccacatc aaagaaaaac ctactcccag agccatggag actaccaata     120
atcggacaca tgcatcatct gataggtacg atgccacatc gtggtgtcat ggaactagcc     180
aggaagcatg gatctctcat gcatctacaa cttggagaag tgtccactat tgtggtctca     240
tccccacgtt gggcaaaaga ggttctgaca acgtacgata ttacgtttgc aaacagaccg     300
gagactttaa ccggtgagat tgttgcatat cacaataccg atattgtcct tgctccgtat     360
ggtgaatact ggaggcagtt gcgaaagctt tgcaccttgg agcttttaag caacaagaaa     420
gtgaagtcgt ttcagtccct tcgtgaggag gaatgttgga atctggttaa agacattcga     480
tcaactgggc agggatcccc aatcaatctt tcagaaaaca ttttcaagat gattgccacc     540
atacttagta gggcagcatt cggaaaggga atcaaagacc aaatgaaatt tacagaatta     600
```

```
gtaaaagaaa tactaaggct tacgggaggt tttgatgtgg cggacatctt tccttctaaa      660
aagttacttc accatctttc aggcaagaga gctaagttaa ccaacataca caataagctt      720
gacaatttga tcaacaatat catcgctgag caccctggaa accgtacaag ctcatcacag      780
gagactctac ttgatgttct gttaagactg aaagaaagcg cagagtttcc attgacagca      840
gacaatgtca aagcagtcat tttggatatg tttggagctg cacggatac ttcgtcagcc       900 acaattgaat gggcaatctc agaattgata aggtgtccga gagccatgga gaaagttcaa      960
acagaattaa ggcaagcact aaatggaaag gaaaggatcc aagaagaaga tctacaggaa     1020
ctaaattacc taaagctagt gatcaaagaa acattgaggt tgcatccacc actaccgttg     1080
gttatgccta gagagtgtag ggagccatgt gtgttggggg gatacgatat acccagcaag     1140
acgaaactta ttgtcaacgt gtttgccata acagggatc ctgaatactg aaagatgct       1200 gaaactttca tgccagagag atttgaaaac agccccatca ctgtaatggg ttcagagtat     1260
gagtatctcc cgtttggtgc aggaagaaga atgtgtccag cgctgccct tggtttagcc      1320 aacgtggaac ttcctcttgc tcatatactt tactacttca attggaagct cccaaatgga     1380
aaaacatttg aagacttgga catgactgag agctttggag ccactgtcca agaaagacg      1440 gagttgttac tagttccaac ggatttccaa acacttacgg catctactta atgactcgag     1500
```

<210> SEQ ID NO 2
<211> LENGTH: 496
<212> TYPE: PRT
<213> ORGANISM: Cichorium intybus

<400> SEQUENCE: 2

```
Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
                20                  25                  30

Pro Glu Pro Trp Arg Leu Pro Ile Ile Gly His Met His His Leu Ile
            35                  40                  45

Gly Thr Met Pro His Arg Gly Val Met Glu Leu Ala Arg Lys His Gly
        50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
```

```
                  210                 215                 220
His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255

Ser Ser Ser Gln Glu Thr Leu Leu Asp Val Leu Leu Arg Leu Lys Glu
            260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Leu Gln Glu Leu Asn Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Gly Gly Tyr Asp Ile Pro Ser Lys Thr Lys Leu Ile
370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Lys Thr Phe Glu
450                 455                 460

Asp Leu Asp Met Thr Glu Ser Phe Gly Ala Thr Val Gln Arg Lys Thr
465                 470                 475                 480

Glu Leu Leu Leu Val Pro Thr Asp Phe Gln Thr Leu Thr Ala Ser Thr
                485                 490                 495

<210> SEQ ID NO 3
<211> LENGTH: 1473
<212> TYPE: DNA
<213> ORGANISM: Artificial Sequence
<220> FEATURE:
<223> OTHER INFORMATION: CYP71AV8-65188 DNA sequence

<400> SEQUENCE: 3
atggcactct tactggcagt attctggtcc gccctgatca ttcttgtaac ccgcacgact    60
agcaaaaaga tctgttgcc ggagccatgg cgtctgccga ttatcggtca catgcaccat   120
ttgatcggca ccatgccgca tcgtggtgtt atggaactgg cccgtaagca tggcagcctg   180
atgcacctgc aactgggtga agtctctacg attgttgtca gcagcccgcg ttgggcgaaa   240
gaggtcttga ccacctatga tatcaccttc gccaatcgcc cggaaaccct gactggcgag   300
atcgtcgcat accacaacac ggatatcgtc ctggcgccgt atggtgagta ttggcgtcaa   360
ctgcgtaaac tgtgcacgct ggagctgctg agcaacaaga agtgaagag cttccagagc   420 ctgcgcgaag aagagtgttg gaacctggtc aaggacatcc gcagcaccgg ccaaggtagc   480
```

```
ccaatcaatc tgtcggagaa cattttcaag atgattgcga cgattctgag ccgtgctgcg      540
ttcggtaagg gtattaagga tcaaatgaag tttaccgaac tggtgaaaga aatcctgcgt      600
ctgaccggcg gttttgatgt cgctgacatc ttccctagca agaagttgct gcaccacctg      660
agcggcaagc gtgcaaaact gaccaatatc cataacaagc tggataatct gatcaataac      720
atcatcgcag agcacccggg caaccgtacc tcgtcctccc aggaaacgct gctggacgtt      780
ctgctgcgcc tgaaagagtc tgcggagttt ccgctgaccg ccgacaacgt taaagcagtg      840
atcctggata tgttcggcgc tggtacggat accagcagcg cgacgatcga gtgggcgatt      900
agcgagctga ttcgctgccc tcgcgcgatg gagaaagtgc agacggaatt cgtcaggca      960 ctgaatggca aagagcgtat tcaggaagag gatttgcagg agctgaatta tctgaagctg     1020
gtgattaaag aaaccctgcg cctgcatccg ccgttgccgc tggtgatgcc gcgtgagtgc     1080
cgtgaaccgt gtgttttggg cggttacgac attccgagca aaacgaagct gatcgttaat     1140
gttttcgcga ttaaccgtga cccggaatac tggaaagacg cggaaacgtt tatgccggag     1200
cgttttgaga atagcccgat taccgttatg ggttccgagt acgaatacct gccatttggt     1260
gctggtcgtc gtatgtgtcc tggtgcagcg ctgggtctgg ccaacgtgga actgccgctg     1320
gcgcacattc tgtactattt caactggaaa ctgccgaacg gcaagacctt cgaagatttg     1380
gacatgaccg agagctttgg tgccactgtg cagcgcaaaa ccgagctgct gctggttccg     1440
accgactttc aaacgctgac tgcgagcacc taa                                  1473
```

<210> SEQ ID NO 4
<211> LENGTH: 490
<212> TYPE: PRT
<213> ORGANISM: Artificial Sequence
<220> FEATURE:
<223> OTHER INFORMATION: CYP71AV8-65188 amino acid sequence

<400> SEQUENCE: 4

```
Met Ala Leu Leu Leu Ala Val Phe Trp Ser Ala Leu Ile Ile Leu Val
1               5                   10                  15

Thr Arg Thr Thr Ser Lys Lys Asn Leu Leu Pro Glu Pro Trp Arg Leu
            20                  25                  30

Pro Ile Ile Gly His Met His His Leu Ile Gly Thr Met Pro His Arg
        35                  40                  45

Gly Val Met Glu Leu Ala Arg Lys His Gly Ser Leu Met His Leu Gln
    50                  55                  60

Leu Gly Glu Val Ser Thr Ile Val Val Ser Ser Pro Arg Trp Ala Lys
65                  70                  75                  80

Glu Val Leu Thr Thr Tyr Asp Ile Thr Phe Ala Asn Arg Pro Glu Thr
                85                  90                  95

Leu Thr Gly Glu Ile Val Ala Tyr His Asn Thr Asp Ile Val Leu Ala
            100                 105                 110

Pro Tyr Gly Glu Tyr Trp Arg Gln Leu Arg Lys Leu Cys Thr Leu Glu
        115                 120                 125

Leu Leu Ser Asn Lys Lys Val Lys Ser Phe Gln Ser Leu Arg Glu Glu
    130                 135                 140

Glu Cys Trp Asn Leu Val Lys Asp Ile Arg Ser Thr Gly Gln Gly Ser
145                 150                 155                 160

Pro Ile Asn Leu Ser Glu Asn Ile Phe Lys Met Ile Ala Thr Ile Leu
                165                 170                 175

Ser Arg Ala Ala Phe Gly Lys Gly Ile Lys Asp Gln Met Lys Phe Thr
            180                 185                 190
```

```
Glu Leu Val Lys Glu Ile Leu Arg Leu Thr Gly Gly Phe Asp Val Ala
            195                 200                 205
Asp Ile Phe Pro Ser Lys Lys Leu Leu His His Leu Ser Gly Lys Arg
        210                 215                 220
Ala Lys Leu Thr Asn Ile His Asn Lys Leu Asp Asn Leu Ile Asn Asn
225                 230                 235                 240
Ile Ile Ala Glu His Pro Gly Asn Arg Thr Ser Ser Gln Glu Thr
                245                 250                 255
Leu Leu Asp Val Leu Leu Arg Leu Lys Glu Ser Ala Glu Phe Pro Leu
            260                 265                 270
Thr Ala Asp Asn Val Lys Ala Val Ile Leu Asp Met Phe Gly Ala Gly
        275                 280                 285
Thr Asp Thr Ser Ser Ala Thr Ile Glu Trp Ala Ile Ser Glu Leu Ile
        290                 295                 300
Arg Cys Pro Arg Ala Met Glu Lys Val Gln Thr Glu Leu Arg Gln Ala
305                 310                 315                 320
Leu Asn Gly Lys Glu Arg Ile Gln Glu Asp Leu Gln Glu Leu Asn
            325                 330                 335
Tyr Leu Lys Leu Val Ile Lys Glu Thr Leu Arg Leu His Pro Pro Leu
            340                 345                 350
Pro Leu Val Met Pro Arg Glu Cys Arg Glu Pro Cys Val Leu Gly Gly
            355                 360                 365
Tyr Asp Ile Pro Ser Lys Thr Lys Leu Ile Val Asn Val Phe Ala Ile
        370                 375                 380
Asn Arg Asp Pro Glu Tyr Trp Lys Asp Ala Thr Phe Met Pro Glu
385                 390                 395                 400
Arg Phe Glu Asn Ser Pro Ile Thr Val Met Gly Ser Glu Tyr Glu Tyr
            405                 410                 415
Leu Pro Phe Gly Ala Gly Arg Arg Met Cys Pro Gly Ala Ala Leu Gly
            420                 425                 430
Leu Ala Asn Val Glu Leu Pro Leu Ala His Ile Leu Tyr Tyr Phe Asn
        435                 440                 445
Trp Lys Leu Pro Asn Gly Lys Thr Phe Glu Asp Leu Asp Met Thr Glu
        450                 455                 460
Ser Phe Gly Ala Thr Val Gln Arg Lys Thr Glu Leu Leu Leu Val Pro
465                 470                 475                 480
Thr Asp Phe Gln Thr Leu Thr Ala Ser Thr
        485                 490

<210> SEQ ID NO 5
<211> LENGTH: 1509
<212> TYPE: DNA
<213> ORGANISM: Artificial Sequence
<220> FEATURE:
<223> OTHER INFORMATION: CYP71AV8-P2 DNA sequence

<400> SEQUENCE: 5
atggctctgt tattagcagt tttttggtcg gcgcttataa tcctcgtagt aacctacacc      60
atatccctcc taatcaacca atggcgaaaa ccgaaacccc aagggaagtt ccccccgggc     120
ccatggcgtc tgccgattat cggtcacatg caccatttga tcggcaccat gccgcatcgt     180
ggtgttatgg aactggcccg taagcatggc agcctgatgc acctgcaact gggtgaagtc     240
tctacgattg ttgtcagcag cccgcgttgg gcgaaagagg tcttgaccac ctatgatatc     300
accttcgcca atcgcccgga aaccctgact ggcgagatcg tcgcatacca caacacggat     360
```

-continued

```
atcgtcctgg cgccgtatgg tgagtattgg cgtcaactgc gtaaactgtg cacgctggag    420
ctgctgagca acaagaaagt gaagagcttc cagagcctgc gcgaagaaga gtgttggaac    480
ctggtcaagg acatccgcag caccggccaa ggtagcccaa tcaatctgtc ggagaacatt    540
ttcaagatga ttgcgacgat tctgagccgt gctgcgttcg taagggtat  taaggatcaa    600 atgaagttta ccgaactggt gaaagaaatc ctgcgtctga ccggcggttt tgatgtcgct    660
gacatcttcc ctagcaagaa gttgctgcac cacctgagcg gcaagcgtgc aaaactgacc    720
aatatccata caagctgga  taatctgatc aataacatca tcgcagagca cccgggcaac    780
cgtacctcgt cctcccagga  acgctgctga cgttctgc  tgcgcctgaa agagtctgcg    840
gagtttccgc tgaccgccga caacgttaaa gcagtgatcc tggatatgtt cggcgctggt    900
acggatacca gcagcgcgac gatcgagtgg gcgattagcg agctgattcg ctgccctcgc    960
gcgatggaga aagtgcagac ggaattgcgt caggcactga atggcaaaga gcgtattcag   1020
gaagaggatt tgcaggagct gaattatctg aagctggtga ttaaagaaac cctgcgcctg   1080
catccgccgt tgccgctggt gatgccgcgt gagtgccgtg aaccgtgtgt tttgggcggt   1140
tacgacattc cgagcaaaac gaagctgatc gttaatgttt tcgcgattaa ccgtgacccg   1200
gaatactgga agacgcgga  aacgtttatg ccggagcgtt ttgagaatag cccgattacc   1260
gttatgggtt ccgagtacga ataccgtgcca tttggtgctg tcgtcgtat  tgtcctggt   1320 gcagcgctgg gtctggccaa cgtggaactg ccgctggcgc acattctgta ctatttcaac   1380
tggaaactgc cgaacggcaa gaccttcgaa gatttggaca tgaccgagag ctttggtgcc   1440
actgtgcagc gcaaaaccga gctgctgctg gttccgaccg actttcaaac gctgactgcg   1500
agcacctaa                                                           1509
```

<210> SEQ ID NO 6
<211> LENGTH: 502
<212> TYPE: PRT
<213> ORGANISM: Artificial Sequence
<220> FEATURE:
<223> OTHER INFORMATION: CYP71AV8-P2 amino acid sequence

<400> SEQUENCE: 6

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
                20                  25                  30

Pro Gln Gly Lys Phe Pro Pro Gly Pro Trp Arg Leu Pro Ile Ile Gly
            35                  40                  45

His Met His His Leu Ile Gly Thr Met Pro His Arg Gly Val Met Glu
        50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
```

```
                145                 150                 155                 160
Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
                180                 185                 190

Phe Gly Lys Gly Ile Lys Asp Gln Met Lys Phe Thr Glu Leu Val Lys
                195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Ile Ile Ala Glu
                245                 250                 255

His Pro Gly Asn Arg Thr Ser Ser Gln Glu Thr Leu Leu Asp Val
                260                 265                 270

Leu Leu Arg Leu Lys Glu Ser Ala Glu Phe Pro Leu Thr Ala Asp Asn
                275                 280                 285

Val Lys Ala Val Ile Leu Asp Met Phe Gly Ala Gly Thr Asp Thr Ser
290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
                340                 345                 350

Val Ile Lys Glu Thr Leu Arg Leu His Pro Pro Leu Pro Leu Val Met
                355                 360                 365

Pro Arg Glu Cys Arg Glu Pro Cys Val Leu Gly Gly Tyr Asp Ile Pro
                370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
                420                 425                 430

Ala Gly Arg Arg Met Cys Pro Gly Ala Ala Leu Gly Leu Ala Asn Val
                435                 440                 445

Glu Leu Pro Leu Ala His Ile Leu Tyr Tyr Phe Asn Trp Lys Leu Pro
                450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
                500

<210> SEQ ID NO 7
<211> LENGTH: 1509
<212> TYPE: DNA
<213> ORGANISM: Artificial Sequence
<220> FEATURE:
<223> OTHER INFORMATION: CYP71AV8-P2O DNA sequence

<400> SEQUENCE: 7
atggcactgt tgctggctgt cttttggtct gctctgatta ttttggtggt tacctacacc    60
```

```
atctccctgc tgattaacca gtggcgtaaa ccgaaaccac agggtaaatt cccgccgggt    120
ccgtggcgtc tgccgattat cggtcacatg caccatttga tcggcaccat gccgcatcgt    180
ggtgttatgg aactggcccg taagcatggc agcctgatgc acctgcaact gggtgaagtc    240
tctacgattg ttgtcagcag cccgcgttgg gcgaaagagg tcttgaccac ctatgatatc    300
accttcgcca tcgcccgga aaccctgact ggcgagatcg tcgcatacca acacggat      360 atcgtcctgg cgccgtatgg tgagtattgg cgtcaactgc gtaaactgtg cacgctggag    420
ctgctgagca acaagaaagt gaagagcttc cagagcctgc gcgaagaaga gtgttggaac    480
ctggtcaagg acatccgcag caccggccaa ggtagcccaa tcaatctgtc ggagaacatt    540
ttcaagatga ttgcgacgat tctgagccgt gctgcgttcg gtaagggtat taaggatcaa    600
atgaagttta ccgaactggt gaaagaaatc ctgcgtctga ccggcggttt tgatgtcgct    660
gacatcttcc ctagcaagaa gttgctgcac cacctgagcg gcaagcgtgc aaaactgacc    720
aatatccata caagctgga taatctgatc aataacatca tcgcagagca cccgggcaac    780
cgtacctcgt cctcccagga aacgctgctg acgttctgc tgcgcctgaa agagtctgcg    840
gagtttccgc tgaccgccga caacgttaaa gcagtgatcc tggatatgtt cggcgctggt    900
acggatacca gcagcgcgac gatcgagtgg gcgattagcg agctgattcg ctgccctcgc    960
gcgatggaga aagtgcagac ggaattgcgt caggcactga atggcaaaga gcgtattcag   1020
gaagaggatt tgcaggagct gaattatctg aagctggtga ttaaagaaac cctgcgcctg   1080
catccgccgt tgccgctggt gatgccgcgt gagtgccgtg aaccgtgtgt tttgggcggt   1140
tacgacattc cgagcaaaac gaagctgatc gttaatgttt tcgcgattaa ccgtgacccg   1200
gaatactgga agacgcgga aacgtttatg ccggagcgtt ttgagaatag cccgattacc   1260
gttatgggtt ccgagtacga atacctgcca tttggtgctg gtcgtcgtat tgtgtcctggt   1320 gcagcgctgg gtctggccaa cgtggaactg ccgctggcgc acattctgta ctatttcaac   1380
tggaaactgc cgaacggcaa gaccttcgaa gatttggaca tgaccgagag ctttggtgcc   1440
actgtgcagc gcaaaaccga gctgctgctg gttccgaccg actttcaaac gctgactgcg   1500
agcacctaa                                                            1509
```

<210> SEQ ID NO 8
<211> LENGTH: 502
<212> TYPE: PRT
<213> ORGANISM: Artificial Sequence
<220> FEATURE:
<223> OTHER INFORMATION: CYP71AV8-P2O amino acid sequence

<400> SEQUENCE: 8

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95
```

```
Thr Tyr Asp Ile Thr Phe Ala Asn Arg Pro Glu Thr Leu Thr Gly Glu
                100                 105                 110

Ile Val Ala Tyr His Asn Thr Asp Ile Val Leu Ala Pro Tyr Gly Glu
            115                 120                 125

Tyr Trp Arg Gln Leu Arg Lys Leu Cys Thr Leu Glu Leu Leu Ser Asn
        130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
            245                 250                 255

His Pro Gly Asn Arg Thr Ser Ser Gln Glu Thr Leu Leu Asp Val
        260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
        290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Leu Pro Leu Val Met
        355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
            405                 410                 415

Ser Pro Ile Thr Val Met Gly Ser Glu Tyr Glu Tyr Leu Pro Phe Gly
        420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
        450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 9
<211> LENGTH: 2133
<212> TYPE: DNA
<213> ORGANISM: Mentha piperita

<400> SEQUENCE: 9

| | | |
|---|---|---|
| atggaaccta gctctcagaa actgtctccg ttggaatttg ttgctgctat cctgaagggc | 60 |
| gactacagca gcggtcaggt tgaaggtggt ccaccgccag gtctggcagc tatgttgatg | 120 |
| gaaaataagg atttggtgat ggttctgacg acgtccgtgg cagtcctgat cggctgtgtc | 180 |
| gtggtcctgg catggcgtcg tgcggcaggt agcggtaagt acaagcaacc tgaactgcct | 240 |
| aaaactggtg tcccgaaagc agccgaaccg gaggaggcag aggatgataa aaccaagatc | 300 |
| agcgtgtttt tcggcaccca aaccggtacg gcagaaggtt tcgcgaaggc ttttgttgaa | 360 |
| gaggccaagg cgcgttatca gcaggcccgt ttcaaagtta tcgacctgga cgactatgcg | 420 |
| gcagacgatg acgagtacga agagaaactg aagaaggaaa acttggcatt cttcttcttg | 480 |
| gcgtcctacg gtgacggcga ccgacggac aacgcggcac gcttttacaa atggtttacg | 540 |
| gagggtaagg accgtggtga atggctgaac aatctgcagt acggcgtttt tggtctgggt | 600 |
| aaccgtcaat atgagcattt caataagatc gccattgtcg tcgatgatct gatcttcgag | 660 |
| caaggtggca agaagctggt tccggtgggt ctgggtgacg atgaccagtg cattgaggat | 720 |
| gattttgcgg cgtggcgtga actggtctgg ccggaactgg ataaactgct gcgtaacgaa | 780 |
| gacgacgcta ccgtggcaac cccgtacagc gccgctgtgc tgcaataccg cgtggttttc | 840 |
| cacgatcaca ttgacggcct gattagcgaa acggtagcc cgaacggtca tgctaatggc | 900 |
| aataccgtgt acgatgcgca cacccgtgc cgtagcaacg tcgcggtcaa gaaggaattg | 960 |
| catactccgg cgagcgatcg cagctgcacc cacctggaat ttaacattag cggtaccggc | 1020 |
| ctgatgtacg agacgggtga ccacgtcggt gtgtattgcg agaacctgtt ggaaaccgtg | 1080 |
| gaggaggccg agaagttgtt gaacctgagc ccgcagacgt acttctccgt tcacaccgac | 1140 |
| aacgaggacg gtacgccgtt gagcggcagc agcctgccgc caccgtttcc gccgtgcacc | 1200 |
| ttgcgcacgg cattgaccaa atacgcagac ttgacttctg caccgaaaaa gtcggtgctg | 1260 |
| gtggcgctgg ccgagtacgc atctgaccag ggtgaagcgg atcgtttgcg tttcttggcg | 1320 |
| agcccgagcg gcaaagagga atatgcacag tacatcttgg caagccagcg cacgctgctg | 1380 |
| gaggtcatgg cggagttccc gtcggcgaaa ccgccgctgg gtgtcttttt cgcgggtgtc | 1440 |
| gctccgcgcc tgcagccgcg tttctattcc attagctcta gcccgaagat cgcaccgttc | 1500 |
| cgtattcacg tgacctgcgc cctggtttat gacaaatccc ctaccggtcg cgttcataag | 1560 |
| ggcatctgta gcacgtggat gaaaaatgcg gtcccgctgg aagaaagcaa cgattgttcc | 1620 |
| tgggctccga tcttcgtccg caacagcaac ttcaagctgc cgaccgaccc gaaggttccg | 1680 |
| attatcatga ttggtccggg taccggtctg gccccttttc gtggcttttt gcaagagcgc | 1740 |
| ttggcgttga agagagcgg tgctgaattg ggtccggcga tcttgttctt ggttgccgt | 1800 |
| aaccgtaaaa tggactttat ttacgaggat gaactgaatg atttcgtcaa agcgggcgtt | 1860 |
| gtcagcgagc tgatcgtcgc tttagccgc gaaggcccga tgaaagaata cgtgcaacac | 1920 |
| aaaatgagcc aacgtgcctc cgatgtgtgg aacatcatta gcgacggtgg ttatgtttat | 1980 |
| gtttgcggtg acgcgaaggg tatggctcgt gatgttcacc gtaccctgca taccatcgca | 2040 |
| caggagcaag gtagcatgtc cagctcggag gccgaaggta tggtcaaaaa cctgcaaacc | 2100 |
| accggtcgtt acctgcgtga tgtgtggtaa taa | 2133 |

<210> SEQ ID NO 10
<211> LENGTH: 709
<212> TYPE: PRT
<213> ORGANISM: Mentha piperita

<400> SEQUENCE: 10

```
Met Glu Pro Ser Ser Gln Lys Leu Ser Pro Leu Glu Phe Val Ala Ala
1               5                   10                  15

Ile Leu Lys Gly Asp Tyr Ser Ser Gly Gln Val Glu Gly Gly Pro Pro
            20                  25                  30

Pro Gly Leu Ala Ala Met Leu Met Glu Asn Lys Asp Leu Val Met Val
        35                  40                  45

Leu Thr Thr Ser Val Ala Val Leu Ile Gly Cys Val Val Val Leu Ala
    50                  55                  60

Trp Arg Arg Ala Ala Gly Ser Gly Lys Tyr Lys Gln Pro Glu Leu Pro
65                  70                  75                  80

Lys Leu Val Val Pro Lys Ala Ala Glu Pro Glu Glu Ala Glu Asp Asp
                85                  90                  95

Lys Thr Lys Ile Ser Val Phe Phe Gly Thr Gln Thr Gly Thr Ala Glu
            100                 105                 110

Gly Phe Ala Lys Ala Phe Val Glu Glu Ala Lys Ala Arg Tyr Gln Gln
        115                 120                 125

Ala Arg Phe Lys Val Ile Asp Leu Asp Asp Tyr Ala Ala Asp Asp Asp
    130                 135                 140

Glu Tyr Glu Glu Lys Leu Lys Lys Glu Asn Leu Ala Phe Phe Phe Leu
145                 150                 155                 160

Ala Ser Tyr Gly Asp Gly Glu Pro Thr Asp Asn Ala Ala Arg Phe Tyr
                165                 170                 175

Lys Trp Phe Thr Glu Gly Lys Asp Arg Gly Glu Trp Leu Asn Asn Leu
            180                 185                 190

Gln Tyr Gly Val Phe Gly Leu Gly Asn Arg Gln Tyr Glu His Phe Asn
        195                 200                 205

Lys Ile Ala Ile Val Val Asp Asp Leu Ile Phe Glu Gln Gly Gly Lys
    210                 215                 220

Lys Leu Val Pro Val Gly Leu Gly Asp Asp Asp Gln Cys Ile Glu Asp
225                 230                 235                 240

Asp Phe Ala Ala Trp Arg Glu Leu Val Trp Pro Glu Leu Asp Lys Leu
                245                 250                 255

Leu Arg Asn Glu Asp Asp Ala Thr Val Ala Thr Pro Tyr Ser Ala Ala
            260                 265                 270

Val Leu Gln Tyr Arg Val Val Phe His Asp His Ile Asp Gly Leu Ile
        275                 280                 285

Ser Glu Asn Gly Ser Pro Asn Gly His Ala Asn Gly Asn Thr Val Tyr
    290                 295                 300

Asp Ala Gln His Pro Cys Arg Ser Asn Val Ala Val Lys Lys Glu Leu
305                 310                 315                 320

His Thr Pro Ala Ser Asp Arg Ser Cys Thr His Leu Glu Phe Asn Ile
                325                 330                 335

Ser Gly Thr Gly Leu Met Tyr Glu Thr Gly Asp His Val Gly Val Tyr
            340                 345                 350

Cys Glu Asn Leu Leu Glu Thr Val Glu Glu Ala Glu Lys Leu Leu Asn
        355                 360                 365

Leu Ser Pro Gln Thr Tyr Phe Ser Val His Thr Asp Asn Glu Asp Gly
    370                 375                 380
```

```
Thr Pro Leu Ser Gly Ser Ser Leu Pro Pro Pro Phe Pro Pro Cys Thr
385                 390                 395                 400

Leu Arg Thr Ala Leu Thr Lys Tyr Ala Asp Leu Thr Ser Ala Pro Lys
            405                 410                 415

Lys Ser Val Leu Val Ala Leu Ala Glu Tyr Ala Ser Asp Gln Gly Glu
        420                 425                 430

Ala Asp Arg Leu Arg Phe Leu Ala Ser Pro Ser Gly Lys Glu Glu Tyr
            435                 440                 445

Ala Gln Tyr Ile Leu Ala Ser Gln Arg Thr Leu Leu Glu Val Met Ala
        450                 455                 460

Glu Phe Pro Ser Ala Lys Pro Pro Leu Gly Val Phe Ala Gly Val
465                 470                 475                 480

Ala Pro Arg Leu Gln Pro Arg Phe Tyr Ser Ile Ser Ser Ser Pro Lys
            485                 490                 495

Ile Ala Pro Phe Arg Ile His Val Thr Cys Ala Leu Val Tyr Asp Lys
        500                 505                 510

Ser Pro Thr Gly Arg Val His Lys Gly Ile Cys Ser Thr Trp Met Lys
            515                 520                 525

Asn Ala Val Pro Leu Glu Glu Ser Asn Asp Cys Ser Trp Ala Pro Ile
530                 535                 540

Phe Val Arg Asn Ser Asn Phe Lys Leu Pro Thr Asp Pro Lys Val Pro
545                 550                 555                 560

Ile Ile Met Ile Gly Pro Gly Thr Gly Leu Ala Pro Phe Arg Gly Phe
            565                 570                 575

Leu Gln Glu Arg Leu Ala Leu Lys Glu Ser Gly Ala Glu Leu Gly Pro
        580                 585                 590

Ala Ile Leu Phe Phe Gly Cys Arg Asn Arg Lys Met Asp Phe Ile Tyr
            595                 600                 605

Glu Asp Glu Leu Asn Asp Phe Val Lys Ala Gly Val Val Ser Glu Leu
610                 615                 620

Ile Val Ala Phe Ser Arg Glu Gly Pro Met Lys Glu Tyr Val Gln His
625                 630                 635                 640

Lys Met Ser Gln Arg Ala Ser Asp Val Trp Asn Ile Ile Ser Asp Gly
            645                 650                 655

Gly Tyr Val Tyr Val Cys Gly Asp Ala Lys Gly Met Ala Arg Asp Val
        660                 665                 670

His Arg Thr Leu His Thr Ile Ala Gln Glu Gln Gly Ser Met Ser Ser
            675                 680                 685

Ser Glu Ala Glu Gly Met Val Lys Asn Leu Gln Thr Thr Gly Arg Tyr
        690                 695                 700

Leu Arg Asp Val Trp
705
```

<210> SEQ ID NO 11
<211> LENGTH: 1992
<212> TYPE: DNA
<213> ORGANISM: Artemisia annua

<400> SEQUENCE: 11

```
atggcactgg acaaactgga cctgtacgta atcatcacct tagtcgtcgc cgtggccgcg    60
tattttgcga aaaatcgccg ctcgtctagc gcagccaaga aagccgcgga gagcccggtt   120
attgtcgtcc gaagaaggt tacgaggac gaagtggacg acggtcgtaa aaaggtcacg    180
gtgttcttcg gcacgcagac tggtaccgct gaaggtttcg cgaaggcgct ggttgaagaa   240
```

-continued

```
gcaaaggcgc gctatgaaaa ggcagtgttc aaggttatcg atctggacga ttacgccgca    300
gaggacgacg aatacgagga gaagttgaaa aaggagtccc tcgccttctt cttcctggcg    360
acgtacggcg atggtgagcc gaccgataac gcagctcgtt tctacaagtg gttcaccgag    420
ggtgaggaga agggtgagtg gctggataaa ctgcaatatg cggtctttgg tctgggcaac    480
cgccaatatg agcacttcaa taagatcgca aaggttgtgg atgagaaact ggtcgagcag    540
ggtgccaagc gcctggtgcc ggttggcatg ggtgatgacg atcagtgcat cgaggatgac    600
ttcaccgcct ggaaggagct ggtgtggccg agctggacc aactgttgcg cgacgaagat     660
gacaccagcg ttgcgacgcc gtataccgcg gcagttggcg aatatcgtgt tgtttttcat    720
gataagccgg aaacctacga tcaggatcaa ctgaccaatg gtcatgctgt gcatgacgcg    780
cagcacccgt gcagaagcaa tgttgctgtt aagaaagaat gcactctcc gctgtccgat     840 cgcagctgca cccacctgga atttgacatc agcaataccg gtttgagcta cgaaacgggc    900
gatcacgtcg gtgtgtatgt ggaaaatctg agcgaagttg tcgatgaggc tgagaagctg    960
atcggtttac caccgcacac ctacttcagc gtgcatactg acaatgagga tggcaccccca  1020 ctgggcggtg ctagcctgcc accgcctttc ccgccttgca ccctgcgcaa agccctcgct   1080
agctacgctg atgtgctgag cagcccgaag aagagcgcac tgctggcact ggcagcacac   1140
gctaccgatt ccaccgaagc cgatcgcctg aagttttcg ctagcccggc aggcaaggac    1200
gagtatgcgc agtggattgt cgcgagccac cgtagcctgc tggaagtgat ggaggcgttc   1260
ccgagcgcga agcctccgct cggcgtcttt ttcgcatcgg ttgcgcctcg cctgcaaccg   1320
cgttattact caatcagcag ctctccgaaa ttcgcgccga atcgtattca cgttacttgc   1380
gcgctggttt atgagcaaac tccgagcggt cgtgttcaca agggcgtttg ctctacctgg   1440
atgaaaaacg cggttcctat gacggagagc caagactgta gctgggctcc gatttatgtt   1500
cgcacgtcta actttcgcct gcctagcgac ccgaaggtgc cagtgattat gattggtccg   1560
ggtaccggtc tggcaccgtt ccgcggtttc ctgcaagaac gtctggcaca gaaagaagct   1620
ggtacggaat tgggcaccgc aattctgttc tttggttgtc gtaatcgtaa agtggacttt   1680
atctatgagg atgaactgaa caacttcgtg gaaaccggtg ccctgagcga attggtgacg   1740 gcttttctc gtgagggtgc gaccaaagaa tacgtgcagc acaagatgac gcagaaagca    1800
agcgacattt ggaatctgct gtccgaaggt gcgtacctgt atgtctgtgg cgacgcgaag   1860
ggcatggcaa agacgttca ccgtaccctg cacaccattg tgcaggagca aggtagcctg     1920
gactcttcga aggcggaatt gtacgtcaaa aacctgcaaa tggccggtcg ttatctgcgt   1980
gacgtttggt aa                                                         1992
```

<210> SEQ ID NO 12
<211> LENGTH: 663
<212> TYPE: PRT
<213> ORGANISM: Artemisia annua

<400> SEQUENCE: 12

```
Met Ala Leu Asp Lys Leu Asp Leu Tyr Val Ile Ile Thr Leu Val Val
1               5                   10                  15

Ala Val Ala Ala Tyr Phe Ala Lys Asn Arg Arg Ser Ser Ser Ala Ala
            20                  25                  30

Lys Lys Ala Ala Glu Ser Pro Val Ile Val Val Pro Lys Lys Val Thr
        35                  40                  45

Glu Asp Glu Val Asp Asp Gly Arg Lys Lys Val Thr Val Phe Phe Gly
```

```
                50                  55                  60
Thr Gln Thr Gly Thr Ala Glu Gly Phe Ala Lys Ala Leu Val Glu Glu
65                  70                  75                  80

Ala Lys Ala Arg Tyr Glu Lys Ala Val Phe Lys Val Ile Asp Leu Asp
                85                  90                  95

Asp Tyr Ala Ala Glu Asp Glu Tyr Glu Lys Leu Lys Lys Glu
            100                 105                 110

Ser Leu Ala Phe Phe Phe Leu Ala Thr Tyr Gly Asp Gly Glu Pro Thr
            115                 120                 125

Asp Asn Ala Ala Arg Phe Tyr Lys Trp Phe Thr Glu Gly Glu Lys
            130                 135                 140

Gly Glu Trp Leu Asp Lys Leu Gln Tyr Ala Val Phe Gly Leu Gly Asn
145                 150                 155                 160

Arg Gln Tyr Glu His Phe Asn Lys Ile Ala Lys Val Val Asp Glu Lys
                165                 170                 175

Leu Val Glu Gln Gly Ala Lys Arg Leu Val Pro Val Gly Met Gly Asp
            180                 185                 190

Asp Asp Gln Cys Ile Glu Asp Phe Thr Ala Trp Lys Glu Leu Val
            195                 200                 205

Trp Pro Glu Leu Asp Gln Leu Leu Arg Asp Glu Asp Thr Ser Val
210                 215                 220

Ala Thr Pro Tyr Thr Ala Ala Val Gly Glu Tyr Arg Val Val Phe His
225                 230                 235                 240

Asp Lys Pro Glu Thr Tyr Asp Gln Asp Gln Leu Thr Asn Gly His Ala
            245                 250                 255

Val His Asp Ala Gln His Pro Cys Arg Ser Asn Val Ala Val Lys Lys
            260                 265                 270

Glu Leu His Ser Pro Leu Ser Asp Arg Ser Cys Thr His Leu Glu Phe
            275                 280                 285

Asp Ile Ser Asn Thr Gly Leu Ser Tyr Glu Thr Gly Asp His Val Gly
            290                 295                 300

Val Tyr Val Glu Asn Leu Ser Glu Val Val Asp Glu Ala Glu Lys Leu
305                 310                 315                 320

Ile Gly Leu Pro Pro His Thr Tyr Phe Ser Val His Thr Asp Asn Glu
                325                 330                 335

Asp Gly Thr Pro Leu Gly Gly Ala Ser Leu Pro Pro Phe Pro Pro
            340                 345                 350

Cys Thr Leu Arg Lys Ala Leu Ala Ser Tyr Ala Asp Val Leu Ser Ser
            355                 360                 365

Pro Lys Lys Ser Ala Leu Leu Ala Leu Ala His Ala Thr Asp Ser
370                 375                 380

Thr Glu Ala Asp Arg Leu Lys Phe Phe Ala Ser Pro Ala Gly Lys Asp
385                 390                 395                 400

Glu Tyr Ala Gln Trp Ile Val Ala Ser His Arg Ser Leu Leu Glu Val
                405                 410                 415

Met Glu Ala Phe Pro Ser Ala Lys Pro Pro Leu Gly Val Phe Phe Ala
            420                 425                 430

Ser Val Ala Pro Arg Leu Gln Pro Arg Tyr Tyr Ser Ile Ser Ser Ser
            435                 440                 445

Pro Lys Phe Ala Pro Asn Arg Ile His Val Thr Cys Ala Leu Val Tyr
450                 455                 460

Glu Gln Thr Pro Ser Gly Arg Val His Lys Gly Val Cys Ser Thr Trp
465                 470                 475                 480
```

Met Lys Asn Ala Val Pro Met Thr Glu Ser Gln Asp Cys Ser Trp Ala
              485                 490                 495

Pro Ile Tyr Val Arg Thr Ser Asn Phe Arg Leu Pro Ser Asp Pro Lys
              500                 505                 510

Val Pro Val Ile Met Ile Gly Pro Gly Thr Gly Leu Ala Pro Phe Arg
              515                 520                 525

Gly Phe Leu Gln Glu Arg Leu Ala Gln Lys Glu Ala Gly Thr Glu Leu
              530                 535                 540

Gly Thr Ala Ile Leu Phe Phe Gly Cys Arg Asn Arg Lys Val Asp Phe
545                   550                 555                 560

Ile Tyr Glu Asp Glu Leu Asn Asn Phe Val Glu Thr Gly Ala Leu Ser
              565                 570                 575

Glu Leu Val Thr Ala Phe Ser Arg Glu Gly Ala Thr Lys Glu Tyr Val
              580                 585                 590

Gln His Lys Met Thr Gln Lys Ala Ser Asp Ile Trp Asn Leu Leu Ser
              595                 600                 605

Glu Gly Ala Tyr Leu Tyr Val Cys Gly Asp Ala Lys Gly Met Ala Lys
              610                 615                 620

Asp Val His Arg Thr Leu His Thr Ile Val Gln Glu Gln Gly Ser Leu
625                   630                 635                 640

Asp Ser Ser Lys Ala Glu Leu Tyr Val Lys Asn Leu Gln Met Ala Gly
              645                 650                 655

Arg Tyr Leu Arg Asp Val Trp
              660

<210> SEQ ID NO 13
<211> LENGTH: 3534
<212> TYPE: DNA
<213> ORGANISM: Artificial Sequence
<220> FEATURE:
<223> OTHER INFORMATION: pCWori-CYP71AV8-P2-aaCPR insert DNA sequence

<400> SEQUENCE: 13

| | | | | | |
|---|---|---|---|---|---|
| catatggctc | tgttattagc | agttttttgg | tcggcgctta | taatcctcgt | agtaacctac | 60 |
| accatatccc | tcctaatcaa | ccaatggcga | aaaccgaaac | cccaagggaa | gttcccccccg | 120 |
| ggcccatggc | gtctgccgat | tatcggtcac | atgcaccatt | tgatcggcac | catgccgcat | 180 |
| cgtggtgtta | tggaactggc | ccgtaagcat | ggcagcctga | tgcacctgca | actgggtgaa | 240 |
| gtctctacga | ttgttgtcag | cagcccgcgt | tgggcgaaag | aggtcttgac | cacctatgat | 300 |
| atcaccttcg | ccaatcgccc | ggaaaccctg | actggcgaga | tcgtcgcata | ccacaacacg | 360 |
| gatatcgtcc | tggcgccgta | tggtgagtat | tggcgtcaac | tgcgtaaact | gtgcacgctg | 420 |
| gagctgctga | gcaacaagaa | agtgaagagc | ttccagagcc | tgcgcgaaga | agagtgttgg | 480 |
| aacctggtca | aggacatccg | cagcaccggc | caaggtagcc | aatcaatctc | gtcggagaac | 540 |
| attttcaaga | tgattgcgac | gattctgagc | cgtgctgcgt | tcggtaaggg | tattaaggat | 600 |
| caaatgaagt | ttaccgaact | ggtgaaagaa | atcctgcgtc | tgaccggcgg | ttttgatgtc | 660 |
| gctgacatct | tccctagcaa | gaagttgctg | caccacctga | gcggcaagcg | tgcaaaactg | 720 |
| accaatatcc | ataacaagct | ggataatctg | atcaataaca | tcatcgcaga | gcacccgggc | 780 |
| aaccgtacct | cgtcctccca | ggaaacgctg | ctggacgttc | tgctgcgcct | gaaagagtct | 840 |
| gcggagtttc | cgctgaccgc | cgacaacgtt | aaagcagtga | tcctggatat | gttcggcgct | 900 |
| ggtacggata | ccagcagcgc | gacgatcgag | tgggcgatta | gcgagctgat | tcgctgccct | 960 |

```
cgcgcgatgg agaaagtgca gacggaattg cgtcaggcac tgaatggcaa agagcgtatt    1020
caggaagagg atttgcagga gctgaattat ctgaagctgg tgattaaaga aaccctgcgc    1080
ctgcatccgc cgttgccgct ggtgatgccg cgtgagtgcc gtgaaccgtg tgttttgggc    1140
ggttacgaca ttccgagcaa aacgaagctg atcgttaatg ttttcgcgat taaccgtgac    1200
ccggaatact ggaaagacgc ggaaacgttt atgccggagc gttttgagaa tagcccgatt    1260
accgttatgg gttccgagta cgaatacctg ccatttggtg ctggtcgtcg tatgtgtcct    1320
ggtgcagcgc tgggtctggc caacgtggaa ctgccgctgg cgcacattct gtactatttc    1380
aactggaaac tgccgaacgg caagaccttc gaagatttgg acatgaccga gagctttggt    1440
gccactgtgc agcgcaaaac cgagctgctg ctggttccga ccgactttca aacgctgact    1500
gcgagcacct aatgagtcga cagaggaaga tataccatgg cactggacaa actggacctg    1560
tacgtaatca tcaccttagt cgtcgccgtg ccgcgtatt ttgcgaaaaa tcgccgctcg    1620
tctagcgcag ccaagaaagc cgcggagagc ccggttattg tcgtcccgaa gaaggttacg    1680
gaggacgaag tggacgacgg tcgtaaaaag gtcacggtgt tcttcggcac gcagactggt    1740
accgctgaag gtttcgcgaa ggcgctggtt gaagaagcaa aggcgcgcta tgaaaaggca    1800
gtgttcaagg ttatcgatct ggacgattac gccgcagagg acgacgaata cgaggagaag    1860
ttgaaaaagg agtccctcgc cttcttcttc ctggcgacgt acggcgatgg tgagccgacc    1920
gataacgcag ctcgtttcta caagtggttc accgagggtg aggagaaggg tgagtggctg    1980
gataaactgc aatatgcggt ctttggtctg ggcaaccgcc aatatgagca cttcaataag    2040
atcgcaaagg ttgtgatga aaactggtc gagcagggtg ccaagcgcct ggtgccggtt    2100
ggcatgggtg atgacgatca gtgcatcgag gatgacttca ccgcctggaa ggagctggtg    2160
tggccggagc tggaccaact gttgcgcgac gaagatgaca ccagcgttgc gacgccgtat    2220
accgcggcag ttggcgaata tcgtgttgtt tttcatgata agccggaaac ctacgatcag    2280
gatcaactga ccaatggtca tgctgtgcat gacgcgcagc acccgtgcag aagcaatgtt    2340
gctgttaaga aagaattgca ctctccgctg tccgatcgca gctgcaccca cctggaattt    2400
gacatcagca ataccggttt gagctacgaa acgggcgatc acgtcggtgt gtatgtggaa    2460
aatctgagcg aagttgtcga tgaggctgag aagctgatcg gtttaccacc gcacacctac    2520
ttcagcgtgc atactgacaa tgaggatggc accccactgg gcggtgctag cctgccaccg    2580
cctttcccgc cttgcaccct gcgcaaagcc ctcgctagct acgctgatgt gctgagcagc    2640
ccgaagaaga gcgcactgct ggcactggca gcacacgcta ccgattccac cgaagccgat    2700
cgcctgaagt ttttcgctag cccggcaggc aaggacgagt atgcgcagtg gattgtcgcg    2760
agccaccgta gctgctgga agtgatggag gcgttcccga gcgcgaagcc tccgctcggc    2820 gtcttttttcg catcggttgc gcctcgcctg caaccgcgtt attactcaat cagcagctct    2880
ccgaaattcg cgccgaatcg tattcacgtt acttgcgcgc tggtttatga gcaaactccg    2940
agcggtcgtg ttcacaaggg cgtttgctct acctggatga aaaacgcggt tcctatgacg    3000
gagagccaag actgtagctg ggctccgatt tatgttcgca cgtctaactt tcgcctgcct    3060
agcgacccga aggtgccagt gattatgatt ggtccgggta ccggtctggc accgttccgc    3120
ggtttcctgc aagaacgtct ggcacagaaa gaagctggta cggaattggg caccgcaatt    3180
ctgttctttg gttgtcgtaa tcgtaaagtg gactttatct atgaggatga actgaacaac    3240
ttcgtggaaa ccggtgccct gagcgaattg gtgacggctt tttctcgtga gggtgcgacc    3300
aaagaatacg tgcagcacaa gatgacgcag aaagcaagcg acatttggaa tctgctgtcc    3360
```

```
gaaggtgcgt acctgtatgt ctgtggcgac gcgaagggca tggcaaaaga cgttcaccgt   3420
accctgcaca ccattgtgca ggagcaaggt agcctggact cttcgaaggc ggaattgtac   3480
gtcaaaaacc tgcaaatggc cggtcgttat ctgcgtgacg tttggtaaaa gctt         3534
```

<210> SEQ ID NO 14
<211> LENGTH: 3534
<212> TYPE: DNA
<213> ORGANISM: Artificial Sequence
<220> FEATURE:
<223> OTHER INFORMATION: pCWori-CYP71AV8-P2O-aaCPR insert DNA sequence

<400> SEQUENCE: 14

```
catatggcac tgttgctggc tgtcttttgg tctgctctga ttattttggt ggttacctac     60
accatctccc tgctgattaa ccagtggcgt aaaccgaaac cacagggtaa attcccgccg    120
ggtccgtggc gtctgccgat tatcggtcac atgccacatt tgatcggcac catgccgcat    180
cgtggtgtta tggaactggc ccgtaagcat ggcagcctga tgcacctgca actgggtgaa    240
gtctctacga ttgttgtcag cagcccgcgt tgggcgaaag aggtcttgac cacctatgat    300
atcaccttcg ccaatcgccc ggaaaccctg actggcgaga tcgtcgcata ccacaacacg    360
gatatcgtcc tggcgccgta tggtgagtat tggcgtcaac tgcgtaaact gtgcacgctg    420
gagctgctga gcaacaagaa agtgaagagc ttccagagcc tgcgcaagaa agagtgttgg    480
aacctggtca aggacatccg cagcaccggc caaggtagcc aatcaatct gtcggagaac     540 attttcaaga tgattgcgac gattctgagc cgtgctgcgt tcggtaaggg tattaaggat    600
caaatgaagt ttaccgaact ggtgaaagaa atcctgcgtc tgaccggcgg ttttgatgtc    660
gctgacatct tccctagcaa gaagttgctg caccacctga gcggcaagcg tgcaaaactg    720
accaatatcc ataacaagct ggataatctg atcaataaca tcatcgcaga gcacccgggc    780
aaccgtacct cgtcctccca ggaaacgctg ctggacgttc tgctgcgcct gaaagagtct    840
gcggagtttc cgctgaccgc cgacaacgtt aaagcagtga tcctggatat gttcggcgct    900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtgaaa ctgccgctgg cgcacattct gtactatttc   1380
aactggaaac tgccgaacgg caagaccttc gaagatttgg acatgaccga gctttggt    1440 gccactgtgc agcgcaaaac cgagctgctg ctggttccga ccgactttca aacgctgact   1500
gcgagcacct aatgagtcga cagaggaaga tataccatgg cactggacaa actggaccgt   1560
tacgtaatca tcaccttagt cgtcgccgtg gccgcgtatt ttgcgaaaaa tcgccgctcg   1620
tctagcgcag ccaagaaagc cgcggagagc ccggttattg tcgtcccgaa gaaggttacg   1680
gaggacgaag tggacgacgg tcgtaaaaag gtcacggtgt tcttcggcac gcagactggt   1740
accgctgaag gttcgcgcaa ggcgctggtt gaagaagcaa aggcgcgcta tgaaaaggca   1800
gtgttcaagg ttatcgatct ggacgattac gccgcagagg acgacgaata cgaggagaag   1860
```

```
ttgaaaaagg agtccctcgc cttcttcttc ctggcgacgt acggcgatgg tgagccgacc    1920
gataacgcag ctcgtttcta caagtggttc accgagggtg aggagaaggg tgagtggctg    1980
gataaactgc aatatgcggt ctttggtctg ggcaaccgcc aatatgagca cttcaataag    2040
atcgcaaagg ttgtggatga gaaactggtc gagcagggtg ccaagcgcct ggtgccggtt    2100
ggcatgggtg atgacgatca gtgcatcgag gatgacttca ccgcctggaa ggagctggtg    2160
tggccggagc tggaccaact gttgcgcgac gaagatgaca ccagcgttgc gacgccgtat    2220
accgcggcag ttggcgaata tcgtgttgtt tttcatgata agccggaaac ctacgatcag    2280
gatcaactga ccaatggtca tgctgtgcat gacgcgcagc acccgtgcag aagcaatgtt    2340
gctgttaaga aagaattgca ctctccgctg tccgatcgca gctgcaccca cctggaattt    2400
gacatcagca ataccggttt gagctacgaa acgggcgatc acgtcggtgt gtatgtggaa    2460
aatctgagcg aagttgtcga tgaggctgag aagctgatcg gtttaccacc gcacacctac    2520
ttcagcgtgc atactgacaa tgaggatggc accccactgg gcggtgctag cctgccaccg    2580
cctttcccgc cttgcaccct gcgcaaagcc ctcgctagct acgctgatgt gctgagcagc    2640
ccgaagaaga gcgcactgct ggcactggca gcacacgcta ccgattccac cgaagccgat    2700
cgcctgaagt ttttcgctag cccggcaggc aaggacgagt atgcgcagtg gattgtcgcg    2760
agccaccgta gcctgctgga agtgatggag gcgttcccga gcgcgaagcc tccgctcggc    2820 gtcttttttcg catcggttgc gcctcgcctg caaccgcgtt attactcaat cagcagctct    2880
ccgaaattcg cgccgaatcg tattcacgtt acttgcgcgc tggtttatga gcaaactccg    2940
agcggtcgtg ttcacaaggg cgtttgctct acctggatga aaaacgcggt tcctatgacg    3000
gagagccaag actgtagctg ggctccgatt tatgttcgca cgtctaactt cgcctgcct    3060 agcgacccga aggtgccagt gattatgatt ggtccgggta ccggtctggc accgttccgc    3120
ggtttcctgc aagaacgtct ggcacagaaa gaagctggta cggaattggg caccgcaatt    3180
ctgttctttg gttgtcgtaa tcgtaaagtg gactttatct atgaggatga actgaacaac    3240
ttcgtggaaa ccggtgccct gagcgaattg gtgacggctt tttctcgtga gggtgcgacc    3300
aaagaatacg tgcagcacaa gatgacgcag aaagcaagcg acatttggaa tctgctgtcc    3360
gaaggtgcgt acctgtatgt ctgtggcgac gcgaagggca tggcaaaaga cgttcaccgt    3420
accctgcaca ccattgtgca ggagcaaggt agcctggact cttcgaaggc ggaattgtac    3480
gtcaaaaacc tgcaaatggc cggtcgttat ctgcgtgacg tttggtaaaa gctt    3534
```

<210> SEQ ID NO 15
<211> LENGTH: 3684
<212> TYPE: DNA
<213> ORGANISM: Artificial Sequence
<220> FEATURE:
<223> OTHER INFORMATION: pCWori-CYP71AV8-P2-CPRm insert DNA sequence

<400> SEQUENCE: 15

```
catatggctc tgttattagc agttttttgg tcggcgctta taatcctcgt agtaacctac     60
accatatccc tcctaatcaa ccaatggcga aaaccgaaac cccaagggaa gttccccccg    120
ggcccatggc gtctgccgat tatcggtcac atgcaccatt tgatcggcac catgccgcat    180
cgtggtgtta tggaactggc ccgtaagcat ggcagcctga tgcacctgca actgggtgaa    240
gtctctacga ttgttgtcag cagcccgcgt tgggcgaaag aggtcttgac cacctatgat    300
atcaccttcg ccaatcgccc ggaaaccctg actggcgaga tcgtcgcata ccacaacacg    360
gatatcgtcc tggcgccgta tggtgagtat tggcgtcaac tgcgtaaact gtgcacgctg    420
```

```
gagctgctga gcaacaagaa agtgaagagc ttccagagcc tgcgcgaaga agagtgttgg    480
aacctggtca aggacatccg cagcaccggc caaggtagcc caatcaatct gtcggagaac    540
attttcaaga tgattgcgac gattctgagc cgtgctgcgt tcggtaaggg tattaaggat    600
caaatgaagt ttaccgaact ggtgaaagaa atcctgcgtc tgaccggcgg ttttgatgtc    660
gctgacatct ccctagcaa gaagttgctg caccacctga gcggcaagcg tgcaaaactg    720
accaatatcc ataacaagct ggataatctg atcaataaca tcatcgcaga gcacccgggc    780
aaccgtacct cgtcctccca ggaaacgctg ctggacgttc tgctgcgcct gaaagagtct    840
gcggagtttc cgctgaccgc cgacaacgtt aaagcagtga tcctggatat gttcggcgct    900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaataccctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aaccctgact   1500
gcgagcacct aatgagtcga ctaactttaa gaaggagata tatccatgga acctagctct   1560
cagaaactgt ctccgttgga atttgttgct gctatcctga agggcgacta cagcagcggt   1620
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gttttttcggc   1860 acccaaaccg gtacggcaga aggtttcgcg aaggcttttg ttgaagaggc caaggcgcgt   1920
tatcagcagg cccgttttca agttatcgac ctggacgact atgcggcaga cgatgacgag   1980
tacgaagaga aactgaagaa ggaaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gttttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta cgaagacga cgctaccgtg   2340 gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
ggtgaccacg tcggtgtgta ttgcgagaac ctgttggaaa ccgtggagga ggccgagaag   2640
ttgttgaacc tgagcccgca gacgtacttc tccgttcaca ccgacaacga ggacggtacg   2700
ccgttgagcg gcagcagcct gccgccaccg tttccgccgt gcaccttgcg cacggcattg   2760
```

```
accaaatacg cagacttgac ttctgcaccg aaaaagtcgg tgctggtggc gctggccgag    2820
tacgcatctg accagggtga agcggatcgt ttgcgtttct tggcgagccc gagcggcaaa    2880
gaggaatatg cacagtacat cttggcaagc cagcgcacgc tgctggaggt catggcggag    2940
ttcccgtcgg cgaaaccgcc gctggtgtgtc tttttcgcgg tgtcgctcc gcgcctgcag    3000
ccgcgtttct attccattag ctctagcccg aagatcgcac cgttccgtat tcacgtgacc    3060
tgcgccctgg tttatgacaa atcccctacc ggtcgcgttc ataagggcat ctgtagcacg    3120
tggatgaaaa atgcggtccc gctggaagaa agcaacgatt gttcctgggc tccgatcttc    3180
gtccgcaaca gcaacttcaa gctgccgacc gacccgaagg ttccgattat catgattggt    3240
ccgggtaccg gtctggcccc ttttcgtggc tttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420
gtcgcttta gccgcgaagg cccgatgaaa gaatacgtgc aacacaaaat gagccaacgt    3480
gcctccgatg tgtggaacat cattagcgac ggtggttatg tttatgtttg cggtgacgcg    3540
aagggtatgg ctcgtgatgt tcaccgtacc ctgcatacca tcgcacagga gcaaggtagc    3600
atgtccagct cggaggccga aggtatggtc aaaaacctgc aaaccaccgg tcgttacctg    3660
cgtgatgtgt ggtaataaaa gctt                                          3684
```

<210> SEQ ID NO 16
<211> LENGTH: 3684
<212> TYPE: DNA
<213> ORGANISM: Artificial Sequence
<220> FEATURE:
<223> OTHER INFORMATION: pCWori-CYP71AV8-P2O-CPRm insert DNA sequence

<400> SEQUENCE: 16

```
catatggcac tgttgctggc tgtcttttgg tctgctctga ttattttggt ggttacctac      60
accatctccc tgctgattaa ccagtggcgt aaaccgaaac cacagggtaa attcccgccg     120
ggtccgtggc gtctgccgat tatcggtcac atgcaccatt tgatcggcac catgccgcat     180
cgtggtgtta tggaactggc ccgtaagcat ggcagcctga tgcacctgca actgggtgaa     240
gtctctacga ttgttgtcag cagcccgcgt tgggcgaaag aggtcttgac cacctatgat     300
atcaccttcg ccaatcgccc ggaaaccctg actggcgaga tcgtcgcata ccacaacacg     360
gatatcgtcc tggcgccgta tggtgagtat tggcgtcaac tgcgtaaact gtgcacgctg     420
gagctgctga gcaacaagaa agtgaagagc ttccagagcc tgcgcgaaga agagtgttgg     480
aacctggtca aggacatccg cagcaccggc caaggtagcc aatcaatctc tgcggagaac     540
atttcaaga tgattgcgac gattctgagc cgtgctgcgt tcggtaaggg tattaaggat     600
caaatgaagt ttaccgaact ggtgaaagaa atcctgcgtc tgaccggcgg ttttgatgtc     660
gctgacatct tccctagcaa gaagttgctg caccacctga gcggcaagcg tgcaaaactg     720
accaatatcc ataacaagct ggataatctg atcaataaca tcatcgcaga gcacccgggc     780
aaccgtacct cgtcctccca ggaaacgctg ctggacgttc tgctgcgcct gaaagagtct     840
gcggagtttc cgctgaccgc cgacaacgtt aaagcagtga tcctggatat gttcggcgct     900
ggtacggata ccagcagcgc gacgatcgag tgggcgatta gcgagctgat tcgctgccct     960
cgcgcgatgg agaaagtgca gacggaattg cgtcaggcac tgaatggcaa agagcgtatt    1020
caggaagagg atttgcagga gctgaattat ctgaagctgg tgattaaaga aaccctgcgc    1080
ctgcatccgc cgttgccgct ggtgatgccg cgtgagtgcc gtgaaccgtg tgttttgggc    1140
```

```
ggttacgaca ttccgagcaa aacgaagctg atcgttaatg ttttcgcgat taaccgtgac    1200
ccggaatact ggaaagacgc ggaaacgttt atgccggagc gttttgagaa tagcccgatt    1260
accgttatgg gttccgagta cgaatacctg ccatttggtg ctggtcgtcg tatgtgtcct    1320
ggtgcagcgc tgggtctggc caacgtggaa ctgccgctgg cgcacattct gtactatttc    1380
aactggaaac tgccgaacgg caagaccttc gaagatttgg acatgaccga gagctttggt    1440
gccactgtgc agcgcaaaac cgagctgctg ctggttccga ccgactttca aacgctgact    1500
gcgagcacct aatgagtcga ctaactttaa gaaggagata tatccatgga acctagctct    1560
cagaaactgt ctccgttgga atttgttgct gctatcctga agggcgacta cagcagcggt    1620
caggttgaag gtggtccacc gccaggtctg gcagctatgt tgatggaaaa taaggatttg    1680
gtgatggttc tgacgacgtc cgtggcagtc ctgatcggct gtgtcgtggt cctggcatgg    1740
cgtcgtgcgg caggtagcgg taagtacaag caacctgaac tgcctaaact ggtggtcccg    1800
aaagcagccg aaccggagga ggcagaggat gataaaacca agatcagcgt ttttttcggc    1860
acccaaaccg gtacggcaga aggtttcgcg aaggcttttg ttgaagaggc caaggcgcgt    1920
tatcagcagg cccgttttca agttatcgac ctggacgact atgcggcaga cgatgacgag    1980
tacgaagaga aactgaagaa ggaaaacttg gcattcttct tcttggcgtc ctacggtgac    2040
ggcgagccga cggacaacgc ggcacgcttt tacaaatggt ttacgagggg taaggaccgt    2100
ggtgaatggc tgaacaatct gcagtacggc gtttttggtc tgggtaaccg tcaatatgag    2160
catttcaata agatcgccat tgtcgtcgat gatctgatct tcgagcaagg tggcaagaag    2220
ctggttccgg tgggtctggg tgacgatgac cagtgcattg aggatgattt tgcggcgtgg    2280
cgtgaactgg tctggccgga actggataaa ctgctgcgta acgaagacga cgctaccgtg    2340
gcaaccccgt acagcgccgc tgtgctgcaa taccgcgtgg ttttccacga tcacattgac    2400
ggcctgatta gcgaaaacgg tagcccgaac ggtcatgcta atggcaatac cgtgtacgat    2460
gcgcaacacc cgtgccgtag caacgtcgcg gtcaagaagg aattgcatac tccggcgagc    2520
gatcgcagct gcacccacct ggaatttaac attagcggta ccggcctgat gtacgagacg    2580
ggtgaccacg tcggtgtgta ttgcgagaac ctgttggaaa ccgtggagga ggccgagaag    2640
ttgttgaacc tgagcccgca gacgtacttc tccgttcaca ccgacaacga ggacggtacg    2700
ccgttgagcg gcagcagcct gccgccaccg tttccgccgt gcaccttgcg cacggcattg    2760
accaaatacg cagacttgac ttctgcaccg aaaaagtcgg tgctggtggc gctggccgag    2820
tacgcatctg accagggtga agcggatcgt ttgcgtttct tggcgagccc gagcggcaaa    2880
gaggaatatg cacagtacat cttggcaagc cagcgcacgc tgctggaggt catggcggag    2940
ttcccgtcgc cgaaaccgcc gctggggtgtc ttttttcgcgg gtgtcgctcc cgcctgcag    3000 ccgcgttttct attccattag ctctagcccg aagatcgcac cgttccgtat tcacgtgacc    3060
tgcgccctgg tttatgacaa atcccctacc ggtcgcgttc ataagggcat ctgtagcacg    3120
tggatgaaaa atgcggtccc gctggaagaa agcaacgatt gttcctgggc tccgatcttc    3180
gtccgcaaca gcaacttcaa gctgccgacc gacccgaagg ttccgattat catgattggt    3240
ccgggtaccg gtctggcccc ttttcgtggc ttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420
gtcgctttta gccgcgaagg cccgatgaaa gaatacgtgc aacacaaaat gagccaacgt    3480
```

```
gcctccgatg tgtggaacat cattagcgac ggtggttatg tttatgtttg cggtgacgcg   3540
aagggtatgg ctcgtgatgt tcaccgtacc ctgcatacca tcgcacagga gcaaggtagc   3600
atgtccagct cggaggccga aggtatggtc aaaaacctgc aaaccaccgg tcgttacctg   3660
cgtgatgtgt ggtaataaaa gctt                                          3684
```

<210> SEQ ID NO 17
<211> LENGTH: 3498
<212> TYPE: DNA
<213> ORGANISM: Artificial Sequence
<220> FEATURE:
<223> OTHER INFORMATION: pCWori-CYP71AV8-65188-aaCPR insert DNA sequence

<400> SEQUENCE: 17

```
catatggcac tcttactggc agtattctgg tccgccctga tcattcttgt aacccgcacg     60
actagcaaaa agaatctgtt gccggagcca tggcgtctgc cgattatcgg tcacatgcac    120
catttgatcg gcaccatgcc gcatcgtggt gttatggaac tggcccgtaa gcatggcagc    180
ctgatgcacc tgcaactggg tgaagtctct acgattgttg tcagcagccc gcgttgggcg    240
aaagaggtct tgaccaccta tgatatcacc ttcgccaatc gcccggaaac cctgactggc    300
gagatcgtcg cataccacaa cacgatatc gtcctggcgc gtatggtga gtattggcgt     360 caactgcgta aactgtgcac gctggagctg ctgagcaaca agaaagtgaa gagcttccag    420
agcctgcgcg aagaagagtg ttggaacctg gtcaaggaca tccgcagcac cggccaaggt    480
agcccaatca atctgtcgga gaacatttc aagatgattg cgacgattct gagccgtgct    540
gcgttcggta agggtattaa ggatcaaatg aagtttaccg aactggtgaa agaaatcctg    600
cgtctgaccg gcggttttga tgtcgctgac atcttcccta gcaagaagtt gctgcaccac    660
ctgagcggca agcgtgcaaa actgaccaat atccataaca agctggataa tctgatcaat    720
aacatcatcg cagagcaccc gggcaaccgt acctcgtcct cccaggaaac gctgctggac    780
gttctgctgc gcctgaaaga gtctgcggag ttccgctga ccgccgacaa cgttaaagca    840
gtgatcctgg atatgttcgg cgctggtacg gataccagca gcgcgacgat cgagtgggcg    900
attagcgagc tgattcgctg ccctcgcgcg atggagaaag tgcagacgga attgcgtcag    960
gcactgaatg gcaaagagcg tattcaggaa gaggatttgc aggagctgaa ttatctgaag   1020
ctggtgatta agaaaccct cgcctgcat ccgccgttgc cgctggtgat gccgcgtgag    1080
tgccgtgaac cgtgtgtttt ggcggttac gacattccga gcaaaacgaa gctgatcgtt    1140
aatgttttcg cgattaaccg tgacccgaa tactggaaag acgcggaaac gtttatgccg    1200
gagcgttttg agaatagccc gattaccgtt atgggttccg agtacgaata cctgccatt    1260 ggtgctggtc gtcgtatgtg tcctggtgca gcgctgggtc tggccaacgt ggaactgccg    1320
ctggcgcaca ttctgtacta ttcaactgg aaactgccga acggcaagac cttcgaagat    1380
ttggacatga ccgagagctt tggtgccact gtgcagcgca aaaccgagct gctgctggtt    1440
ccgaccgact ttcaaacgct gactgcgagc acctaatgag tcgacagagg aagatatacc    1500
atggcactgg acaaactgga cctgtacgta atcatcacct tagtcgtcgc cgtggccgcg    1560
tattttgcga aaatcgccg ctcgtctagc gcagccaaga agccgcgga gagcccggtt    1620 attgtcgtcc cgaagaaggt tacggaggac gaagtggacg acggtcgtaa aaaggtcacg    1680
gtgttcttcg gcacgcagac tggtaccgct gaaggtttcg cgaaggcgct ggttgaagaa    1740
gcaaaggcgc gctatgaaaa ggcagtgttc aaggttatcg atctggacga ttacgccgca    1800
gaggacgacg aatacgagga gaagttgaaa aaggagtccc tcgccttctt cttcctggcg    1860
```

```
acgtacggcg atggtgagcc gaccgataac gcagctcgtt tctacaagtg gttcaccgag   1920
ggtgaggaga agggtgagtg gctggataaa ctgcaatatg cggtctttgg tctgggcaac   1980
cgccaatatg agcacttcaa taagatcgca aaggttgtgg atgagaaact ggtcgagcag   2040
ggtgccaagc gcctggtgcc ggttggcatg ggtgatgacg atcagtgcat cgaggatgac   2100
ttcaccgcct ggaaggagct ggtgtggccg agctggacc aactgttgcg cgacgaagat    2160
gacaccagcg ttgcgacgcc gtataccgcg gcagttggcg aatatcgtgt tgttttcat    2220 gataagccgg aaacctacga tcaggatcaa ctgaccaatg gtcatgctgt gcatgacgcg   2280
cagcacccgt gcagaagcaa tgttgctgtt aagaaagaat gcactctcc gctgtccgat    2340 cgcagctgca cccacctgga atttgacatc agcaataccg gtttgagcta cgaaacgggc   2400
gatcacgtcg gtgtgtatgt ggaaaatctg agcgaagttg tcgatgaggc tgagaagctg   2460
atcggtttac caccgcacac ctacttcagc gtgcatactg acaatgagga tggcaccca    2520 ctgggcggtg ctagcctgcc accgcctttc ccgccttgca ccctgcgcaa agccctcgct   2580
agctacgctg atgtgctgag cagcccgaag aagagcgcac tgctggcact ggcagcacac   2640
gctaccgatt ccaccgaagc cgatcgcctg aagttttcg ctagcccggc aggcaaggac    2700
gagtatgcgc agtggattgt cgcgagccac cgtagcctgc tggaagtgat ggaggcgttc   2760
ccgagcgcga agcctccgct cggcgtcttt ttcgcatcgg ttgcgcctcg cctgcaaccg   2820
cgttattact caatcagcag ctctccgaaa ttcgcgccga atcgtattca cgttacttgc   2880
gcgctggttt atgagcaaac tccgagcggt cgtgttcaca agggcgtttg ctctacctgg   2940
atgaaaaacg cggttcctat gacggagagc caagactgta gctgggctcc gatttatgtt   3000
cgcacgtcta actttcgcct gcctagcgac ccgaaggtgc cagtgattat gattggtccg   3060
ggtaccggtc tggcaccgtt ccgcggtttc ctgcaagaac gtctggcaca gaaagaagct   3120
ggtacggaat ggcaccgc aattctgttc tttggttgtc gtaatcgtaa agtggacttt    3180
atctatgagg atgaactgaa caacttcgtg gaaaccggtg ccctgagcga attggtgacg   3240 gcttttctc gtgagggtgc gaccaaagaa tacgtcagc acaagatgac gcagaaagca    3300
agcgacattt ggaatctgct gtccgaaggt gcgtacctgt atgtctgtgg cgacgcgaag   3360
ggcatggcaa agacgttca ccgtacccctg cacaccattg tgcaggagca aggtagcctg   3420
gactcttcga aggcggaatt gtacgtcaaa aacctgcaaa tggccggtcg ttatctgcgt   3480
gacgtttggt aaaagctt                                                 3498
```

<210> SEQ ID NO 18
<211> LENGTH: 3648
<212> TYPE: DNA
<213> ORGANISM: Artificial Sequence
<220> FEATURE:
<223> OTHER INFORMATION: pCWori-CYP71AV8-65188-CPRm insert DNA sequence

<400> SEQUENCE: 18

```
catatggcac tcttactggc agtattctgg tccgccctga tcattcttgt aacccgcacg     60
actagcaaaa agaatctgtt gccggagcca tggcgtctgc cgattatcgg tcacatgcac    120
catttgatcg gcaccatgcc gcatcgtggt gttatggaac tggcccgtaa gcatggcagc    180
ctgatgcacc tgcaactggg tgaagtctct acgattgttg tcagcagccc gcgttgggcg    240
aaagaggtct tgaccaccta tgatatcacc ttcgccaatc gcccggaaac cctgactggc    300
gagatcgtcg cataccacaa cacgcgatatc gtcctggcgc cgtatggtga gtattggcgt    360
```

```
caactgcgta aactgtgcac gctggagctg ctgagcaaca agaaagtgaa gagcttccag    420
agcctgcgcg aagaagagtg ttggaacctg gtcaaggaca tccgcagcac cggccaaggt    480
agcccaatca atctgtcgga gaacattttc aagatgattg cgacgattct gagccgtgct    540
gcgttcggta agggtattaa ggatcaaatg aagtttaccg aactggtgaa agaaatcctg    600
cgtctgaccg gcggttttga tgtcgctgac atcttcccta gcaagaagtt gctgcaccac    660
ctgagcggca agcgtgcaaa actgaccaat atccataaca agctggataa tctgatcaat    720
aacatcatcg cagagcaccc gggcaaccgt acctcgtcct cccaggaaac gctgctggac    780
gttctgctgc gcctgaaaga gtctgcggag tttccgctga ccgccgacaa cgttaaagca    840
gtgatcctgg atatgttcgg cgctggtacg gataccagca gcgcgacgat cgagtgggcg    900
attagcgagc tgattcgctg ccctcgcgcg atggagaaag tgcagacgga attgcgtcag    960
gcactgaatg gcaaagagcg tattcaggaa gaggatttgc aggagctgaa ttatctgaag   1020
ctggtgatta agaaaccct gcgcctgcat ccgccgttgc cgctggtgat gccgcgtgag   1080
tgccgtgaac cgtgtgtttt gggcggttac gacattccga gcaaaacgaa gctgatcgtt   1140
aatgttttcg cgattaaccg tgaccccgaa tactggaaag acgcggaaac gtttatgccg   1200
gagcgttttg agaatagccc gattaccgtt atgggttccg agtacgaata cctgccattt   1260
ggtgctggtc gtcgtatgtg tcctggtgca gcgctgggtc tggccaacgt ggaactgccg   1320
ctggcgcaca ttctgtacta tttcaactgg aaactgccga acggcaagac cttcgaagat   1380
ttggacatga ccgagagctt tggtgccact gtgcagcgca aaaccgagct gctgctggtt   1440
ccgaccgact ttcaaacgct gactgcgagc acctaatgag tcgactaact ttaagaagga   1500
gatatatcca tggaacctag ctctcagaaa ctgtctccgt ggaatttgt tgctgctatc   1560
ctgaagggcg actacagcag cggtcaggtt gaaggtggtc accgccagg tctggcagct   1620
atgttgatgg aaaataagga tttggtgatg gttctgacga cgtccgtggc agtcctgatc   1680
ggctgtgtcg tggtcctggc atggcgtcgt cggcaggta gcgtaagta caagcaacct   1740
gaactgccta aactggtggt cccgaaagca gccgaaccgg aggaggcaga ggatgataaa   1800
accaagatca gcgtgttttt cggcacccaa accggtacgg cagaaggttt cgcgaaggct   1860
tttgttgaag aggccaaggc gcgttatcag caggcccgtt tcaaagttat cgacctggac   1920
gactatgcgg cagacgatga cgagtacgaa gagaaactga gaaggaaaa cttggcattc   1980
ttcttcttgg cgtcctacgg tgacggcgag ccgacggaca acgcggcacg cttttacaaa   2040
tggtttacgg agggtaagga ccgtggtgaa tggctgaaca atctgcagta cggcgttttt   2100
ggtctgggta accgtcaata tgagcatttc aataagatcg ccattgtcgt cgatgatctg   2160
atcttcgagc aaggtggcaa gaagctggtt ccggtgggtc tgggtgacga tgaccagtgc   2220
attgaggatg atttttgcggc gtggcgtgaa ctggtctggc cggaactgga taaactgctg   2280
cgtaacgaag acgacgctac cgtggcaacc ccgtacagcg ccgctgtgct gcaataccgc   2340
gtggttttcc acgatcacat tgacggcctg attagcgaaa acggtagccc gaacggtcat   2400
gctaatggca ataccgtgta cgatgcgcaa cacccgtgcc gtagcaacgt cgcggtcaag   2460
aaggaattgc atactccggc gagcgatcgc agctgcaccc acctggaatt taacattagc   2520
ggtaccggcc tgatgtacga gacgggtgac cacgtcggtg tgtattgcga gaacctgttg   2580
gaaaccgtgg aggaggccga gaagttgttg aacctgagcc gcagacgta cttctccgtt   2640
cacaccgaca acgaggacgg tacgccgttg agcggcagca gcctgccgcc accgtttccg   2700
ccgtgcacct tgcgcacggc attgaccaaa tacgcagact tgacttctgc accgaaaaag   2760
```

```
tcggtgctgg tggcgctggc cgagtacgca tctgaccagg gtgaagcgga tcgtttgcgt    2820
ttcttggcga gcccgagcgg caaagaggaa tatgcacagt acatcttggc aagccagcgc    2880
acgctgctgg aggtcatggc ggagttcccg tcggcgaaac cgccgctggg tgtcttttc     2940 gcgggtgtcg ctccgcgcct gcagccgcgt ttctattcca ttagctctag cccgaagatc    3000
gcaccgttcc gtattcacgt gacctgcgcc ctggtttatg acaaatcccc taccggtcgc    3060
gttcataagg gcatctgtag cacgtggatg aaaaatgcgg tcccgctgga agaaagcaac    3120
gattgttcct gggctccgat cttcgtccgc aacagcaact tcaagctgcc gaccgacccg    3180
aaggttccga ttatcatgat tggtccgggt accggtctgg cccctttcg tggcttttg      3240 caagagcgct tggcgttgaa agagagcggt gctgaattgg gtccggcgat cttgttcttt    3300
ggttgccgta accgtaaaat ggactttatt tacgaggatg aactgaatga tttcgtcaaa    3360
gcgggcgttg tcagcgagct gatcgtcgct tttagccgcg aaggcccgat gaaagaatac    3420 gtgcaaacaca aaatgagcca acgtgcctcc gatgtgtgga acatcattag cgacggtggt    3480
tatgtttatg tttgcggtga cgccgaaggg atggctcgtg atgttcaccg tacccctgcat   3540 accatcgcac aggagcaagg tagcatgtcc agctcggagg ccgaaggtat ggtcaaaaac    3600
ctgcaaacca ccggtcgtta cctgcgtgat gtgtggtaat aaaagctt                 3648
```

<210> SEQ ID NO 19
<211> LENGTH: 1665
<212> TYPE: DNA
<213> ORGANISM: Artificial Sequence
<220> FEATURE:
<223> OTHER INFORMATION: alpha-santalene synthase optimized cDNA
      sequence

<400> SEQUENCE: 19

```
atggaccaca tgtctaccca gcaggttagc tccgagaata tcgttcgcaa cgcggcgaac     60
ttccacccga atatctgggg taatcatttc ttgacgtgtc caagccagac gatcgattct    120
tggacgcaac aacaccataa agagctgaaa gaagaggtcc gcaagatgat ggtgagcgac    180
gcaaacaaac cggcacaacg tctgcgtctg attgacaccg ttcaacgttt gggcgtggcg    240
tatcatttcg aaaagagaat cgatgacgct ctggaaaaga tcggtcacga tccgtttgac    300
gataaggatg acctgtatat cgttagcctg tgttttcgcc tgctgcgtca gcatggcatc    360
aagattagct gcgatgtttt tgagaagttc aaagacgacg atggcaagtt taaggcttcc    420
ctgatgaatg atgtccaagg tatgctgtcg ttgtatgaag cggcccacct ggcaattcat    480
ggcgaggaca tcctggatga ggctattgtc tttacgacca cccacctgaa gagcaccgtt    540
tctaactccc cggtcaattc caccttgcg aacagattc gccacagcct gcgtgtgccg      600
ctgcgtaagg cagtcccgcg ttttggagagc cgctacttcc tggatatcta tagccgtgac    660
gacctgcacg acaagactct gctgaacttt gccaaactgg acttcaacat cctgcaggcg    720
atgcaccaga aagaggcaag cgagatgacc cgttggtggc gtgatttcga tttcctgaag    780
aagctgccgt acattcgtga tcgcgtggtt gaactgtact ttttggattt ggtcggtgtg    840
agctaccaac cgaaattcag cacgggtcgt atctttttga gcaagattat ctgtctggaa    900 acctggtgg acgacacgtt tgatgcgtac ggtacttcg acgaactggc cattttcacc      960
gaggccgtta cgcgttggga cctgggtcat cgcgacgcgc tgcctgagta catgaaattc   1020
attttcaaga ccctgattga tgtgtacagc gaggcggaac aagagctggc aaaagagggc   1080
cgctcctata gcattcacta tgcgatccgt agcttccagg agttggtcat gaagtacttt   1140
```

```
tgcgaggcga aatggctgaa taagggttat gttccgagcc tggatgacta caagagcgtc   1200
agcctgcgca gcatcggctt cctgccgatc gccgtggctt cttttgtttt catgggcgac   1260
attgctacga aagaggtttt tgagtgggaa atgaataacc cgaaaatcat catcgcagcc   1320
gaaaccattt tccgctttct ggatgacatt gcaggtcatc gcttcgaaca aaaacgtgag   1380
cacagcccga gcgcaatcga gtgctacaaa aaccaacatg gtgtctcgga agaagaggca   1440
gtgaaagcgc tgagcttgga ggtcgccaat tcgtggaaag acattaacga agagctgctg   1500
ctgaacccta tggcaattcc actgccgttg ctgcaggtga tcctggattt gagccgtagc   1560
gcggacttca tgtacggtaa tgcgcaggac cgtttcacgc actccaccat gatgaaagat   1620
caagttgacc tggttctgaa agatccggtg aaactggacg attaa               1665

<210> SEQ ID NO 20
<211> LENGTH: 554
<212> TYPE: PRT
<213> ORGANISM: Artificial Sequence
<220> FEATURE:
<223> OTHER INFORMATION: alpha-santalene synthase amino acid sequence

<400> SEQUENCE: 20

Met Asp His Met Ser Thr Gln Gln Val Ser Ser Glu Asn Ile Val Arg
1               5                   10                  15

Asn Ala Ala Asn Phe His Pro Asn Ile Trp Gly Asn His Phe Leu Thr
            20                  25                  30

Cys Pro Ser Gln Thr Ile Asp Ser Trp Thr Gln Gln His His Lys Glu
        35                  40                  45

Leu Lys Glu Glu Val Arg Lys Met Met Val Ser Asp Ala Asn Lys Pro
    50                  55                  60

Ala Gln Arg Leu Arg Leu Ile Asp Thr Val Gln Arg Leu Gly Val Ala
65                  70                  75                  80

Tyr His Phe Glu Lys Glu Ile Asp Asp Ala Leu Glu Lys Ile Gly His
                85                  90                  95

Asp Pro Phe Asp Asp Lys Asp Asp Leu Tyr Ile Val Ser Leu Cys Phe
            100                 105                 110

Arg Leu Leu Arg Gln His Gly Ile Lys Ile Ser Cys Asp Val Phe Glu
        115                 120                 125

Lys Phe Lys Asp Asp Gly Lys Phe Lys Ala Ser Leu Met Asn Asp
    130                 135                 140

Val Gln Gly Met Leu Ser Leu Tyr Glu Ala Ala His Leu Ala Ile His
145                 150                 155                 160

Gly Glu Asp Ile Leu Asp Glu Ala Ile Val Phe Thr Thr Thr His Leu
                165                 170                 175

Lys Ser Thr Val Ser Asn Ser Pro Val Asn Ser Thr Phe Ala Glu Gln
            180                 185                 190

Ile Arg His Ser Leu Arg Val Pro Leu Arg Lys Ala Val Pro Arg Leu
        195                 200                 205

Glu Ser Arg Tyr Phe Leu Asp Ile Tyr Ser Arg Asp Asp Leu His Asp
    210                 215                 220

Lys Thr Leu Leu Asn Phe Ala Lys Leu Asp Phe Asn Ile Leu Gln Ala
225                 230                 235                 240

Met His Gln Lys Glu Ala Ser Glu Met Thr Arg Trp Trp Arg Asp Phe
                245                 250                 255

Asp Phe Leu Lys Lys Leu Pro Tyr Ile Arg Asp Arg Val Val Glu Leu
            260                 265                 270
```

```
Tyr Phe Trp Ile Leu Val Gly Val Ser Tyr Gln Pro Lys Phe Ser Thr
            275                 280                 285

Gly Arg Ile Phe Leu Ser Lys Ile Ile Cys Leu Glu Thr Leu Val Asp
        290                 295                 300

Asp Thr Phe Asp Ala Tyr Gly Thr Phe Asp Glu Leu Ala Ile Phe Thr
305                 310                 315                 320

Glu Ala Val Thr Arg Trp Asp Leu Gly His Arg Asp Ala Leu Pro Glu
                325                 330                 335

Tyr Met Lys Phe Ile Phe Lys Thr Leu Ile Asp Val Tyr Ser Glu Ala
            340                 345                 350

Glu Gln Glu Leu Ala Lys Glu Gly Arg Ser Tyr Ser Ile His Tyr Ala
        355                 360                 365

Ile Arg Ser Phe Gln Glu Leu Val Met Lys Tyr Phe Cys Glu Ala Lys
    370                 375                 380

Trp Leu Asn Lys Gly Tyr Val Pro Ser Leu Asp Asp Tyr Lys Ser Val
385                 390                 395                 400

Ser Leu Arg Ser Ile Gly Phe Leu Pro Ile Ala Val Ala Ser Phe Val
                405                 410                 415

Phe Met Gly Asp Ile Ala Thr Lys Glu Val Phe Glu Trp Glu Met Asn
            420                 425                 430

Asn Pro Lys Ile Ile Ile Ala Ala Glu Thr Ile Phe Arg Phe Leu Asp
        435                 440                 445

Asp Ile Ala Gly His Arg Phe Glu Gln Lys Arg Glu His Ser Pro Ser
    450                 455                 460

Ala Ile Glu Cys Tyr Lys Asn Gln His Gly Val Ser Glu Glu Glu Ala
465                 470                 475                 480

Val Lys Ala Leu Ser Leu Glu Val Ala Asn Ser Trp Lys Asp Ile Asn
                485                 490                 495

Glu Glu Leu Leu Leu Asn Pro Met Ala Ile Pro Leu Pro Leu Leu Gln
            500                 505                 510

Val Ile Leu Asp Leu Ser Arg Ser Ala Asp Phe Met Tyr Gly Asn Ala
        515                 520                 525

Gln Asp Arg Phe Thr His Ser Thr Met Met Lys Asp Gln Val Asp Leu
    530                 535                 540

Val Leu Lys Asp Pro Val Lys Leu Asp Asp
545                 550
```

<210> SEQ ID NO 21
<211> LENGTH: 1728
<212> TYPE: DNA
<213> ORGANISM: Artificial Sequence
<220> FEATURE:
<223> OTHER INFORMATION: SaTps8201-1-FL_optEc (alpha/santalene synthase optimized full-length cDNA) including RBS region and restriction sites

<400> SEQUENCE: 21

```
aggaggtaaa acatatggac agcagcaccg ccaccgcaat gaccgcacca ttcatcgacc    60
cgacggatca tgtgaatctg aaaaccgaca cggatgcgag cgaaaatcgt cgtatgggta   120
actacaagcc gagcatttgg aactacgatt ttctgcagtc cctggcgacg caccacaaca   180
ttgttgaaga gcgtcaccty aagctggcag agaaactgaa aggtcaagtg aaattcatgt   240
tcggtgcgcc gatggagcca ttggctaagt tggagctggt tgatgtggtg caacgcttgg   300
gtctgaacca cctgttcgag actgaaatca agaagctctc gttcagcatc tacaaagatg   360
```

```
gcagcaatgg ctggtggttt ggccatctgc atgctacctc tttgcgcttc cgtctgttgc    420
gccaatgtgg cctgtttatc ccgcaggacg ttttcaaaac ctttcaaaac aagaccggtg    480
agtttgacat gaagctgtgg gacaacgtta agggcctgct gagcctgtac gaggcgagct    540
acctgggctg gaagggcgag aacatcttgg atgaagcaaa ggcgttcacg accaagtgcc    600
tgaagagcgc atgggagaac attagcgaga agtggctggc gaagcgtgtt aaacatgcgt    660
tggcgctgcc gctgcactgg cgtgttccgc gtattgaagc acgctggttt atcgaggtgt    720
acgaacaaga ggccaatatg aatccgacgc tgctgaaact ggcgaaactg gacttcaaca    780
tggtccaaag cattcaccag aaagaaatcg gtgaactggc ccgctggtgg gttactaccg    840
gcctggacaa gctggatttc gcacgcaaca atctgttgca gtcttatatg tggagctgcg    900
ccatcgcgtc cgacccgaaa ttcaaactgg cgcgtgaaac cattgtcgag atcggttccg    960
tgttgacggt tgtcgacgac ggctatgatg tgtacggttc tatggatgag ctggacctgt   1020
acaccagctc ggtggagcgt tggtcctgtg tcaaaattga caagctgcct aatacgctga   1080
agctgatctt tatgtctatg ttcaacaaaa ccaacgaggg gggtctgcgt gttcaacacg   1140
agcgtggtta caatagcatc ccgaccttca ttaaggcgtg ggtggaacag tgtaagagct   1200
atcaaaaaga ggcgcgttgg tttcatggtg gtcacacgcc tccgctggaa gaatacagcc   1260
tgaacggtct ggtcagcatt ggttttccgc tgttgctgat caccggctat gttgcgattg   1320
ctgagaatga agcagccctg gataaagtcc acccgctgcc ggacctgctg cattattcca   1380
gcttgctgag ccgtctgatt aatgatatcg cactagccc ggatgaaatg gcgcgtggtg   1440
acaatctgaa gagcattcac tgctatatga atgaaaccgg tgccagcgaa gaggtcgcac   1500
gcgagcacat caaaggcgtc atcgaagaga attggaaaat tctgaaccag tgttgctttg   1560
accagtccca gttccaggag ccgttcatca cgtttaacct gaacagcgtg cgcggctcgc   1620
atttcttcta tgaatttggt gatggttttg gtgttaccga cagctggacc aaggtggata   1680
tgaaaagcgt cctgattgat ccgattccgc tgggtgaaga gtaagctt              1728
```

<210> SEQ ID NO 22
<211> LENGTH: 569
<212> TYPE: PRT
<213> ORGANISM: Artificial Sequence
<220> FEATURE:
<223> OTHER INFORMATION: SaTps8201-1-FL (alpha/beta santalene synthase
      full-length) amino acid sequence

<400> SEQUENCE: 22

Met Asp Ser Ser Thr Ala Thr Ala Met Thr Ala Pro Phe Ile Asp Pro
1               5                   10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu
    50                  55                  60

Ala Glu Lys Leu Lys Gly Gln Val Lys Phe Met Phe Gly Ala Pro Met
65                  70                  75                  80

Glu Pro Leu Ala Lys Leu Glu Leu Val Asp Val Gln Arg Leu Gly
                85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr

```
                115                 120                 125
Ser Leu Arg Phe Arg Leu Leu Arg Gln Cys Gly Leu Phe Ile Pro Gln
130                 135                 140

Asp Val Phe Lys Thr Phe Gln Asn Lys Thr Gly Glu Phe Asp Met Lys
145                 150                 155                 160

Leu Trp Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
                180                 185                 190

Thr Lys Cys Leu Lys Ser Ala Trp Glu Asn Ile Ser Glu Lys Trp Leu
                195                 200                 205

Ala Lys Arg Val Lys His Ala Leu Ala Leu Pro Leu His Trp Arg Val
210                 215                 220

Pro Arg Ile Glu Ala Arg Trp Phe Ile Glu Val Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
                260                 265                 270

Val Thr Thr Gly Leu Asp Lys Leu Asp Phe Ala Arg Asn Asn Leu Leu
                275                 280                 285

Gln Ser Tyr Met Trp Ser Cys Ala Ile Ala Ser Asp Pro Lys Phe Lys
                290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Met Asp Glu Leu Asp Leu Tyr
                325                 330                 335

Thr Ser Ser Val Glu Arg Trp Ser Cys Val Lys Ile Asp Lys Leu Pro
                340                 345                 350

Asn Thr Leu Lys Leu Ile Phe Met Ser Met Phe Asn Lys Thr Asn Glu
                355                 360                 365

Val Gly Leu Arg Val Gln His Glu Arg Gly Tyr Asn Ser Ile Pro Thr
370                 375                 380

Phe Ile Lys Ala Trp Val Glu Gln Cys Lys Ser Tyr Gln Lys Glu Ala
385                 390                 395                 400

Arg Trp Phe His Gly Gly His Thr Pro Leu Glu Glu Tyr Ser Leu
                405                 410                 415

Asn Gly Leu Val Ser Ile Gly Phe Pro Leu Leu Leu Ile Thr Gly Tyr
                420                 425                 430

Val Ala Ile Ala Glu Asn Glu Ala Ala Leu Asp Lys Val His Pro Leu
                435                 440                 445

Pro Asp Leu Leu His Tyr Ser Leu Leu Ser Arg Leu Ile Asn Asp
                450                 455                 460

Ile Gly Thr Ser Pro Asp Glu Met Ala Arg Gly Asp Asn Leu Lys Ser
465                 470                 475                 480

Ile His Cys Tyr Met Asn Glu Thr Gly Ala Ser Glu Glu Val Ala Arg
                485                 490                 495

Glu His Ile Lys Gly Val Ile Glu Glu Asn Trp Lys Ile Leu Asn Gln
                500                 505                 510

Cys Cys Phe Asp Gln Ser Gln Phe Gln Glu Pro Phe Ile Thr Phe Asn
                515                 520                 525

Leu Asn Ser Val Arg Gly Ser His Phe Phe Tyr Glu Phe Gly Asp Gly
                530                 535                 540
```

Phe Gly Val Thr Asp Ser Trp Thr Lys Val Asp Met Lys Ser Val Leu
545                 550                 555                 560

Ile Asp Pro Ile Pro Leu Gly Glu Glu
            565

<210> SEQ ID NO 23
<211> LENGTH: 5361
<212> TYPE: DNA
<213> ORGANISM: Artificial Sequence
<220> FEATURE:
<223> OTHER INFORMATION: DNA sequence of the synthetic operon containing
      CYP71AV-P2, CPRm, and ClASS including the NdeI and HindIII
      restriction sites in 3' and 5' ends

<400> SEQUENCE: 23

| | | | | |
|---|---|---|---|---|
| catatggctc | tgttattagc | agttttttgg | tcggcgctta | taatcctcgt agtaacctac | 60 |
| accatatccc | tcctaatcaa | ccaatggcga | aaaccgaaac | cccaagggaa gttcccccg | 120 |
| ggcccatggc | gtctgccgat | tatcggtcac | atgcaccatt | tgatcggcac catgccgcat | 180 |
| cgtggtgtta | tggaactggc | ccgtaagcat | ggcagcctga | tgcacctgca actgggtgaa | 240 |
| gtctctacga | ttgttgtcag | cagcccgcgt | tgggcgaaag | aggtcttgac cacctatgat | 300 |
| atcaccttcg | ccaatcgccc | ggaaaccctg | actggcgaga | tcgtcgcata ccacaacacg | 360 |
| gatatcgtcc | tggcgccgta | tggtgagtat | tggcgtcaac | tgcgtaaact gtgcacgctg | 420 |
| gagctgctga | gcaacaagaa | agtgaagagc | ttccagagcc | tgcgcgaaga agagtgttgg | 480 |
| aacctggtca | aggacatccg | cagcaccggc | caagtagcc | caatcaatct gtcggagaac | 540 |
| attttcaaga | tgattgcgac | gattctgagc | cgtgctgcgt | tcggtaaggg tattaaggat | 600 |
| caaatgaagt | ttaccgaact | ggtgaaagaa | atcctgcgtc | tgaccggcgg ttttgatgtc | 660 |
| gctgacatct | tccctagcaa | gaagttgctg | caccacctga | gcggcaagcg tgcaaaactg | 720 |
| accaatatcc | ataacaagct | ggataatctg | atcaataaca | tcatcgcaga gcacccgggc | 780 |
| aaccgtacct | cgtcctccca | ggaaacgctg | ctggacgttc | tgctgcgcct gaaagagtct | 840 |
| gcggagtttc | cgctgaccgc | cgacaacgtt | aaagcagtga | tcctggatat gttcggcgct | 900 |
| ggtacggata | ccagcagcgc | gacgatcgag | tgggcgatta | gcgagctgat tcgctgccct | 960 |
| cgcgcgatgg | agaaagtgca | gacggaattg | cgtcaggcac | tgaatggcaa agagcgtatt | 1020 |
| caggaagagg | atttgcagga | gctgaattat | ctgaagctgg | tgattaaaga aaccctgcgc | 1080 |
| ctgcatccgc | cgttgccgct | ggtgatgccg | cgtgagtgcc | gtgaaccgtg tgtttttgggc | 1140 |
| ggttacgaca | ttccgagcaa | aacgaagctg | atcgttaatg | ttttcgcgat taaccgtgac | 1200 |
| ccggaatact | ggaaagacgc | ggaaacgttt | atgccggagc | gttttgagaa tagcccgatt | 1260 |
| accgttatgg | gttccgagta | cgaatacctg | ccatttggtg | ctggtcgtcg tatgtgtcct | 1320 |
| ggtgcagcgc | tgggtctggc | caacgtggaa | ctgccgctgg | cgcacattct gtactatttc | 1380 |
| aactggaaac | tgccgaacgg | caagaccttc | gaagatttgg | acatgaccga gagctttggt | 1440 |
| gccactgtgc | agcgcaaaac | cgagctgctg | ctggttccga | ccgactttca aacgctgact | 1500 |
| gcgagcacct | aatgagtcga | ctaactttaa | gaaggagata | tatccatgga acctagctct | 1560 |
| cagaaactgt | ctccgttgga | atttgttgct | gctatcctga | agggcgacta cagcagcggt | 1620 |
| caggttgaag | tggtccacc | gccaggtctg | gcagctatgt | tgatggaaaa taaggatttg | 1680 |
| gtgatggttc | tgacgacgtc | cgtggcagtc | ctgatcggct | gtgtcgtggt cctggcatgg | 1740 |
| cgtcgtgcgg | caggtagcgg | taagtacaag | caacctgaac | tgcctaaact ggtggtcccg | 1800 |

```
aaagcagccg aaccggagga ggcagaggat gataaaacca agatcagcgt gttttcgcc    1860 acccaaaccg gtacggcaga aggtttcgcg aaggcttttg ttgaagaggc caaggcgcgt    1920
tatcagcagg cccgtttcaa agttatcgac ctggacgact atgcggcaga cgatgacgag    1980
tacgaagaga aactgaagaa ggaaaacttg gcattcttct tcttggcgtc ctacggtgac    2040
ggcgagccga cggacaacgc ggcacgcttt tacaaatggt ttacgaggg taaggaccgt     2100 ggtgaatggc tgaacaatct gcagtacggc gttttggtc tgggtaaccg tcaatatgag     2160
catttcaata agatcgccat tgtcgtcgat gatctgatct tcgagcaagg tggcaagaag    2220
ctggttccgg tgggtctggg tgacgatgac cagtgcattg aggatgattt tgcggcgtgg    2280
cgtgaactgg tctggccgga actggataaa ctgctgcgta acgaagacga cgctaccgtg    2340
gcaaccccgt acagcgccgc tgtgctgcaa taccgcgtgg ttttccacga tcacattgac    2400
ggcctgatta gcgaaaacgg tagcccgaac ggtcatgcta atggcaatac cgtgtacgat    2460
gcgcaacacc cgtgccgtag caacgtcgcg gtcaagaagg aattgcatac tccggcgagc    2520
gatcgcagct gcacccacct ggaatttaac attagcggta ccggcctgat gtacgagacg    2580
ggtgaccacg tcggtgtgta ttgcgagaac ctgttggaaa ccgtggagga ggccgagaag    2640
ttgttgaacc tgagcccgca gacgtacttc tccgttcaca ccgacaacga ggacggtacg    2700
ccgttgagcg gcagcagcct gccgccaccg tttccgccgt gcaccttgcg cacggcattg    2760
accaaatacg cagacttgac ttctgcaccg aaaaagtcgg tgctggtggc gctggccgag    2820
tacgcatctg accagggtga agcggatcgt ttgcgtttct tggcgagccc gagcggcaaa    2880
gaggaatatg cacagtacat cttggcaagc cagcgcacgc tgctggaggt catggcggag    2940
ttcccgtcgg cgaaaccgcc gctgggtgtc tttttcgcgg gtgtcgctcc gcgcctgcag    3000
ccgcgtttct attccattag ctctagcccg aagatcgcac cgttccgtat tcacgtgacc    3060
tgcgccctgg tttatgacaa atcccctacc ggtcgcgttc ataagggcat ctgtagcacg    3120
tggatgaaaa atgcggtccc gctggaagaa agcaacgatt gttcctgggc tccgatcttc    3180
gtccgcaaca gcaacttcaa gctgccgacc gacccgaagg ttccgattat catgattggt    3240
ccgggtaccg gtctggcccc ttttcgtggc ttttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420
gtcgctttta gccgcgaagg cccgatgaaa gaatacgtgc aacacaaaat gagccaacgt    3480
gcctccgatg tgtggaacat cattagcgac ggtggttatg tttatgtttg cggtgacgcg    3540
aagggtatgg ctcgtgatgt tcaccgtacc ctgcatacca tcgcacagga gcaaggtagc    3600
atgtccagct cggaggccga aggtatggtc aaaaacctgc aaaccaccgg tcgttacctg    3660
cgtgatgtgt ggtaataaaa gcttgaagga gatatactaa tgtctaccca gcaggttagc    3720
tccgagaata tcgttcgcaa cgcggcgaac ttccacccga atatctgggg taatcatttc    3780
ttgacgtgtc caagccagac gatcgattct tggacgcaac aacaccataa agagctgaaa    3840
gaagaggtcc gcaagatgat ggtgagcgac gcaaacaaac cggcacaacg tctgcgtctg    3900
attgacaccg ttcaacgttt gggcgtggcg tatcatttcg aaaagaaat cgatgacgct    3960 ctggaaaaga tcggtcacga tccgtttgac gataaggatg acctgtatat cgttagcctg    4020
tgttttcgcc tgctgcgtca gcatggcatc aagattagct gcgatgtttt tgagaagttc    4080
aaagacgacg atggcaagtt taaggcttcc ctgatgaatg atgtccaagg tatgctgtcg    4140
ttgtatgaag cggcccacct ggcaattcat ggcgaggaca tcctggatga ggctattgtc    4200
```

```
tttacgacca cccacctgaa gagcaccgtt tctaactccc cggtcaattc cacctttgcg    4260
gaacagattc gccacagcct gcgtgtgccg ctgcgtaagg cagtcccgcg tttggagagc    4320
cgctacttcc tggatatcta tagccgtgac gacctgcacg acaagactct gctgaacttt    4380
gccaaactgg acttcaacat cctgcaggcg atgcaccaga aagaggcaag cgagatgacc    4440
cgttggtggc gtgatttcga tttcctgaag aagctgccgt acattcgtga tcgcgtggtt    4500
gaactgtact tttggatttt ggtcggtgtg agctaccaac cgaaattcag cacgggtcgt    4560 atcttttttga gcaagattat ctgtctggaa accctggtgg acgacacgtt tgatgcgtac    4620
ggtactttcg acgaactggc cattttcacc gaggccgtta cgcgttggga cctgggtcat    4680
cgcgacgcgc tgcctgagta catgaaattc attttcaaga ccctgattga tgtgtacagc    4740
gaggcggaac aagagctggc aaaagagggc cgctccatata gcattcacta tgcgatccgt    4800
agcttccagg agttggtcat gaagtacttt tgcgaggcga atggctgaa taagggttat    4860 gttccgagcc tggatgacta caagagcgtc agcctgcgca gcatcggctt cctgccgatc    4920
gccgtggctt cttttgtttt catgggcgac attgctacga aagaggtttt tgagtgggaa    4980
atgaataacc cgaaaatcat catcgcagcc gaaaccattt tccgctttct ggatgacatt    5040
gcaggtcatc gcttcgaaca aaaacgtgag cacagcccga gcgcaatcga gtgctacaaa    5100
aaccaacatg gtgtctcgga agaagaggca gtgaaagcgc tgagcttgga ggtcgccaat    5160
tcgtggaaag acattaacga gagctgctg ctgaaccca tggcaattcc actgccgttg    5220
ctgcaggtga tcctggattt gagccgtagc gcggacttca tgtacggtaa tgcgcaggac    5280
cgtttcacgc actccaccat gatgaaagat caagttgacc tggttctgaa agatccggtg    5340
aaactggacg attaagaatt c                                              5361
```

<210> SEQ ID NO 24
<211> LENGTH: 5414
<212> TYPE: DNA
<213> ORGANISM: Artificial Sequence
<220> FEATURE:
<223> OTHER INFORMATION: DNA sequence of the synthetic operon containing
      CYP71AV-P2, CPRm, and SaSAS including the NdeI and HindIII
      restriction sites in 3' and 5' ends

<400> SEQUENCE: 24

```
catatggctc tgttattagc agttttttgg tcggcgctta taatcctcgt agtaacctac      60
accatatccc tcctaatcaa ccaatggcga aaaccgaaac cccaagggaa gttcccccg     120 ggcccatggc gtctgccgat tatcggtcac atgcaccatt tgatcggcac catgccgcat     180
cgtggtgtta tggaactggc ccgtaagcat ggcagcctga tgcacctgca actgggtgaa     240
gtctctacga ttgttgtcag cagcccgcgt tgggcgaaag aggtcttgac cacctatgat     300
atcaccttcg ccaatcgccc ggaaaccctg actggcgaga tcgtcgcata ccacaacacg     360
gatatcgtcc tggcgccgta tgtgagtat tggcgtcaac tgcgtaaact gtgcacgctg     420
gagctgctga gcaacaagaa agtgaagagc ttccagagcc tgcgcgaaga agagtgttgg     480
aacctggtca aggacatccg cagcaccggc caaggtagcc caatcaatct gtcggagaac     540
attttcaaga tgattgcgac gattctgagc cgtgctgcgt tcggtaaggg tattaaggat     600
caaatgaagt ttaccgaact ggtgaaagaa atcctgcgtc tgaccggcgg ttttgatgtc     660
gctgacatct tccctagcaa gaagttgctg caccacctga gcggcaagcg tgcaaaactg     720
accaatatcc ataacaagct ggataatctg atcaataaca tcatcgcaga gcacccgggc     780
```

```
aaccgtacct cgtcctccca ggaaacgctg ctggacgttc tgctgcgcct gaaagagtct   840
gcggagtttc cgctgaccgc cgacaacgtt aaagcagtga tcctggatat gttcggcgct   900
ggtacggata ccagcagcgc gacgatcgag tgggcgatta gcgagctgat tcgctgccct   960
cgcgcgatgg agaaagtgca gacggaattg cgtcaggcac tgaatggcaa agagcgtatt  1020
caggaagagg atttgcagga gctgaattat ctgaagctgg tgattaaaga aaccctgcgc  1080
ctgcatccgc cgttgccgct ggtgatgccg cgtgagtgcc gtgaaccgtg tgttttgggc  1140
ggttacgaca ttccgagcaa aacgaagctg atcgttaatg ttttcgcgat taaccgtgac  1200
ccggaatact ggaaagacgc ggaaacgttt atgccggagc gttttgagaa tagcccgatt  1260
accgttatgg gttccgagta cgaatacctg ccatttggtg ctggtcgtcg tatgtgtcct  1320
ggtgcagcgc tggtctggc caacgtggaa ctgccgctgg cgcacattct gtactatttc  1380
aactggaaac tgccgaacgg caagaccttc gaagatttgg acatgaccga gagctttggt  1440
gccactgtgc agcgcaaaac cgagctgctg ctggttccga ccgactttca aaccctgact  1500
gcaagcacct aatgagtcga ctaactttaa gaaggagata tatccatgga acctagctct  1560
cagaaactgt ctccgttgga atttgttgct gctatcctga agggcgacta cagcagcggt  1620
caggttgaag gtggtccacc gccaggtctg gcagctatgt tgatggaaaa taaggatttg  1680
gtgatggttc tgacgacgtc cgtggcagtc ctgatcggct gtgtcgtggt cctggcatgg  1740
cgtcgtgcgg caggtagcgg taagtacaag caacctgaac tgcctaaact ggtggtcccg  1800
aaagcagccg aaccggagga ggcagaggat gataaaacca agatcagcgt gtttttcggc  1860
acccaaaccg gtacggcaga aggtttcgcg aaggcttttg ttgaagaggc caaggcgcgt  1920
tatcagcagg cccgtttcaa agttatcgac ctggacgact atgcggcaga cgatgacgag  1980
tacgaagaga aactgaagaa ggaaaacttg gcattcttct tcttggcgtc ctacggtgac  2040
ggcgagccga cggacaacgc ggcacgcttt tacaaatggt ttacggaggg taaggaccgt  2100
ggtgaatggc tgaacaatct gcagtacggc gttttggtc tgggtaaccg tcaatatgag  2160
catttcaata agatcgccat tgtcgtcgat gatctgatct tcgagcaagg tggcaagaag  2220
ctggttccgg tgggtctggg tgacgatgac cagtgcattg aggatgattt tgcggcgtgg  2280
cgtgaactgg tctggccgga actggataaa ctgctgcgta cgaagacga cgctaccgtg  2340
gcaaccccgt acagcgccgc tgtgctgcaa taccgcgtgg ttttccacga tcacattgac  2400
ggcctgatta gcgaaaacgg tagcccgaac ggtcatgcta atggcaatac cgtgtacgat  2460
gcgcaacacc cgtgccgtag caacgtcgcg gtcaagaagg aattgcatac tccggcgagc  2520
gatcgcagct gcacccacct ggaatttaac attagcggta ccggcctgat gtacgagacg  2580
ggtgaccacg tcggtgtgta ttgcgagaac ctgttggaaa ccgtggagga ggccgagaag  2640
ttgttgaacc tgagcccgca gacgtacttc tccgttcaca ccgacaacga ggacggtacg  2700
ccgttgagcg gcagcagcct gccgccaccg tttccgccgt gcaccttgcg cacggcattg  2760
accaaatacg cagacttgac ttctgcaccg aaaaagtcgg tgctggtggc gctggccgag  2820
tacgcatctg accagggtga agcggatcgt ttgcgtttct tggcgagccc gagcggcaaa  2880
gaggaatatg cacagtacat cttggcaagc cagcgcacgc tgctgaggt catggcggag  2940
ttcccgtcgg cgaaaccgcc gctgggtgtc ttttttcgcgg gtgtcgctcc gcgcctgcag  3000
ccgcgttct attccattag ctctagcccg aagatcgcac cgttccgtat tcacgtgacc  3060
tgcgccctgt tttatgacaa atcccctacc ggtcgcgttc ataagggcat ctgtagcacg  3120
tggatgaaaa atgcggtccc gctggaagaa agcaacgatt gttcctgggc tccgatcttc  3180
```

```
gtccgcaaca gcaacttcaa gctgccgacc gacccgaagg ttccgattat catgattggt    3240
ccgggtaccg gtctggcccc ttttcgtggc tttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420
gtcgctttta gccgcgaagg cccgatgaaa gaatacgtgc aacacaaaat gagccaacgt    3480
gcctccgatg tgtggaacat cattagcgac ggtggttatg tttatgtttg cggtgacgcg    3540
aagggtatgg ctcgtgatgt tcaccgtacc ctgcatacca tcgcacagga gcaaggtagc    3600
atgtccagct cggaggccga aggtatggtc aaaaacctgc aaaccaccgg tcgttacctg    3660
cgtgatgtgt ggtaataaaa gcttaggagg taaaacatat ggacagcagc accgccaccg    3720
caatgaccgc accattcatc gacccgacgg atcatgtgaa tctgaaaacc gacacggatg    3780
cgagcgaaaa tcgtcgtatg ggtaactaca agccgagcat ttggaactac gattttctgc    3840
agtccctggc gacgcaccac aacattgttg aagagcgtca cctgaagctg cagagaaac    3900 tgaaaggtca agtgaaattc atgttcggtg cgccgatgga gccattggct aagttggagc    3960
tggttgatgt ggtgcaacgc ttgggtctga accacctgtt cgagactgaa atcaaagaag    4020
ctctgttcag catctacaaa gatggcagca atggctggtg gtttggccat ctgcatgcta    4080
cctctttgcg cttccgtctg ttgcgccaat gtggcctgtt tatcccgcag gacgttttca    4140
aaaccttcca aaacaagacc ggtgagtttg acatgaagct gtgggacaac gttaagggcc    4200
tgctgagcct gtacgaggcg agctacctgg gctggaaggg cgagaacatc ttggatgaag    4260
caaaggcgtt cacgaccaag tgcctgaaga gcgcatggga gaacattagc gagaagtggc    4320
tggcgaagcg tgttaaacat gcgttggcgc tgccgctgca ctggcgtgtt ccgcgtattg    4380
aagcacgctg gtttatcgag gtgtacgaac aagaggccaa tatgaatccg acgctgctga    4440
aactggcgaa actggacttc aacatggtcc aaagcattca ccagaaagaa atcggtgaac    4500
tggcccgctg gtgggttact accggcctgg acaagctgga tttcgcacgc aacaatctgt    4560
tgcagtctta tatgtggagc tgcgccatcg cgtccgaccc gaaattcaaa ctggcgcgtg    4620
aaaccattgt cgagatcggt tccgtgttga cggttgtcga cgacggctat gatgtgtacg    4680
gttctatgga tgagctggac ctgtacacca gctcggtgga gcgttggtcc tgtgtcaaaa    4740
ttgacaagct gcctaatacg ctgaagctga tctttatgtc tatgttcaac aaaaccaacg    4800
aggtgggtct gcgtgttcaa cacgagcgtg gttacaatag catcccgacc ttcattaagg    4860
cgtgggtgga acagtgtaag agctatcaaa agaggcgcg ttggtttcat ggtggtcaca    4920
cgcctccgct ggaagaatac agcctgaacg gtctggtcag cattggtttt ccgctgttgc    4980
tgatcaccgg ctatgttgcg attgctgaga atgaagcagc cctggataaa gtccaccgc    5040 tgccggacct gctgcattat tccagcttgc tgagccgtct gattaatgat atcggcacta    5100
gcccggatga aatggcgcgt ggtgacaatc tgaagagcat tcactgctat atgaatgaaa    5160
ccggtgccag cgaagaggtc gcacgcgagc acatcaaagg cgtcatcgaa gagaattgga    5220
aaattctgaa ccagtgttgc tttgaccagt cccagttcca ggagccgttc atcacgttta    5280
acctgaacag cgtgcgcggc tcgcatttct tctatgaatt tggtgatggt tttggtgtta    5340
ccgacagctg gaccaaggtg gatatgaaaa gcgtcctgat tgatccgatt ccgctgggtg    5400
aagagtaagc ttgc                                                     5414

<210> SEQ ID NO 25
```

<211> LENGTH: 5361
<212> TYPE: DNA
<213> ORGANISM: Artificial Sequence
<220> FEATURE:
<223> OTHER INFORMATION: DNA sequence of the synthetic operon containing CYP71AV-P2O, CPRm, and ClASS including the NdeI and HindIII restriction sites in 3' and 5' ends

<400> SEQUENCE: 25

| | | | | | |
|---|---|---|---|---|---|
| catatggcac | tgttgctggc | tgtcttttgg | tctgctctga | ttattttggt | ggttacctac | 60 |
| accatctccc | tgctgattaa | ccagtggcgt | aaaccgaaac | cacagggtaa | attcccgccg | 120 |
| ggtccgtggc | gtctgccgat | tatcggtcac | atgcaccatt | tgatcggcac | catgccgcat | 180 |
| cgtggtgtta | tggaactggc | ccgtaagcat | ggcagcctga | tgcacctgca | actgggtgaa | 240 |
| gtctctacga | ttgttgtcag | cagcccgcgt | tgggcgaaag | aggtcttgac | cacctatgat | 300 |
| atcaccttcg | ccaatcgccc | ggaaaccctg | actggcgaga | tcgtcgcata | ccacaacacg | 360 |
| gatatcgtcc | tggcgccgta | tggtgagtat | tggcgtcaac | tgcgtaaact | gtgcacgctg | 420 |
| gagctgctga | gcaacaagaa | agtgaagagc | ttccagagcc | tgcgcaagag | agagtgttgg | 480 |
| aacctggtca | aggacatccg | cagcaccggc | caaggtagcc | aatcaatct | gtcggagaac | 540 |
| attttcaaga | tgattgcgac | gattctgagc | cgtgctgcgt | tcggtaaggg | tattaaggat | 600 |
| caaatgaagt | taccgaact | ggtgaaagaa | atcctgcgtc | tgaccggcgg | ttttgatgtc | 660 |
| gctgacatct | tccctagcaa | gaagttgctg | caccacctga | gcggcaagcg | tgcaaaactg | 720 |
| accaatatcc | ataacaagct | ggataatctg | atcaataaca | tcatcgcaga | gcacccgggc | 780 |
| aaccgtacct | cgtcctccca | ggaaacgctg | ctggacgttc | tgctgcgcct | gaaagagtct | 840 |
| gcggagtttc | gctgaccgc | cgacaacgtt | aaagcagtga | tcctggatat | gttcggcgct | 900 |
| ggtacggata | ccagcagcgc | gacgatcgag | tgggcgatta | gcgagctgat | tcgctgccct | 960 |
| cgcgcgatgg | agaaagtgca | gacggaattg | cgtcaggcac | tgaatggcaa | agagcgtatt | 1020 |
| caggaagagg | atttgcagga | gctgaattat | ctgaagctgg | tgattaaaga | aaccctgcgc | 1080 |
| ctgcatccgc | cgttgccgct | ggtgatgccg | cgtgagtgcc | gtgaaccgtg | tgttttgggc | 1140 |
| ggttacgaca | ttccgagcaa | aacgaagctg | atcgttaatg | ttttcgcgat | taaccgtgac | 1200 |
| ccggaatact | ggaaagacgc | ggaaacgttt | atgccggagc | gttttgagaa | tagcccgatt | 1260 |
| accgttatgg | gttccgagta | cgaatacctg | ccatttggtg | ctggtcgtcg | tatgtgtcct | 1320 |
| ggtgcagcgc | tgggtctggc | caacgtggaa | ctgccgctgg | cgcacattct | gtactatttc | 1380 |
| aactggaaac | tgccgaacgg | caagaccttc | gaagatttgg | acatgaccga | gagctttggt | 1440 |
| gccactgtgc | agcgcaaaac | cgagctgctg | ctggttccga | ccgactttca | aacgctgact | 1500 |
| gcgagcacct | aatgagtcga | ctaactttaa | gaaggagata | tatccatgga | acctagctct | 1560 |
| cagaaactgt | ctccgttgga | atttgttgct | gctatcctga | agggcgacta | cagcagcggt | 1620 |
| caggttgaag | tggtccacc | gccaggtctg | gcagctatgt | tgatggaaaa | taaggatttg | 1680 |
| gtgatggttc | tgacgacgtc | cgtggcagtc | ctgatcggct | gtgtcgtggt | cctggcatgg | 1740 |
| cgtcgtgcgg | caggtagcgg | taagtacaag | caacctgaac | tgcctaaact | ggtggtcccg | 1800 |
| aaagcagccg | aaccggagga | ggcagaggat | gataaaacca | agatcagcgt | gttttttcggc | 1860 |
| acccaaaccg | gtacggcaga | aggtttcgcg | aaggcttttg | ttgaagaggc | caaggcgcgt | 1920 |
| tatcagcagg | cccgttttca | agttatcgac | ctggacgact | atgcggcaga | cgatgacgag | 1980 |
| tacgaagaga | aactgaagaa | ggaaaacttg | gcattcttct | tcttggcgtc | ctacggtgac | 2040 |
| ggcgagccga | cggacaacgc | ggcacgcttt | tacaaatggt | ttacggaggg | taaggaccgt | 2100 |

```
ggtgaatggc tgaacaatct gcagtacggc gttttTggtc tgggtaaccg tcaatatgag    2160
catttcaata agatcgccat tgtcgtcgat gatctgatct tcgagcaagg tggcaagaag    2220
ctggttccgg tgggtctggg tgacgatgac cagtgcattg aggatgattt tgcggcgtgg    2280
cgtgaactgg tctggccgga actggataaa ctgctgcgta acgaagacga cgctaccgtg    2340
gcaaccccgt acagcgccgc tgtgctgcaa taccgcgtgg ttttccacga tcacattgac    2400
ggcctgatta gcgaaaacgg tagcccgaac ggtcatgcta atggcaatac cgtgtacgat    2460
gcgcaacacc cgtgccgtag caacgtcgcg gtcaagaagg aattgcatac tccggcgagc    2520
gatcgcagct gcacccacct ggaatttaac attagcggta ccggcctgat gtacgagacg    2580
ggtgaccacg tcggtgtgta ttgcgagaac ctgttggaaa ccgtggagga ggccgagaag    2640
ttgttgaacc tgagcccgca gacgtacttc tccgttcaca ccgacaacga ggacggtacg    2700
ccgttgagcg gcagcagcct gccgccaccg tttccgccgt gcaccttgcg cacggcattg    2760
accaaatacg cagacttgac ttctgcaccg aaaaagtcgg tgctggtggc gctggccgag    2820
tacgcatctg accagggtga agcggatcgt ttgcgtttct tggcgagccc gagcggcaaa    2880
gaggaatatg cacagtacat cttggcaagc cagcgcacgc tgctggaggt catggcggag    2940
ttcccgtcgg cgaaaccgcc gctgggtgtc tttttcgcgg gtgtcgctcc gcgcctgcag    3000
ccgcgtttct attccattag ctctagcccg aagatcgcac cgttccgtat tcacgtgacc    3060
tgcgccctgg tttatgacaa atcccctacc ggtcgcgttc ataagggcat ctgtagcacg    3120
tggatgaaaa atgcggtccc gctggaagaa agcaacgatt gttcctgggc tccgatcttc    3180
gtccgcaaca gcaacttcaa gctgccgacc gacccgaagg ttccgattat catgattggt    3240
ccgggtaccg tctgccccc ttttcgtggc tttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420 gtcgcttttta gccgcgaagg cccgatgaaa gaatacgtgc aacacaaaat gagccaacgt    3480
gcctccgatg tgtggaacat cattagcgac ggtggttatg tttatgtttg cggtgacgcg    3540
aagggtatgg ctcgtgatgt tcaccgtacc ctgcatacca tcgcacagga gcaaggtagc    3600
atgtccagct cggaggccga aggtatggtc aaaaacctgc aaaccaccgg tcgttacctg    3660
cgtgatgtgt ggtaataaaa gcttgaagga gatatactaa tgtctaccca gcaggttagc    3720
tccgagaata tcgttcgcaa cgcggcgaac ttccacccga atatctgggg taatcatttc    3780
ttgacgtgtc caagccagac gatcgattct tggacgcaac aacaccataa agagctgaaa    3840
gaagaggtcc gcaagatgat ggtgagcgac gcaaacaaac cggcacaacg tctgcgtctg    3900
attgacaccg ttcaacgttt gggcgtggcg tatcatttcg aaaagaaat cgatgacgct    3960 ctggaaaaga tcggtcacga tccgtttgac gataaggatg acctgtatat cgttagcctg    4020
tgttttcgcc tgctgcgtca gcatggcatc aagattagct gcgatgtttt tgagaagttc    4080
aaagacgacg atggcaagtt taaggcttcc ctgatgaatg atgtccaagg tatgctgtcg    4140
ttgtatgaag cggcccacct ggcaattcat ggcgaggaca tcctggatga ggctattgtc    4200
tttacgacca cccacctgaa gagcaccgtt tctaactccc cggtcaattc caccttgcg    4260 gaacagattc gccacagcct gcgtgtgccg ctgcgtaagg cagtcccgcg tttggagagc    4320
cgctacttcc tggatatcta tagccgtgac gacctgcacg acaagactct gctgaacttt    4380
gccaaactgg acttcaacat cctgcaggcg atgcaccaga aagaggcaag cgagatgacc    4440
```

```
cgttggtggc gtgatttcga tttcctgaag aagctgccgt acattcgtga tcgcgtggtt    4500
gaactgtact tttggatttt ggtcggtgtg agctaccaac cgaaattcag cacgggtcgt    4560
atcttttga  gcaagattat ctgtctggaa accctggtgg acgacacgtt tgatgcgtac    4620
ggtactttcg acgaactggc cattttcacc gaggccgtta cgcgttggga cctgggtcat    4680
cgcgacgcgc tgcctgagta catgaaattc attttcaaga ccctgattga tgtgtacagc    4740
gaggcggaac aagagctggc aaaagagggc cgctccctata gcattcacta tgcgatccgt   4800
agcttccagg agttggtcat gaagtacttt tgcgaggcga atggctgaa  taagggttat    4860
gttccgagcc tggatgacta caagagcgtc agcctgcgca gcatcggctt cctgccgatc    4920
gccgtggctt cttttgtttt catgggcgac attgctacga aagaggtttt tgagtgggaa    4980
atgaataacc cgaaaatcat catcgcagcc gaaaccattt tccgctttct ggatgacatt    5040
gcaggtcatc gcttcgaaca aaaacgtgag cacagcccga gcgcaatcga gtgctacaaa    5100
aaccaacatg gtgtctcgga agaagaggca gtgaaagcgc tgagcttgga ggtcgccaat    5160
tcgtggaaag acattaacga gagctgctg  ctgaacccta tggcaattcc actgccgttg    5220
ctgcaggtga tcctggattt gagccgtagc gcggacttca tgtacggtaa tgcgcaggac    5280
cgtttcacgc actccaccat gatgaaagat caagttgacc tggttctgaa agatccggtg    5340
aaactggacg attaagaatt c                                              5361
```

<210> SEQ ID NO 26
<211> LENGTH: 5414
<212> TYPE: DNA
<213> ORGANISM: Artificial Sequence
<220> FEATURE:
<223> OTHER INFORMATION: DNA sequence of the synthetic operon containing CYP71AV-P2O, CPRm, and SaSAS including the NdeI and HindIII restriction sites in 3' and 5' ends

<400> SEQUENCE: 26

```
catatggcac tgttgctggc tgtcttttgg tctgctctga ttattttggt ggttacctac      60
accatctccc tgctgattaa ccagtggcgt aaaccgaaac cacagggtaa attcccgccg     120
ggtccgtggc gtctgccgat tatcggtcac atgcaccatt tgatcggcac catgccgcat     180
cgtggtgtta tggaactggc ccgtaagcat ggcagcctga tgcacctgca actgggtgaa     240
gtctctacga ttgttgtcag cagcccgcgt tgggcgaaag aggtcttgac cacctatgat     300
atcaccttcg ccaatcgccc ggaaaccctg actggcgaga tcgtcgcata ccacaacacg     360
gatatcgtcc tggcgccgta tggtgagtat tggcgtcaac tgcgtaaact gtgcacgctg     420
gagctgctga gcaacaagaa agtgaagagc ttccagagcc tgcgcgaaga agagtgttgg    480
aacctggtca aggacatccg cagcaccggc caaggtagcc caatcaatct gtcggagaac     540
attttcaaga tgattgcgac gattctgagc cgtgctgcgt tcggtaaggg tattaaggat     600
caaatgaagt ttaccgaact ggtgaaagaa atcctgcgtc tgaccggcgg ttttgatgtc     660
gctgacatct tccctagcaa gaagttgctg caccacctga cgcgcaagcg tgcaaaactg     720
accaatatcc ataacaagct ggataatctg atcaataaca tcatcgcaga gcacccgggc     780
aaccgtacct cgtcctccca ggaaacgctg ctggacgttc tgctgcgcct gaaagagtct     840
gcggagtttc cgctgaccgc cgacaacgtt aaagcagtga tcctggatat gttcggcgct     900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc    1080
```

```
ctgcatccgc cgttgccgct ggtgatgccg cgtgagtgcc gtgaaccgtg tgttttgggc    1140
ggttacgaca ttccgagcaa aacgaagctg atcgttaatg ttttcgcgat taaccgtgac    1200
ccggaatact ggaaagacgc ggaaacgttt atgccggagc gttttgagaa tagcccgatt    1260
accgttatgg gttccgagta cgaatacctg ccatttggtg ctggtcgtcg tatgtgtcct    1320
ggtgcagcgc tgggtctggc aacgtggaa ctgccgctgg cgcacattct gtactatttc    1380
aactggaaac tgccgaacgg caagaccttc gaagatttgg acatgaccga gagctttggt    1440
gccactgtgc agcgcaaaac cgagctgctg ctggttccga ccgactttca aacgctgact    1500
gcgagcacct aatgagtcga ctaactttaa gaaggagata tatccatgga acctagctct    1560
cagaaactgt ctccgttgga atttgttgct gctatcctga agggcgacta cagcagcggt    1620
caggttgaag gtggtccacc gccaggtctg cagctatgt tgatggaaaa taaggatttg    1680
gtgatggttc tgacgacgtc cgtggcagtc ctgatcggct gtgtcgtggt cctggcatgg    1740
cgtcgtgcgg caggtagcgg taagtacaag caacctgaac tgcctaaact ggtggtcccg    1800
aaagcagccg aaccggagga ggcagaggat gataaaacca agatcagcgt gttttcggc    1860
acccaaaccg gtacggcaga aggtttcgcg aaggcttttg ttgaagaggc caaggcgcgt    1920
tatcagcagg cccgtttcaa agttatcgac ctggacgact atgcggcaga cgatgacgag    1980
tacgaagaga aactgaagaa ggaaaaacttg gcattcttct tcttggcgtc ctacggtgac    2040
ggcgagccga cggacaacgc ggcacgcttt tacaaatggt ttacgagggg taaggaccgt    2100
ggtgaatggc tgaacaatct gcagtacggc gttttggtc tgggtaaccg tcaatatgag    2160
catttcaata agatcgccat tgtcgtcgat gatctgatct tcgagcaagg tggcaagaag    2220
ctggttccgg tgggtctggg tgacgatgac cagtgcattg aggatgattt tgcggcgtgg    2280
cgtgaactgg tctggccgga actggataaa ctgctgcgta acgaagacga cgctaccgtg    2340
gcaaccccgt acagcgccgc tgtgctgcaa taccgcgtgg ttttccacga tcacattgac    2400
ggcctgatta gcgaaaacgg tagcccgaac ggtcatgcta atggcaatac cgtgtacgat    2460
gcgcaacacc cgtgccgtag caacgtcgcg gtcaagaagg aattgcatac tccggcgagc    2520
gatcgcagct gcacccacct ggaatttaac attagcggta ccggcctgat gtacgagacg    2580
ggtgaccacg tcggtgtgta ttgcgagaac ctgttggaaa ccgtggagga ggccgagaag    2640
ttgttgaacc tgagcccgca gacgtacttc tccgttcaca ccgacaacga ggacggtacg    2700
ccgttgagcg gcagcagcct gccgccaccg tttccgccgt gcaccttgcg cacggcattg    2760
accaaatacg cagacttgac ttctgcaccg aaaaagtcgg tgctggtggc gctggccgag    2820
tacgcatctg accagggtga agcggatcgt ttgcgtttct tggcgagccc gagcggcaaa    2880
gaggaatatg cacagtacat cttggcaagc cagcgcacgc tgctgaggt catggcgag    2940
ttcccgtcgg cgaaaccgcc gctgggtgtc ttttcgcgg gtgtcgctcc gcgcctgcag    3000
ccgcgtttct attccattag ctctagcccg aagatcgcac cgttccgtat tcacgtgacc    3060
tgcgccctgg tttatgacaa atcccctacc ggtcgcgttc ataagggcat ctgtagcacg    3120
tggatgaaaa atgcggtccc gctggaagaa agcaacgatt gttcctgggc tccgatcttc    3180
gtccgcaaca gcaacttcaa gctgccgacc gacccgaagg ttccgattat catgattggt    3240
ccgggtaccg gtctggcccc ttttcgtggc ttttttgcaag agcgcttggc gttgaaagag    3300
agcggtgctg aattgggtcc ggcgatcttg ttctttggtt gccgtaaccg taaaatggac    3360
tttatttacg aggatgaact gaatgatttc gtcaaagcgg gcgttgtcag cgagctgatc    3420
```

-continued

```
gtcgctttta gccgcgaagg cccgatgaaa gaatacgtgc aacacaaaat gagccaacgt      3480
gcctccgatg tgtggaacat cattagcgac ggtggttatg tttatgtttg cggtgacgcg      3540
aagggtatgg ctcgtgatgt tcaccgtacc ctgcatacca tcgcacagga gcaaggtagc      3600
atgtccagct cggaggccga aggtatggtc aaaaacctgc aaaccaccgg tcgttacctg      3660
cgtgatgtgt ggtaataaaa gcttaggagg taaaacatat ggacagcagc accgccaccg      3720
caatgaccgc accattcatc gacccgacgg atcatgtgaa tctgaaaacc gacacggatg      3780
cgagcgaaaa tcgtcgtatg ggtaactaca agccgagcat ttggaactac gattttctgc      3840
agtccctggc gacgcaccac aacattgttg aagagcgtca cctgaagctg cagagaaaac      3900
tgaaaggtca agtgaaattc atgttcggtg cgccgatgga gccattggct aagttggagc      3960
tggttgatgt ggtgcaacgc ttgggtctga ccacctgtt cgagactgaa atcaaagaag       4020
ctctgttcag catctacaaa gatggcagca atggctggtg gtttggccat ctgcatgcta      4080
cctctttgcg cttccgtctg ttgcgccaat gtggcctgtt tatcccgcag acgttttca       4140 aaacctttca aaacaagacc ggtgagtttg acatgaagct gtgggacaac gttaagggcc      4200
tgctgagcct gtacgaggcg agctacctgg gctggaaggg cgagaacatc ttggatgaag      4260
caaaggcgtt cacgaccaag tgcctgaaga gcgcatggga gaacattagc gagaagtggc      4320
tggcgaagcg tgttaaacat gcgttggcgc tgccgctgca ctggcgtgtt ccgcgtattg      4380
aagcacgctg gtttatcgag gtgtacgaac aagaggccaa tatgaatccg acgctgctga      4440
aactggcgaa actggacttc aacatggtcc aaagcattca ccagaaagaa atcggtgaac      4500
tggcccgctg gtgggttact accggcctgg acaagctgga tttcgcacgc aacaatctgt      4560
tgcagtctta tatgtggagc tgcgccatcg cgtccgaccc gaaattcaaa ctggcgcgtg      4620
aaaccattgt cgagatcggt tccgtgttga cggttgtcga cgacggctat gatgtgtacg      4680
gttctatgga tgagctggac ctgtacacca gctcggtgga gcgttggtcc tgtgtcaaaa      4740
ttgacaagct gcctaatacg ctgaagctga tctttatgtc tatgttcaac aaaaccaacg      4800
aggtgggtct gcgtgttcaa cacgagcgtg gttacaatag catcccgacc ttcattaagg      4860
cgtgggtgga acagtgtaag agctatcaaa aagaggcgcg ttggtttcat ggtggtcaca      4920
cgcctccgct ggaagaatac agcctgaacg gtctggtcag cattggtttt ccgctgttgc      4980
tgatcaccgg ctatgttgcg attgctgaga atgaagcagc cctggataaa gtccaccgc      5040 tgccggacct gctgcattat tccagcttgc tgagccgtct gattaatgat atcggcacta      5100
gcccggatga aatggcgcgt ggtgacaatc tgaagagcat tcactgctat atgaatgaaa      5160
ccggtgccag cgaagaggtc gcacgcgagc acatcaaagg cgtcatcgaa gagaattgga      5220
aaattctgaa ccagtgttgc tttgaccagt cccagttcca ggagccgttc atcacgttta      5280
acctgaacag cgtgcgcggc tcgcatttct tctatgaatt tggtgatggt tttggtgtta      5340
ccgacagctg gaccaaggtg gatatgaaaa gcgtcctgat tgatccgatt ccgctgggtg      5400
aagagtaagc ttgc                                                       5414
```

<210> SEQ ID NO 27
<211> LENGTH: 1512
<212> TYPE: DNA
<213> ORGANISM: Artificial Sequence
<220> FEATURE:
<223> OTHER INFORMATION: CYP71AV8-L358A DNA sequence

<400> SEQUENCE: 27

```
atggctctgt tattagcagt tttttggtcg gcgcttataa tcctcgtagt aacctacacc       60
```

```
atatccctcc taatcaacca atggcgaaaa ccgaaacccc aagggaagtt ccccccgggc      120
ccatggcgtc tgccgattat cggtcacatg caccatttga tcggcaccat gccgcatcgt      180
ggtgttatgg aactggcccg taagcatggc agcctgatgc acctgcaact gggtgaagtc      240
tctacgattg ttgtcagcag cccgcgttgg gcgaaagagg tcttgaccac ctatgatatc      300
accttcgcca tcgcccgga aaccctgact ggcgagatcg tcgcatacca aacacggat       360 atcgtcctgg cgccgtatgg tgagtattgg cgtcaactgc gtaaactgtg cacgctggag      420
ctgctgagca caagaaagt gaagagcttc cagagcctgc gcgaagaaga gtgttggaac      480
ctggtcaagg acatccgcag caccggccaa ggtagcccaa tcaatctgtc ggagaacatt      540
ttcaagatga ttgcgacgat tctgagccgt gctgcgttcg gtaagggtat taaggatcaa      600
atgaagttta ccgaactggt gaaagaaatc ctgcgtctga ccggcggttt tgatgtcgct      660
gacatcttcc ctagcaagaa gttgctgcac cacctgagcg gcaagcgtgc aaaactgacc      720
aatatccata caagctgga taatctgatc aataacatca tcgcagagca cccgggcaac      780
cgtacctcgt cctcccagga aacgctgctg gacgttctgc tgcgcctgaa agagtctgcg      840
gagtttccgc tgaccgccga caacgttaaa gcagtgatcc tggatatgtt cggcgctggt      900
acggatacca gcagcgcgac gatcgagtgg gcgattagcg agctgattcg ctgccctcgc      960
gcgatggaga agtgcagac ggaattgcgt caggcactga atggcaaaga gcgtattcag     1020
gaagaggatt tgcaggagct gaattatctg aagctggtga ttaaagaaac cctgcgcctg     1080
catccgccgg ctccgctggt gatgccgcgt gagtgccgtg aaccgtgtgt tttgggcggt     1140
tacgacattc cgagcaaaac gaagctgatc gttaatgttt tcgcgattaa ccgtgacccg     1200
gaatactgga agacgcgga aacgtttatg ccggagcgtt ttgagaatag cccgattacc     1260
gttatgggtt ccgagtacga atacctgcca tttggtgctg gtcgtcgtat gtgtcctggt     1320
gcagcgctgg gtctgccaa cgtggaactg ccgctggcgc acattctgta ctatttcaac     1380
tggaaactgc cgaacggcaa gaccttcgaa gatttggaca tgaccgagag cttggtgcc     1440 actgtgcagc gcaaaaccga gctgctgctg gttccgaccg actttcaaac cctgactgcg     1500
agcacctaat ga                                                         1512
```

<210> SEQ ID NO 28
<211> LENGTH: 502
<212> TYPE: PRT
<213> ORGANISM: Artificial Sequence
<220> FEATURE:
<223> OTHER INFORMATION: CYP71AV8-L358A amino acid sequence

<400> SEQUENCE: 28

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95
```

```
Thr Tyr Asp Ile Thr Phe Ala Asn Arg Pro Glu Thr Leu Thr Gly Glu
                100                 105                 110

Ile Val Ala Tyr His Asn Thr Asp Ile Val Leu Ala Pro Tyr Gly Glu
            115                 120                 125

Tyr Trp Arg Gln Leu Arg Lys Leu Cys Thr Leu Glu Leu Leu Ser Asn
        130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
            245                 250                 255

His Pro Gly Asn Arg Thr Ser Ser Gln Glu Thr Leu Leu Asp Val
        260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
        290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Ala Pro Leu Val Met
        355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
            405                 410                 415

Ser Pro Ile Thr Val Met Gly Ser Glu Tyr Glu Tyr Leu Pro Phe Gly
        420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 29
<211> LENGTH: 1512
<212> TYPE: DNA
<213> ORGANISM: Artificial Sequence
<220> FEATURE:
<223> OTHER INFORMATION: CYP71AV8-L358F DNA sequence

<400> SEQUENCE: 29

```
atggctctgt tattagcagt tttttggtcg gcgcttataa tcctcgtagt aacctacacc      60
atatccctcc taatcaacca atggcgaaaa ccgaaacccc aagggaagtt ccccccgggc     120
ccatggcgtc tgccgattat cggtcacatg caccatttga tcggcaccat gccgcatcgt     180
ggtgttatgg aactggcccg taagcatggc agcctgatgc acctgcaact gggtgaagtc     240
tctacgattg ttgtcagcag cccgcgttgg gcgaagagg tcttgaccac ctatgatatc      300
accttcgcca atcgcccgga aaccctgact ggcgagatcg tcgcatacca caacacggat     360
atcgtcctgg cgccgtatgg tgagtattgg cgtcaactgc gtaaactgtg cacgctggag     420
ctgctgagca acaagaaagt gaagagcttc cagagcctgc gcgaagaaga gtgttggaac     480
ctggtcaagg acatccgcag caccggccaa ggtagcccaa tcaatctgtc ggagaacatt     540
ttcaagatga ttgcgacgat tctgagccgt gctgcgttcg gtaagggtat taaggatcaa     600
atgaagttta ccgaactggt gaaagaaatc ctgcgtctga ccggcggttt tgatgtcgct     660
gacatcttcc ctagcaagaa gttgctgcac cacctgagcg gcaagcgtgc aaaactgacc     720
aatatccata caagctgga taatctgatc aataacatca tcgcagagca cccgggcaac     780
cgtacctcgt cctcccagga aacgctgctg acgttctgc tgcgcctgaa agagtctgcg     840
gagtttccgc tgaccgccga caacgttaaa gcagtgatcc tggatatgtt cggcgctggt     900
acggatacca gcagcgcgac gatcgagtgg gcgattagcg agctgattcg ctgccctcgc     960
gcgatggaga aagtgcagac ggaattgcgt caggcactga atggcaaaga gcgtattcag    1020
gaagaggatt tgcaggagct gaattatctg aagctggtga ttaaagaaac cctgcgcctg    1080
catccgccgt ttccgctggt gatgccgcgt gagtgccgtg aaccgtgtgt tttgggcggt    1140
tacgacattc cgagcaaaac gaagctgatc gttaatgttt tcgcgattaa ccgtgacccg    1200
gaatactgga aagacgcgga aacgtttatg ccggagcgtt ttgagaatag cccgattacc    1260
gttatgggtt ccgagtacga ataccctgcca tttggtgctg gtcgtcgtat gtgtcctggt    1320
gcagcgctgg gtctgccaa cgtggaactg ccgctggcgc acattctgta ctatttcaac    1380
tggaaactgc cgaacggcaa gaccttcgaa gatttggaca tgaccgagag ctttggtgcc    1440
actgtgcagc gcaaaaccga gctgctgctg gttccgaccg actttcaaac gctgactgcg    1500
agcacctaat ga                                                        1512
```

<210> SEQ ID NO 30
<211> LENGTH: 502
<212> TYPE: PRT
<213> ORGANISM: Artificial Sequence
<220> FEATURE:
<223> OTHER INFORMATION: CYP71AV8-L358F amino acid sequence

<400> SEQUENCE: 30

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
                20                  25                  30

Pro Gln Gly Lys Phe Pro Pro Gly Pro Trp Arg Leu Pro Ile Ile Gly
            35                  40                  45

```
His Met His His Leu Ile Gly Thr Met Pro His Arg Gly Val Met Glu
         50                  55                  60

Leu Ala Arg Lys His Gly Ser Leu Met His Leu Gln Leu Gly Glu Val
 65                  70                  75                  80

Ser Thr Ile Val Val Ser Ser Pro Arg Trp Ala Lys Glu Val Leu Thr
                     85                  90                  95

Thr Tyr Asp Ile Thr Phe Ala Asn Arg Pro Glu Thr Leu Thr Gly Glu
                100                 105                 110

Ile Val Ala Tyr His Asn Thr Asp Ile Val Leu Ala Pro Tyr Gly Glu
             115                 120                 125

Tyr Trp Arg Gln Leu Arg Lys Leu Cys Thr Leu Glu Leu Leu Ser Asn
         130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
                 165                 170                 175

Ser Glu Asn Ile Phe Lys Met Ile Ala Thr Ile Leu Ser Arg Ala Ala
             180                 185                 190

Phe Gly Lys Gly Ile Lys Asp Gln Met Lys Phe Thr Glu Leu Val Lys
         195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                 245                 250                 255

His Pro Gly Asn Arg Thr Ser Ser Ser Gln Glu Thr Leu Leu Asp Val
             260                 265                 270

Leu Leu Arg Leu Lys Glu Ser Ala Glu Phe Pro Leu Thr Ala Asp Asn
         275                 280                 285

Val Lys Ala Val Ile Leu Asp Met Phe Gly Ala Gly Thr Asp Thr Ser
290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                 325                 330                 335

Glu Arg Ile Gln Glu Glu Asp Leu Gln Glu Leu Asn Tyr Leu Lys Leu
             340                 345                 350

Val Ile Lys Glu Thr Leu Arg Leu His Pro Pro Phe Pro Leu Val Met
         355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                 405                 410                 415

Ser Pro Ile Thr Val Met Gly Ser Glu Tyr Glu Tyr Leu Pro Phe Gly
             420                 425                 430

Ala Gly Arg Arg Met Cys Pro Gly Ala Ala Leu Gly Leu Ala Asn Val
         435                 440                 445

Glu Leu Pro Leu Ala His Ile Leu Tyr Tyr Phe Asn Trp Lys Leu Pro
450                 455                 460
```

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
            500

<210> SEQ ID NO 31
<211> LENGTH: 1512
<212> TYPE: DNA
<213> ORGANISM: Artificial Sequence
<220> FEATURE:
<223> OTHER INFORMATION: CYP71AV8-L358T DNA Sequence

<400> SEQUENCE: 31

| | | | | |
|---|---|---|---|---|
| atggctctgt | tattagcagt | ttttggtcg | gcgcttataa | tcctcgtagt aacctacacc | 60 |
| atatccctcc | taatcaacca | atggcgaaaa | ccgaaacccc | aagggaagtt cccccgggc | 120 |
| ccatggcgtc | tgccgattat | cggtcacatg | caccatttga | tcggcaccat gccgcatcgt | 180 |
| ggtgttatgg | aactggcccg | taagcatggc | agcctgatgc | acctgcaact gggtgaagtc | 240 |
| tctacgattg | ttgtcagcag | cccgcgttgg | gcgaaagagg | tcttgaccac ctatgatatc | 300 |
| accttcgcca | atcgcccgga | aaccctgact | ggcgagatcg | tcgcatacca caacacggat | 360 |
| atcgtcctgg | cgccgtatgg | tgagtattgg | cgtcaactgc | gtaaactgtg cacgctggag | 420 |
| ctgctgagca | acaagaaagt | gaagagcttc | cagagcctgc | gcgaagaaga gtgttggaac | 480 |
| ctggtcaagg | acatccgcag | caccggccaa | ggtagcccaa | tcaatctgtc ggagaacatt | 540 |
| ttcaagatga | ttgcgacgat | tctgagccgt | gctgcgttcg | gtaagggtat taaggatcaa | 600 |
| atgaagttta | ccgaactggt | gaaagaaatc | ctgcgtctga | ccggcggttt tgatgtcgct | 660 |
| gacatcttcc | ctagcaagaa | gttgctgcac | cacctgagcg | gcaagcgtgc aaaactgacc | 720 |
| aatatccata | caagctgga | taatctgatc | aataacatca | tcgcagagca cccgggcaac | 780 |
| cgtacctcgt | cctcccagga | aacgctgctg | gacgttctgc | tgcgcctgaa agagtctgcg | 840 |
| gagtttccgc | tgaccgccga | caacgttaaa | gcagtgatcc | tggatatgtt cggcgctggt | 900 |
| acggatacca | gcagcgcgac | gatcgagtgg | gcgattagca | gctgattcg ctgccctcgc | 960 |
| gcgatggaga | agtgcagac | ggaattgcgt | caggcactga | atggcaaaga gcgtattcag | 1020 |
| gaagaggatt | tgcaggagct | gaattatctg | aagctggtga | ttaaagaaac cctgcgcctg | 1080 |
| catccgccga | ctccgctggg | gatgccgcgt | gagtgccgtg | aaccgtgtgt tttgggcggt | 1140 |
| tacgacattc | cgagcaaaac | gaagctgatc | gttaatgttt | tcgcgattaa ccgtgacccg | 1200 |
| gaatactgga | agacgcgga | aacgtttatg | ccggagcgtt | ttgagaatag cccgattacc | 1260 |
| gttatgggtt | ccgagtacga | atacctgcca | tttggtctg | tcgtcgtat gtgtcctggt | 1320 |
| gcagcgctgg | gtctggccaa | cgtggaactg | ccgctggcgc | acattctgta ctatttcaac | 1380 |
| tggaaactgc | cgaacggcaa | gaccttcgaa | gatttggaca | tgaccgagag ctttggtgcc | 1440 |
| actgtgcagc | gcaaaaccga | gctgctgctg | gttccgaccg | actttcaaac cctgactgcg | 1500 |
| agcacctaat | ga | | | | 1512 |

<210> SEQ ID NO 32
<211> LENGTH: 502
<212> TYPE: PRT
<213> ORGANISM: Artificial Sequence
<220> FEATURE:
<223> OTHER INFORMATION: CYP71AV8-L358T amino acid sequence

<400> SEQUENCE: 32

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
            115                 120                 125

Tyr Trp Arg Gln Leu Arg Lys Leu Cys Thr Leu Glu Leu Leu Ser Asn
    130                 135                 140

Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
            165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ala Glu
            245                 250                 255

His Pro Gly Asn Arg Thr Ser Ser Gln Glu Thr Leu Leu Asp Val
        260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
            325                 330                 335

Glu Arg Ile Gln Glu Asp Leu Gln Glu Leu Asn Tyr Leu Lys Leu
        340                 345                 350

Val Ile Lys Glu Thr Leu Arg Leu His Pro Pro Thr Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
            405                 410                 415
```

```
Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
            435                 440                 445

Glu Leu Pro Leu Ala His Ile Leu Tyr Tyr Phe Asn Trp Lys Leu Pro
450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
            500

<210> SEQ ID NO 33
<211> LENGTH: 1512
<212> TYPE: DNA
<213> ORGANISM: Artificial Sequence
<220> FEATURE:
<223> OTHER INFORMATION: CYP71AV8-L358S DNA sequence

<400> SEQUENCE: 33
atggctctgt tattagcagt tttttggtcg gcgcttataa tcctcgtagt aacctacacc      60
atatccctcc taatcaacca atggcgaaaa ccgaaacccc aagggaagtt cccccccggc     120
ccatggcgtc tgccgattat cggtcacatg caccatttga tcggcaccat gccgcatcgt     180
ggtgttatgg aactggcccg taagcatggc agcctgatgc acctgcaact gggtgaagtc     240
tctacgattg ttgtcagcag cccgcgttgg gcgaaagagg tcttgaccac ctatgatatc     300
accttcgcca atcgcccgga aaccctgact ggcgagatcg tcgcatacca caacacggat     360
atcgtcctgg cgccgtatgg tgagtattgg cgtcaactgc gtaaactgtg cacgctggag     420
ctgctgagca caagaaagt gaagagcttc cagagcctgc gcgaagaaga gtgttggaac     480
ctggtcaagg acatccgcag caccggccaa ggtagcccaa tcaatctgtc ggagaacatt     540
ttcaagatga ttgcgacgat tctgagccgt gctgcgttcg gtaagggtat taaggatcaa     600
atgaagttta ccgaactggt gaaagaaatc ctgcgtctga ccggcggttt tgatgtcgct     660
gacatcttcc ctagcaagaa gttgctgcac cacctgagcg gcaagcgtgc aaaactgacc     720
aatatccata caagctgga taatctgatc aataacatca tcgcagagca cccgggcaac     780
cgtacctcgt cctcccagga aacgctgctg gacgttctgc tgcgcctgaa agagtctgcg     840
gagtttccgc tgaccgccga caacgttaaa gcagtgatcc tggatatgtt cggcgctggt     900
acggatacca gcagcgcgac gatcgagtgg gcgattagcg agctgattcg ctgccctcgc     960
gcgatggaga aagtgcagac ggaattgcgt caggcactga atggcaaaga gcgtattcag    1020
gaagaggatt tgcaggagct gaattatctg aagctggtga ttaaagaaac cctgcgcctg    1080
catccgccgt ctccgctggt gatgccgcgt gagtgccgtg aaccgtgtgt tttgggcggt    1140
tacgacattc cgagcaaaac gaagctgatc gttaatgttt tcgcgattaa ccgtgacccg    1200
gaatactgga agacgcgga aacgtttatg ccggagcgtt ttgagaatag cccgattacc    1260 gttatggggtt ccgagtacga atacctgcca tttggtgctg tcgtcgtat gtgtcctggt    1320 gcagcgctgg gtctggccaa cgtggaactg ccgctggcgc acattctgta ctatttcaac    1380
tggaaactgc cgaacggcaa gaccttcgaa gatttggaca tgaccgagag ctttggtgcc    1440
actgtgcagc gcaaaaccga gctgctgctg gttccgaccg actttcaaac cctgactgcg    1500
```
agcacctaat ga 1512

<210> SEQ ID NO 34
<211> LENGTH: 502
<212> TYPE: PRT
<213> ORGANISM: Artificial Sequence
<220> FEATURE:
<223> OTHER INFORMATION: CYP71AV8-L358S amino acid sequence

<400> SEQUENCE: 34

```
Met Ala Leu Leu Leu Ala Val Phe Trp Ser Ala Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
    275                 280                 285

Val Lys Ala Val Ile Leu Asp Met Phe Gly Ala Gly Thr Asp Thr Ser
290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Ser Pro Leu Val Met
```

```
                355                 360                 365
Pro Arg Glu Cys Arg Glu Pro Cys Val Leu Gly Gly Tyr Asp Ile Pro
            370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
                435                 440                 445

Glu Leu Pro Leu Ala His Ile Leu Tyr Tyr Phe Asn Trp Lys Leu Pro
            450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500

<210> SEQ ID NO 35
<211> LENGTH: 1512
<212> TYPE: DNA
<213> ORGANISM: Artificial Sequence
<220> FEATURE:
<223> OTHER INFORMATION: CYP71AV8-L358V DNA sequence

<400> SEQUENCE: 35
atggctctgt tattagcagt tttttggtcg gcgcttataa tcctcgtagt aacctacacc    60
atatccctcc taatcaacca atggcgaaaa ccgaaacccc aagggaagtt ccccccgggc   120
ccatggcgtc tgccgattat cggtcacatg caccatttga tcggcaccat gccgcatcgt   180
ggtgttatgg aactggcccg taagcatggc agcctgatgc acctgcaact gggtgaagtc   240
tctacgattg ttgtcagcag cccgcgttgg gcgaaagagg tcttgaccac ctatgatatc   300
accttcgcca atcgcccgga aaccctgact ggcgagatcc tcgcatacca aacacggat   360 atcgtcctgg cgccgtatgg tgagtattgg cgtcaactgc gtaaactgtg cacgctggag   420
ctgctgagca caagaaagt gaagagcttc cagagcctgc gcgaagaaga gtgttggaac   480
ctggtcaagg acatccgcag caccggccaa ggtagcccaa tcaatctgtc ggagaacatt   540
ttcaagatga ttgcgacgat tctgagccgt gctgcgttcg gtaagggtat taaggatcaa   600
atgaagttta ccgaactggt gaaagaaatc ctgcgtctga ccggcggttt tgatgtcgct   660
gacatcttcc ctagcaagaa gttgctgcac cacctgagcg gcaagcgtgc aaaactgacc   720
aatatccata caagctgga taatctgatc aataacatca tcgcagagca cccgggcaac   780
cgtacctcgt cctcccagga aacgctgctg acgttctgc tgcgcctgaa agagtctgcg   840
gagtttccgc tgaccgccga caacgttaaa gcagtgatcc tggatatgtt cggcgctggt   900
acggatacca gcagcgcgac gatcgagtgg gcgattagcg agctgattcg ctgccctcgc   960
gcgatggaga aagtgcagac ggaattgcgt caggcactga atggcaaaga gcgtattcag  1020
gaagaggatt tgcaggagct gaattatctg aagctggtga ttaaagaaac cctgcgcctg  1080
catccgccgg ttccgctggt gatgccgcgt gagtgccgtg aaccgtgtgt tttgggcggt  1140
tacgacattc cgagcaaaac gaagctgatc gttaatgttt tcgcgattaa ccgtgacccg  1200
```

```
gaatactgga aagacgcgga aacgttatg ccggagcgtt ttgagaatag cccgattacc      1260
gttatgggtt ccgagtacga atacctgcca tttggtgctg gtcgtcgtat gtgtcctggt      1320
gcagcgctgg gtctggccaa cgtggaactg ccgctggcgc acattctgta ctatttcaac      1380
tggaaactgc cgaacggcaa gaccttcgaa gatttggaca tgaccgagag ctttggtgcc      1440
actgtgcagc gcaaaaccga gctgctgctg gttccgaccg actttcaaac cctgactgcg      1500
agcacctaat ga                                                          1512
```

```
<210> SEQ ID NO 36
<211> LENGTH: 502
<212> TYPE: PRT
<213> ORGANISM: Artificial Sequence
<220> FEATURE:
<223> OTHER INFORMATION: CYP71AV8-L358V amino acid sequence

<400> SEQUENCE: 36

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300
```

```
Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Val Pro Leu Val Met
            355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
                420                 425                 430

Ala Gly Arg Arg Met Cys Pro Gly Ala Ala Leu Gly Leu Ala Asn Val
                435                 440                 445

Glu Leu Pro Leu Ala His Ile Leu Tyr Tyr Phe Asn Trp Lys Leu Pro
450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500

<210> SEQ ID NO 37
<211> LENGTH: 1512
<212> TYPE: DNA
<213> ORGANISM: Artificial Sequence
<220> FEATURE:
<223> OTHER INFORMATION: CYP71AV8-L358G DNA sequence

<400> SEQUENCE: 37
atggctctgt tattagcagt tttttggtcg gcgcttataa tcctcgtagt aacctacacc      60
atatccctcc taatcaacca atggcgaaaa ccgaaacccc aagggaagtt ccccccgggc     120
ccatggcgtc tgccgattat cggtcacatg caccatttga tcggcaccat gccgcatcgt     180
ggtgttatgg aactggcccg taagcatggc agcctgatgc acctgcaact gggtgaagtc     240
tctacgattg ttgtcagcag cccgcgttgg gcgaaagagg tcttgaccac ctatgatatc     300
accttcgcca atcgcccgga aaccctgact ggcgagatcg tcgcatacca aacacggat      360 atcgtcctgg cgccgtatgg tgagtattgg cgtcaactgc gtaaactgtg cacgctggag     420
ctgctgagca caagaaagt gaagagcttc agagcctgc gcgaagaaga gtgttggaac       480
ctggtcaagg catccgcag caccggccaa ggtagcccaa tcaatctgtc ggagaacatt      540
ttcaagatga ttgcgacgat tctgagccgt gctgcgttcg gtaagggtat taaggatcaa     600
atgaagttta ccgaactggt gaaagaaatc ctgcgtctga ccggcggttt tgatgtcgct     660
gacatcttcc ctagcaagaa gttgctgcac cacctgagcg gcaagcgtgc aaaactgacc     720
aatatccata caagctgga taatctgatc aataacatca tcgcagagca cccgggcaac     780
cgtacctcgt cctcccagga aacgctgctg acgttctgc tgcgcctgaa agagtctgcg     840
gagtttccgc tgaccgccga caacgttaaa gcagtgatcc tggatatgtt cggcgctggt     900
```

```
acggatacca gcagcgcgac gatcgagtgg gcgattagcg agctgattcg ctgccctcgc    960
gcgatggaga aagtgcagac ggaattgcgt caggcactga atggcaaaga gcgtattcag   1020
gaagaggatt tgcaggagct gaattatctg aagctggtga ttaaagaaac cctgcgcctg   1080
catccgccgg ggccgctggt gatgccgcgt gagtgccgtg aaccgtgtgt tttgggcggt   1140
tacgacattc cgagcaaaac gaagctgatc gttaatgttt tcgcgattaa ccgtgacccg   1200
gaatactgga agacgcgga aacgtttatg ccggagcgtt ttgagaatag cccgattacc   1260
gttatgggtt ccgagtacga atacctgcca tttggtgctg gtcgtcgtat gtgtcctggt   1320
gcagcgctgg gtctggccaa cgtggaactg ccgctggcgc acattctgta ctatttcaac   1380
tggaaactgc cgaacggcaa gaccttcgaa gatttggaca tgaccgagag ctttggtgcc   1440
actgtgcagc gcaaaaccga gctgctgctg gttccgaccg actttcaaac cctgactgcg   1500
agcacctaat ga                                                       1512
```

<210> SEQ ID NO 38
<211> LENGTH: 502
<212> TYPE: PRT
<213> ORGANISM: Artificial Sequence
<220> FEATURE:
<223> OTHER INFORMATION: CYP71AV8-L358G amino acid sequence

<400> SEQUENCE: 38

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Ile Ile Ala Glu
                245                 250                 255
```

His Pro Gly Asn Arg Thr Ser Ser Gln Glu Thr Leu Leu Asp Val
            260                 265                 270
Leu Leu Arg Leu Lys Glu Ser Ala Glu Phe Pro Leu Thr Ala Asp Asn
        275                 280                 285
Val Lys Ala Val Ile Leu Asp Met Phe Gly Ala Gly Thr Asp Thr Ser
        290                 295                 300
Ser Ala Thr Ile Glu Trp Ala Ile Ser Glu Leu Ile Arg Cys Pro Arg
305                 310                 315                 320
Ala Met Glu Lys Val Gln Thr Glu Leu Arg Gln Ala Leu Asn Gly Lys
            325                 330                 335
Glu Arg Ile Gln Glu Asp Leu Gln Glu Leu Asn Tyr Leu Lys Leu
        340                 345                 350
Val Ile Lys Glu Thr Leu Arg Leu His Pro Pro Gly Pro Leu Val Met
        355                 360                 365
Pro Arg Glu Cys Arg Glu Pro Cys Val Leu Gly Gly Tyr Asp Ile Pro
    370                 375                 380
Ser Lys Thr Lys Leu Ile Val Asn Val Phe Ala Ile Asn Arg Asp Pro
385                 390                 395                 400
Glu Tyr Trp Lys Asp Ala Glu Thr Phe Met Pro Glu Arg Phe Glu Asn
            405                 410                 415
Ser Pro Ile Thr Val Met Gly Ser Glu Tyr Glu Tyr Leu Pro Phe Gly
        420                 425                 430
Ala Gly Arg Arg Met Cys Pro Gly Ala Ala Leu Gly Leu Ala Asn Val
        435                 440                 445
Glu Leu Pro Leu Ala His Ile Leu Tyr Tyr Phe Asn Trp Lys Leu Pro
    450                 455                 460
Asn Gly Lys Thr Phe Glu Asp Leu Asp Met Thr Glu Ser Phe Gly Ala
465                 470                 475                 480
Thr Val Gln Arg Lys Thr Glu Leu Leu Leu Val Pro Thr Asp Phe Gln
            485                 490                 495
Thr Leu Thr Ala Ser Thr
            500

<210> SEQ ID NO 39
<211> LENGTH: 1512
<212> TYPE: DNA
<213> ORGANISM: Artificial Sequence
<220> FEATURE:
<223> OTHER INFORMATION: CYP71AV8-L358I DNA sequence

<400> SEQUENCE: 39
atggctctgt tattagcagt tttttggtcg gcgcttataa tcctcgtagt aacctacacc      60
atatccctcc taatcaacca atggcgaaaa ccgaaacccc aagggaagtt ccccccgggc     120
ccatggcgtc tgccgattat cggtcacatg caccatttga tcggcaccat gccgcatcgt     180
ggtgttatgg aactggcccg taagcatgga agcctgatgc acctgcaact gggtgaagtc     240
tctacgattg ttgtcagcag cccgcgttgg gcgaaagagg tcttgaccac ctatgatatc     300
accttcgcca atcgcccgga aaccctgact ggcgagatcg tcgcatacca aacacggat     360 atcgtcctgg cgccgtatgg tgagtattgg cgtcaactgc gtaaactgtg cacgctggag     420
ctgctgagca acaagaaagt gaagagcttc agagcctgc gcgaagaaga gtgttggaac     480
ctggtcaagg acatccgcag caccggccaa ggtagcccaa tcaatctgtc ggagaacatt     540
ttcaagatga ttgcgacgat tctgagccgt gctgcgttcg gtaagggtat taaggatcaa    600

```
atgaagttta ccgaactggt gaaagaaatc ctgcgtctga ccggcggttt tgatgtcgct    660
gacatcttcc ctagcaagaa gttgctgcac cacctgagcg gcaagcgtgc aaaactgacc    720
aatatccata caaagctgga taatctgatc aataacatca tcgcagagca cccgggcaac    780
cgtacctcgt cctcccagga aacgctgctg acgttctgc tgcgcctgaa agagtctgcg     840
gagtttccgc tgaccgccga caacgttaaa gcagtgatcc tggatatgtt cggcgctggt    900
acggatacca gcagcgcgac gatcgagtgg gcgattagcg agctgattcg ctgccctcgc    960
gcgatggaga aagtgcagac ggaattgcgt caggcactga atggcaaaga gcgtattcag   1020
gaagaggatt tgcaggagct gaattatctg aagctggtga ttaaagaaac cctgcgcctg   1080
catccgccga ttccgctggt gatgccgcgt gagtgccgtg aaccgtgtgt tttgggcggt   1140
tacgacattc cgagcaaaac gaagctgatc gttaatgttt tcgcgattaa ccgtgacccg   1200
gaatactgga aagacgcgga aacgtttatg ccggagcgtt tgagaatag cccgattacc    1260
gttatgggtt ccgagtacga atacctgcca tttggtgctg tcgtcgtat gtgtcctggt    1320
gcagcgctgg gtctgccaa cgtggaactg ccgctggcgc acattctgta ctatttcaac    1380
tggaaactgc cgaacggcaa gaccttcgaa gatttggaca tgaccgagag ctttggtgcc   1440
actgtgcagc gcaaaaccga gctgctgctg gttccgaccg actttcaaac cctgactgcg   1500
agcacctaat ga                                                       1512
```

<210> SEQ ID NO 40
<211> LENGTH: 502
<212> TYPE: PRT
<213> ORGANISM: Artificial Sequence
<220> FEATURE:
<223> OTHER INFORMATION: CYP71AV8-L358I amino acid sequence

<400> SEQUENCE: 40

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
```

|  | | | 195 | | | 200 | | | 205 | | |
|---|---|---|---|---|---|---|---|---|---|---|---|

Glu Ile Leu Arg Leu Thr Gly Gly Phe Asp Val Ala Asp Ile Phe Pro
          210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
            275                 280                 285

Val Lys Ala Val Ile Leu Asp Met Phe Gly Ala Gly Thr Asp Thr Ser
            290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Ile Pro Leu Val Met
            355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
            435                 440                 445

Glu Leu Pro Leu Ala His Ile Leu Tyr Tyr Phe Asn Trp Lys Leu Pro
450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
            500

<210> SEQ ID NO 41
<211> LENGTH: 1512
<212> TYPE: DNA
<213> ORGANISM: Artificial Sequence
<220> FEATURE:
<223> OTHER INFORMATION: CYP71AV8-L358M DNA sequence

<400> SEQUENCE: 41

| atggctctgt tattagcagt tttttggtcg gcgcttataa tcctcgtagt aacctacacc | 60 |
|---|---|
| atatccctcc taatcaacca atggcgaaaa ccgaaacccc aagggaagtt cccccgggc | 120 |
| ccatggcgtc tgccgattat cggtcacatg caccatttga tcggcaccat gccgcatcgt | 180 |
| ggtgttatgg aactggcccg taagcatgg agcctgatgc acctgcaact gggtgaagtc | 240 |
| tctacgattg ttgtcagcag cccgcgttgg gcgaaagagg tcttgaccac ctatgatatc | 300 |

| | | |
|---|---|---|
| accttcgcca atcgcccgga aaccctgact ggcgagatcg tcgcatacca caacacggat | | 360 |
| atcgtcctgg cgccgtatgg tgagtattgg cgtcaactgc gtaaactgtg cacgctggag | | 420 |
| ctgctgagca acaagaaagt gaagagcttc cagagcctgc gcgaagaaga gtgttggaac | | 480 |
| ctggtcaagg acatccgcag caccggccaa ggtagcccaa tcaatctgtc ggagaacatt | | 540 |
| ttcaagatga ttgcgacgat tctgagccgt gctgcgttcg gtaagggtat taaggatcaa | | 600 |
| atgaagttta ccgaactggt gaaagaaatc ctgcgtctga ccggcggttt tgatgtcgct | | 660 |
| gacatcttcc ctagcaagaa gttgctgcac cacctgagcg gcaagcgtgc aaaactgacc | | 720 |
| aatatccata acaagctgga taatctgatc aataacatca tcgcagagca cccgggcaac | | 780 |
| cgtacctcgt cctcccagga aacgctgctg gacgttctgc tgcgcctgaa agagtctgcg | | 840 |
| gagtttccgc tgaccgccga caacgttaaa gcagtgatcc tggatatgtt cggcgctggt | | 900 |
| acggatacca gcagcgcgac gatcgagtgg gcgattagcg agctgattcg ctgccctcgc | | 960 |
| gcgatggaga aagtgcagac ggaattgcgt caggcactga atggcaaaga gcgtattcag | | 1020 |
| gaagaggatt tgcaggagct gaattatctg aagctggtga ttaaagaaac cctgcgcctg | | 1080 |
| catccgccga tgccgctggt gatgccgcgt gagtgccgtg aaccgtgtgt tttgggcggt | | 1140 |
| tacgacattc cgagcaaaac gaagctgatc gttaatgttt tcgcgattaa ccgtgacccg | | 1200 |
| gaatactgga agacgcgga aacgtttatg ccggagcgtt ttgagaatag cccgattacc | | 1260 |
| gttatgggtt ccgagtacga atacctgcca ttggtgctg tcgtcgtat gtgtcctggt | | 1320 |
| gcagcgctgg gtctggccaa cgtggaactg ccgctggcgc acattctgta ctatttcaac | | 1380 |
| tggaaactgc cgaacggcaa gaccttcgaa gatttggaca tgaccgagag ctttggtgcc | | 1440 |
| actgtgcagc gcaaaaccga gctgctgctg gttccgaccg actttcaaac cctgactgcg | | 1500 |
| agcacctaat ga | | 1512 |

<210> SEQ ID NO 42
<211> LENGTH: 502
<212> TYPE: PRT
<213> ORGANISM: Artificial Sequence
<220> FEATURE:
<223> OTHER INFORMATION: CYP71AV8-L358M amino acid sequence

<400> SEQUENCE: 42

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140
```

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
        165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
            245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
            325                 330                 335

Glu Arg Ile Gln Glu Glu Asp Leu Gln Glu Leu Asn Tyr Leu Lys Leu
        340                 345                 350

Val Ile Lys Glu Thr Leu Arg Leu His Pro Pro Met Pro Leu Val Met
        355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
            405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
                500

<210> SEQ ID NO 43
<211> LENGTH: 1512
<212> TYPE: DNA
<213> ORGANISM: Artificial Sequence
<220> FEATURE:
<223> OTHER INFORMATION: CYP71AV8-L358P DNA sequence

<400> SEQUENCE: 43

```
atggctctgt tattagcagt ttttggtcg gcgcttataa tcctcgtagt aacctacacc    60
atatccctcc taatcaacca atggcgaaaa ccgaaacccc aagggaagtt ccccccgggc   120
ccatggcgtc tgccgattat cggtcacatg caccatttga tcggcaccat gccgcatcgt   180
ggtgttatgg aactggcccg taagcatgg agcctgatgc acctgcaact gggtgaagtc    240
tctacgattg ttgtcagcag cccgcgttgg gcgaaagagg tcttgaccac ctatgatatc   300
accttcgcca tcgcccgga aaccctgact ggcgagatcg tcgcatacca aacacggat     360
atcgtcctgg cgccgtatgg tgagtattgg cgtcaactgc gtaaactgtg cacgctggag   420
ctgctgagca acaagaaagt gaagagcttc cagagcctgc gcgaagaaga gtgttggaac   480
ctggtcaagg acatccgcag caccggccaa ggtagcccaa tcaatctgtc ggagaacatt   540
ttcaagatga ttgcgacgat tctgagccgt gctgcgttcg gtaagggtat taaggatcaa   600
atgaagttta ccgaactggt gaaagaaatc ctgcgtctga ccggcggttt tgatgtcgct   660
gacatcttcc ctagcaagaa gttgctgcac cacctgagcg gcaagcgtgc aaaactgacc   720
aatatccata caagctgga taatctgatc aataacatca tcgcagagca cccgggcaac   780
cgtacctcgt cctcccagga aacgctgctg gacgttctgc tgcgcctgaa agagtctgcg   840
gagtttccgc tgaccgccga caacgttaaa gcagtgatcc tggatatgtt cggcgctggt   900
acggatacca gcagcgcgac gatcgagtgg gcgattagcg agctgattcg ctgccctcgc   960
gcgatggaga aagtgcagac ggaattgcgt caggcactga atggcaaaga gcgtattcag  1020
gaagaggatt tgcaggagct gaattatctg aagctggtga ttaaagaaac cctgcgcctg  1080
catccgccgc tccgctggt gatgccgcgt gagtgccgtg aaccgtgtgt tttgggcggt   1140
tacgacattc cgagcaaaac gaagctgatc gttaatgttt tcgcgattaa ccgtgacccg  1200
gaatactgga agacgcggaa aacgtttatg ccggagcgtt ttgagaatag cccgattacc  1260
gttatgggtt ccgagtacga ataccctgcca tttggtgctg gtcgtcgtat gtgtcctggt  1320
gcagcgctgg gtctgccaa cgtggaactg ccgctggcgc acattctgta ctatttcaac  1380
tggaaactgc cgaacggcaa gaccttcgaa gatttggaca tgaccgagag ctttggtgcc  1440
actgtgcagc gcaaaaccga gctgctgctg gttccgaccg actttcaaac cctgactgcg  1500
agcacctaat ga                                                      1512
```

<210> SEQ ID NO 44
<211> LENGTH: 502
<212> TYPE: PRT
<213> ORGANISM: Artificial Sequence
<220> FEATURE:
<223> OTHER INFORMATION: CYP71AV8-L358P amino acid sequence

<400> SEQUENCE: 44

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95
```

-continued

```
Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
            115                 120                 125

Tyr Trp Arg Gln Leu Arg Lys Leu Cys Thr Leu Glu Leu Leu Ser Asn
            130                 135                 140

Lys Lys Val Lys Ser Phe Gln Ser Leu Arg Glu Glu Cys Trp Asn
145                 150                 155                 160

Leu Val Lys Asp Ile Arg Ser Thr Gly Gln Gly Ser Pro Ile Asn Leu
            165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
            195                 200                 205

Glu Ile Leu Arg Leu Thr Gly Gly Phe Asp Val Ala Asp Ile Phe Pro
            210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
            245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
            275                 280                 285

Val Lys Ala Val Ile Leu Asp Met Phe Gly Ala Gly Thr Asp Thr Ser
            290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
            325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Pro Leu Val Met
            355                 360                 365

Pro Arg Glu Cys Arg Glu Pro Cys Val Leu Gly Gly Tyr Asp Ile Pro
370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
            405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
            435                 440                 445

Glu Leu Pro Leu Ala His Ile Leu Tyr Tyr Phe Asn Trp Lys Leu Pro
            450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
            500
```

<210> SEQ ID NO 45
<211> LENGTH: 1512
<212> TYPE: DNA
<213> ORGANISM: Artificial Sequence
<220> FEATURE:
<223> OTHER INFORMATION: CYP71AV8-L358Y DNA sequence

<400> SEQUENCE: 45

```
atggctctgt tattagcagt tttttggtcg gcgcttataa tcctcgtagt aacctacacc      60
atatccctcc taatcaacca atggcgaaaa ccgaaacccc aagggaagtt cccccgggc     120
ccatggcgtc tgccgattat cggtcacatg caccatttga tcggcaccat gccgcatcgt     180
ggtgttatgg aactggcccg taagcatggc agcctgatgc acctgcaact gggtgaagtc     240
tctacgattg ttgtcagcag cccgcgttgg gcgaaagagg tcttgaccac ctatgatatc     300
accttcgcca atcgcccgga aaccctgact ggcgagatcg tcgcatacca caacacggat     360
atcgtcctgg cgccgtatgg tgagtattgg cgtcaactgc gtaaactgtg cacgctggag     420
ctgctgagca acaagaaagt gaagagcttc cagagcctgc gcgaagaaga gtgttggaac     480
ctggtcaagg acatccgcag caccggccaa ggtagcccaa tcaatctgtc ggagaacatt     540
ttcaagatga ttgcgacgat tctgagccgt gctgcgttcg gtaagggtat taaggatcaa     600
atgaagttta ccgaactggt gaaagaaatc ctgcgtctga ccggcggttt tgatgtcgct     660
gacatcttcc ctagcaagaa gttgctgcac cacctgagcg gcaagcgtgc aaaactgacc     720
aatatccata caagctgga taatctgatc aataacatca tcgcagagca cccgggcaac     780
cgtacctcgt cctcccagga aacgctgctg acgttctgc tgcgcctgaa agagtctgcg     840
gagtttccgc tgaccgccga caacgttaaa gcagtgatcc tggatatgtt cggcgctggt     900
acggatacca gcagcgcgac gatcgagtgg gcgattagcg agctgattcg ctgccctcgc     960
gcgatggaga aagtgcagac ggaattgcgt caggcactga atggcaaaga gcgtattcag    1020
gaagaggatt tgcaggagct gaattatctg aagctggtga ttaaagaaac cctgcgcctg    1080
catccgccgt atccgctggt gatgccgcgt gagtgccgtg aaccgtgtgt tttgggcggt    1140
tacgacattc cgagcaaaac gaagctgatc gttaatgttt tcgcgattaa ccgtgacccg    1200
gaatactgga agacgcgga aacgtttatg ccggagcgtt ttgagaatag cccgattacc    1260
gttatgggtt ccgagtacga ataccttgcca tttggtgctg tcgtcgtat gtgtcctggt    1320
gcagcgctgg gtctggccaa cgtggaactg ccgctggcgc acattctgta ctatttcaac    1380
tggaaactgc cgaacggcaa gaccttcgaa gatttggaca tgaccgagag ctttggtgcc    1440
actgtgcagc gcaaaaccga gctgctgctg gttccgaccg actttcaaac cctgactgcg    1500
agcacctaat ga                                                         1512
```

<210> SEQ ID NO 46
<211> LENGTH: 502
<212> TYPE: PRT
<213> ORGANISM: Artificial Sequence
<220> FEATURE:
<223> OTHER INFORMATION: CYP71AV8-L358Y amino acid sequence

<400> SEQUENCE: 46

Met Ala Leu Leu Leu Ala Val Phe Trp Ser Ala Leu Ile Ile Leu Val
1               5                  10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly

-continued

```
                35                  40                  45
His Met His His Leu Ile Gly Thr Met Pro His Arg Gly Val Met Glu
 50                  55                  60
Leu Ala Arg Lys His Gly Ser Leu Met His Leu Gln Leu Gly Glu Val
 65                  70                  75                  80
Ser Thr Ile Val Val Ser Ser Pro Arg Trp Ala Lys Glu Val Leu Thr
                 85                  90                  95
Thr Tyr Asp Ile Thr Phe Ala Asn Arg Pro Glu Thr Leu Thr Gly Glu
                100                 105                 110
Ile Val Ala Tyr His Asn Thr Asp Ile Val Leu Ala Pro Tyr Gly Glu
                115                 120                 125
Tyr Trp Arg Gln Leu Arg Lys Leu Cys Thr Leu Glu Leu Leu Ser Asn
                130                 135                 140
Lys Lys Val Lys Ser Phe Gln Ser Leu Arg Glu Glu Cys Trp Asn
145                 150                 155                 160
Leu Val Lys Asp Ile Arg Ser Thr Gly Gln Gly Ser Pro Ile Asn Leu
                165                 170                 175
Ser Glu Asn Ile Phe Lys Met Ile Ala Thr Ile Leu Ser Arg Ala Ala
                180                 185                 190
Phe Gly Lys Gly Ile Lys Asp Gln Met Lys Phe Thr Glu Leu Val Lys
                195                 200                 205
Glu Ile Leu Arg Leu Thr Gly Gly Phe Asp Val Ala Asp Ile Phe Pro
210                 215                 220
Ser Lys Lys Leu Leu His His Leu Ser Gly Lys Arg Ala Lys Leu Thr
225                 230                 235                 240
Asn Ile His Asn Lys Leu Asp Asn Leu Ile Asn Asn Ile Ile Ala Glu
                245                 250                 255
His Pro Gly Asn Arg Thr Ser Ser Gln Glu Thr Leu Leu Asp Val
                260                 265                 270
Leu Leu Arg Leu Lys Glu Ser Ala Glu Phe Pro Leu Thr Ala Asp Asn
                275                 280                 285
Val Lys Ala Val Ile Leu Asp Met Phe Gly Ala Gly Thr Asp Thr Ser
290                 295                 300
Ser Ala Thr Ile Glu Trp Ala Ile Ser Glu Leu Ile Arg Cys Pro Arg
305                 310                 315                 320
Ala Met Glu Lys Val Gln Thr Glu Leu Arg Gln Ala Leu Asn Gly Lys
                325                 330                 335
Glu Arg Ile Gln Glu Glu Asp Leu Gln Glu Leu Asn Tyr Leu Lys Leu
                340                 345                 350
Val Ile Lys Glu Thr Leu Arg Leu His Pro Pro Tyr Pro Leu Val Met
                355                 360                 365
Pro Arg Glu Cys Arg Glu Pro Cys Val Leu Gly Gly Tyr Asp Ile Pro
                370                 375                 380
Ser Lys Thr Lys Leu Ile Val Asn Val Phe Ala Ile Asn Arg Asp Pro
385                 390                 395                 400
Glu Tyr Trp Lys Asp Ala Glu Thr Phe Met Pro Glu Arg Phe Glu Asn
                405                 410                 415
Ser Pro Ile Thr Val Met Gly Ser Glu Tyr Glu Tyr Leu Pro Phe Gly
                420                 425                 430
Ala Gly Arg Arg Met Cys Pro Gly Ala Ala Leu Gly Leu Ala Asn Val
                435                 440                 445
Glu Leu Pro Leu Ala His Ile Leu Tyr Tyr Phe Asn Trp Lys Leu Pro
450                 455                 460
```

```
Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
            485                 490                 495

Thr Leu Thr Ala Ser Thr
            500

<210> SEQ ID NO 47
<211> LENGTH: 1512
<212> TYPE: DNA
<213> ORGANISM: Artificial Sequence
<220> FEATURE:
<223> OTHER INFORMATION: CYP71AV8-L358W DNA sequence

<400> SEQUENCE: 47
atggctctgt tattagcagt tttttggtcg gcgcttataa tcctcgtagt aacctacacc        60
atatccctcc taatcaacca atggcgaaaa ccgaaacccc aagggaagtt ccccccgggc       120
ccatggcgtc tgccgattat cggtcacatg caccatttga tcggcaccat gccgcatcgt       180
ggtgttatgg aactggcccg taagcatggc agcctgatgc acctgcaact gggtgaagtc       240
tctacgattg ttgtcagcag cccgcgttgg gcgaaagagg tcttgaccac ctatgatatc       300
accttcgcca tcgcccgga aaccctgact ggcgagatcg tcgcatacca acacggat          360 atcgtcctgg cgccgtatgg tgagtattgg cgtcaactgc gtaaactgtg cacgctggag       420
ctgctgagca acaagaaagt gaagagcttc agagcctgc gcgaagaaga gtgttggaac        480
ctggtcaagg acatccgcag caccggccaa ggtagcccaa tcaatctgtc ggagaacatt       540
ttcaagatga ttgcgacgat tctgagccgt gctgcgttcg gtaagggtat taaggatcaa       600
atgaagttta ccgaactggt gaaagaaatc ctgcgtctga ccggcggttt tgatgtcgct       660
gacatcttcc ctagcaagaa gttgctgcac cacctgagcg gcaagcgtgc aaaactgacc       720
aatatccata caagctgga taatctgatc aataacatca tcgcagagca cccgggcaac       780
cgtacctcgt cctcccagga aacgctgctg gacgttctgc tgcgcctgaa agagtctgcg       840
gagtttccgc tgaccgccga caacgttaaa gcagtgatcc tggatatgtt cggcgctggt       900
acggatacca gcagcgcgac gatcgagtgg gcgattagcg agctgattcg ctgccctcgc       960
gcgatggaga agtgcagac ggaattgcgt caggcactga atggcaaaga gcgtattcag      1020
gaagaggatt tgcaggagct gaattatctg aagctggtga ttaaagaaac cctgcgcctg      1080
catccgccgt ggccgctggt gatgccgcgt gagtgccgtg aacgtgtgt tttgggcggt      1140 tacgacattc cgagcaaaac gaagctgatc gttaatgttt tcgcgattaa ccgtgacccg      1200
gaatactgga agacgcgga aacgtttatg ccggagcgtt ttgagaatag cccgattacc      1260
gttatgggtt ccgagtacga atacctgcca tttggtgctg gtcgtcgtat gtgtcctggt      1320
gcagcgctgg gtctggccaa cgtggaactg ccgctggcgc acattctgta ctatttcaac      1380
tggaaactgc cgaacggcaa gaccttcgaa gatttggaca tgaccgagag ctttggtgcc      1440
actgtgcagc gcaaaaccga gctgctgctg gttccgaccg actttcaaac cctgactgcg      1500
agcacctaat ga                                                         1512

<210> SEQ ID NO 48
<211> LENGTH: 502
<212> TYPE: PRT
<213> ORGANISM: Artificial Sequence
<220> FEATURE:
<223> OTHER INFORMATION: CYP71AV8-L358W amino acid sequence
```

<400> SEQUENCE: 48

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Gly Pro Trp Arg Leu Pro Ile Ile Gly
        35                  40                  45

His Met His His Leu Ile Gly Thr Met Pro His Arg Gly Val Met Glu
        50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
        290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Trp Pro Leu Val Met
        355                 360                 365

Pro Arg Glu Cys Arg Glu Pro Cys Val Leu Gly Gly Tyr Asp Ile Pro
        370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
```

```
                    405                 410                 415
Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
            435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500

<210> SEQ ID NO 49
<211> LENGTH: 1512
<212> TYPE: DNA
<213> ORGANISM: Artificial Sequence
<220> FEATURE:
<223> OTHER INFORMATION: CYP71AV8-L358R DNA sequence

<400> SEQUENCE: 49
```

| | |
|---|---:|
| atggctctgt tattagcagt tttttggtcg gcgcttataa tcctcgtagt aacctacacc | 60 |
| atatccctcc taatcaacca atggcgaaaa ccgaaacccc aagggaagtt cccccgggc | 120 |
| ccatggcgtc tgccgattat cggtcacatg caccatttga tcggcaccat gccgcatcgt | 180 |
| ggtgttatgg aactggcccg taagcatggc agcctgatgc acctgcaact gggtgaagtc | 240 |
| tctacgattg ttgtcagcag cccgcgttgg gcgaaagagg tcttgaccac ctatgatatc | 300 |
| accttcgcca atcgcccgga aaccctgact ggcgagatcg tcgcatacca caacacggat | 360 |
| atcgtcctgg cgccgtatgg tgagtattgg cgtcaactgc gtaaactgtg cacgctggag | 420 |
| ctgctgagca caagaaagt gaagagcttc cagagcctgc gcgaagaaga gtgttggaac | 480 |
| ctggtcaagg acatccgcag caccggccaa gtagcccaa tcaatctgtc ggagaacatt | 540 |
| ttcaagatga ttgcgacgat tctgagccgt gctgcgttcg gtaagggtat taaggatcaa | 600 |
| atgaagttta ccgaactggt gaaagaaatc ctgcgtctga ccggcggttt tgatgtcgct | 660 |
| gacatcttcc ctagcaagaa gttgctgcac cacctgagcg gcaagcgtgc aaaactgacc | 720 |
| aatatccata caagctgga taatctgatc aataacatca tcgcagagca cccgggcaac | 780 |
| cgtacctcgt cctcccagga aacgctgctg acgttctgc tgcgcctgaa agagtctgcg | 840 |
| gagtttccgc tgaccgccga caacgttaaa gcagtgatcc tggatatgtt cggcgctggt | 900 |
| acggatacca gcagcgcgac gatcgagtgg gcgattagcg agctgattcg ctgccctcgc | 960 |
| gcgatggaga aagtgcagac ggaattgcgt caggcactga atggcaaaga gcgtattcag | 1020 |
| gaagaggatt tgcaggagct gaattatctg aagctggtga ttaaagaaac cctgcgcctg | 1080 |
| catccgccgc gtccgctggt gatgccgcgt gagtgccgtg aaccgtgtgt tttgggcggt | 1140 |
| tacgacattc cgagcaaaac gaagctgatc gttaatgttt cgcgattaa ccgtgacccg | 1200 |
| gaatactgga agacgcgga aacgtttatg ccggagcgtt ttgagaatag cccgattacc | 1260 |
| gttatgggtt ccgagtacga ataCCtgcca tttggtgctg gtcgtcgtat gtgtcctggt | 1320 |
| gcagcgctgg gtctggccaa cgtggaactg ccgctggcgc acattctgta ctatttcaac | 1380 |
| tggaaactgc cgaacggcaa gaccttcgaa gatttggaca tgaccgagag ctttggtgcc | 1440 |
| actgtgcagc gcaaaaccga gctgctgctg gttccgaccg actttcaaac cctgactgcg | 1500 | agcacctaat ga                                              1512

<210> SEQ ID NO 50
<211> LENGTH: 502
<212> TYPE: PRT
<213> ORGANISM: Artificial Sequence
<220> FEATURE:
<223> OTHER INFORMATION: CYP71AV8-L358R amino acid sequence

<400> SEQUENCE: 50

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Gln Glu Thr Leu Leu Asp Val
            260                 265                 270

Leu Leu Arg Leu Lys Glu Ser Ala Glu Phe Pro Leu Thr Ala Asp Asn
    275                 280                 285

Val Lys Ala Val Ile Leu Asp Met Phe Gly Ala Gly Thr Asp Thr Ser
        290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

-continued

```
Val Ile Lys Glu Thr Leu Arg Leu His Pro Pro Arg Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 51
<211> LENGTH: 1488
<212> TYPE: DNA
<213> ORGANISM: Artemisia annua

<400> SEQUENCE: 51

| | | |
|---|---|---|
| atgaagagta tactaaaagc aatggcactc tcactgacca cttccattgc tcttgcaacg | 60 |
| atcctttgt tcgtttacaa gttcgctact cgttccaaat ccaccaaaaa aagccttcct | 120 |
| gagccatggc ggcttcccat tattggtcac atgcatcact tgattggtac aacgccacat | 180 |
| cgtggggtta gggatttagc cagaaagtat ggatctttga tgcatttaca gcttggtgaa | 240 |
| gttccaacaa tcgtggtgtc atctccgaaa tgggctaaag agattttgac aacgtacgac | 300 |
| attacctttg ctaacaggcc cgagacttta actggtgaga ttgttttata tcacaatacg | 360 |
| gatgttgttc ttgcacctta tggtgaatac tggaggcaat acgtaaaaat ttgcacattg | 420 |
| gagcttttga gtgttaagaa agtaaagtca tttcagtcac ttcgtgaaga ggagtgttgg | 480 |
| aatttggttc aagagattaa agcttcaggt tcagggagac cggttaaccct ttcagagaat | 540 |
| gttttcaagt tgattgcaac gatacttagt agagccgcat ttgggaaagg gatcaaggac | 600 |
| cagaaagagt taacggagat tgtgaaagag atactgaggc aaactggtgg ttttgatgtg | 660 |
| gcagatatct ttccttcaaa gaaatttctt catcatcttt cgggcaagag agctcggtta | 720 |
| actagccttc gcaaaaagat cgataattta atcgataacc ttgtagctga gcatactgtt | 780 |
| aacacctcca gtaaaactaa cgagacactc ctcgatgttc ttttaaggct caaagacagt | 840 |
| gctgaattcc cattaacatc tgataacatt aaagccatca ttttggatat gtttggagca | 900 |
| ggcacagaca cttcctcatc cacaatcgaa tgggcgattt cggaactcat aaagtgtccg | 960 |
| aaagcaatgg agaaagtaca agcggaattg aggaaagcat tgaacggaaa agaaaagatc | 1020 |
| catgaggaag acattcaaga actaagctac ttgaacatgg taatcaaaga aacattgagg | 1080 |
| ttgcaccctc cactacccct tggttctgcca agagagtgcc gccaaccagt caatttggct | 1140 |
| ggatacaaca tacccaataa gaccaaaactt attgtcaacg tctttgcgat aaatagggac | 1200 |
| cctgaatatt ggaaagacgc tgaagctttc atccctgaac gatttgaaaa tagttctgca | 1260 |

```
actgtcatgg gtgcagaata cgagtatctt ccgtttggag ctgggagaag gatgtgtcct   1320
ggagccgcac ttggtttagc taacgtgcag ctcccgctcg ctaatatact atatcatttc   1380
aactggaaac tccccaatgg tgtgagctat gaccagatcg acatgaccga gagctctgga   1440
gccacgatgc aaagaaagac tgagttgtta ctcgttccaa gtttctag              1488
```

<210> SEQ ID NO 52
<211> LENGTH: 495
<212> TYPE: PRT
<213> ORGANISM: Artemisia annua

<400> SEQUENCE: 52

```
Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Ser Ser Pro Lys Trp Ala Lys Glu Ile Leu
            85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
    290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335
```

```
Lys Glu Lys Ile His Glu Glu Asp Ile Gln Glu Leu Ser Tyr Leu Asn
            340                 345                 350
Met Val Ile Lys Glu Thr Leu Arg Leu His Pro Pro Leu Pro Leu Val
            355                 360                 365
Leu Pro Arg Glu Cys Arg Gln Pro Val Asn Leu Ala Gly Tyr Asn Ile
370                 375                 380
Pro Asn Lys Thr Lys Leu Ile Val Asn Val Phe Ala Ile Asn Arg Asp
385                 390                 395                 400
Pro Glu Tyr Trp Lys Asp Ala Glu Ala Phe Ile Pro Glu Arg Phe Glu
                405                 410                 415
Asn Ser Ser Ala Thr Val Met Gly Ala Glu Tyr Glu Tyr Leu Pro Phe
            420                 425                 430
Gly Ala Gly Arg Arg Met Cys Pro Gly Ala Ala Leu Gly Leu Ala Asn
            435                 440                 445
Val Gln Leu Pro Leu Ala Asn Ile Leu Tyr His Phe Asn Trp Lys Leu
450                 455                 460
Pro Asn Gly Val Ser Tyr Asp Gln Ile Asp Met Thr Glu Ser Ser Gly
465                 470                 475                 480
Ala Thr Met Gln Arg Lys Thr Glu Leu Leu Leu Val Pro Ser Phe
                485                 490                 495

<210> SEQ ID NO 53
<211> LENGTH: 1500
<212> TYPE: DNA
<213> ORGANISM: Artificial Sequence
<220> FEATURE:
<223> OTHER INFORMATION: CYP71AV1 codon optimized DNA sequence

<400> SEQUENCE: 53
atgaccgtac acgacatcat cgcaacgtac ttcactaaat ggtacgtaat tgtgccgctg      60
gcactgattg cgtatcgcgt gctggattat ttctacgcga cccgttctaa aagcactaag     120
aaatctctgc cggaaccgtg gcgtctgcca atcatcggtc acatgcacca cctgatcggc     180 accacccgc accgtggcgt acgcgacctg gcgcgtaagt acggctctct gatgcatctg      240
cagctgggcg aggtacctac tatcgtcgtt cctccccga gtgggccaa agaaatcctg       300 actaccatg acatcacttt cgccaaccgc ccggaaacgc tgaccggcga aattgtcctg      360
taccataaca cggatgtggt tctggccccg tacggtgagt actggcgcca gctgcgcaaa     420
atttgtactc tggaactgct gagcgttaaa aaggttaaat ccttccagag cctgcgtgaa     480
gaggaatgct ggaaccctggt gcaggagatt aaagcgtctg gcagcggtcg tccagttaac     540
ctgtctgaga tgttttttaa actgatcgct actatcctgt ctcgcgcggc attcggtaaa     600
ggtatcaaag atcagaaaga actgaccgaa atcgttaagg aaatcctgcg ccagactggt     660
ggcttcgacg ttgcggacat cttcccgtcc aaaaagttcc tgcaccatct gtctggcaaa     720
cgcgctcgtc tgacctccct gcgtaagaaa attgataacc tgattgacaa cctggtcgct     780
gagcacactg tgaacacctc ttctaaaacc aacgaaaccc tgctggacgt actgctgcgc     840
ctgaaggact ctgccgaatt tccactgact agcgacaata tcaaagcaat catcctggac     900
atgttcggcg ccggtaccga tacgtcctct ccacgattg agtgggctat ttccgaactg     960
atcaaatgcc cgaaggcgat ggaaaaagtg caggcggaac tgcgtaaagc gctgaacggt    1020
aaagagaaaa ttcatgaaga ggacatccag gaactgtcct acctgaatat ggtaatcaaa    1080
gaaactctgc gtctgcatcc gccgctgcca ctggttctgc cgcgtgaatg ccgtcagccg    1140
```

-continued

```
gttaacctgg ccggctacaa cattccgaac aaaacgaagc tgatcgtcaa cgttttcgcg   1200
atcaaccgcg atcctgaata ctggaaagac gcggaagcgt tcattccgga acgctttgag   1260
aactcctctg ccaccgttat gggcgctgaa tacgagtacc tgccgttcgg tgcgggtcgc   1320
cgtatgtgcc cgggtgctgc actgggcctg gcgaacgttc aactgccact ggcgaacatc   1380
ctgtaccact tcaactggaa actgcctaac ggcgtatctt atgatcaaat cgacatgacc   1440
gaaagctccg cgcgaccat gcagcgtaaa accgaactgc tgctggttcc gtccttttaa   1500
```

<210> SEQ ID NO 54
<211> LENGTH: 499
<212> TYPE: PRT
<213> ORGANISM: Artificial Sequence
<220> FEATURE:
<223> OTHER INFORMATION: CYP71AV1 codon optimized amino acid sequence

<400> SEQUENCE: 54

```
Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
                20                  25                  30

Ala Thr Arg Ser Lys Ser Thr Lys Lys Ser Leu Pro Glu Pro Trp Arg
            35                  40                  45

Leu Pro Ile Ile Gly His Met His Leu Ile Gly Thr Thr Pro His
    50                  55                  60

Arg Gly Val Arg Asp Leu Ala Arg Lys Tyr Gly Ser Leu Met His Leu
65                  70                  75                  80

Gln Leu Gly Glu Val Pro Thr Ile Val Val Ser Ser Pro Lys Trp Ala
                85                  90                  95

Lys Glu Ile Leu Thr Thr Tyr Asp Ile Thr Phe Ala Asn Arg Pro Glu
            100                 105                 110

Thr Leu Thr Gly Glu Ile Val Leu Tyr His Asn Thr Asp Val Val Leu
        115                 120                 125

Ala Pro Tyr Gly Glu Tyr Trp Arg Gln Leu Arg Lys Ile Cys Thr Leu
    130                 135                 140

Glu Leu Leu Ser Val Lys Lys Val Lys Ser Phe Gln Ser Leu Arg Glu
145                 150                 155                 160

Glu Glu Cys Trp Asn Leu Val Gln Glu Ile Lys Ala Ser Gly Ser Gly
                165                 170                 175

Arg Pro Val Asn Leu Ser Glu Asn Val Phe Lys Leu Ile Ala Thr Ile
            180                 185                 190

Leu Ser Arg Ala Ala Phe Gly Lys Gly Ile Lys Asp Gln Lys Glu Leu
        195                 200                 205

Thr Glu Ile Val Lys Glu Ile Leu Arg Gln Thr Gly Gly Phe Asp Val
    210                 215                 220

Ala Asp Ile Phe Pro Ser Lys Lys Phe Leu His His Leu Ser Gly Lys
225                 230                 235                 240

Arg Ala Arg Leu Thr Ser Leu Arg Lys Lys Ile Asp Asn Leu Ile Asp
                245                 250                 255

Asn Leu Val Ala Glu His Thr Val Asn Thr Ser Ser Lys Thr Asn Glu
            260                 265                 270

Thr Leu Leu Asp Val Leu Leu Arg Leu Lys Asp Ser Ala Glu Phe Pro
        275                 280                 285

Leu Thr Ser Asp Asn Ile Lys Ala Ile Ile Leu Asp Met Phe Gly Ala
    290                 295                 300
```

```
Gly Thr Asp Thr Ser Ser Thr Ile Glu Trp Ala Ile Ser Glu Leu
305                 310                 315                 320

Ile Lys Cys Pro Lys Ala Met Glu Lys Val Gln Ala Glu Leu Arg Lys
                325                 330                 335

Ala Leu Asn Gly Lys Glu Lys Ile His Glu Glu Asp Ile Gln Glu Leu
                340                 345                 350

Ser Tyr Leu Asn Met Val Ile Lys Glu Thr Leu Arg Leu His Pro Pro
            355                 360                 365

Leu Pro Leu Val Leu Pro Arg Glu Cys Arg Gln Pro Val Asn Leu Ala
        370                 375                 380

Gly Tyr Asn Ile Pro Asn Lys Thr Lys Leu Ile Val Asn Val Phe Ala
385                 390                 395                 400

Ile Asn Arg Asp Pro Glu Tyr Trp Lys Asp Ala Glu Ala Phe Ile Pro
                405                 410                 415

Glu Arg Phe Glu Asn Ser Ser Ala Thr Val Met Gly Ala Glu Tyr Glu
                420                 425                 430

Tyr Leu Pro Phe Gly Ala Gly Arg Arg Met Cys Pro Gly Ala Ala Leu
            435                 440                 445

Gly Leu Ala Asn Val Gln Leu Pro Leu Ala Asn Ile Leu Tyr His Phe
450                 455                 460

Asn Trp Lys Leu Pro Asn Gly Val Ser Tyr Asp Gln Ile Asp Met Thr
465                 470                 475                 480

Glu Ser Ser Gly Ala Thr Met Gln Arg Lys Thr Glu Leu Leu Leu Val
            485                 490                 495

Pro Ser Phe

<210> SEQ ID NO 55
<211> LENGTH: 3150
<212> TYPE: DNA
<213> ORGANISM: Bacillus megaterium

<400> SEQUENCE: 55
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag agacgggtt atttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga cgacctagt agataaaatt     660
attgcagatc gcaaagcaag cggtgaacaa agcgatgatt tattaacgca catgctaaac     720
ggaaaagatc cagaaacggg tgagccgctt gatgacgaga acattcgcta tcaaattatt     780
acattcttaa ttgcgggaca cgaaacaaca agtggtcttt atcatttgc gctgtatttc     840
ttagtgaaaa atccacatgt attacaaaaa gcagcagaag aagcagcacg agttctagta     900
gatcctgttc caagctacaa acaagtcaaa cagcttaaat atgtcggcat ggtctttaaac     960
gaagcgctgc gcttatggcc aactgctcct gcgttttccc tatatgcaaa agaagatacg    1020
```

```
gtgcttggag gagaatatcc tttagaaaaa ggcgacgaac taatggttct gattcctcag    1080
cttcaccgtg ataaaacaat ttggggagac gatgtgaaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctggata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg ctttttatcga tgaaacgctt gccgctaaag gggcagaaaa catcgctgac    1800
cgcggtgaag cagatgcaag cgacgacttt gaaggcacct atgaagaatg gcgtgaacac    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctctcg catgccaaat cagccgaaaa catacgttca gcacgtaatg    2940
gaacaagacg caagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaggc    3120 cgatacgcaa aagacgtgtg ggctgggtaa                                     3150
```

<210> SEQ ID NO 56
<211> LENGTH: 1049
<212> TYPE: PRT
<213> ORGANISM: Bacillus megaterium

<400> SEQUENCE: 56

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
        180                 185                 190

Asn Pro Asp Asp Pro Ala Tyr Asp Glu Asn Lys Arg Gln Phe Gln Glu
    195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
        340                 345                 350

Glu Leu Met Val Leu Ile Pro Gln Leu His Arg Asp Lys Thr Ile Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415
```

```
Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830
```

```
Ser Ser Ser Pro Arg Val Asp Glu Lys Gln Ala Ser Ile Thr Val Ser
        835                 840                 845

Val Val Ser Gly Glu Ala Trp Ser Gly Tyr Gly Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010            1015                1020

Val Ser Glu Ala Asp Ala Arg Leu Trp Leu Gln Gln Leu Glu Glu
    1025            1030                1035

Lys Gly Arg Tyr Ala Lys Asp Val Trp Ala Gly
    1040            1045

<210> SEQ ID NO 57
<211> LENGTH: 3150
<212> TYPE: DNA
<213> ORGANISM: Artificial Sequence
<220> FEATURE:
<223> OTHER INFORMATION: P450-BM3 Variant 7 DNA sequence

<400> SEQUENCE: 57
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag agacggggtt aatcacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga cgacctagt agataaaatt    660 attgcagatc gcaaagcaag cggtgaacaa agcgatgatt tattaacgca catgctaaac    720
ggaaaagatc cagaacggg tgagccgctt gatgacgaga cattcgcta tcaaattatt    780 acattcttaa ttgcgggaca cgaaacaaca agtggtcttt tatcatttgc gctgtatttc    840
```

```
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactatccct gcgttttccc tatatgcaaa agaagatacg   1020
gtgcttggag gagaatatcc tttagaaaaa ggcgacgaac taatggttct gattcctcag   1080
cttcaccgtg ataaaacaat tggggagac gatgtggaag agttccgtcc agagcgtttt   1140
gaaaatccaa gtgcgattcc gcagcatgcg tttaaaccgt tggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg cgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                   3150
```

<210> SEQ ID NO 58
<211> LENGTH: 1049
<212> TYPE: PRT
<213> ORGANISM: Artificial Sequence
<220> FEATURE:
<223> OTHER INFORMATION: P450-BM3 Variant 7 amino acid sequence

<400> SEQUENCE: 58

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ile Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365
```

-continued

```
Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
```

```
                785                 790                 795                 800
        Met Leu Glu Leu Leu Glu Lys Tyr Pro Ala Cys Glu Met Lys Phe Ser
                        805                 810                 815

Glu Phe Ile Ala Leu Leu Pro Ser Ile Arg Pro Arg Tyr Tyr Ser Ile
                        820                 825                 830

Ser Ser Ser Pro Arg Val Asp Glu Lys Gln Ala Ser Ile Thr Val Ser
                        835                 840                 845

Val Val Ser Gly Glu Ala Trp Ser Gly Tyr Gly Glu Tyr Lys Gly Ile
                850                 855                 860

Ala Ser Asn Tyr Leu Ala Glu Leu Gln Glu Gly Asp Thr Ile Thr Cys
        865                 870                 875                 880

Phe Ile Ser Thr Pro Gln Ser Glu Phe Thr Leu Pro Lys Asp Pro Glu
                        885                 890                 895

Thr Pro Leu Ile Met Val Gly Pro Gly Thr Gly Val Ala Pro Phe Arg
                        900                 905                 910

Gly Phe Val Gln Ala Arg Lys Gln Leu Lys Glu Gln Gly Gln Ser Leu
                        915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
        945                 950                 955                 960

Leu His Thr Ala Phe Ser Arg Met Pro Asn Gln Pro Lys Thr Tyr Val
                        965                 970                 975

Gln His Val Met Glu Gln Asp Gly Lys Lys Leu Ile Glu Leu Leu Asp
                        980                 985                 990

Gln Gly Ala His Phe Tyr Ile Cys Gly Asp Gly Ser Gln Met Ala Pro
                        995                 1000                1005

Ala Val  Glu Ala Thr Leu Met  Lys Ser Tyr Ala Asp  Val His Gln
           1010                 1015                 1020

Val Ser  Glu Ala Asp Ala Arg  Leu Trp Leu Gln Gln  Leu Glu Glu
           1025                 1030                 1035

Lys Gly  Arg Tyr Ala Lys Asp  Val Trp Ala Gly
           1040                 1045

<210> SEQ ID NO 59
<211> LENGTH: 3150
<212> TYPE: DNA
<213> ORGANISM: Artificial Sequence
<220> FEATURE:
<223> OTHER INFORMATION: P450-BM3 Variant 17 DNA sequence

<400> SEQUENCE: 59
atgacaatta aagaaatgcc tcagccaaaa acgtttggag agcttaaaaa tttaccgtta      60
ttaaacacag ataaccggt tcaagctttg atgaaaattg cggatgaatt aggagaaatc     120
tttaaattcg aggcgcctgg tcgtgtaacg cgctacttat caagtcagcg tctaattaaa    180
gaagcatgcg atgaatcacg ctttgataaa acttaagtc aagcgcttaa atttgtacgt     240
gattttgcag agacggggtt agttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
```

```
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactatccct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt tggaaacggg tcagcgtgcg   1200
tgtatcggtc agcagttcgc tcttcatgaa gcaacgctgg tacttggtat gatgctaaaa   1260
cactttgact tgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760 ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
```

-continued

```
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

```
<210> SEQ ID NO 60
<211> LENGTH: 1049
<212> TYPE: PRT
<213> ORGANISM: Artificial Sequence
<220> FEATURE:
<223> OTHER INFORMATION: P450-BM3 Variant 17 amino acid sequence

<400> SEQUENCE: 60
```

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala

```
                325                 330                 335
Lys Glu Asp Thr Val Leu Gly Gly Glu Tyr Pro Leu Glu Lys Gly Asp
                340                 345                 350
Glu Leu Met Val Leu Ile Pro Gln Leu His Arg Asp Lys Thr Ile Trp
                355                 360                 365
Gly Asp Asp Val Glu Glu Phe Arg Pro Glu Arg Phe Glu Asn Pro Ser
                370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
                435                 440                 445
Ala Lys Ser Lys Lys Ile Pro Leu Gly Gly Ile Pro Ser Pro Ser Thr
                450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
                515                 520                 525
Ala Val Leu Ile Val Thr Ala Ser Tyr Asn Gly His Pro Pro Asp Asn
                530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Thr Tyr Glu Glu Trp Arg Glu His Met Trp Ser Asp
                610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
                675                 680                 685
Leu Pro Lys Glu Ala Ser Tyr Gln Glu Gly Asp His Leu Gly Val Ile
                690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
```

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 61
<211> LENGTH: 3150
<212> TYPE: DNA
<213> ORGANISM: Artificial Sequence
<220> FEATURE:
<223> OTHER INFORMATION: P450-BM3 Variant 18 DNA sequence

<400> SEQUENCE: 61
atgacaatta agaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa acttaagtc aagcgcttaa atttgtacgt     240
gattttgcag agacgggtt agttacaagc tggacgcatg aaaaaaattg gaaaaaagcg     300
cataatatct tacttccaag cttcagtcag caggcaatga aaggctatca tgcgatgatg     360

```
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactctgcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatcat acaaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaac gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag    2340
cttgaagcct tgcttgaaaa gcaagcctac aaagaacaag tgctggcaaa acgtttaaca    2400
atgcttgaac tgcttgaaaa atacccggcg tgtgaaatga attcagcga atttatcgcc     2460
cttctgccaa gcatacgccc gcgctattac tcgatttctt catcacctcg tgtcgatgaa   2520
aaacaagcaa gcatcaccgt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
```

-continued

```
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc aacctgccgtt gaagcaacgc ttatgaaaag ctatgctgac    3060
gttcaccaag tgagtgaagc agacgctcgc ttatggctgc agcagctaga agaaaaaggc    3120
cgatacgcaa agacgtgtg ggctgggtaa                                       3150
```

<210> SEQ ID NO 62
<211> LENGTH: 1049
<212> TYPE: PRT
<213> ORGANISM: Artificial Sequence
<220> FEATURE:
<223> OTHER INFORMATION: P450-BM3 Variant 18 amino acid sequence

<400> SEQUENCE: 62

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285
```

Gln Lys Ala Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Leu Pro Ala Phe Ser Leu Tyr Ala
                325                 330                 335

Lys Glu Asp Thr Val Leu Gly Gly Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
    690                 695                 700

| | | | | | | | | | | | |
|---|---|---|---|---|---|---|---|---|---|---|---|
|Pro|Arg|Asn|Tyr|Glu|Gly|Ile|Val|Asn|Arg|Val|Thr|Ala|Arg|Phe|Gly|
|705| | | | |710| | | | |715| | | | |720|

Leu Asp Ala Ser Gln Gln Ile Arg Leu Glu Ala Glu Glu Lys Leu
           725           730          735

Ala His Leu Pro Leu Ala Lys Thr Val Ser Val Glu Glu Leu Leu Gln
        740            745            750

Tyr Val Glu Leu Gln Asp Pro Val Thr Arg Thr Gln Leu Arg Ala Met
    755            760            765

Ala Ala Lys Thr Val Cys Pro His Lys Val Leu Glu Ala Leu
770            775            780

Leu Glu Lys Gln Ala Tyr Lys Glu Gln Val Leu Ala Lys Arg Leu Thr
785           790           795          800

Met Leu Glu Leu Leu Glu Lys Tyr Pro Ala Cys Glu Met Lys Phe Ser
        805            810          815

Glu Phe Ile Ala Leu Leu Pro Ser Ile Arg Pro Arg Tyr Tyr Ser Ile
        820            825          830

Ser Ser Ser Pro Arg Val Asp Glu Lys Gln Ala Ser Ile Thr Val Ser
        835            840          845

Val Val Ser Gly Glu Ala Trp Ser Gly Tyr Gly Glu Tyr Lys Gly Ile
850            855            860

Ala Ser Asn Tyr Leu Ala Glu Leu Gln Glu Gly Asp Thr Ile Thr Cys
865           870           875          880

Phe Ile Ser Thr Pro Gln Ser Glu Phe Thr Leu Pro Lys Asp Pro Glu
          885           890         895

Thr Pro Leu Ile Met Val Gly Pro Gly Thr Gly Val Ala Pro Phe Arg
        900            905          910

Gly Phe Val Gln Ala Arg Lys Gln Leu Lys Glu Gln Gly Gln Ser Leu
        915            920          925

Gly Glu Ala His Leu Tyr Phe Gly Cys Arg Ser Pro His Glu Asp Tyr
        930            935          940

Leu Tyr Gln Glu Glu Leu Glu Asn Ala Gln Ser Glu Gly Ile Ile Thr
945           950           955          960

Leu His Thr Ala Phe Ser Arg Met Pro Asn Gln Pro Lys Thr Tyr Val
        965            970          975

Gln His Val Met Glu Gln Asp Gly Lys Lys Leu Ile Glu Leu Leu Asp
        980            985          990

Gln Gly Ala His Phe Tyr Ile Cys Gly Asp Gly Ser Gln Met Ala Pro
        995          1000         1005

Ala Val Glu Ala Thr Leu Met Lys Ser Tyr Ala Asp Val His Gln
      1010          1015         1020

Val Ser Glu Ala Asp Ala Arg Leu Trp Leu Gln Gln Leu Glu Glu
      1025          1030         1035

Lys Gly Arg Tyr Ala Lys Asp Val Trp Ala Gly
      1040          1045

<210> SEQ ID NO 63
<211> LENGTH: 3150
<212> TYPE: DNA
<213> ORGANISM: Artificial Sequence
<220> FEATURE:
<223> OTHER INFORMATION: P450-BM3 Variant 19 DNA sequence

<400> SEQUENCE: 63
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120

```
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt agttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgttcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
```

```
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg ctttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 64
<211> LENGTH: 1049
<212> TYPE: PRT
<213> ORGANISM: Artificial Sequence
<220> FEATURE:
<223> OTHER INFORMATION: P450-BM3 Variant 19 amino acid sequence

<400> SEQUENCE: 64

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240
```

-continued

```
Gly Lys Asp Pro Glu Thr Gly Glu Pro Leu Asp Asp Glu Asn Ile Arg
                245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
        275                 280                 285
Gln Lys Ala Ala Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Val Pro Ala Phe Ser Leu Tyr Ala
                325                 330                 335
Lys Glu Asp Thr Val Leu Gly Gly Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
```

```
            660                 665                 670
Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765

Ala Ala Lys Thr Val Cys Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
            1010                1015                1020

Val Ser Glu Ala Asp Ala Arg Leu Trp Leu Gln Gln Leu Glu Glu
            1025                1030                1035

Lys Gly Arg Tyr Ala Lys Asp Val Trp Ala Gly
            1040                1045

<210> SEQ ID NO 65
<211> LENGTH: 3150
<212> TYPE: DNA
<213> ORGANISM: Artificial Sequence
```

<220> FEATURE:
<223> OTHER INFORMATION: P450-BM3 Variant 20 DNA sequence

<400> SEQUENCE: 65

| | | | | | |
|---|---|---|---|---|---|
| atgacaatta | aagaaatgcc | tcagccaaaa | acgtttggag | agcttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tcgtgtaacg | cgctacttat | caagtcagcg | tctaattaaa | 180 |
| gaagcatgcg | atgaatcacg | ctttgataaa | aacttaagtc | aagcgcttaa | atttgtacgt | 240 |
| gattttgcag | agacgggtt | agttacaagc | tggacgcatg | aaaaaaattg | gaaaaaagcg | 300 |
| cataatatct | tacttccaag | cttcagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtaccgg | aagacatgac | acgtttaacg | cttgatacaa | ttggtctttg | cggctttaac | 480 |
| tatcgcttta | acagctttta | ccgagatcag | cctcatccat | ttattacaag | tatggtccgt | 540 |
| gcactggatg | aagcaatgaa | caagctgcag | cgagcaaatc | cagacgaccc | agcttatgat | 600 |
| gaaaacaagc | gccagtttca | agaagatatc | aaggtgatga | cgacctagt | agataaaatt | 660 |
| attgcagatc | gcaaagcaag | cggtgaacaa | agcgatgatt | tattaacgca | catgctaaac | 720 |
| ggaaaagatc | cagaaacggg | tgagccgctt | gatgacgaga | cattcgcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gcagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactttttcct | gcgttttccc | tatatgcaaa | agaagatacg | 1020 |
| gtgcttggag | gagaatatcc | tttagaaaaa | ggcgacgaac | taatggttct | gattcctcag | 1080 |
| cttcaccgtg | ataaaacaat | tggggagac | gatgtggaag | agttccgtcc | agagcgtttt | 1140 |
| gaaaatccaa | gtgcgattcc | gcagcatgcg | tttaaaccgt | tggaaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctggata | ttaagaaac | tttaacgtta | 1320 |
| aaacctgaag | gctttgtggt | aaaagcaaaa | tcgaaaaaaa | ttccgcttgg | cggtattcct | 1380 |
| tcacctagca | ctgaacagtc | tgctaaaaaa | gtacgcaaaa | aggcagaaaa | cgctcataat | 1440 |
| acgccgctgc | ttgtgctata | cggttcaaat | atgggaacag | ctgaaggaac | ggcgcgtgat | 1500 |
| ttagcagata | ttgcaatgag | caaaggattt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtcgac | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | cttttatcga | tgaaacgctt | gccgctaaag | ggcagaaaa | catcgctgac | 1800 |
| cgcggtgaag | cagatgcaag | cgacgacttt | gaaggcacct | atgaagaatg | gcgtgaacac | 1860 |
| atgtggagtg | acgtagcagc | ctactttaac | ctcgacattg | aaaacagtga | agataataaa | 1920 |
| tctactcttt | cacttcaatt | tgtcgacagc | gccgcggata | tgccgcttgc | gaaaatgcac | 1980 |
| ggtgcgtttt | caacgaacgt | cgtagcaagc | aagaacttc | aacagccagg | cagtgcacga | 2040 |
| agcacgcgac | atcttgaaat | tgaacttcca | aaagaagctt | cttatcaaga | aggagatcat | 2100 |
| ttaggtgtta | ttcctcgcaa | ctatgaagga | atagtaaacc | gtgtaacagc | aaggttcggc | 2160 |
| ctagatgcat | cacagcaaat | ccgtctggaa | gcagaagaag | aaaaattagc | tcatttgcca | 2220 |

-continued

| | |
|---|---|
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taaagtagag | 2340 |
| cttgaagcct tgcttgaaaa gcaagcctac aaagaacaag tgctggcaaa acgtttaaca | 2400 |
| atgcttgaac tgcttgaaaa atacccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct ttgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga agaaaaggc | 3120 |
| cgatacgcaa aagacgtgtg ggctgggtaa | 3150 |

<210> SEQ ID NO 66
<211> LENGTH: 1049
<212> TYPE: PRT
<213> ORGANISM: Artificial Sequence
<220> FEATURE:
<223> OTHER INFORMATION: P450-BM3 Variant 20 amino acid sequence

<400> SEQUENCE: 66

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
```

-continued

```
            195                 200                 205
Asp Ile Lys Val Met Asn Asp Leu Val Asp Lys Ile Ile Ala Asp Arg
210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
                    245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Ala Ala Glu Glu Ala Ala Arg Val Leu Val Asp Pro Val Pro
        290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Phe Pro Ala Phe Ser Leu Tyr Ala
                    325                 330                 335
Lys Glu Asp Thr Val Leu Gly Gly Glu Tyr Pro Leu Glu Lys Gly Asp
                340                 345                 350
Glu Leu Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                    405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
        450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                    485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
        530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                    565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
        610                 615                 620
```

```
Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035
```

Lys Gly Arg Tyr Ala Lys Asp Val Trp Ala Gly
    1040                    1045

<210> SEQ ID NO 67
<211> LENGTH: 3150
<212> TYPE: DNA
<213> ORGANISM: Artificial Sequence
<220> FEATURE:
<223> OTHER INFORMATION: P450-BM3 Variant 23 DNA sequence

<400> SEQUENCE: 67

| | |
|---|---|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg ctttgataaa aacttaagtc aagcgcttaa atttgtacgt | 240 |
| gattttgcag agacgggtt atttacaagc tggacgcatg aaaaaaattg gaaaaaagcg | 300 |
| cataatatct tcttccaag cttcagtcag caggcaatga aggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta acagctttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca agaagatatc aaggtgatga acgacctagt agataaaatt | 660 |
| attgcagatc gcaaagcaag cggtgaacaa agcgatgatt tattaacgca catgctaaac | 720 |
| ggaaaagatc cagaaacggg tgagccgctt gatgacgaga cattcgcta tcaaattatt | 780 |
| acattcttaa ttgcgggaca cgaaacaaca agtggtcttt tatcatttgc gctgtatttc | 840 |
| ttagtgaaaa atccacatgt attacaaaaa gcagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgttcct gcgttttccc tatatgcaaa agaagatacg | 1020 |
| gtgcttggag gagaatatcc tttagaaaaa ggcgacgaac taatggttct gattcctcag | 1080 |
| cttcaccgtg ataaaacaat tgggggagac gatgtggaag agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact tgaagatca tacaaactac gagctggata ttaaagaaac tttaacgtta | 1320 |
| aaacctgaag ctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg ctttatcga tgaaacgctt gccgctaaag ggcagaaaa catcgctgac | 1800 |
| cgcggtgaag cagatgcaag cgacgacttt gaaggcacct atgaagaatg cgtgaacac | 1860 |
| atgtggagtg acgtagcagc ctactttaac ctcgacattg aaacagtga agataataaa | 1920 |
| tctactcttt cacttcaatt tgtcgacagc gccgcggata tgccgcttgc gaaaatgcac | 1980 |

-continued

```
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                     3150
```

<210> SEQ ID NO 68
<211> LENGTH: 1049
<212> TYPE: PRT
<213> ORGANISM: Artificial Sequence
<220> FEATURE:
<223> OTHER INFORMATION: P450-BM3 Variant 23 amino acid sequence

<400> SEQUENCE: 68

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160
```

```
Tyr Arg Phe Asn Ser Phe Tyr Arg Asp Gln Pro His Pro Phe Ile Thr
            165                 170                 175

Ser Met Val Arg Ala Leu Asp Glu Ala Met Asn Lys Leu Gln Arg Ala
        180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Val Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575
```

```
Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
```

```
             995                1000               1005
Ala Val Glu Ala Thr Leu Met Lys Ser Tyr Ala Asp Val His Gln
        1010                1015               1020

Val Ser Glu Ala Asp Ala Arg Leu Trp Leu Gln Gln Leu Glu Glu
        1025                1030               1035

Lys Gly Arg Tyr Ala Lys Asp Val Trp Ala Gly
        1040                1045

<210> SEQ ID NO 69
<211> LENGTH: 2051
<212> TYPE: DNA
<213> ORGANISM: Santalum album

<400> SEQUENCE: 69
```

| | | | | | |
|---|---|---|---|---|---|
| atgtacgtat | ccatcagcaa | tgatcgacct | tataaaggag | ccgagacact | ctcaccttca | 60 |
| atccactcat | ccctacattc | ttttgctaac | tcctttgttg | ccagcaagta | tatctcttac | 120 |
| gttaaacgtt | ttacttcctc | aacatgtctc | cggcaacagc | cgttatcctc | actctcctcg | 180 |
| tggccctagg | gctatccatc | cttttgcggc | ggcgccaaaa | agaaataat | ctacctcccg | 240 |
| gtccacccgc | tttaccgatc | atcggaaaca | tccacatatt | ggggacccct | cctcaccaga | 300 |
| gcctctacaa | cttggccaag | aagtatggtc | ccatcatgtc | aatgaggctg | ggctcgtgc | 360 |
| cggctgttgt | gatatcctct | ccggaggccg | ccgagctcgt | cctcaagacc | cacgatatcg | 420 |
| ttttcgccag | ccggcccaga | ctccaagttg | cggactactt | ccattacggg | acaaagggcg | 480 |
| tcatcctgac | ggagtatggt | acatattggc | gcaacatgcg | aaggctgtgc | accgtgaagc | 540 |
| ttctcaacac | ggtgaaaatc | gattctttcg | cagggacaag | gaagaaggag | gtggcatcgt | 600 |
| tcgtgcagtc | ccttaaggag | gcttcggtgg | cacacaaaat | ggtgaatttg | agcgcgaggg | 660 |
| tggcgaacgt | cattgaaaac | atggtgtgcc | ttatggtgat | cgggcgaagt | agcgatgaga | 720 |
| ggtttaagct | aaaggaggtc | atccaggagg | cagcgcagtt | ggcgggagct | ttcaatatag | 780 |
| gggattatgt | tccattcctt | atgccccttg | acctacaggg | attaactcgg | cgcataaagt | 840 |
| caggaagtaa | agctttcgac | gacatcttgg | aagtcataat | cgacgagcac | gtgcaagaca | 900 |
| ttaaggacca | tgatgatgaa | caacatggag | acttcattga | tgtgttgctg | gcaatgatga | 960 |
| acaagcccat | ggattcgcgg | gagggtctta | gtatcattga | ccgaacaaac | atcaaagcga | 1020 |
| tcctagtgga | catgattgga | gctgcaatgg | acacttcaac | aagtgcgtc | gagtgggcga | 1080 |
| tttcagagct | catcaagcat | ccgcgggtaa | tgaaaaagct | ccaagacgag | gtcaaaactg | 1140 |
| tcatcggaat | gaataggatg | gtcgaggagg | ccgacttgcc | taagctacca | tacctcgaca | 1200 |
| tggtagtgaa | agagaccatg | aggttacacc | ctcctggacc | attgctcgtg | ccccgagagt | 1260 |
| ccatggaaga | catcacaatc | aacgatact | acatacctaa | gaaatcgcga | atcattgtca | 1320 |
| acgcctgggc | aattgggcgt | gatacaaacg | cctggtctaa | taacgcgcac | gagttcttcc | 1380 |
| cagagaggtt | tatgagtagc | aatgtggact | acagggaca | agatttccaa | cttatcccat | 1440 |
| tcgggtcagg | tcggagaggg | tgccccggga | tgcgcctagg | cctcacaacc | gttcgattag | 1500 |
| tgttagcgca | gctcattcat | tgtttcgact | tggagcttcc | taagggaacc | gtggcgaccg | 1560 |
| acttggacat | gagtgagaaa | ttcggggttgg | caatgcccag | agcccagcac | ttgcttgcat | 1620 |
| ttccaaccta | tcgcttggag | tcctaaacca | ttgaggaaga | tgcgtttata | tttcatattg | 1680 |
| cagtgttaca | ataagtagca | gtcgttttca | tggtgaagag | gcaattcccc | ctacactacc | 1740 |
| tgtcttatgc | tatgcccctc | cccaactttc | accgtatgtg | tcttgtcatc | atgtatcatg | 1800 |

-continued

| | |
|---|---|
| tccacatcaa taagatatta tatagaaatt gtcggtacgc aagatcgga ctcaatatgt | 1860 |
| atcagctttg agctctgtac acaaaatttg atacacgaac agagaaggtc gcgaattttg | 1920 |
| ggccactcgt ctcagatata tacccttcaa gtggctaatg gggagatccc tctcctttgc | 1980 |
| atttaaagcc tctgcttccc gaaccctagc ccacaaaatt ttggccgaaa ccggataggc | 2040 |
| atacacgaca g | 2051 |

<210> SEQ ID NO 70
<211> LENGTH: 1503
<212> TYPE: DNA
<213> ORGANISM: Santalum album

<400> SEQUENCE: 70

| | |
|---|---|
| atgtctccgg caacagccgt tatcctcact ctcctcgtgg ccctagggct atccatcctt | 60 |
| ttgcggcggc gccaaaaaag aaataatcta cctcccggtc cacccgcttt accgatcatc | 120 |
| ggaaacatcc acatattggg gacccttcct caccagagcc tctacaactt ggccaagaag | 180 |
| tatggtccca tcatgtcaat gaggctgggg ctcgtgccgg ctgttgtgat atcctctccg | 240 |
| gaggccgccg agctcgtcct caagacccac gatatcgttt cgccagccg gcccagactc | 300 |
| caagttgcg actacttcca ttacgggaca aagggcgtca tcctgacgga gtatggtaca | 360 |
| tattggcgca acatgcgaag gctgtgcacc gtgaagcttc tcaacacggt gaaaatcgat | 420 |
| tctttcgcag gacaaggaa gaggaggtg gcatcgttcg tgcagtccct taaggaggct | 480 |
| tcggtggcac acaaaatggt gaatttgagc gcgagggtgg cgaacgtcat gaaaacatg | 540 |
| gtgtgcctta tggtgatcgg gcgaagtagc gatgagaggt ttaagctaaa ggaggtcatc | 600 |
| caggaggcag cgcagttggc gggagctttc aatataggg attatgttcc attccttatg | 660 |
| ccccttgacc tacagggatt aactcggcgc ataaagtcag gaagtaaagc tttcgacgac | 720 |
| atcttggaag tcataatcga cgagcacgtg caagacatta aggaccatga tgatgaacaa | 780 |
| catggagact tcattgatgt gttgctggca atgatgaaca gcccatggga ttcgcgggag | 840 |
| ggtcttagta tcattgaccg aacaaacatc aaagcgatcc tagtggacat gattggagct | 900 |
| gcaatggaca cttcaacaag tggcgtcgag tgggcgattt cagagctcat caagcatccg | 960 |
| cgggtaatga aaaagctcca agacgaggtc aaaactgtca tcggaatgaa taggatggtc | 1020 |
| gaggaggccg acttgcctaa gctaccatac ctcgacatgg tagtgaaaga gaccatgagg | 1080 |
| ttacaccctc ctggaccatt gctcgtgccc cgagagtcca tggaagacat cacaatcaac | 1140 |
| ggatactaca tacctaagaa atcgcgaatc attgtcaacg cctgggcaat ggggcgtgat | 1200 |
| acaaacgcct ggtctaataa cgcgcacgag ttcttcccag agaggtttat gagtagcaat | 1260 |
| gtggacttac agggacaaga tttccaactt atcccattcg ggtcaggtcg gagagggtgc | 1320 |
| cccgggatgc gcctaggcct cacaaccgtt cgattagtgt tagcgcagct cattcattgt | 1380 |
| ttcgacttgg agcttcctaa gggaaccgtg gcgaccgact tggacatgag tgagaaattc | 1440 |
| gggttggcaa tgcccagagc ccagcacttg cttgcatttc aacctatcg cttggagtcc | 1500 |
| taa | 1503 |

<210> SEQ ID NO 71
<211> LENGTH: 500
<212> TYPE: PRT
<213> ORGANISM: Santalum album

<400> SEQUENCE: 71

Met Ser Pro Ala Thr Ala Val Ile Leu Thr Leu Leu Val Ala Leu Gly

-continued

```
1               5                   10                  15
Leu Ser Ile Leu Leu Arg Arg Gln Lys Arg Asn Asn Leu Pro Pro
                20                  25                  30
Gly Pro Pro Ala Leu Pro Ile Ile Gly Asn Ile His Ile Leu Gly Thr
                35                  40                  45
Leu Pro His Gln Ser Leu Tyr Asn Leu Ala Lys Lys Tyr Gly Pro Ile
 50                  55                  60
Met Ser Met Arg Leu Gly Leu Val Pro Ala Val Val Ile Ser Ser Pro
 65                  70                  75                  80
Glu Ala Ala Glu Leu Val Leu Lys Thr His Asp Ile Val Phe Ala Ser
                 85                  90                  95
Arg Pro Arg Leu Gln Val Ala Asp Tyr Phe His Tyr Gly Thr Lys Gly
                100                 105                 110
Val Ile Leu Thr Glu Tyr Gly Thr Tyr Trp Arg Asn Met Arg Arg Leu
                115                 120                 125
Cys Thr Val Lys Leu Leu Asn Thr Val Lys Ile Asp Ser Phe Ala Gly
                130                 135                 140
Thr Arg Lys Lys Glu Val Ala Ser Phe Val Gln Ser Leu Lys Glu Ala
145                 150                 155                 160
Ser Val Ala His Lys Met Val Asn Leu Ser Ala Arg Val Ala Asn Val
                165                 170                 175
Ile Glu Asn Met Val Cys Leu Met Val Ile Gly Arg Ser Ser Asp Glu
                180                 185                 190
Arg Phe Lys Leu Lys Glu Val Ile Gln Glu Ala Ala Gln Leu Ala Gly
                195                 200                 205
Ala Phe Asn Ile Gly Asp Tyr Val Pro Phe Leu Met Pro Leu Asp Leu
210                 215                 220
Gln Gly Leu Thr Arg Arg Ile Lys Ser Gly Ser Lys Ala Phe Asp Asp
225                 230                 235                 240
Ile Leu Glu Val Ile Ile Asp Glu His Val Gln Asp Ile Lys Asp His
                245                 250                 255
Asp Asp Glu Gln His Gly Asp Phe Ile Asp Val Leu Leu Ala Met Met
                260                 265                 270
Asn Lys Pro Met Asp Ser Arg Glu Gly Leu Ser Ile Ile Asp Arg Thr
                275                 280                 285
Asn Ile Lys Ala Ile Leu Val Asp Met Ile Gly Ala Ala Met Asp Thr
                290                 295                 300
Ser Thr Ser Gly Val Glu Trp Ala Ile Ser Glu Leu Ile Lys His Pro
305                 310                 315                 320
Arg Val Met Lys Lys Leu Gln Asp Glu Val Lys Thr Val Ile Gly Met
                325                 330                 335
Asn Arg Met Val Glu Glu Ala Asp Leu Pro Lys Leu Pro Tyr Leu Asp
                340                 345                 350
Met Val Val Lys Glu Thr Met Arg Leu His Pro Pro Gly Pro Leu Leu
                355                 360                 365
Val Pro Arg Glu Ser Met Glu Asp Ile Thr Ile Asn Gly Tyr Tyr Ile
                370                 375                 380
Pro Lys Lys Ser Arg Ile Ile Val Asn Ala Trp Ala Ile Gly Arg Asp
385                 390                 395                 400
Thr Asn Ala Trp Ser Asn Asn Ala His Glu Phe Phe Pro Glu Arg Phe
                405                 410                 415
Met Ser Ser Asn Val Asp Leu Gln Gly Gln Asp Phe Gln Leu Ile Pro
                420                 425                 430
```

```
Phe Gly Ser Gly Arg Arg Gly Cys Pro Gly Met Arg Leu Gly Leu Thr
        435                 440                 445

Thr Val Arg Leu Val Leu Ala Gln Leu Ile His Cys Phe Asp Leu Glu
    450                 455                 460

Leu Pro Lys Gly Thr Val Ala Thr Asp Leu Asp Met Ser Glu Lys Phe
465                 470                 475                 480

Gly Leu Ala Met Pro Arg Ala Gln His Leu Leu Ala Phe Pro Thr Tyr
                485                 490                 495

Arg Leu Glu Ser
        500

<210> SEQ ID NO 72
<211> LENGTH: 1534
<212> TYPE: DNA
<213> ORGANISM: Artificial Sequence
<220> FEATURE:
<223> OTHER INFORMATION: SaCP120293, optimized DNA sequence for SaCP816

<400> SEQUENCE: 72
```

| | | | | | |
|---|---|---|---|---|---|
| aggaggtaaa | acatatggca | ctgttgttgg | cggttttctg | gagcgctttg | attattctgg | 60 |
| ttagcatctt | attgcgtcgt | cgtcaaaaac | gcaacaattt | gccaccgggc | ccaccggccc | 120 |
| tgccgatcat | cggtaacatt | cacattctgg | gcaccctgcc | gcaccagagc | ctgtacaatc | 180 |
| tggcgaagaa | gtacggtccg | atcatgtcca | tgcgtttggg | cttggttccg | gcggtggtca | 240 |
| tcagcagccc | ggaagcggcc | gagctggtcc | tgaaaaccca | cgacatcgtt | tttgcttctc | 300 |
| gccctcgtct | gcaagttgca | gattactttc | actatggcac | caaaggcgtg | attctgaccg | 360 |
| aatatggtac | ctactggcgt | aacatgcgtc | gcctgtgcac | ggtcaaactg | ctgaacaccg | 420 |
| ttaagattga | tagctttgca | ggcacccgca | gaaagaagt | cgctagcttc | gttcagagcc | 480 |
| tgaaagaagc | aagcgtggcg | cacaaaatgg | ttaacctgtc | cgcacgcgtc | gctaatgtta | 540 |
| ttgagaatat | ggtttgtctg | atggttattg | gtagatcgtc | tgacgagcgt | ttcaagctga | 600 |
| agaagtgat | ccaagaagcg | gcacagctgg | cgggtgcctt | caatattggt | gactatgtcc | 660 |
| cgtttctgat | gccgctggat | ctgcagggcc | tgactcgccg | tatcaagagc | ggtagcaagg | 720 |
| cattcgatga | catcctcgag | gtcattatcg | acgagcatgt | gcaagacatt | aaagatcatg | 780 |
| acgatgagca | gcatggtgac | ttcatcgacg | tgctgctggc | gatgatgaat | aagccgatgg | 840 |
| attctcgtga | gggtctgtcc | atcattgatc | gcacgaacat | taaagcgatc | ctggtggata | 900 |
| tgatcggtgc | cgcgatggac | acgagcacca | gcggtgtgga | gtgggcgatt | tcggagctga | 960 |
| ttaagcatcc | tcgtgtcatg | aagaaactgc | aagacgaagt | gaaaaccgta | atcggtatga | 1020 |
| accgcatggt | ggaagaagcg | gatctgccga | aactgccgta | cctggacatg | gttgtcaagg | 1080 |
| aaacgatgcg | tctgcatccg | ccaggcccgc | tgctggtgcc | gcgtgaaagc | atggaagata | 1140 |
| ttacgatcaa | cggttactat | atcccgaaga | aatcccgcat | tattgtgaat | gcatgggcga | 1200 |
| tcggccgtga | caccaacgcc | tggagcaata | atgcgcacga | gttttccct | gagcgtttta | 1260 |
| tgagctctaa | cgttgatctg | caaggccagg | acttccagct | gatcccgttc | ggtagcggtc | 1320 |
| gtcgcggttg | tccgggcatg | cgtctgggtc | tgacgacggt | ccgcttggtg | ctggcccaac | 1380 |
| tgattcactg | cttcgacctg | gagcttccga | agggcaccgt | cgcgactgac | ctggatatga | 1440 |
| gcgagaagtt | tggtctggca | atgccgcgtg | cgcagcactt | actggccttt | ccgacctacc | 1500 |
| gtctggagag | ctaagtcgac | accatggaaa | gctt | | | 1534 |

```
<210> SEQ ID NO 73
<211> LENGTH: 499
<212> TYPE: PRT
<213> ORGANISM: Artificial Sequence
<220> FEATURE:
<223> OTHER INFORMATION: SaCP120293 amino acid sequence, N-terminal
      modified SaCP816

<400> SEQUENCE: 73

Met Ala Leu Leu Leu Ala Val Phe Trp Ser Ala Leu Ile Ile Leu Val
1               5                   10                  15

Ser Ile Leu Leu Arg Arg Arg Gln Lys Arg Asn Asn Leu Pro Pro Gly
                20                  25                  30

Pro Pro Ala Leu Pro Ile Ile Gly Asn Ile His Ile Leu Gly Thr Leu
            35                  40                  45

Pro His Gln Ser Leu Tyr Asn Leu Ala Lys Lys Tyr Gly Pro Ile Met
        50                  55                  60

Ser Met Arg Leu Gly Leu Val Pro Ala Val Val Ile Ser Ser Pro Glu
65                  70                  75                  80

Ala Ala Glu Leu Val Leu Lys Thr His Asp Ile Val Phe Ala Ser Arg
                85                  90                  95

Pro Arg Leu Gln Val Ala Asp Tyr Phe His Tyr Gly Thr Lys Gly Val
            100                 105                 110

Ile Leu Thr Glu Tyr Gly Thr Tyr Trp Arg Asn Met Arg Arg Leu Cys
        115                 120                 125

Thr Val Lys Leu Leu Asn Thr Val Lys Ile Asp Ser Phe Ala Gly Thr
130                 135                 140

Arg Lys Lys Glu Val Ala Ser Phe Val Gln Ser Leu Lys Glu Ala Ser
145                 150                 155                 160

Val Ala His Lys Met Val Asn Leu Ser Ala Arg Val Ala Asn Val Ile
                165                 170                 175

Glu Asn Met Val Cys Leu Met Val Ile Gly Arg Ser Ser Asp Glu Arg
            180                 185                 190

Phe Lys Leu Lys Glu Val Ile Gln Glu Ala Ala Gln Leu Ala Gly Ala
        195                 200                 205

Phe Asn Ile Gly Asp Tyr Val Pro Phe Leu Met Pro Leu Asp Leu Gln
210                 215                 220

Gly Leu Thr Arg Arg Ile Lys Ser Gly Ser Lys Ala Phe Asp Asp Ile
225                 230                 235                 240

Leu Glu Val Ile Ile Asp Glu His Val Gln Asp Ile Lys Asp His Asp
                245                 250                 255

Asp Glu Gln His Gly Asp Phe Ile Asp Val Leu Leu Ala Met Met Asn
            260                 265                 270

Lys Pro Met Asp Ser Arg Glu Gly Leu Ser Ile Ile Asp Arg Thr Asn
        275                 280                 285

Ile Lys Ala Ile Leu Val Asp Met Ile Gly Ala Ala Met Asp Thr Ser
290                 295                 300

Thr Ser Gly Val Glu Trp Ala Ile Ser Glu Leu Ile Lys His Pro Arg
305                 310                 315                 320

Val Met Lys Lys Leu Gln Asp Glu Val Lys Thr Val Ile Gly Met Asn
                325                 330                 335

Arg Met Val Glu Glu Ala Asp Leu Pro Lys Leu Pro Tyr Leu Asp Met
            340                 345                 350

Val Val Lys Glu Thr Met Arg Leu His Pro Pro Gly Pro Leu Leu Val
        355                 360                 365
```

```
Pro Arg Glu Ser Met Glu Asp Ile Thr Ile Asn Gly Tyr Tyr Ile Pro
    370                 375                 380

Lys Lys Ser Arg Ile Ile Val Asn Ala Trp Ala Ile Gly Arg Asp Thr
385                 390                 395                 400

Asn Ala Trp Ser Asn Asn Ala His Glu Phe Phe Pro Glu Arg Phe Met
                405                 410                 415

Ser Ser Asn Val Asp Leu Gln Gly Gln Asp Phe Gln Leu Ile Pro Phe
            420                 425                 430

Gly Ser Gly Arg Arg Gly Cys Pro Gly Met Arg Leu Gly Leu Thr Thr
                435                 440                 445

Val Arg Leu Val Leu Ala Gln Leu Ile His Cys Phe Asp Leu Glu Leu
    450                 455                 460

Pro Lys Gly Thr Val Ala Thr Asp Leu Asp Met Ser Glu Lys Phe Gly
465                 470                 475                 480

Leu Ala Met Pro Arg Ala Gln His Leu Leu Ala Phe Pro Thr Tyr Arg
                485                 490                 495

Leu Glu Ser
```

<210> SEQ ID NO 74
<211> LENGTH: 3672
<212> TYPE: DNA
<213> ORGANISM: Artificial Sequence
<220> FEATURE:
<223> OTHER INFORMATION: synthetic operon encoding for SaCP816 and CPRm

<400> SEQUENCE: 74

```
catatggcac tgttgttggc ggttttctgg agcgctttga ttattctggt tagcatctta    60
ttgcgtcgtc gtcaaaaacg caacaatttg ccaccgggcc caccggccct gccgatcatc   120
ggtaacattc acattctggg caccctgccg caccagagcc tgtacaatct ggcgaagaag   180
tacggtccga tcatgtccat gcgtttgggc ttggttccgg cggtggtcat cagcagcccg   240
gaagcggccg agctggtcct gaaaacccac gacatcgttt ttgcttctcg ccctcgtctg   300
caagttgcag attactttca ctatggcacc aaaggcgtga ttctgaccga atatggtacc   360
tactggcgta acatgcgtcg cctgtgcacg gtcaaactgc tgaacaccgt taagattgat   420
agctttgcag gcacccgcaa gaaagaagtc gctagcttcg ttcagagcct gaagaagca    480
agcgtggcgc acaaaatggt taacctgtcc gcacgcgtcg ctaatgttat tgagaatatg   540
gtttgtctga tggttattgg tagatcgtct gacgagcgtt tcaagctgaa agaagtgatc   600
caagaagcgg cacagctggc gggtgccttc aatattggtg actatgtccc gtttctgatg   660
ccgctggatc tgcagggcct gactcgccgt atcaagagcg gtagcaaggc attcgatgac   720
atcctcgagg tcattatcga cgagcatgtg caagacatta aagatcatga cgatgagcag   780
catggtgact tcatcgacgt gctgctggcg atgatgaata gccgatgga ttctcgtgag   840
ggtctgtcca tcattgatcg cacgaacatt aaagcgatcc tggtggatat gatcggtgcc   900
gcgatggaca cgagcaccag cggtgtggag tgggcgattt cggagctgat taagcatcct   960
cgtgtcatga agaaactgca agacgaagtg aaaaccgtaa tcggtatgaa ccgcatggtg  1020
gaagaagcgg atctgccgaa actgccgtac ctggacatgt tgtcaagga acgatgcgt   1080
ctgcatccgc aggcccgct gctggtgccg cgtgaaagca tggaagatat tacgatcaac  1140
ggttactata tcccgaagaa atcccgcatt attgtgaatg catgggcgat cggccgtgac  1200
accaacgcct ggagcaataa tgcgcacgag tttttccctg agcgttttat gagctctaac  1260
gttgatctgc aaggccagga cttccagctg atcccgttcg gtagcggtcg tcgcggttgt  1320
```

```
ccgggcatgc gtctgggtct gacgacggtc cgcttggtgc tggcccaact gattcactgc    1380
ttcgacctgg agcttccgaa gggcaccgtc gcgactgacc tggatatgag cgagaagttt    1440
ggtctggcaa tgccgcgtgc gcagcactta ctggcctttc cgacctaccg tctggagagc    1500
taagtcgact aactttaaga aggagatata tccatggaac ctagctctca gaaactgtct    1560
ccgttggaat tgttgctgc tatcctgaag ggcgactaca gcagcggtca ggttgaaggt    1620
ggtccaccgc caggtctggc agctatgttg atggaaaata aggatttggt gatggttctg    1680
acgacgtccg tggcagtcct gatcggctgt gtcgtggtcc tggcatggcg tcgtgcggca    1740
ggtagcggta agtacaagca acctgaactg cctaaactgg tggtcccgaa agcagccgaa    1800
ccggaggagg cagaggatga taaaaccaag atcagcgtgt ttttcggcac ccaaaccggt    1860
acggcagaag gttcgcgaa ggcttttgtt gaagaggcca aggcgcgtta tcagcaggcc    1920
cgtttcaaag ttatcgacct ggacgactat gcggcagacg atgacgagta cgaagagaaa    1980
ctgaagaagg aaaacttggc attcttcttc ttggcgtcct acggtgacgg cgagccgacg    2040
gacaacgcgg cacgctttta caaatggttt acggagggta aggaccgtgg tgaatggctg    2100
aacaatctgc agtacggcgt ttttggtctg ggtaaccgtc aatatgagca tttcaataag    2160
atcgccattg tcgtcgatga tctgatcttc gagcaaggtg caagaagct ggttccggtg    2220 ggtctgggtg acgatgacca gtgcattgag gatgattttg cggcgtggcg tgaactggtc    2280
tggccggaac tggataaact gctgcgtaac gaagacgacg ctaccgtggc aaccccgtac    2340
agcgccgctg tgctgcaata ccgcgtggtt ttccacgatc acattgacgg cctgattagc    2400
gaaaacggta gcccgaacgg tcatgctaat ggcaataccg tgtacgatgc gcaacacccg    2460
tgccgtagca acgtcgcggt caagaaggaa ttgcatactc cggcgagcga tcgcagctgc    2520
acccacctgg aatttaacat tagcggtacc ggcctgatgt acgagacggg tgaccacgtc    2580
ggtgtgtatt gcgagaacct gttggaaacc gtggaggagg ccgagaagtt gttgaacctg    2640
agcccgcaga cgtacttctc cgttcacacc gacaacgagg acggtacgcc gttgagcggc    2700
agcagcctgc cgccaccgtt tccgccgtgc accttgcgca cggcattgac caaatacgca    2760
gacttgactt ctgcaccgaa aaagtcggtg ctggtggcgc tggccgagta cgcatctgac    2820
cagggtgaag cggatcgttt gcgtttcttg gcgagcccga gcggcaaaga ggaatatgca    2880
cagtacatct tggcaagcca gcgcacgctg ctggaggtca tggcggagtt cccgtcggcg    2940
aaaccgccgc tgggtgtctt tttcgcgggt gtcgctccgc gcctgcagcc gcgtttctat    3000
tccattagct ctagcccgaa gatcgcaccg ttccgtattc acgtgacctg cgccctggtt    3060
tatgacaaat cccctaccgg tcgcgttcat aagggcatct gtagcacgtg gatgaaaaat    3120
gcggtcccgc tggaagaaag caacgattgt tcctgggctc cgatcttcgt ccgcaacagc    3180
aacttcaagc tgccgaccga cccgaaggtt ccgattatca tgattggtcc gggtaccggt    3240 ctggccccctt ttcgtggctt tttgcaagag cgcttggcgt tgaaagagag cggtgctgaa    3300
ttgggtccgg cgatcttgtt cttggttgc cgtaaccgta aaatggactt tatttacgag    3360
gatgaactga atgatttcgt caaagcgggc gttgtcagcg agctgatcgt cgcttttagc    3420
cgcgaaggcc cgatgaaaga atacgtgcaa cacaaaatga ccaacgtgc ctccgatgtg    3480 tggaacatca ttagcgacgg tggttatgtt tatgtttgcg gtgacgcgaa gggtatggct    3540
cgtgatgttc accgtaccct gcataccatc gcacaggagc aaggtagcat gtccagctcg    3600
gaggccgaag gtatggtcaa aaacctgcaa accaccggtc gttacctgcg tgatgtgtgg    3660
```

-continued

| | |
|---|---|
| taataaaagc tt | 3672 |

<210> SEQ ID NO 75
<211> LENGTH: 5349
<212> TYPE: DNA
<213> ORGANISM: Artificial Sequence
<220> FEATURE:
<223> OTHER INFORMATION: Synthetic operon encoding for SaCP816, CPRm and ClASS

<400> SEQUENCE: 75

| | |
|---|---|
| catatggcac tgttgttggc ggttttctgg agcgctttga ttattctggt tagcatctta | 60 |
| ttgcgtcgtc gtcaaaaacg caacaatttg ccaccgggcc caccggccct gccgatcatc | 120 |
| ggtaacattc acattctggg caccctgccg caccagagcc tgtacaatct ggcgaagaag | 180 |
| tacggtccga tcatgtccat gcgtttgggc ttggttccgg cggtggtcat cagcagcccg | 240 |
| gaagcggccg agctggtcct gaaaacccac gacatcgttt ttgcttctcg ccctcgtctg | 300 |
| caagttgcag attactttca ctatggcacc aaaggcgtga ttctgaccga atatggtacc | 360 |
| tactggcgta acatgcgtcg cctgtgcacg gtcaaactgc tgaacaccgt taagattgat | 420 |
| agctttgcag gcacccgcaa gaaagaagtc gctagcttcg ttcagagcct gaaagaagca | 480 |
| agcgtggcgc acaaaatggt taacctgtcc gcacgcgtcg ctaatgttat tgagaatatg | 540 |
| gtttgtctga tggttattgg tagatcgtct gacgagcgtt tcaagctgaa agaagtgatc | 600 |
| caagaagcgg cacagctggc gggtgccttc aatattggtg actatgtccc gtttctgatg | 660 |
| ccgctggatc tgcagggcct gactcgccgt atcaagagcg gtagcaaggc attcgatgac | 720 |
| atcctcgagg tcattatcga cgagcatgtg caagacatta agatcatga cgatgagcag | 780 |
| catggtgact tcatcgacgt gctgctggcg atgatgaata gccgatgga ttctcgtgag | 840 |
| ggtctgtcca tcattgatcg cacgaacatt aaagcgatcc tggtggatat gatcggtgcc | 900 |
| gcgatggaca cgagcaccag cggtgtggag tgggcgattt cggagctgat taagcatcct | 960 |
| cgtgtcatga agaaactgca agacgaagtg aaaaccgtaa tcggtatgaa ccgcatggtg | 1020 |
| gaagaagcgg atctgccgaa actgccgtac ctggacatgg ttgtcaagga acgatgcgt | 1080 |
| ctgcatccgc caggcccgct gctggtgccg cgtgaaagca tggaagatat tacgatcaac | 1140 |
| ggttactata tcccgaagaa atcccgcatt attgtgaatg catgggcgat cggccgtgac | 1200 |
| accaacgcct ggagcaataa tgcgcacgag tttttccctg agcgttttat gagctctaac | 1260 |
| gttgatctgc aaggccagga cttccagctg atcccgttcg gtagcggtcg tcgcggttgt | 1320 |
| ccgggcatgc gtctgggtct gacgacggtc cgcttggtgc tggcccaact gattcactgc | 1380 |
| ttcgacctgg agcttccgaa gggcaccgtc gcgactgacc tggatatgag cgagaagttt | 1440 |
| ggtctggcaa tgccgcgtgc gcagcactta ctggcctttc cgacctaccg tctggagagc | 1500 |
| taagtcgact aactttaaga aggagatata tccatggaac ctagctctca gaaactgtct | 1560 |
| ccgttggaat tgttgctgc tatcctgaag ggcgactaca gcagcggtca ggttgaaggt | 1620 |
| ggtccaccgc caggtctggc agctatgttg atggaaaata aggatttggt gatggttctg | 1680 |
| acgacgtccg tggcagtcct gatcggctgt gtcgtggtcc tggcatggcg tcgtgcggca | 1740 |
| ggtagcggta agtacaagca acctgaactg cctaaactgg tggtcccgaa agcagccgaa | 1800 |
| ccggaggagg cagaggatga taaaaccaag atcagcgtgt ttttcggcac ccaaaccggt | 1860 |
| acggcagaag gtttcgcgaa ggcttttgtt gaagaggcca aggcgcgtta tcagcaggcc | 1920 |
| cgtttcaaag ttatcgacct ggacgactat gcggcagacg atgacgagta cgaagagaaa | 1980 |

```
ctgaagaagg aaaacttggc attcttcttc ttggcgtcct acggtgacgg cgagccgacg    2040
gacaacgcgg cacgctttta caaatggttt acggagggta aggaccgtgg tgaatggctg    2100
aacaatctgc agtacggcgt ttttggtctg ggtaaccgtc aatatgagca tttcaataag    2160
atcgccattg tcgtcgatga tctgatcttc gagcaaggtg gcaagaagct ggttccggtg    2220
ggtctgggtg acgatgacca gtgcattgag gatgattttg cggcgtggcg tgaactggtc    2280
tggccggaac tggataaact gctgcgtaac gaagacgacg ctaccgtggc aaccccgtac    2340
agcgccgctg tgctgcaata ccgcgtggtt ttccacgatc acattgacgg cctgattagc    2400
gaaaacggta gcccgaacgg tcatgctaat ggcaataccg tgtacgatgc gcaacacccg    2460
tgccgtagca acgtcgcggt caagaaggaa ttgcatactc cggcgagcga tcgcagctgc    2520
acccacctgg aatttaacat tagcggtacc ggcctgatgt acgagacggg tgaccacgtc    2580
ggtgtgtatt gcgagaacct gttggaaacc gtggaggagg ccgagaagtt gttgaacctg    2640
agcccgcaga cgtacttctc cgttcacacc gacaacgagg acggtacgcc gttgagcggc    2700
agcagcctgc cgccaccgtt tccgccgtgc accttgcgca cggcattgac caaatacgca    2760
gacttgactt ctgcaccgaa aaagtcggtg ctggtggcgc tggccgagta cgcatctgac    2820
cagggtgaag cggatcgttt gcgtttcttg gcgagcccga gcggcaaaga gaatatgca    2880 cagtacatct tggcaagcca gcgcacgctg ctggaggtca tggcggagtt cccgtcggcg    2940
aaaccgccgc tgggtgtctt tttcgcgggt gtcgctccgc gcctgcagcc gcgtttctat    3000
tccattagct ctagcccgaa gatcgcaccg ttccgtattc acgtgacctg cgccctggtt    3060
tatgacaaat cccctaccgg tcgcgttcat aagggcatct gtagcacgtg gatgaaaaat    3120
gcggtcccgc tggaagaaag caacgattgt tcctgggctc cgatcttcgt ccgcaacagc    3180
aacttcaagc tgccgaccga cccgaaggtt ccgattatca tgattggtcc gggtaccggt    3240 ctggccccctt ttcgtggctt tttgcaagag cgcttggcgt tgaaagagag cggtgctgaa    3300
ttgggtccgg cgatcttgtt cttttggttgc cgtaaccgta aaatggactt tatttacgag    3360
gatgaactga atgatttcgt caaagcgggc gttgtcagcg agctgatcgt cgcttttagc    3420
cgcgaaggcc cgatgaaaga atacgtgcaa cacaaaatga gccaacgtgc ctccgatgtg    3480
tggaacatca ttagcgacgg tggttatgtt tatgtttgcg gtgacgcgaa gggtatggct    3540
cgtgatgttc accgtaccct gcataccatc gcacaggagc aaggtagcat gtccagctcg    3600
gaggccgaag gtatggtcaa aaacctgcaa accaccggtc gttacctgcg tgatgtgtgg    3660
taataaaagc ttgaaggaga tatactaatg tctacccagc aggttagctc cgagaatatc    3720
gttcgcaacg cggcgaactt ccacccgaat atctggggta atcatttctt gacgtgtcca    3780
agccagacga tcgattcttg gacgcaacaa caccataaag agctgaaaga agaggtccgc    3840
aagatgatgg tgagcgacgc aaacaaaccg gcacaacgtc tgcgtctgat tgacaccgtt    3900
caacgtttgg gcgtggcgta tcatttcgaa aaagaaatcg atgacgctct ggaaaagatc    3960
ggtcacgatc cgtttgacga taaggatgac ctgtatatcg ttagcctgtg ttttcgcctg    4020
ctgcgtcagc atggcatcaa gattagctgc gatgttttg agaagttcaa agacgacgat    4080
ggcaagttta aggcttccct gatgaatgat gtccaaggta tgctgtcgtt gtatgaagcg    4140
gcccacctgg caattcatgg cgaggacatc ctggatgagg ctattgtctt tacgaccacc    4200
cacctgaaga gcaccgtttc taactccccg gtcaattcca cctttgcgga acagattcgc    4260
cacagcctgc gtgtgccgct gcgtaaggca gtccgcgctt tggagagccg ctacttcctg    4320
gatatctata gccgtgacga cctgcacgac aagactctgc tgaactttgc caaactggac    4380
```

```
ttcaacatcc tgcaggcgat gcaccagaaa gaggcaagcg agatgacccg ttggtggcgt    4440
gatttcgatt tcctgaagaa gctgccgtac attcgtgatc gcgtggttga actgtacttt    4500
tggattttgg tcggtgtgag ctaccaaccg aaattcagca cgggtcgtat cttttttgagc   4560 aagattatct gtctggaaac cctggtggac gacacgtttg atgcgtacgg tactttcgac    4620
gaactggcca ttttcaccga ggccgttacg cgttgggacc tgggtcatcg cgacgcgctg    4680
cctgagtaca tgaaattcat tttcaagacc ctgattgatg tgtacagcga ggcggaacaa    4740
gagctggcaa agagggccg ctcctatagc attcactatg cgatccgtag cttccaggag     4800
ttggtcatga agtactttg cgaggcgaaa tggctgaata agggttatgt tccgagcctg     4860
gatgactaca agagcgtcag cctgcgcagc atcggcttcc tgccgatcgc cgtggcttct    4920
tttgttttca tgggcgacat tgctacgaaa gaggttttg agtgggaaat gaataacccg      4980
aaaatcatca tcgcagccga aaccattttc cgctttctgg atgacattgc aggtcatcgc    5040
ttcgaacaaa aacgtgagca cagcccgagc gcaatcgagt gctacaaaaa ccaacatggt    5100
gtctcggaag aagaggcagt gaaagcgctg agcttggagg tcgccaattc gtggaaagac    5160
attaacgaag agctgctgct gaaccctatg gcaattccac tgccgttgct gcaggtgatc    5220
ctggatttga gccgtagcgc ggacttcatg tacggtaatg cgcaggaccg tttcacgcac    5280
tccaccatga tgaaagatca agttgacctg gttctgaaag atccggtgaa actggacgat    5340
taagaattc                                                             5349

<210> SEQ ID NO 76
<211> LENGTH: 5402
<212> TYPE: DNA
<213> ORGANISM: Artificial Sequence
<220> FEATURE:
<223> OTHER INFORMATION: synthetic operon encoding for SaCP816, CPRm and
      SaSAS

<400> SEQUENCE: 76
catatggcac tgttgttggc ggttttctgg agcgctttga ttattctggt tagcatctta      60
ttgcgtcgtc gtcaaaaacg caacaatttg ccaccgggcc caccggccct gccgatcatc     120
ggtaacattc acattctggg caccctgccg caccagagcc tgtacaatct ggcgaagaag     180
tacggtccga tcatgtccat gcgtttgggc ttggttccgg cggtggtcat cagcagcccg     240
gaagcggccg agctggtcct gaaaacccac gacatcgttt ttgcttctcg ccctcgtctg     300
caagttgcag attactttca ctatggcacc aaaggcgtga ttctgaccga atatggtacc     360
tactggcgta acatgcgtcg cctgtgcacg gtcaaactgc tgaacaccgt taagattgat     420
agctttgcag gcacccgcaa gaaagaagtc gctagcttcg ttcagagcct gaaagaagca    480
agcgtggcgc acaaaatggt taacctgtcc gcacgcgtcg ctaatgttat tgagaatatg    540
gtttgtctga tggttattgg tagatcgtct gacgagcgtt tcaagctgaa agaagtgatc    600
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta aagatcatga cgatgagcag    780
catggtgact tcatcgacgt gctgctggcg atgatgaata agccgatgga ttctcgtgag    840
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
```

```
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag ttttccctg agcgtttat gagctctaac   1260 gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt ttttcggcac ccaaaccggt   1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgcttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggcccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
```

```
gatgaactga atgatttcgt caaagcgggc gttgtcagcg agctgatcgt cgcttttagc      3420
cgcgaaggcc cgatgaaaga atacgtgcaa cacaaaatga gccaacgtgc ctccgatgtg      3480
tggaacatca ttagcgacgg tggttatgtt tatgtttgcg gtgacgcgaa gggtatggct      3540
cgtgatgttc accgtaccct gcataccatc gcacaggagc aaggtagcat gtccagctcg      3600
gaggccgaag gtatggtcaa aaacctgcaa accaccggtc gttacctgcg tgatgtgtgg      3660
taataaaagc ttaggaggta aaacatatgg acagcagcac cgccaccgca atgaccgcac      3720
cattcatcga cccgacggat catgtgaatc tgaaaaccga cacggatgcg agcgaaaatc      3780
gtcgtatggg taactacaag ccgagcattt ggaactacga ttttctgcag tccctggcga      3840
cgcaccacaa cattgttgaa gagcgtcacc tgaagctggc agagaaactg aaaggtcaag      3900
tgaaattcat gttcggtgcg ccgatggagc cattggctaa gttggagctg ttgatgtgg       3960 tgcaacgctt gggtctgaac cacctgttcg agactgaaat caaagaagct ctgttcagca      4020
tctacaaaga tggcagcaat ggctggtggt ttggccatct gcatgctacc tctttgcgct      4080
tccgtctgtt gcgccaatgt ggcctgttta tcccgcagga cgttttcaaa accttttcaaa     4140 acaagaccgg tgagtttgac atgaagctgt gggacaacgt taagggcctg ctgagcctgt      4200
acgaggcgag ctacctgggc tggaagggcg agaacatctt ggatgaagca aaggcgttca      4260
cgaccaagtg cctgaagagc gcatgggaga acattagcga agtggctg cgaagcgtg         4320 ttaaacatgc gttggcgctg ccgctgcact ggcgtgttcc gcgtattgaa gcacgctggt      4380
ttatcgaggt gtacgaacaa gaggccaata tgaatccgac gctgctgaaa ctggcgaaac      4440
tggacttcaa catggtccaa agcattcacc agaaagaaat cggtgaactg gcccgctggt      4500
gggttactac cggcctggac aagctggatt cgcacgcaa caatctgttg cagtcttata      4560
tgtggagctg cgccatcgcg tccgacccga aattcaaact ggcgcgtgaa accattgtcg      4620
agatcggttc cgtgttgacg gttgtcgacg acggctatga tgtgtacggt tctatggatg      4680
agctggacct gtacaccagc tcggtggagc gttggtcctg tgtcaaaatt gacaagctgc      4740
ctaatacgct gaagctgatc tttatgtcta tgttcaacaa aaccaacgag gtgggtctgc      4800
gtgttcaaca cgagcgtggt tacaatagca tcccgacctt cattaaggcg tgggtggaac      4860
agtgtaagag ctatcaaaaa gaggcgcgtt ggtttcatgg tggtcacacg cctccgctgg      4920
aagaatacag cctgaacggt ctggtcagca ttggttttcc gctgttgctg atcaccggct      4980
atgttgcgat tgctgagaat gaagcagccc tggataaagt ccacccgctg ccggacctgc      5040
tgcattattc cagcttgctg agccgtctga ttaatgatat cggcactagc ccggatgaaa      5100
tggcgcgtgg tgacaatctg aagagcattc actgctatat gaatgaaacc ggtgccagcg      5160
aagaggtcgc acgcgagcac atcaaaggcg tcatcgaaga gaattggaaa attctgaacc      5220
agtgttgctt tgaccagtcc cagttccagg agccgttcat cacgtttaac ctgaacagcg      5280
tgcgcggctc gcatttcttc tatgaatttg gtgatggttt tggtgttacc gacagctgga      5340
ccaaggtgga tatgaaaagc gtcctgattg atccgattcc gctgggtgaa gagtaagctt      5400
gc                                                                     5402
```

<210> SEQ ID NO 77
<211> LENGTH: 1880
<212> TYPE: DNA
<213> ORGANISM: Santalum album

<400> SEQUENCE: 77

```
atataaaagc aatagagaaa cgcactttcc cacaccatcc caccagtaag tcactttgcc        60
```

```
caagtcccta atacggtgga aagggcaaaa aaaaataacg gaaagggtaa aatatcccgc    120
aaatgtctcc gaccactgtc gccgtcgccg tcgccatcat cggagcactc tggctcctca    180
cgcgaaagcg ccggaagggg ccgggcctcc cgccaggccc acgggcctac ccgatcatcg    240
ggaacctcca catgatgggc cagctcccgc accacaacct ccgcgagctg gcccgggagt    300
acggccccat catgtcgatg cggctcggcc tcgtccccgc catcgtggtc tcctccccgg    360
aggcggcgca gctcttcctg aagacgcatg atacggtgtt cgcgagccgg ccgaagacgg    420
agacggcgaa gtacttccac tacgggatca agggtctcat cctgaccgag tacgggccgt    480
actggcgcaa catccggcgg ctgagcacgg tcaagctgct gaacgcggcg aagatcgatt    540
cgttcgcggc gatgaggcgg agcgaggtgg agaggctggt ggcgtcggtg aggggtcgg     600 cggtgcggcg ggaggtggtg gacgtgagct cgaaggtggc ggaggcaatg gagaacatgg    660
tgtgtcagat ggtgattggg aggagtgggg acgataggtt taagctgaag gagacgtttc    720
aggaggggac tcagttggcc ggagctttca attttgggga gttcgttccc tttctcctgc    780
cacttgacct tcagggaata acacggcgca taaaagaagt aagcacgagg ttcaacaaaa    840
tcttggattt aatcgtcgac gagcacatca gagacgccgc tggaaccaaa aattccggcg    900
gtcgagacag cgacaacttc ctcgacgtcc tcctttccct aatgaacacc tccatcagcg    960
actccaacga caccggcgac aacaaccgca caacgtcat tgaacgagac aacatcaaag    1020
cgatcctcac cgatatgctc ggcgccgcca tggacacctc cgccagcacc gtcgagtgga    1080
ccatctccga gctcttccgc cacccaaaaa caatgcaaaa gctccaggcc gagattcggg    1140
gtgtcgtggg cccgacccgg aacgtgtctg aagacgacct cccaaagctc acttacctgg    1200
acatggtggt gaaggagggg atgcggcttc accggcggt gccgctgctc ctcccccacg    1260
agtccctgga ggaggcgaca atcgatggtt attacattcc gaagggggtct cggatcctga    1320 tcaatgtgtg ggccatcggg cgcgacccga aggcctggcc tgatcgcccg gaggagttca    1380
tcccggagag gtttgagaaa agcaatgtgg atgtgctggg gagggatttc caactccttc    1440
cgttcggctc gggccgtaga gggtgcgccg ggattcggtt agggttgatt ttcgtgcgat    1500
tggtgctagc tcagctggtg cattgtttcg attgggagct cgcccgcaac atggcttcgt    1560
caccggagaa gttggacatg aagagaaagt tcgggctagc tgtgcataga gttaaccatt    1620
tgaaagcact gccgacttat cgcttggaat gctaaaagtt gctttctacc tatatatata    1680
cactcgctag gaaataaatg atgttttcaa atggaataat tttcttttttt aatgaaatag    1740 cataagtatt gttggttgtt atttaccaaa aaaaagaag tattgtcggt tgtttacgat    1800
ggtggtatta atgtgtttg atgcatgggt atatccatca tttatttta acttagctaa    1860 tttttgagtt attgatgtat                                                1880

<210> SEQ ID NO 78
<211> LENGTH: 1533
<212> TYPE: DNA
<213> ORGANISM: Santalum album

<400> SEQUENCE: 78
atgtctccga ccactgtcgc cgtcgccgtc gccatcatcg gagcactctg gctcctcacg     60
cgaaagcgcc ggaaggggcc gggcctcccg ccaggcccac gggcctaccc gatcatcggg    120
aacctccaca tgatgggcca gctcccgcac acaacctcc gcgagctggc ccggagtac     180 ggccccatca tgtcgatgcg gctcggcctc gtccccgcca tcgtggtctc ctccccggag    240
```

```
gcggcgcagc tcttcctgaa gacgcatgat acggtgttcg cgagccggcc gaagacggag    300
acggcgaagt acttccacta cgggatcaag ggtctcatcc tgaccgagta cgggccgtac    360
tggcgcaaca tccggcggct gagcacggtc aagctgctga acgcggcgaa gatcgattcg    420
ttcgcggcga tgaggcggag cgaggtggag aggctggtgg cgtcggtgag ggggtcggcg    480
gtgcggcggg aggtggtgga cgtgagctcg aaggtggcgg aggcaatgga gaacatggtg    540
tgtcagatgg tgattgggag gagtggggac gataggttta agctgaagga gacgtttcag    600
gaggggactc agttggccgg agctttcaat tttggggagt tcgttcccct tctcctgcca    660
cttgaccttc agggaataac acggcgcata aagaagtaa gcacgaggtt caacaaaatc    720
ttggatttaa tcgtcgacga gcacatcaga gacgccgctg gaaccaaaaa ttccggcggt    780
cgagacagcg acaacttcct cgacgtcctc ctttccctaa tgaacacctc catcagcgac    840
tccaacgaca ccggcgacaa caaccgcaac aacgtcattg aacgagacaa catcaaagcg    900
atcctcaccg atatgctcgg cgccgccatg gacacctccg ccagcaccgt cgagtggacc    960
atctccgagc tcttccgcca cccaaaaaca atgcaaaagc tccaggccga gattcggggt   1020
gtcgtgggcc cgacccggaa cgtgtctgaa gacgacctcc caaagctcac ttacctggac   1080
atggtggtga aggaggggat gcggcttcac ccggcggtgc cgctgctcct cccccacgag   1140
tccctggagg aggcgacaat cgatggttat tacattccga aggggtctcg gatcctgatc   1200
aatgtgtggg ccatcgggcg cgacccgaag gcctggcctg atcgcccgga ggagttcatc   1260
ccggagaggt ttgagaaaag caatgtggat gtgctgggga gggatttcca actccttccg   1320
ttcggctcgg gccgtagagg gtgcgccggg attcggttag ggttgatttt cgtgcgattg   1380
gtgctagctc agctggtgca ttgtttcgat tgggagctcg cccgcaacat ggcttcgtca   1440
ccggagaagt tggacatgga agagaagttc gggctagctg tgcatagagt taaccatttg   1500
aaagcactgc cgacttatcg cttggaatgc taa                                 1533
```

<210> SEQ ID NO 79
<211> LENGTH: 510
<212> TYPE: PRT
<213> ORGANISM: Santalum album

<400> SEQUENCE: 79

```
Met Ser Pro Thr Thr Val Ala Val Ala Ile Ile Gly Ala Leu
1               5                   10                  15

Trp Leu Leu Thr Arg Lys Arg Lys Gly Pro Gly Leu Pro Pro Gly
                20                  25                  30

Pro Arg Ala Tyr Pro Ile Ile Gly Asn Leu His Met Met Gly Gln Leu
            35                  40                  45

Pro His His Asn Leu Arg Glu Leu Ala Arg Glu Tyr Gly Pro Ile Met
        50                  55                  60

Ser Met Arg Leu Gly Leu Val Pro Ala Ile Val Val Ser Ser Pro Glu
65                  70                  75                  80

Ala Ala Gln Leu Phe Leu Lys Thr His Asp Thr Val Phe Ala Ser Arg
                85                  90                  95

Pro Lys Thr Glu Thr Ala Lys Tyr Phe His Tyr Gly Ile Lys Gly Leu
            100                 105                 110

Ile Leu Thr Glu Tyr Gly Pro Tyr Trp Arg Asn Ile Arg Arg Leu Ser
        115                 120                 125

Thr Val Lys Leu Leu Asn Ala Ala Lys Ile Asp Ser Phe Ala Ala Met
    130                 135                 140
```

```
Arg Arg Ser Glu Val Glu Arg Leu Val Ala Ser Val Arg Gly Ser Ala
145                 150                 155                 160

Val Arg Arg Glu Val Val Asp Val Ser Ser Lys Val Ala Glu Ala Met
                165                 170                 175

Glu Asn Met Val Cys Gln Met Val Ile Gly Arg Ser Gly Asp Asp Arg
            180                 185                 190

Phe Lys Leu Lys Glu Thr Phe Gln Glu Gly Thr Gln Leu Ala Gly Ala
        195                 200                 205

Phe Asn Phe Gly Glu Phe Val Pro Phe Leu Leu Pro Leu Asp Leu Gln
210                 215                 220

Gly Ile Thr Arg Arg Ile Lys Glu Val Ser Thr Arg Phe Asn Lys Ile
225                 230                 235                 240

Leu Asp Leu Ile Val Asp Glu His Ile Arg Asp Ala Ala Gly Thr Lys
                245                 250                 255

Asn Ser Gly Gly Arg Asp Ser Asp Asn Phe Leu Asp Val Leu Leu Ser
            260                 265                 270

Leu Met Asn Thr Ser Ile Ser Asp Ser Asn Asp Thr Gly Asp Asn Asn
        275                 280                 285

Arg Asn Asn Val Ile Glu Arg Asp Asn Ile Lys Ala Ile Leu Thr Asp
290                 295                 300

Met Leu Gly Ala Ala Met Asp Thr Ser Ala Ser Thr Val Glu Trp Thr
305                 310                 315                 320

Ile Ser Glu Leu Phe Arg His Pro Lys Thr Met Gln Lys Leu Gln Ala
                325                 330                 335

Glu Ile Arg Gly Val Val Gly Pro Thr Arg Asn Val Ser Glu Asp Asp
            340                 345                 350

Leu Pro Lys Leu Thr Tyr Leu Asp Met Val Val Lys Glu Gly Met Arg
        355                 360                 365

Leu His Pro Ala Val Pro Leu Leu Pro His Glu Ser Leu Glu Glu
370                 375                 380

Ala Thr Ile Asp Gly Tyr Tyr Ile Pro Lys Gly Ser Arg Ile Leu Ile
385                 390                 395                 400

Asn Val Trp Ala Ile Gly Arg Asp Pro Lys Ala Trp Pro Asp Arg Pro
                405                 410                 415

Glu Glu Phe Ile Pro Glu Arg Phe Glu Lys Ser Asn Val Asp Val Leu
            420                 425                 430

Gly Arg Asp Phe Gln Leu Leu Pro Phe Gly Ser Gly Arg Arg Gly Cys
        435                 440                 445

Ala Gly Ile Arg Leu Gly Leu Ile Phe Val Arg Leu Val Leu Ala Gln
450                 455                 460

Leu Val His Cys Phe Asp Trp Glu Leu Ala Arg Asn Met Ala Ser Ser
465                 470                 475                 480

Pro Glu Lys Leu Asp Met Glu Glu Lys Phe Gly Leu Ala Val His Arg
                485                 490                 495

Val Asn His Leu Lys Ala Leu Pro Thr Tyr Arg Leu Glu Cys
            500                 505                 510
```

<210> SEQ ID NO 80
<211> LENGTH: 1555
<212> TYPE: DNA
<213> ORGANISM: Artificial Sequence
<220> FEATURE:
<223> OTHER INFORMATION: SaCP120292, optimized cDNA encoding for N-term modified SaCP10374

<400> SEQUENCE: 80

```
aggaggtaaa acatatggca ctgctgctgg ctgtcttttg gagcgcactg attattctga      60
cccgcaaacg ccgcaaaggt ccgggtctgc caccgggtcc gcgtgcgtac ccgattattg     120
gcaatctgca catgatgggc cagctgccac accacaattt gcgtgagctg cacgtgagt     180
atggtccgat tatgagcatg cgcctgggtc tggtgccggc aatcgtggtt agctctcctg     240
aggctgcgca gctgttcctc aagacgcatg ataccgtttt cgcgagccgt ccaaagaccg     300
agactgccaa atacttccat tacggtatca aggtctgat cctgaccgag tatggcccgt     360
actggcgcaa tattcgtcgt ttgagcaccg ttaagctgtt gaatgccgcg aaaatcgata     420
gcttcgcggc tatgcgtaga agcgaagttg aacgcctggt cgcgtccgtt cgtggttcgg     480
cggttcgtcg tgaggttgtg gacgtcagca gcaaagtggc ggaagctatg gagaatatgg     540
tctgccagat ggttatcggc cgttcaggtg acgatcgttt taagctgaaa gaaacctttc     600
aagagggcac ccaactggca ggcgcgttca attttggtga gtttgtgccg tttctgctgc     660
cgctggactt gcaaggtatt acccgtcgca tcaaagaagt cagcactcgt ttcaataaga     720
ttttggacct gatcgttgac gagcacattc gcgatgccgc tggtaccaaa acagcggcg     780
gtcgtgatag cgacaatttt ctggatgttc tgctgtcctt gatgaacacc tctattagcg     840
atagcaatga cacgggtgac aacaaccgta caacgtgat cgagcgtgat aacattaaag     900
cgatcctgac ggacatgctg ggtgcagcga tggacacgag cgcgagcacg tcgagtggaa     960
cgatctccga actgtttcgc caccgaaaa ccatgcagaa gctgcaagca gaaatccgtg    1020
gtgtcgtggg cccgacccgc aatgtgagcg aagatgactt gccgaagctg acctatctgg    1080
acatggtcgt taaggaaggc atgcgtttgc atccggccgt gccgctgctt ctgccgcatg    1140
agtctctgga agaagccacg atcgatggct actacattcc gaagggttcc cgcattctga    1200
tcaacgtctg ggcgattggt cgcgacccga aggcctggcc ggatcgtcct gaagagttca    1260
tcccggagcg tttcgagaaa agcaacgtgg atgtgctggg ccgtgacttc agctgctgc    1320
cgtttggttc gggtcgtcgc ggttgtgcag gcattcgcct gggcctgatc ttcgtacgtc    1380
tggttctggc acagttagtt cactgtttcg actgggaact ggcgcgcaac atggcgagca    1440
gcccggagaa gttggatatg gaagagaagt tcggcctggc ggtgcatcgt gtcaaccacc    1500
tgaaagccct gccgacgtat cgtctggagt gctaagtcga caccatggaa agctt    1555
```

<210> SEQ ID NO 81
<211> LENGTH: 506
<212> TYPE: PRT
<213> ORGANISM: Artificial Sequence
<220> FEATURE:
<223> OTHER INFORMATION: SaCP10374opt, N-terminal modified, amino acid
      sequence

<400> SEQUENCE: 81

Met Ala Leu Leu Leu Ala Val Phe Trp Ser Ala Leu Ile Ile Leu Thr
1               5                   10                  15

Arg Lys Arg Arg Lys Gly Pro Gly Leu Pro Pro Gly Pro Arg Ala Tyr
                20                  25                  30

Pro Ile Ile Gly Asn Leu His Met Met Gly Gln Leu Pro His His Asn
            35                  40                  45

Leu Arg Glu Leu Ala Arg Glu Tyr Gly Pro Ile Met Ser Met Arg Leu
        50                  55                  60

Gly Leu Val Pro Ala Ile Val Val Ser Ser Pro Glu Ala Ala Gln Leu
65                  70                  75                  80

```
Phe Leu Lys Thr His Asp Thr Val Phe Ala Ser Arg Pro Lys Thr Glu
                85                  90                  95
Thr Ala Lys Tyr Phe His Tyr Gly Ile Lys Gly Leu Ile Leu Thr Glu
            100                 105                 110
Tyr Gly Pro Tyr Trp Arg Asn Ile Arg Arg Leu Ser Thr Val Lys Leu
        115                 120                 125
Leu Asn Ala Ala Lys Ile Asp Ser Phe Ala Ala Met Arg Arg Ser Glu
    130                 135                 140
Val Glu Arg Leu Val Ala Ser Val Arg Gly Ser Ala Val Arg Arg Glu
145                 150                 155                 160
Val Val Asp Val Ser Ser Lys Val Ala Glu Ala Met Glu Asn Met Val
                165                 170                 175
Cys Gln Met Val Ile Gly Arg Ser Gly Asp Asp Arg Phe Lys Leu Lys
            180                 185                 190
Glu Thr Phe Gln Glu Gly Thr Gln Leu Ala Gly Ala Phe Asn Phe Gly
        195                 200                 205
Glu Phe Val Pro Phe Leu Leu Pro Leu Asp Leu Gln Gly Ile Thr Arg
    210                 215                 220
Arg Ile Lys Glu Val Ser Thr Arg Phe Asn Lys Ile Leu Asp Leu Ile
225                 230                 235                 240
Val Asp Glu His Ile Arg Asp Ala Ala Gly Thr Lys Asn Ser Gly Gly
                245                 250                 255
Arg Asp Ser Asp Asn Phe Leu Asp Val Leu Leu Ser Leu Met Asn Thr
            260                 265                 270
Ser Ile Ser Asp Ser Asn Asp Thr Gly Asp Asn Arg Asn Asn Val
        275                 280                 285
Ile Glu Arg Asp Asn Ile Lys Ala Ile Leu Thr Asp Met Leu Gly Ala
    290                 295                 300
Ala Met Asp Thr Ser Ala Ser Thr Val Glu Trp Thr Ile Ser Glu Leu
305                 310                 315                 320
Phe Arg His Pro Lys Thr Met Gln Lys Leu Gln Ala Glu Ile Arg Gly
                325                 330                 335
Val Val Gly Pro Thr Arg Asn Val Ser Glu Asp Asp Leu Pro Lys Leu
            340                 345                 350
Thr Tyr Leu Asp Met Val Val Lys Glu Gly Met Arg Leu His Pro Ala
        355                 360                 365
Val Pro Leu Leu Leu Pro His Glu Ser Leu Glu Glu Ala Thr Ile Asp
    370                 375                 380
Gly Tyr Tyr Ile Pro Lys Gly Ser Arg Ile Leu Ile Asn Val Trp Ala
385                 390                 395                 400
Ile Gly Arg Asp Pro Lys Ala Trp Pro Asp Arg Pro Glu Glu Phe Ile
                405                 410                 415
Pro Glu Arg Phe Glu Lys Ser Asn Val Asp Val Leu Gly Arg Asp Phe
            420                 425                 430
Gln Leu Leu Pro Phe Gly Ser Gly Arg Arg Gly Cys Ala Gly Ile Arg
        435                 440                 445
Leu Gly Leu Ile Phe Val Arg Leu Val Leu Ala Gln Leu Val His Cys
    450                 455                 460
Phe Asp Trp Glu Leu Ala Arg Asn Met Ala Ser Ser Pro Glu Lys Leu
465                 470                 475                 480
Asp Met Glu Glu Lys Phe Gly Leu Ala Val His Arg Val Asn His Leu
                485                 490                 495
Lys Ala Leu Pro Thr Tyr Arg Leu Glu Cys
```

<210> SEQ ID NO 82
<211> LENGTH: 3693
<212> TYPE: DNA
<213> ORGANISM: Artificial Sequence
<220> FEATURE:
<223> OTHER INFORMATION: SaCP10374-CPRm, synthetic operon encoding for SaCP10374 and CPRm

<400> SEQUENCE: 82

```
catatggcac tgctgctggc tgtcttttgg agcgcactga ttattctgac cgcaaacgc      60
cgcaaaggtc cgggtctgcc accgggtccg cgtgcgtacc cgattattgg caatctgcac    120
atgatgggcc agctgccaca ccacaatttg cgtgagctgg cacgtgagta tggtccgatt    180
atgagcatgc gcctgggtct ggtgccggca atcgtggtta gctctcctga ggctgcgcag    240
ctgttcctca agacgcatga taccgttttc gcgagccgtc aaagaccga gactgccaaa     300
tacttccatt acggtatcaa aggtctgatc ctgaccgagt atggcccgta ctggcgcaat    360
attcgtcgtt tgagcaccgt taagctgttg aatgccgcga aaatcgatag cttcgcggct    420
atgcgtagaa gcgaagttga acgcctggtc gcgtccgttc gtggttcggc ggttcgtcgt    480
gaggttgtgg acgtcagcag caaagtggcg gaagctatgg agaatatggt ctgccagatg    540
gttatcggcc gttcaggtga cgatcgtttt aagctgaaag aaacctttca agagggcacc    600
caactggcag gcgcgttcaa ttttggtgag tttgtgccgt ttctgctgcc gctggacttg    660
caaggtatta cccgtcgcat caaagaagtc agcactcgtt tcaataagat tttggacctg    720
atcgttgacg agcacattcg cgatgccgct ggtaccaaaa acagcggcgg tcgtgatagc    780
gacaattttc tggatgttct gctgtccttg atgaacacct ctattagcga tagcaatgac    840
acgggtgaca acaaccgtaa caacgtgatc gagcgtgata acattaaagc gatcctgacg    900
gacatgctgg gtgcagcgat ggacacgagc gcgagcacgg tcgagtggac gatctccgaa    960
ctgtttcgcc acccgaaaac catgcagaag ctgcaagcag aaatccgtgg tgtcgtgggc   1020
ccgacccgca atgtgagcga agatgacttg ccgaagctga cctatctgga catggtcgtt   1080
aaggaaggca tgcgtttgca tccggccgtg ccgctgcttc tgccgcatga gtctctggaa   1140
gaagccacga tcgatggcta ctacattccg aagggttccc gcattctgat caacgtctgg   1200
gcgattggtc gcgacccgaa ggcctggcg atcgtcctg aagagttcat cccggagcgt   1260
ttcgagaaaa gcaacgtgga tgtgctgggc cgtgacttcc agctgctgcc gtttggttcg   1320
ggtcgtcgcg gttgtgcagg cattcgcctg ggcctgatct tcgtacgtct ggttctggca   1380
cagttagttc actgtttcga ctgggaactg gcgcgcaaca tggcgagcag cccggagaag   1440
ttggatatgg aagagaagtt cggcctggcg gtgcatcgtg tcaaccacct gaaagccctg   1500
ccgacgtatc gtctggagtg ctaagtcgac taactttaag aaggagatat atccatggaa   1560
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga agcagccga accggaggag gcagaggatg ataaaaccaa gatcagcgtg   1860
ttttcggca cccaaaccgg tacgcagaa ggtttcgcga aggcttttgt tgaagaggcc   1920
aaggcgcgtt atcagcaggc ccgtttcaaa gttatcgacc tggacgacta tgcggcagac   1980
```

```
gatgacgagt acgaagagaa actgaagaag gaaaacttgg cattcttctt cttggcgtcc    2040
tacggtgacg gcgagccgac ggacaacgcg gcacgctttt acaaatggtt tacggagggt    2100
aaggaccgtg gtgaatggct gaacaatctg cagtacggcg ttttttggtct gggtaaccgt   2160 caatatgagc atttcaataa gatcgccatt gtcgtcgatg atctgatctt cgagcaaggt    2220
ggcaagaagc tggttccggt gggtctgggt gacgatgacc agtgcattga ggatgatttt    2280
gcggcgtggc gtgaactggt ctggccggaa ctggataaac tgctgcgtaa cgaagacgac    2340
gctaccgtgg caaccccgta cagcgccgct gtgctgcaat accgcgtggt tttccacgat    2400
cacattgacg gcctgattag cgaaaacggt agcccgaacg gtcatgctaa tggcaatacc    2460
gtgtacgatg cgcaacaccc gtgccgtagc aacgtcgcgg tcaagaagga attgcatact    2520
ccggcgagcg atcgcagctg cacccacctg gaatttaaca ttagcggtac cggcctgatg    2580
tacgagacgg gtgaccacgt cggtgtgtat tgcgagaacc tgttggaaac cgtggaggag    2640
gccgagaagt tgttgaacct gagcccgcag acgtacttct ccgttcacac cgacaacgag    2700
gacggtacgc cgttgagcgg cagcagcctg ccgccaccgt ttccgccgtg caccttgcgc    2760
acggcattga ccaaatacgc agacttgact tctgcaccga aaaagtcggt gctggtggcg    2820
ctggccgagt acgcatctga ccagggtgaa gcggatcgtt tgcgtttctt ggcgagcccg    2880
agcggcaaag aggaatatgc acagtacatc ttggcaagcc agcgcacgct gctggaggtc    2940
atggcggagt cccgtcggc gaaaccgccg ctgggtgtct ttttcgcggg tgtcgctccg    3000
cgcctgcagc gcgtttcta ttccattagc tctagcccga agatcgcacc gttccgtatt    3060
cacgtgacct gcgccctggt ttatgacaaa tcccctaccg gtcgcgttca taagggcatc    3120
tgtagcacgt ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggccct tttcgtggct ttttgcaaga gcgcttggcg    3300
ttgaaagaga gcggtgctga attgggtccg gcgatcttgt tctttggttg ccgtaaccgt    3360
aaaatggact ttatttacga ggatgaactg aatgatttcg tcaaagcggg cgttgtcagc    3420
gagctgatcg tcgcttttag ccgcgaaggc ccgatgaaag aatacgtgca acacaaaatg    3480
agccaacgtg cctccgatgt gtggaacatc attagcgacg gtggttatgt ttatgtttgc    3540
ggtgacgcga agggtatggc tcgtgatgtt caccgtaccc tgcataccat cgcacaggag    3600
caaggtagca tgtccagctc ggaggccgaa ggtatggtca aaaacctgca aaccaccggt    3660
cgttacctgc gtgatgtgtg gtaataaaag ctt                                 3693
```

<210> SEQ ID NO 83
<211> LENGTH: 5339
<212> TYPE: DNA
<213> ORGANISM: Artificial Sequence
<220> FEATURE:
<223> OTHER INFORMATION: SaCP816-CPRm-SaTPs647, synthetic operon encoding for SaCP816, CPRm and a sesquisabiene B synthase

<400> SEQUENCE: 83

```
catatggcac tgttgttggc ggttttctgg agcgctttga ttattctggt tagcatcttg    60
ttgcgtcgtc gtcaaaaacg caacaatttg ccaccgggcc caccggccct gccgatcatc    120
ggtaacattc acattctggg caccctgccg caccagagcc tgtacaatct ggcgaagaag    180
tacggtccga tcgtgtccat gcgttttggc ttggttccgg cggtggtcat cagcagcccg    240
gaagcggccg agctggtcct gaaaacccac gacatcgttt ttgcttctcg ccctcgtctg    300
```

```
caagttgcag attactttca ctatggcacc aaaggcgtga ttctgaccga atatggtacc    360
tactggcgta acatgcgtcg cctgtgcacg gtcaaactgc tgaacaccgt taagattgat    420
agctttgcag gcacccgcaa gaaagaagtc gctagcttcg ttcagagcct gaaagaagca    480
agcgtggcgc acaaaatggt taacctgtcc gcacgcgtcg ctaatgttat tgagaatatg    540
gtttgtctga tggttattgg tagatcgtct gacgagcgtt tcaagctgaa agaagtgatc    600
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta agatcatga cgatgagcag    780
catggtgact tcatcgacgt gctgctggcg atgatgaata agccgatgga ttctcgtgag    840
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag ttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc gacctaccg tctggagagc   1500
taagtcgact aactttaaga aggagatata tccatggaac ctagctctca gaaactgtct   1560
ccgttggaat tgttgctgc tatcctgaag ggcgactaca gcagcggtca ggttgaaggt   1620
ggtccaccgc aggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt ttttcggcac ccaaaccggt   1860
acggcagaag gttcgcgaaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
```

```
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggccccett ttcgtggctt tttgcaagag cgcttggcgt tgaaagagag cggtgctgaa   3300
ttgggtccgg cgatcttgtt cttttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga gccaacgtgc ctccgatgtg   3480
tggaacatca ttagcgacgg tggttatgtt tatgtttgcg gtgacgcgaa gggtatggct   3540
cgtgatgttc accgtacccct gcataccatc gcacaggagc aaggtagcat gtccagctcg   3600
gaggccgaag gtatggtcaa aaacctgcaa accaccggtc gttacctgcg tgatgtgtgg   3660
taataaaagc ttaggaggta aaaatggcga ccgttgtgga tgattctagc gtcgttcgtc   3720
gttctgcaaa ctaccgccg aatttgtggg actatgagtt cctgcaatcc ctgggtgacc   3780
agtgtacggt cgaagaaaaa cacctgaagc tggccgacaa gttgaaagaa gaagtaaat   3840
ccctgattaa acagacgatg gagccgctgg caaaactgga gttcatcgat accgtgcgtc   3900
gtttgggttt gaaatatcag tttgagaccg aggtgaagga ggccgttgtt atggttagca   3960
aatatgagaa tgatgcgtgg tggattgata atctgcacgc taccagcctg cgtttccgca   4020
tcatgcgtga gaatggtatc ttcgtgccgc aagatgtgtt tgaacgtttc aaagataccg   4080
acggctttaa aaaccaactg tgcgaagacg tgaagggtct gttgtctctg tatgaggcga   4140
gctttctggg ttgggagggc gaggatatct tggatgaggc acgcaccttt gcgaccagca   4200
agctgaagag cattgaaggc aaaattccga gcccgagcct ggctaagaaa gtgagccacg   4260
cgctggactt gcctctgcac tggcgtacca ttcgctacga agcgcgctgg ttcatcgaca   4320
cctacggtga agaagaggac gtgaatctga cgttgctgcg ttacgccaaa ctggacttca   4380
acattgttca atcttttac caaaagaga tcggccgtct gtcccgctgg tgggtgggta   4440
ctggcctgga taaaatgccg tttgctcgta atggtctgat tcagagctat atgtacgcaa   4500
ttggtatgct gttcgagcct aacctggcg aggtgcgtga gatggaggcg aaggtcggcg   4560
ccttgattac cacgatcgac gacgtgtatg acgtttacgg cacgatggag gagttggagc   4620
tgttcaccga tattaccaat cgttgggaca tcagcaaagc ggatcaactg ccgcgtaaca   4680
tccgcatgcc gctgctgacg atgttcaaca ccagcaatga tatcggttat tgggctctga   4740
aagagcgtgg tttcaatggc attccgtgta ccgcaaaagt ctggtccgac caactgaaga   4800
gctacaccaa ggaggctaaa tggttccacg aaggccataa accgactctg gaggagtatc   4860
tggacaatgc gctggtcagc atcggcttcc cgaacctgct ggtcacgtct tatctgttga   4920
ccgttgagaa tccgaccaaa gaaaagctgg actatgtgaa cagcctgccg ttgttcgttc   4980
gcgcgagctg catcctgtgt cgtatcatta acgatctggg tacgagcccg gatgaaatgg   5040
```

```
agcgtggtga caatctgaaa agcatccagt gctatatgaa cgaaaccggt gcgagccaag    5100
aggttgcgcg tgagcacatc gaaggcctgg ttcgtatgtg gtggaaacgt ctgaacaagt    5160
gcctgtttga gccgagcccg ttcactgagc cgttcctgag ctttacgatt aacgtggtcc    5220
gtggtagcca cttttcctat cagtacggcg atggctacgg caacgcagag agctggacca    5280
agaaccaggg tatgtcggtg ctgatccacc cgattaccct ggatgaagag taagaattc     5339

<210> SEQ ID NO 84
<211> LENGTH: 5360
<212> TYPE: DNA
<213> ORGANISM: Artificial Sequence
<220> FEATURE:
<223> OTHER INFORMATION: SaCP10374-CPRm-saTPs647, synthetic operon
      encoding for SaCP10374, CPRm and a sesquisabiene B synthase

<400> SEQUENCE: 84
catatggcac tgctgctggc tgtcttttgg agcgcactga ttattctgac ccgcaaacgc      60
cgcaaaggtc cgggtctgcc accgggtccg cgtgcgtacc cgattattgg caatctgcac     120
atgatgggcc agctgccaca ccacaatttg cgtgagctgg cacgtgagta tggtccgatt     180
atgagcatgc gcctgggtct ggtgccggca atcgtggtta gctctcctga ggctgcgcag     240
ctgttcctca agacgcatga taccgttttc gcgagccgtc aaagaccgga gactgccaaa     300
tacttccatt acggtatcaa aggtctgatc ctgaccgagt atggcccgta ctggcgcaat     360
attcgtcgtt tgagcaccgt taagctgttg aatgccgcga aaatcgatag cttcgcggct     420
atgcgtagaa gcgaagttga acgcctggtc gcgtccgttc gtggttcggc ggttcgtcgt     480
gaggttgtgg acgtcagcag caaagtggcg gaagctatgg agaatatggt ctgccagatg     540
gttatcggcc gttcaggtga cgatcgtttt aagctgaaag aaaccttcca agagggcacc     600
caactggcag gcgcgttcaa ttttggtgag tttgtgccgt ttctgctgcc gctggacttg     660
caaggtatta cccgtcgcat caaagaagtc agcactcgtt tcaataagat tttggacctg     720
atcgttgacg agcacattcg cgatgccgct ggtaccaaaa acagcggcgg tcgtgatagc     780 gacaatttc tggatgttct gctgtccttg atgaacacct ctattagcga tagcaatgac     840
acgggtgaca acaaccgtaa caacgtgatc gagcgtgata acattaaagc gatcctgacg     900
gacatgctgg tgcagcgat ggacacgagc gcgagcacgg tcgagtggac gatctccgaa     960
ctgtttcgcc acccgaaaac catgcagaag ctgcaagcag aaatccgtgg tgtcgtgggc    1020
ccgacccgca atgtgagcga agatgacttg ccgaagctga cctatctgga catggtcgtt    1080
aaggaaggca tgcgtttgca tccggccgtg ccgctgcttc tgccgcatga gtctctggaa    1140
gaagccacga tcgatggcta ctacattccg aagggttccc gcattctgat caacgtctgg    1200
gcgattggtc gcgacccgaa ggcctggcg atcgtcctg aagagttcat cccggagcgt    1260
ttcgagaaaa gcaacgtgga tgtgctgggc cgtgacttcc agctgctgcc gtttggttcg    1320
ggtcgtcgcg gttgtgcagg cattcgcctg ggcctgatct tcgtacgtct ggttctggca    1380
cagttagttc actgtttcga ctgggaactg gcgcgcaaca tggcgagcag cccggagaag    1440
ttggatatgg aagagaagtt cggcctggcg gtgcatcgtg tcaaccacct gaaagccctg    1500
ccgacgtatc gtctggagag ctaagtcgac taactttaag aaggagatat atccatggaa    1560
cctagctctc agaaactgtc tccgttggaa tttgttgctg ctatcctgaa gggcgactac    1620
agcagcggtc aggttgaagg tggtccaccg ccaggtctgg cagctatgtt gatgaaaaat    1680
aaggatttgg tgatggttct gacgacgtcc gtggcagtcc tgatcggctg tgtcgtggtc    1740
```

```
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
tttttcggca cccaaaccgg tacggcagaa ggtttcgcga aggcttttgt tgaagaggcc   1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacgagggt    2100 aaggaccgtg gtgaatggct gaacaatctg cagtacggcg ttttttggtct gggtaaccgt   2160 caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaagtcggt gctggtggcg   2820 ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct ttttcgcggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct ttttgcaaga gcgcttggcg   3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaaatggcg accgttgtgg   3720
atgattctag cgtcgttcgt cgttctgcaa actacccgcc gaatttgtgg gactatgagt   3780
tcctgcaatc cctgggtgac cagtgtacgg tcgaagaaaa acacctgaag ctggccgaca   3840
agttgaaaga agaagttaaa tccctgatta acagacgat ggagccgctg gcaaaactgg    3900
agttcatcga taccgtgcgt cgtttgggtt tgaaatatca gtttgagacc gaggtgaagg   3960
aggccgttgt tatggttagc aaatatgaga atgatgcgtg gtggattgat aatctgcacg   4020
ctaccagcct gcgtttccgc atcatgcgtg agaatgtat cttcgtgccg caagatgtgt    4080
ttgaacgttt caaagatacc gacggcttta aaaaccaact gtgcgaagac gtgaagggtc   4140
```

```
tgttgtctct gtatgaggcg agctttctgg gttgggaggg cgaggatatc ttggatgagg    4200
cacgcacctt tgcgaccagc aagctgaaga gcattgaagg caaaattccg agcccgagcc    4260
tggctaagaa agtgagccac gcgctggact tgcctctgca ctggcgtacc attcgctacg    4320
aagcgcgctg gttcatcgac acctacggtg aagaagagga cgtgaatctg acgttgctgc    4380
gttacgccaa actggacttc aacattgttc aatctttta ccaaaaagag atcggccgtc    4440
tgtcccgctg gtgggtgggt actggcctgg ataaaatgcc gtttgctcgt aatggtctga    4500
ttcagagcta tatgtacgca attggtatgc tgttcgagcc taacctgggc gaggtgcgtg    4560
agatggaggc gaaggtcggc gccttgatta ccacgatcga cgacgtgtat gacgtttacg    4620
gcacgatgga ggagttggag ctgttcaccg atattaccaa tcgttgggac atcagcaaag    4680
cggatcaact gccgcgtaac atccgcatgc cgctgctgac gatgttcaac accagcaatg    4740
atatcggtta ttgggctctg aaagagcgtg gtttcaatgg cattccgtgt accgcaaaag    4800
tctggtccga ccaactgaag agctacacca aggaggctaa atggttccac gaaggccata    4860
aaccgactct ggaggagtat ctggacaatg cgctggtcag catcggcttc ccgaacctgc    4920
tggtcacgtc ttatctgttg accgttgaga atccgaccaa agaaaagctg gactatgtga    4980
acagcctgcc gttgttcgtt cgcgcgagct gcatcctgtg tcgtatcatt aacgatctgg    5040
gtacgagccc ggatgaaatg gagcgtggtg acaatctgaa aagcatccag tgctatatga    5100
acgaaaccgg tgcgagccaa gaggttgcgc gtgagcacat cgaaggcctg gttcgtatgt    5160
ggtggaaacg tctgaacaag tgcctgtttg agccgagccc gttcactgag ccgttcctga    5220
gctttacgat taacgtggtc cgtggtagcc actttttcta tcagtacggc gatggctacg    5280
gcaacgcaga gagctggacc aagaaccagg gtatgtcggt gctgatccac ccgattaccc    5340
tggatgaaga gtaagaattc                                                5360

<210> SEQ ID NO 85
<211> LENGTH: 5420
<212> TYPE: DNA
<213> ORGANISM: Artificial Sequence
<220> FEATURE:
<223> OTHER INFORMATION: SaCP816-CPRm-SaTPs30, synthetic operon encoding
      for SaCP816, CPRm and a Beta-bisabolene synthase

<400> SEQUENCE: 85
catatggcac tgttgttggc ggttttctgg agcgctttga ttattctggt tagcatctta     60
ttgcgtcgtc gtcaaaaacg caacaatttg ccaccgggcc caccggccct gccgatcatc    120
ggtaacattc acattctggg caccctgccg caccagagcc tgtacaatct ggcgaagaag    180
tacggtccga tcatgtccat gcgtttgggc ttggttccgg cggtggtcat cagcagcccg    240
gaagcggccg agctggtcct gaaaacccac gacatcgttt ttgcttctcg ccctcgtctg    300
caagttgcag attactttca ctatggcacc aaaggcgtga ttctgaccga atatggtacc    360
tactggcgta acatgcgtcg cctgtgcacg gtcaaactgc tgaacaccgt taagattgat    420
agctttgcag gcaccgcaa gaaagaagtc gctagcttcg ttcagagcct gaaagaagca    480
agcgtggcgc acaaaatggt taacctgtcc gcacgcgtcg ctaatgttat tgagaatatg    540
gtttgtctga tggttattgg tagatcgtct gacgagcgtt tcaagctgaa agaagtgatc    600
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta agatcatga cgatgagcag    780
```

```
catggtgact tcatcgacgt gctgctggcg atgatgaata agccgatgga ttctcgtgag      840
ggtctgtcca tcattgatcg cacgaacatt aaagcgatcc tggtggatat gatcggtgcc      900
gcgatggaca cgagcaccag cggtgtggag tgggcgattt cggagctgat taagcatcct      960
cgtgtcatga agaaactgca agacgaagtg aaaaccgtaa tcggtatgaa ccgcatggtg     1020
gaagaagcgg atctgccgaa actgccgtac ctggacatgg ttgtcaagga acgatgcgt     1080
ctgcatccgc caggcccgct gctggtgccg cgtgaaagca tggaagatat tacgatcaac     1140
ggttactata tcccgaagaa atcccgcatt attgtgaatg catgggcgat cggccgtgac     1200
accaacgcct ggagcaataa tgcgcacgag ttttccctg agcgttttat gagctctaac     1260
gttgatctgc aaggccagga cttccagctg atcccgttcg gtagcggtcg tcgcggttgt     1320
ccgggcatgc gtctgggtct gacgacggtc cgcttggtgc tggcccaact gattcactgc     1380
ttcgacctgg agcttccgaa gggcaccgtc gcgactgacc tggatatgag cgagaagttt     1440
ggtctggcaa tgccgcgtgc gcagcactta ctggcctttc cgacctaccg tctggagagc     1500
taagtcgact aactttaaga aggagatata ccatggaac ctagctctca gaaactgtct      1560
ccgttggaat ttgttgctgc tatcctgaag ggcgactaca gcagcggtca ggttgaaggt     1620
ggtccaccgc caggtctggc agctatgttg atggaaaata aggatttggt gatggttctg     1680
acgacgtccg tggcagtcct gatcggctgt gtcgtggtcc tggcatggcg tcgtgcggca     1740
ggtagcggta agtacaagca acctgaactg cctaaactgg tggtcccgaa agcagccgaa     1800
ccggaggagg cagaggatga taaaaccaag atcagcgtgt ttttcggcac ccaaaccggt     1860
acggcagaag gtttcgcgaa ggcttttgtt gaagaggcca aggcgcgtta tcagcaggcc     1920
cgtttcaaag ttatcgacct ggacgactat gcggcagacg atgacgagta cgaagagaaa     1980
ctgaagaagg aaaacttggc attcttcttc ttggcgtcct acggtgacgg cgagccgacg     2040
gacaacgcgg cacgctttta caaatggttt acggagggta aggaccgtgg tgaatggctg     2100
aacaatctgc agtacggcgt ttttggtctg ggtaaccgtc aatatgagca tttcaataag     2160
atcgccattg tcgtcgatga tctgatcttc agcaaggtg gcaagaagct ggttccggtg     2220
ggtctgggtg acgatgacca gtgcattgag atgattttg cggcgtggcg tgaactggtc     2280
tggccggaac tggataaact gctgcgtaac gaagacgacg ctaccgtggc aaccccgtac     2340
agcgccgctg tgctgcaata ccgcgtggtt ttccacgatc acattgacgg cctgattagc     2400
gaaaacggta gcccgaacgg tcatgctaat ggcaataccg tgtacgatgc gcaacacccg     2460
tgccgtagca acgtcgcggt caagaaggaa ttgcatactc cggcgagcga tcgcagctgc     2520
acccacctgg aatttaacat tagcggtacc ggcctgatgt acgagacggg tgaccacgtc     2580
ggtgtgtatt gcgagaacct gttggaaacc gtggaggagg ccgagaagtt gttgaacctg     2640
agcccgcaga cgtacttctc cgttcacacc gacaacgagg acggtacgcc gttgagcggc     2700
agcagcctgc cgccaccgtt tccgccgtgc accttgcgca cggcattgac caaatacgca     2760
gacttgactt ctgcaccgaa aaagtcggtg ctggtggcgc tggccgagta cgcatctgac     2820
cagggtgaag cggatcgttt gcgtttcttg gcgagcccga gcggcaaaga ggaatatgca     2880
cagtacatct tggcaagcca gcgcacgctg ctggaggtca tggcggagtt cccgtcggcg     2940
aaaccgccgc tgggtgtctt tttcgcgggt gtcgctccgc gcctgcagcc gcgtttctat     3000
tccattagct ctagcccgaa gatcgcaccg ttccgtattc acgtgacctg cgccctggtt     3060
tatgacaaat cccctaccgg tcgcgttcat aagggcatct gtagcacgtg gatgaaaaat     3120
```

```
gcggtcccgc tggaagaaag caacgattgt tcctgggctc cgatcttcgt ccgcaacagc    3180
aacttcaagc tgccgaccga cccgaaggtt ccgattatca tgattggtcc gggtaccggt    3240
ctggccccct ttcgtggctt tttgcaagag cgcttggcgt tgaaagagag cggtgctgaa    3300
ttgggtccgg cgatcttgtt ctttggttgc cgtaaccgta aaatggactt tatttacgag    3360
gatgaactga atgatttcgt caaagcgggc gttgtcagcg agctgatcgt cgcttttagc    3420
cgcgaaggcc cgatgaaaga atacgtgcaa cacaaaatga ccaacgtgc ctccgatgtg    3480 tggaacatca ttagcgacgg tggttatgtt tatgtttgcg gtgacgcgaa gggtatggct    3540
cgtgatgttc accgtaccct gcataccatc gcacaggagc aaggtagcat gtccagctcg    3600
gaggccgaag gtatggtcaa aaacctgcaa accaccggtc gttacctgcg tgatgtgtgg    3660
taataaaagc ttaggaggta aaaatggacg cattcgcaac gagcccgacc agcgcactga    3720
ttaaggcggt taactgcatc gcgcacgtga ccccgatggc aggtgaagat tcctccgaaa    3780
accgccgtgc atcgaactac aaaccgagca cctgggacta tgaatttctg caaagcctgg    3840
ccacgagcca taacaccgtc caggaaaagc acatgaagat ggctgagaaa ttgaaggaag    3900
aggtgaagag catgatcaag ggtcagatgg agccggtggc gaagttggaa ctgatcaaca    3960
tcctgcagcg tctgggtttg aaatatcgct ttgaatccga gatcaaggaa gagctgttt     4020 ccctgtacaa ggacggtact gatgcgtggt gggttgataa tctgcatgca acggcgctgc    4080
gttttagact gctgcgcgag aatggtattt tcgtgccgca agaagtattc gaaactttaa    4140
aggataagag cggtaagttt aagagccagc tgtgcaagga cgttcgtggt ctgctgagct    4200
tgtacgaggc gtcctacctg ggttgggagg gtgaggactt gctggacgag gccaagaagt    4260
tcagcaccac caacctgaac aatgtgaaag aaagcatcag cagcaacact ctgggtcgct    4320
tggtcaagca cgcccgaac ctgccgctgc actggtctgc ggcacgttac gaggcgagat     4380
ggtttattga cgagtacgaa aaagaagaaa acgttaaccc gaacctgctg aagtacgcga    4440
agtttgactt taacatcgtt cagagcattc accaacgtga gctcggtaac ctcgcgcgtt    4500
ggtgggtaga aaccggcctg gataaactga gcttcgtgcg caatacgttg atgcagaatt    4560
tcatgtgggg ctgtgcgatg gtgttcgaac cgcagtacgg caaggttcgc gatgcggccg    4620
tcaagcaggc cagcctgatt gcgatggtcg acgacgtgta tgacgtttat ggcagcctgg    4680
aagaactgga aatctttacc gatatcgtgg accgttggga tatcaccggt atcgacaagc    4740
tgccgcgtaa catctctatg attctgctga cgatgttcaa taccgcgaat cagattggtt    4800
acgacttgct gcgtgaccgc ggttttaacg gcatcccgca cattgctcag gcgtgggcca    4860
ccctgtgtaa gaaatatctg aaagaggcga gtggtatca tagcggttac aagccaactc     4920
tggaggagta cctggaaaac ggtcttgttt ctattagctt tgtgctgagc cttgttaccg    4980
catatctgca gaccgaaacc ctggagaatc tgacgtatga gtccgctgcg tacgtgaata    5040
gcgtaccgcc actggtccgc tacagcggcc tgctgaatcg tctgtacaac gatctcggta    5100
cgtcaagcgc agaaattgca cgtggtgaca cccctgaaaag catccagtgt tatatgaccc    5160
aaaccggtgc aaccgaggaa gcagcgcgcg agcacattaa aggtctggtt cacgaagcgt    5220
ggaagggcat gaacaaatgc ttgttcgagc agacgccatt cgcggagccg tttgtcggtt    5280
tcaacgtcaa taccgtccgc ggttcccaat tcttctacca gcatggcgac ggctacgcgg    5340
ttacggaaag ctggacgaag gacctgagcc tgtcggtgct gattcacccg atcccgctga    5400
atgaagagga ctaagaattc                                               5420
```

<210> SEQ ID NO 86
<211> LENGTH: 5441
<212> TYPE: DNA
<213> ORGANISM: Artificial Sequence
<220> FEATURE:
<223> OTHER INFORMATION: SaCP10374-CPRm-SaTPs30, synthetic operon
      encoding for SaCP10374, CPRm and a Beta-bisabolene synthase

<400> SEQUENCE: 86

```
catatggcac tgctgctggc tgtcttttgg agcgcactga ttattctgac ccgcaaacgc      60
cgcaaaggtc cgggtctgcc accgggtccg cgtgcgtacc cgattattgg caatctgcac     120
atgatgggcc agctgccaca ccacaatttg cgtgagctgg cacgtgagta tggtccgatt     180
atgagcatgc gcctgggtct ggtgccggca atcgtggtta gctctcctga ggctgcgcag     240
ctgttcctca agacgcatga taccgttttc gcgagccgtc aaagaccgag actgccaaaa     300
tacttccatt acggtatcaa aggtctgatc ctgaccgagt atggcccgta ctggcgcaat     360
attcgtcgtt tgagcaccgt taagctgttg aatgccgcga aaatcgatag cttcgcggct     420
atgcgtagaa gcgaagttga acgcctgtc gcgtccgttc gtggttcggc ggttcgtcgt     480
gaggttgtgg acgtcagcag caaagtggcg gaagctatgg agaatatggt ctgccagatg     540
gttatcggcc gttcaggtga cgatcgtttt aagctgaaag aaacctttca agagggcacc     600
caactggcag gcgcgttcaa ttttggtgag tttgtgccgt ttctgctgcc gctggacttg     660
caaggtatta cccgtcgcat caaagaagtc agcactcgtt tcaataagat tttgacctg      720
atcgttgacg agcacattcg cgatgccgct ggtaccaaaa acagcggcgg tcgtgatagc     780
gacaattttc tggatgttct gctgtccttg atgaacacct ctattagcga tagcaatgac     840
acgggtgaca caaccgtaa caacgtgatc gagcgtgata acattaaagc gatcctgacg     900
gacatgctgg gtgcagcgat ggacacgagc gcgagcacgg tcgagtggac gatctccgaa     960
ctgtttcgcc acccgaaaac catgcagaag ctgcaagcag aaatccgtgg tgtcgtgggc    1020
ccgacccgca atgtgagcga agatgacttg ccgaagctga cctatctgga catggtcgtt    1080
aaggaaggca tgcgtttgca tccggccgtg ccgctgcttc tgccgcatga gtctctggaa    1140
gaagccacga tcgatggcta ctacattccg aagggttccc gcattctgat caacgtctgg    1200
gcgattggtc gcgacccgaa ggcctggccg gatcgtcctg aagagttcat cccggagcgt    1260
ttcgagaaaa gcaacgtgga tgtgctgggc cgtgacttcc agctgctgcc gtttggttcg    1320
ggtcgtcgcg gttgtgcagg cattcgcctg ggcctgatct tcgtacgtct ggttctggca    1380
cagttagttc actgtttcga ctgggaactg gcgcgcaaca tggcgagcag cccggagaag    1440
ttggatatgg aagagaagtt cggcctggcg gtgcatcgtg tcaaccacct gaaagccctg    1500
ccgacgtatc gtctggagag ctaagtcgac taactttaag aaggagatat atccatggaa    1560
cctagctctc agaaactgtc tccgttggaa tttgttgctg ctatcctgaa gggcgactac    1620
agcagcggtc aggttgaagg tggtccaccg ccaggtctgg cagctatgtt gatgaaaat     1680
aaggatttgg tgatggttct gacgacgtcc gtggcagtcc tgatcggctg tgtcgtggtc    1740
ctggcatggc gtcgtgcggc aggtagcggt aagtacaagc aacctgaact gcctaaactg    1800
gtggtcccga agcagccga accggaggag cagaggatat aaaaccaa gatcagcgtg       1860
tttttcggca cccaaaccgg tacggcagaa ggtttcgcga aggcttttgt tgaagaggcc    1920
aaggcgcgtt atcagcaggc ccgtttcaaa gttatcgacc tggacgacta tgcggcagac    1980
gatgacgagt acgaagagaa actgaagaag gaaaacttgg cattcttctt cttggcgtcc    2040
tacggtgacg cgcagccgac ggacaacgcg gcacgctttt acaaatggtt tacggagggt    2100
```

-continued

```
aaggaccgtg gtgaatggct gaacaatctg cagtacggcg ttttggtct gggtaaccgt    2160 caatatgagc atttcaataa gatcgccatt gtcgtcgatg atctgatctt cgagcaaggt    2220
ggcaagaagc tggttccggt gggtctgggt gacgatgacc agtgcattga ggatgatttt    2280
gcggcgtggc gtgaactggt ctggccggaa ctggataaac tgctgcgtaa cgaagacgac    2340
gctaccgtgg caaccccgta cagcgccgct gtgctgcaat accgcgtggt tttccacgat    2400
cacattgacg gcctgattag cgaaaacggt agcccgaacg gtcatgctaa tggcaatacc    2460
gtgtacgatg cgcaacaccc gtgccgtagc aacgtcgcgg tcaagaagga attgcatact    2520
ccggcgagcg atcgcagctg cacccacctg gaatttaaca ttagcggtac cggcctgatg    2580
tacgagacgg gtgaccacgt cggtgtgtat tgcgagaacc tgttggaaac cgtggaggag    2640
gccgagaagt tgttgaacct gagcccgcag acgtacttct ccgttcacac cgacaacgag    2700
gacggtacgc cgttgagcgg cagcagcctg ccgccaccgt ttccgccgtg caccttgcgc    2760
acggcattga ccaaatacgc agacttgact tctgcaccga aaagtcggt gctggtggcg    2820 ctggccgagt acgcatctga ccagggtgaa gcggatcgtt tgcgtttctt ggcgagcccg    2880
agcggcaaag aggaatatgc acagtacatc ttggcaagcc agcgcacgct gctggaggtc    2940
atggcggagt tcccgtcggc gaaaccgccg ctgggtgtct ttttcgcggg tgtcgctccg    3000
cgcctgcagc gcgtttcta ttccattagc tctagcccga agatcgcacc gttccgtatt    3060
cacgtgacct gcgccctggt ttatgacaaa tcccctaccg gtcgcgttca taagggcatc    3120
tgtagcacgt ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggcccct tttcgtggct ttttgcaaga gcgcttggcg    3300
ttgaaagaga gcggtgctga attgggtccg gcgatcttgt tctttggttg ccgtaaccgt    3360
aaaatggact ttattacga ggatgaactg aatgatttcg tcaaagcggg cgttgtcagc    3420
gagctgatcg tcgcttttag ccgcgaaggc ccgatgaaag aatacgtgca acacaaaatg    3480
agccaacgtg cctccgatgt gtggaacatc attagcgacg gtggttatgt ttatgtttgc    3540
ggtgacgcga agggtatggc tcgtgatgtt caccgtaccc tgcataccat cgcacaggag    3600
caaggtagca tgtccagctc ggaggccgaa ggtatggtca aaaacctgca accaccggt    3660 cgttacctgc gtgatgtgtg gtaataaaag cttaggaggt aaaaatggac gcattcgcaa    3720
cgagcccgac cagcgcactg attaaggcgg ttaactgcat cgcgcacgtg accccgatgg    3780
caggtgaaga ttcctccgaa aaccgccgtg catcgaacta caaccgagc acctgggact    3840 atgaatttct gcaaagcctg gccacgagcc ataacaccgt ccaggaaaag cacatgaaga    3900
tggctgagaa attgaaggaa gaggtgaaga gcatgatcaa gggtcagatg gagccggtgg    3960
cgaagttgga actgatcaac atcctgcagc gtctgggttt gaaatatcgc tttgaatccg    4020
agatcaagga gagctgtttt ccctgtaca aggacggtac tgatgcgtgg tgggttgata    4080
atctgcatgc aacggcgctg cgttttagac tgctgcgcga atggtatt ttcgtgccgc    4140 aagaagtatt cgaaacttta aaggataaga gcggtaagtt taagagccag ctgtgcaagg    4200
acgttcgtgg tctgctgagc ttgtacgagg cgtcctacct gggttgggag ggtgaggact    4260
tgctggacga ggccaagaag ttcagcacca ccaacctgaa caatgtgaaa gaaagcatca    4320
gcagcaacac tctgggtcgc ttggtcaagc acgccctgaa cctgccgctg cactggtctg    4380
cggcacgtta cgaggcgaga tggtttattg acgagtacga aaagaagaa aacgttaacc    4440
```

```
cgaacctgct gaagtacgcg aagtttgact ttaacatcgt tcagagcatt caccaacgtg    4500
agctcggtaa cctcgcgcgt tggtgggtag aaaccggcct ggataaactg agcttcgtgc    4560
gcaatacgtt gatgcagaat tcatgtggg gctgtgcgat ggtgttcgaa ccgcagtacg     4620
gcaaggttcg cgatgcggcc gtcaagcagg ccagcctgat tgcgatggtc gacgacgtgt    4680
atgacgttta tggcagcctg gaagaactgg aaatctttac cgatatcgtg gaccgttggg    4740
atatcaccgg tatcgacaag ctgccgcgta acatctctat gattctgctg acgatgttca    4800
ataccgcgaa tcagattggt tacgacttgc tgcgtgaccg cggttttaac ggcatcccgc    4860
acattgctca ggcgtgggcc accctgtgta agaaatatct gaaagaggcg aagtggtatc    4920
atagcggtta caagccaact ctggaggagt acctggaaaa cggtcttgtt tctattagct    4980
ttgtgctgag ccttgttacc gcatatctgc agaccgaaac cctggagaat ctgacgtatg    5040
agtccgctgc gtacgtgaat agcgtaccgc cactggtccg ctacagcggc ctgctgaatc    5100
gtctgtacaa cgatctcggt acgtcaagcg cagaaattgc acgtggtgac accctgaaaa    5160
gcatccagtg ttatatgacc caaaccgtg caaccgagga agcagcgcgc gagcacatta     5220
aaggtctggt tcacgaagcg tggaagggca tgaacaaatg cttgttcgag cagacgccat    5280
tcgcggagcc gtttgtcggt ttcaacgtca ataccgtccg cggttcccaa ttcttctacc    5340
agcatggcga cggctacgcg gttacggaaa gctggacgaa ggacctgagc ctgtcggtgc    5400
tgattcaccc gatcccgctg aatgaagagg actaagaatt c                        5441

<210> SEQ ID NO 87
<211> LENGTH: 5414
<212> TYPE: DNA
<213> ORGANISM: Artificial Sequence
<220> FEATURE:
<223> OTHER INFORMATION: SaCP816-CPRm-AaBFS, synthetic operon encoding
      for SaCP816, CPRm and a Beta-farnesene synthase

<400> SEQUENCE: 87
catatggcac tgttgttggc ggttttctgg agcgctttga ttattctggt tagcatctta      60
ttgcgtcgtc gtcaaaaacg caacaatttg ccaccgggcc caccggccct gccgatcatc     120
ggtaacattc acattctggg caccctgccg caccagagcc tgtacaatct ggcgaagaag     180
tacggtccga tcatgtccat gcgttttggg cttggttccgg cggtggtcat cagcagcccg    240
gaagcggccg agctggtcct gaaaacccac gacatcgtct ttgcttctcg ccctcgtctg    300
caagttgcag attactttca ctatggcacc aaaggcgtga ttctgaccga atatggtacc    360
tactggcgta acatgcgtcg cctgtgcacg gtcaaactgc tgaacaccgt taagattgat    420
agctttgcag gcacccgcaa gaaagaagtc gctagcttcg ttcagagcct gaaagaagca    480
agcgtggcgc acaaaatggt taacctgtcc gcacgcgtcg ctaatgttat tgagaatatg    540
gtttgtctga tggttattgg tagatcgtct gacgagcgtt tcaagctgaa agaagtgatc    600
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta agatcatga cgatgagcag    780 catggtgact tcatcgacgt gctgctgcg atgatgaata agccgatgga ttctcgtgag    840
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
```

```
gaagaagcgg atctgccgaa actgccgtac ctggacatgg ttgtcaagga aacgatgcgt    1080
ctgcatccgc caggcccgct gctggtgccg cgtgaaagca tggaagatat tacgatcaac    1140
ggttactata tcccgaagaa atcccgcatt attgtgaatg catgggcgat cggccgtgac    1200
accaacgcct ggagcaataa tgcgcacgag ttttcccctg agcgttttat gagctctaac    1260
gttgatctgc aaggccagga cttccagctg atcccgttcg gtagcggtcg tcgcggttgt    1320 ccggcatgc gtctgggtct gacgacggtc cgcttggtgc tggcccaact gattcactgc    1380
ttcgacctgg agcttccgaa gggcaccgtc gcgactgacc tggatatgag cgagaagttt    1440
ggtctggcaa tgccgcgtgc gcagcactta ctggcctttc cgacctaccg tctggagagc    1500
taagtcgact aactttaaga aggagatata tccatggaac ctagctctca gaaactgtct    1560
ccgttggaat tgttgctgc tatcctgaag ggcgactaca gcagcggtca ggttgaaggt    1620
ggtccaccgc caggtctggc agctatgttg atggaaaata aggatttggt gatggttctg    1680
acgacgtccg tggcagtcct gatcggctgt gtcgtggtcc tggcatggcg tcgtgcggca    1740
ggtagcggta agtacaagca acctgaactg cctaaactgg tggtcccgaa agcagccgaa    1800
ccggaggagg cagaggatga taaaaccaag atcagcgtgt ttttcggcac ccaaaccggt    1860
acggcagaag gtttcgcgaa ggcttttgtt gaagaggcca aggcgcgtta tcagcaggcc    1920
cgtttcaaag ttatcgacct ggacgactat gcggcagacg atgacgagta cgaagagaaa    1980
ctgaagaagg aaaacttggc attcttcttc ttggcgtcct acggtgacgg cgagccgacg    2040
gacaacgcgg cacgcttta caaatggttt acggagggta aggaccgtgg tgaatggctg    2100
aacaatctgc agtacggcgt ttttggtctg ggtaaccgtc aatatgagca tttcaataag    2160
atcgccattg tcgtcgatga tctgatcttc gagcaaggtg gcaagaagct ggttccggtg    2220
ggtctgggtg acgatgacca gtgcattgag atgattttg cggcgtggcg tgaactggtc    2280
tggccggaac tggataaact gctgcgtaac gaagacgacg ctaccgtggc aaccccgtac    2340
agcgccgctg tgctgcaata ccgcgtggtt ttccacgatc acattgacgg cctgattagc    2400
gaaaacggta gcccgaacgg tcatgctaat ggcaataccg tgtacgatgc gcaacacccg    2460
tgccgtagca acgtcgcggt caagaaggaa ttgcatactc cggcgagcga tcgcagctgc    2520
acccacctgg aatttaacat tagcggtacc ggcctgatgt acgagacggg tgaccacgtc    2580
ggtgtgtatt gcgagaacct gttggaaacc gtggaggagg ccgagaagtt gttgaacctg    2640
agcccgcaga cgtacttctc cgttcacacc gacaacgagg acggtacgcc gttgagcggc    2700
agcagcctgc cgccaccgtt tccgccgtgc accttgcgca cggcattgac caaatacgca    2760
gacttgactt ctgcaccgaa aaagtcggtg ctggtggcgc tggccgagta cgcatctgac    2820
cagggtgaag cggatcgttt gcgtttcttg gcgagcccga gcggcaaaga ggaatatgca    2880
cagtacatct tggcaagcca gcgcacgctg ctggaggtca tggcggagtt cccgtcggcg    2940
aaaccgccgc tgggtgtctt tttcgcgggt tcgctccgc gcctgcagcc gcgtttctat    3000
tccattagct ctagcccgaa gatcgcaccg ttccgtattc acgtgacctg cgccctggtt    3060
tatgacaaat cccctaccgg tcgcgttcat aagggcatct gtagcacgtg gatgaaaaat    3120
gcggtcccgg tggaagaaag caacgattgt tcctgggctc cgatcttcgt ccgcaacagc    3180
aacttcaagc tgccgaccga cccgaaggtt ccgattatca tgattggtcc gggtaccggt    3240
ctggcccctt tcgtggcttt ttgcaagag cgcttggcgt tgaaagagag cggtgctgaa    3300
ttgggtccgg cgatcttgtt ctttggttgc cgtaaccgta aaatggactt tatttacgag    3360
gatgaactga atgatttcgt caaagcgggc gttgtcagcg agctgatcgt cgcttttagc    3420
```

```
cgcgaaggcc cgatgaaaga atacgtgcaa cacaaaatga gccaacgtgc ctccgatgtg    3480
tggaacatca ttagcgacgg tggttatgtt tatgtttgcg gtgacgcgaa gggtatggct    3540
cgtgatgttc accgtaccct gcataccatc gcacaggagc aaggtagcat gtccagctcg    3600
gaggccgaag gtatggtcaa aaacctgcaa accaccggtc gttacctgcg tgatgtgtgg    3660
taataaaagc ttaggaggta aaatgtctca ccctgccaat ttcttctgtg tcctttagct    3720
ccagcacttc gccactggtt gtcgatgaca aggtgagcac gaaaccggat gtgatccgtc    3780
acacgatgaa cttcaacgcg agcatttggg gcgatcaatt cctgacctat gacgagccgg    3840
aagatctggt aatgaagaaa caactggttg aggaacttaa agaagaagtg aagaaagaat    3900
tgatcaccat caagggtagc aacgagccga tgcaacatgt caagctgatc gagttgatcg    3960
acgcagttca acgcctgggc attgcctacc actttgaaga agagattgaa gaggccctgc    4020
agcacattca tgtcacctac ggtgagcagt gggtggacaa agagaatttg caatccatca    4080
gcctgtggtt tcgtctgctg cgtcaacagg gcttcaacgt gagcagcggt gtgtttaaag    4140
atttcatgga cgaaaagggt aagtttaaag agtccctgtg caatgatgca cagggtattt    4200
tggcgctgta tgaggccgca ttcatgcgcg ttgaagatga aaccattctg gacaacgctc    4260
tggagttcac caaggtgcat ctggacatca tcgctaagga cccgagctgt gattctagcc    4320
tgcgcacgca gattcaccag gctctgaagc agccgctgcg ccgtcgcctg gcacgtattg    4380
aggcgttaca ctatatgccg atctatcagc aagagactag ccatgacgaa gttctgctga    4440
aactggcaaa gctggacttt agcgttctgc agagcatgca caagaaagaa ctcagccata    4500
tttgcaagtg gtggaaagat ctggatctgc agaataagct gccgtacgtt cgtgaccgtg    4560
tcgttgaggg ctatttctgg atcttgagca tttactacga gccgcaacat gcgcgtaccc    4620
gtatgttcct gatgaaaacc tgtatgtggt tggttgtgct ggacgacacg tttgataact    4680
acggcacgta cgaagagttg gagattttca cccaagcggt agaacgttgg agcatctcgt    4740
gtctggacat gctgcctgag tatatgaagc tgatctacca ggaactggtc aatttacacg    4800
tcgagatgga agagagcctg gagaaagaag gcaagaccta tcagattcac tatgtgaaag    4860
aaatggcgaa agaactggtc cgcaactacc tggttgaggc gcgctggctg aaagagggct    4920
acatgccgac cctggaagag tatatgagcg tgagcatggt cacgggtacg tacggtctga    4980
tgatcgcccg cagctacgtc ggtcgtggcg acatcgttac cgaagatacc ttcaaatggg    5040
tttctagcta cccgccgatt atcaaggcaa gctgcgttat cgtgcgtttg atggatgata    5100
ttgttagcca caagaagaa caagagcgtg gtcatgttgc tagcagcatt gagtgctaca    5160
gcaaagagtc cggtgcaagc gaagaagaag cgtgcgagta tatcagccgt aaggtcgagg    5220
acgcgtggaa agtcattaat cgcgagtccc tgcgtccgac cgcggttccg tttccgctgc    5280
tgatgcctgc gattaatctg gcgcgtatgt gtgaggtcct gtacagcgtg aatgacggtt    5340 tacgcacgc cgagggtgat atgaaaagct atatgaagtc attctttgtg cacccgatgg    5400
ttgtgtaaga attc                                                      5414
```

<210> SEQ ID NO 88
<211> LENGTH: 5435
<212> TYPE: DNA
<213> ORGANISM: Artificial Sequence
<220> FEATURE:
<223> OTHER INFORMATION: SaCP10374-CPRm-AaBFS, synthetic operon encoding for SaCP10374, CPRm and a Beta-farnesene synthase

<400> SEQUENCE: 88

```
catatggcac tgctgctggc tgtcttttgg agcgcactga ttattctgac ccgcaaacgc    60
cgcaaaggtc cgggtctgcc accgggtccg cgtgcgtacc cgattattgg caatctgcac   120
atgatgggcc agctgccaca ccacaatttg cgtgagctgg cacgtgagta tggtccgatt   180
atgagcatgc gcctgggtct ggtgccggca atcgtggtta gctctcctga ggctgcgcag   240
ctgttcctca agacgcatga taccgttttc gcgagccgtc caaagaccga gactgccaaa   300
tacttccatt acggtatcaa aggtctgatc ctgaccgagt atgggcccgta ctggcgcaat   360 attcgtcgtt tgagcaccgt taagctgttg aatgccgcga aaatcgatag cttcgcggct   420
atgcgtagaa gcgaagttga acgcctggtc gcgtccgttc gtggttcggc ggttcgtcgt   480
gaggttgtgg acgtcagcag caaagtggcg gaagctatgg agaatatggt ctgccagatg   540
gttatcggcc gttcaggtga cgatcgtttt aagctgaaag aaacctttca agagggcacc   600
caactggcag gcgcgttcaa ttttggtgag tttgtgccgt ttctgctgcc gctggacttg   660
caaggtatta cccgtcgcat caaagaagtc agcactcgtt tcaataagat tttggacctg   720
atcgttgacg agcacattcg cgatgccgct ggtaccaaaa acagcggcgg tcgtgatagc   780
gacaattttc tggatgttct gctgtccttg atgaacacct ctattagcga tagcaatgac   840
acgggtgaca acaaccgtaa caacgtgatc gagcgtgata acattaaagc gatcctgacg   900
gacatgctgg gtgcagcgat ggacacgagc gcgagcacgg tcgagtggac gatctccgaa   960
ctgtttcgcc acccgaaaac catgcagaag ctgcaagcag aaatccgtgg tgtcgtgggc  1020
ccgacccgca atgtgagcga agatgacttg ccgaagctga cctatctgga catggtcgtt  1080
aaggaaggca tgcgtttgca tccggccgtg ccgctgcttc tgccgcatga gtctctggaa  1140
gaagccacga tcgatggcta ctacattccg aagggttccc gcattctgat caacgtctgg  1200
gcgattggtc gcgacccgaa ggcctggccg gatcgtcctg aagagttcat cccggagcgt  1260
ttcgagaaaa gcaacgtgga tgtgctgggc cgtgacttcc agctgctgcc gtttggttcg  1320
ggtcgtcgcg gttgtgcagg cattcgcctg ggcctgatct tcgtacgtct ggttctggca  1380
cagttagttc actgtttcga ctgggaactg gcgcgcaaca tggcgagcag cccggagaag  1440
ttggatatgg aagagaagtt cggcctggcg gtgcatcgtg tcaaccacct gaaagccctg  1500
ccgacgtatc gtctggagag ctaagtcgac taactttaag aaggagatat atccatggaa  1560
cctagctctc agaaactgtc tccgttggaa tttgttgctg ctatcctgaa gggcgactac  1620
agcagcggtc aggttgaagg tggtccaccg ccaggtctgg cagctatgtt gatggaaaat  1680
aaggatttgg tgatggttct gacgacgtcc gtggcagtcc tgatcggctg tgtcgtggtc  1740
ctggcatggc gtcgtgcggc aggtagcggt aagtacaagc aacctgaact gcctaaactg  1800
gtggtcccga aagcagccga accggaggag gcagaggata taaaaccaa gatcagcgtg  1860 tttttcggca cccaaaccgg tacggcagaa ggtttcgcga aggcttttgt tgaagaggcc  1920
aaggcgcgtt atcagcaggc ccgtttcaaa gttatcgacc tggacgacta tgcggcagac  1980
gatgacgagt acgaagagaa actgaagaag gaaaacttgg cattcttctt cttggcgtcc  2040
tacggtgacg gcgagccgac ggacaacgcg gcacgctttt acaaatggtt tacggagggt  2100
aaggaccgtg gtgaatggct gaacaatctg cagtacggcg tttttggtct gggtaaccgt  2160
caatatgagc atttcaataa gatcgccatt gtcgtcgatg atctgatctt cgagcaaggt  2220
ggcaagaagc tggttccggt gggtctgggt gacgatgacc agtgcattga ggatgatttt  2280
gcggcgtggc gtgaactggt ctggccggaa ctggataaac tgctgcgtaa cgaagacgac  2340
```

```
gctaccgtgg caaccccgta cagcgccgct gtgctgcaat accgcgtggt tttccacgat    2400
cacattgacg gcctgattag cgaaaacggt agcccgaacg gtcatgctaa tggcaatacc    2460
gtgtacgatg cgcaacaccc gtgccgtagc aacgtcgcgg tcaagaagga attgcatact    2520
ccggcgagcg atcgcagctg cacccacctg gaatttaaca ttagcggtac cggcctgatg    2580
tacgagacgg gtgaccacgt cggtgtgtat tgcgagaacc tgttggaaac cgtggaggag    2640
gccgagaagt tgttgaacct gagcccgcag acgtacttct ccgttcacac cgacaacgag    2700
gacggtacgc cgttgagcgg cagcagcctg ccgccaccgt ttccgccgtg caccttgcgc    2760
acggcattga ccaaatacgc agacttgact tctgcaccga aaaagtcggt gctggtggcg    2820
ctggccgagt acgcatctga ccagggtgaa gcggatcgtt tgcgtttctt ggcgagcccg    2880
agcggcaaag aggaatatgc acagtacatc ttggcaagcc agcgcacgct gctggaggtc    2940
atggcggagt tcccgtcggc gaaaccgccg ctgggtgtct ttttcgcggg tgtcgctccg    3000
cgcctgcagc cgcgtttcta ttccattagc tctagcccga agatcgcacc gttccgtatt    3060
cacgtgacct gcgccctggt ttatgacaaa tcccctaccg gtcgcgttca taagggcatc    3120
tgtagcacgt ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggccccct tttcgtggct ttttgcaaga gcgcttggcg    3300
ttgaaagaga gcggtgctga attgggtccg gcgatcttgt tctttggttg ccgtaaccgt    3360
aaaatggact ttatttacga ggatgaactg aatgatttcg tcaaagcggg cgttgtcagc    3420
gagctgatcg tcgcttttag ccgcgaaggc ccgatgaaag aatacgtgca acacaaaatg    3480
agccaacgtg cctccgatgt gtggaacatc attagcgacg gtggttatgt ttatgtttgc    3540
ggtgacgcga agggtatggc tcgtgatgtt caccgtaccc tgcataccat cgcacaggag    3600
caaggtagca tgtccagctc ggaggccgaa ggtatggtca aaaacctgca aaccaccggt    3660
cgttacctgc gtgatgtgtg gtaataaaag cttaggaggt aaaaatgtct accctgccaa    3720
tttcttctgt gtcctttagc tccagcactt cgccactggt tgtcgatgac aaggtgagca    3780
cgaaaccgga tgtgatccgt cacacgatga acttcaacgc gagcatttgg ggcgatcaat    3840
tcctgaccta tgacgagccg gaagatctgg taatgaagaa acaactggtt gaggaactta    3900
aagaagaagt gaagaaagaa ttgatcacca tcaagggtag caacgagccg atgcaacatg    3960
tcaagctgat cgagttgatc gacgcagttc aacgcctggg cattgcctac cacttgaaag    4020
aagagattga agaggccctg cagcacattc atgtcaccta cggtgagcag tgggtggaca    4080
aagagaattt gcaatccatc agcctgtggt tcgtctgct gcgtcaacag ggcttcaacg    4140
tgagcagcgc tgtgtttaaa gatttcatgg acgaaaaggg taagtttaaa gagtccctgt    4200
gcaatgatgc acagggtatt ttggcgctgt atgaggccgc attcatgcgc gttgaagatg    4260
aaaccattct ggacaacgct ctggagttca ccaaggtgca tctggacatc atcgctaagg    4320
acccgagctg tgattctagc ctgcgcacgc agattcacca ggctctgaag cagccgctgc    4380
gccgtcgcct ggcacgtatt gaggcgttac actatatgcc gatctatcag caagagacta    4440
gccatgacga agttctgctg aaactggcaa agctggactt tagcgttctg cagagcatgc    4500
acaagaaaga actcagccat atttgcaagt ggtggaaaga tctggatctg cagaataagc    4560
tgccgtacgt tcgtgaccgt gtcgttgagg gctatttctg gatcttgagc atttactacg    4620
agccgcaaca tgcgcgtacc cgtatgttcc tgatgaaaac ctgtatgtgg ttggttgtgc    4680
tggacgacac gtttgataac tacggcacgt acgaagagtt ggagattttc acccaagcgg    4740
```

```
tagaacgttg gagcatctcg tgtctggaca tgctgcctga gtatatgaag ctgatctacc    4800
aggaactggt caatttacac gtcgagatgg aagagagcct ggagaaagaa ggcaagacct    4860
atcagattca ctatgtgaaa gaaatggcga agaactggt ccgcaactac ctggttgagg     4920
cgcgctggct gaaagagggc tacatgccga ccctggaaga gtatatgagc gtgagcatgg    4980
tcacgggtac gtacggtctg atgatcgccc gcagctacgt cggtcgtggc gacatcgtta    5040
ccgaagatac cttcaaatgg gtttctagct acccgccgat tatcaaggca agctgcgtta    5100
tcgtgcgttt gatggatgat attgttagcc acaagaaga acaagagcgt ggtcatgttg     5160
ctagcagcat tgagtgctac agcaaagagt ccggtgcaag cgaagaagaa gcgtgcgagt    5220
atatcagccg taaggtcgag gacgcgtgga aagtcattaa tcgcgagtcc ctgcgtccga    5280
ccgcggttcc gtttccgctg ctgatgcctg cgattaatct ggcgcgtatg tgtgaggtcc    5340
tgtacagcgt gaatgacggt tttacgcacg ccgagggtga tatgaaaagc tatatgaagt    5400
cattctttgt gcacccgatg gttgtgtaag aattc                               5435

<210> SEQ ID NO 89
<211> LENGTH: 5432
<212> TYPE: DNA
<213> ORGANISM: Artificial Sequence
<220> FEATURE:
<223> OTHER INFORMATION: SaCP816-CPRm-PaAFS, synthetic operon encoding
      for SaCP816, CPRm and an alpha-farnesene synthase

<400> SEQUENCE: 89
catatggcac tgttgttggc ggttttctgg agcgctttga ttattctggt tagcatctta      60
ttgcgtcgtc gtcaaaaacg caacaatttg ccaccgggcc caccggccct gccgatcatc     120
ggtaacattc acattctggg caccctgccg caccagagcc tgtacaatct ggcgaagaag     180
tacggtccga tcatgtccat gcgtttgggc ttggttccgg cggtggtcat cagcagcccg     240
gaagcggccg agctggtcct gaaaacccac gacatcgttt ttgcttctcg ccctcgtctg     300
caagttgcag attactttca ctatggcacc aaaggcgtga ttctgaccga atatggtacc     360
tactggcgta acatgcgtcg cctgtgcacg gtcaaactgc tgaacaccgt taagattgat     420
agctttgcag gcacccgcaa gaaagaagtc gctagcttcg ttcagagcct gaaagaagca     480
agcgtggcgc acaaaatggt taacctgtcc gcacgcgtcg ctaatgttat tgagaatatg     540
gtttgtctga tggttattgg tagatcgtct gacgagcgtt tcaagctgaa agaagtgatc     600
caagaagcgg cacagctggc gggtgccttc aatattggtg actatgtccc gtttctgatg     660
ccgctggatc tgcagggcct gactcgccgt atcaagagcg gtagcaaggc attcgatgac     720
atcctcgagg tcattatcga cgagcatgtg caagacatta aagatcatga cgatgagcag     780
catggtgact tcatcgacgt gctgctggcg atgatgaata agccgatgga ttctcgtgag     840
ggtctgtcca tcattgatcg cacgaacatt aaagcgatcc tggtggatat gatcggtgcc     900
gcgatggaca cgagcaccag cggtgtggag tgggcgattt cggagctgat taagcatcct     960
cgtgtcatga agaaactgca agacgaagtg aaaaccgtaa tcggtatgaa ccgcatggtg    1020
gaagaagcgg atctgccgaa actgccgtac ctggacatgt tgtcaagga acgatgcgt     1080 ctgcatccgc caggcccgct gctggtgccg cgtgaaagca tggaagatat tacgatcaac    1140
ggttactata tcccgaagaa atcccgcatt attgtgaatg catgggcgat cggccgtgac    1200
accaacgcct ggagcaataa tgcgcacgag ttttttccctg agcgttttat gagctctaac    1260
gttgatctgc aaggccagga cttccagctg atcccgttcg gtagcggtcg tcgcggttgt    1320
```

```
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat tgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt ttttcggcac ccaaaccggt   1860
acggcagaag gttcgcgaaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga gaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg atgaaaaat   3120
gcggtccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggccccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga ccaacgtgc ctccgatgtg   3480
tggaacatca ttagcgacgg tggttatgtt tatgtttgcg gtgacgcgaa gggtatggct   3540
cgtgatgttc accgtaccct gcataccatc gcacaggagc aaggtagcat gtccagctcg   3600
gaggccgaag gtatggtcaa aaacctgcaa accaccggtc gttacctgcg tgatgtgtgg   3660
```

```
taataaaagc ttaggaggta aaaatggatc tggcagtgga aatcgcaatg gacctggcag      3720
tggatgatgt tgaacgccgt gtgggtgact atcattccaa tctgtgggac gacgacttca      3780
tccaaagcct gagcaccccg tatggcgcca gctcttaccg cgagcgtgcg gagcgcttgg      3840
tcggcgaggt caaagaaatg tttacgagca tcagcatcga ggatggtgag ctgacctctg      3900
acttgcttca cgcctgtggg atggttgaca acgttgagcg cctgggcatt agccgtcact      3960
tcgagaatga aatcaaggct gcaattgatt acgtctacag ctattggtcc gacaagggta      4020
ttgtccgtgg tagagatagc gccgtgccgg atctgaacag cattgctctg ggtttccgta      4080
cgttgcgtct gcatggttac accgttagca gcgatgtttt caaggtcttt caagaccgca      4140
aaggtgagtt tgcatgtagc gcgattccga cggaaggtga catcaaaggc gtactgaatc      4200
tgctgcgtgc aagctacatc gcgttccctg gtgagaaagt gatggagaaa gcgcagacct      4260 tgccgcaac ttatctgaaa gaagcactgc agaagatcca agtgtctagc ctgagccgcg      4320
agatcgaata cgttctggag tatggctggc tgaccaattt tccgcgcctg gaagcgcgta      4380
actacatcga cgttttcggt gaggaaattt gtccgtactt caagaaaccg tgtattatgg      4440
ttgataagct gctggaactg gcgaaactgg agttcaattt gtttcactcg ctgcaacaga      4500
ccgagctgaa acacgtttcc cgttggtgga aggatagcgg ctttagccag ctgaccttca      4560
cgcgtcatcg tcacgtggag ttttacaccc tggctagctg tattgcaatt gaaccgaaac      4620
attctgcgtt tcgtttgggt ttcgcgaagg tctgctacct gggcattgtg ctggacgata      4680
tctatgacac gttcggtaaa atgaaagaac tggagttatt cacggcggca atcaagcgtt      4740 gggaccccgag cacgaccgag tgcctgcctg agtatatgaa aggtgtctac atggcgtttt      4800
acaactgcgt taatgaactg gcgctgcaag ccgagaaaac ccagggccgt gacatgttga      4860
actatgcacg taaggcgtgg gaagccctgt tcgatgcgtt cctggaagaa gcgaagtgga      4920
ttagctccgg ctatctgccg acctttgagg aatacctgga gaacggcaaa gtgtccttcg      4980
gttatcgtgc tgccactctg cagccaatcc tgacccctgga cattccgttg ccgctgcaca      5040
tcttgcagca gatcgatttc ccgagccgct taatgacct ggccagctca atttgcgtc      5100 tgcgcggtga tatctgcggt tatcaagccg agcgttctcg tggcgaagag gcgagcagca      5160
ttagctgcta catgaaggac aatccgggtt ccaccgagga agatgcgctg agccacatta      5220
acgcgatgat ttcggacaac atcaacgaac tgaattggga gctgctgaag ccgaacagca      5280
atgttccaat cagcagcaaa aagcacgctt tcgatatcct gcgtgcgttt taccatctct      5340
ataagtaccg tgatggtttt agcattgcga agattgaaac gaagaacctg gtgatgcgca      5400
ccgtcctgga gccggtcccg atgtaagaat tc                                   5432
```

<210> SEQ ID NO 90
<211> LENGTH: 5453
<212> TYPE: DNA
<213> ORGANISM: Artificial Sequence
<220> FEATURE:
<223> OTHER INFORMATION: SaCP10374-CPRm-PaAFS, synthetic operon encoding
      for SaCP10374, CPRm and an alpha-farnesene synthase

<400> SEQUENCE: 90

```
catatggcac tgctgctggc tgtcttttgg agcgcactga ttattctgac ccgcaaacgc       60
cgcaaaggtc cgggtctgcc accgggtccg cgtgcgtacc cgattattgg caatctgcac      120
atgatgggcc agctgccaca ccacaatttg cgtgagctgg cacgtgagta tggtccgatt      180
atgagcatgc gcctgggtct ggtgccggca atcgtggtta gctctcctga ggctgcgcag      240
```

-continued

```
ctgttcctca agacgcatga taccgttttc gcgagccgtc caaagaccga gactgccaaa    300
tacttccatt acggtatcaa aggtctgatc ctgaccgagt atggcccgta ctggcgcaat    360
attcgtcgtt tgagcaccgt taagctgttg aatgccgcga aaatcgatag cttcgcggct    420
atgcgtagaa gcgaagttga acgcctggtc gcgtccgttc gtggttcggc ggttcgtcgt    480
gaggttgtgg acgtcagcag caaagtggcg gaagctatgg agaatatggt ctgccagatg    540
gttatcggcc gttcaggtga cgatcgtttt aagctgaaag aaaccttca agagggcacc     600
caactggcag gcgcgttcaa ttttggtgag tttgtgccgt ttctgctgcc gctggacttg    660
caaggtatta cccgtcgcat caaagaagtc agcactcgtt tcaataagat tttggacctg    720
atcgttgacg agcacattcg cgatgccgct ggtaccaaaa acagcggcgg tcgtgatagc    780
gacaattttc tggatgttct gctgtccttg atgaacacct ctattagcga tagcaatgac    840
acgggtgaca acaaccgtaa caacgtgatc gagcgtgata acattaaagc gatcctgacg    900
gacatgctgg gtgcagcgat ggacacgagc gcgagcacgg tcgagtggac gatctccgaa    960
ctgtttcgcc acccgaaaac catgcagaag ctgcaagcag aaatccgtgg tgtcgtgggc   1020
ccgacccgca atgtgagcga agatgacttg ccgaagctga cctatctgga catggtcgtt   1080
aaggaaggca tgcgtttgca tccggccgtg ccgctgcttc tgccgcatga gtctctggaa   1140
gaagccacga tcgatggcta ctacattccg aagggttccc gcattctgat caacgtctgg   1200
gcgattggtc gcgacccgaa ggcctggccg atcgtcctg aagagttcat cccggagcgt    1260
ttcgagaaaa gcaacgtgga tgtgctgggc cgtgacttcc agctgctgcc gtttggttcg   1320
ggtcgtcgcg gttgtgcagg cattcgcctg ggcctgatct tcgtacgtct ggttctggca   1380
cagttagttc actgtttcga ctgggaactg gcgcgcaaca tggcgagcag cccggagaag   1440
ttggatatgg aagagaagtt cggcctggcg gtgcatcgtg tcaaccacct gaaagccctg   1500
ccgacgtatc gtctggagtg ctaagtcgac taactttaag aaggagatat atccatggaa   1560
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
ttttcggca cccaaaccgg tacggcagaa ggtttcgcga aggcttttgt tgaagaggcc    1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacgagggt    2100
aaggaccgtg gtgaatggct gaacaatctg cagtacggcg ttttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg tcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
```

```
gccgagaagt tgttgaacct gagcccgcag acgtacttct ccgttcacac cgacaacgag    2700
gacggtacgc cgttgagcgg cagcagcctg ccgccaccgt ttccgccgtg caccttgcgc    2760
acggcattga ccaaatacgc agacttgact tctgcaccga aaaagtcggt gctggtggcg    2820
ctggccgagt acgcatctga ccagggtgaa gcggatcgtt tgcgtttctt ggcgagcccg    2880
agcggcaaag aggaatatgc acagtacatc ttggcaagcc agcgcacgct gctggaggtc    2940
atggcggagt tcccgtcggc gaaaccgccg ctgggtgtct ttttcgcggg tgtcgctccg    3000
cgcctgcagc cgcgtttcta ttccattagc tctagcccga agatcgcacc gttccgtatt    3060
cacgtgacct cgcgccctgg t ttatgacaaa tcccctaccg gtcgcgttca taagggcatc    3120
tgtagcacgt ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggcccct tttcgtggct ttttgcaaga gcgcttggcg    3300
ttgaaagaga gcggtgctga attgggtccg gcgatcttgt tctttggttg ccgtaaccgt    3360
aaaatggact ttatttacga ggatgaactg aatgatttcg tcaaagcggg cgttgtcagc    3420
gagctgatcg tcgcttttag ccgcgaaggc ccgatgaaag aatacgtgca acacaaaatg    3480
agccaacgtg cctccgatgt gtggaacatc attagcgacg gtggttatgt ttatgtttgc    3540
ggtgacgcga agggtatggc tcgtgatgtt caccgtaccc tgcataccat cgcacaggag    3600
caaggtagca tgtccagctc ggaggccgaa ggtatggtca aaaacctgca aaccaccggt    3660
cgttacctgc gtgatgtgtg gtaataaaag cttaggaggt aaaaatggat ctggcagtgg    3720
aaatcgcaat ggacctggca gtggatgatg ttgaacgccg tgtgggtgac tatcattcca    3780
atctgtggga cgacgacttc atccaaagcc tgagcacccc gtatggcgcc agctcttacc    3840
gcgagcgtgc ggagcgcttg gtcggcgagg tcaaagaaat gtttacgagc atcagcatcg    3900
aggatggtga gctgacctct gacttgcttc aacgcctgtg gatggttgac aacgttgagc    3960
gcctgggcat tagccgtcac ttcgagaatg aaatcaaggc tgcaattgat tacgtctaca    4020
gctattggtc cgacaagggt attgtccgtg gtagagatag cgccgtgccg gatctgaaca    4080
gcattgctct gggtttccgt acgttgcgtc tgcatggtta caccgttagc agcgatgttt    4140
tcaaggtctt tcaagaccgc aaaggtgagt tgcatgtag cgcgattccg acggaaggtg    4200
acatcaaagg cgtactgaat ctgctgcgtg caagctacat cgcgttccct ggtgagaaag    4260
tgatggagaa agcgcagacc tttgccgcaa cttatctgaa agaagcactg cagaagatcc    4320
aagtgtctag cctgagccgc gagatcgaat acgttctgga gtatggctgg ctgaccaatt    4380
ttccgcgcct ggaagcgcgt aactacatcg acgttttcgg tgaggaaatt tgtccgtact    4440
tcaagaaacc gtgtattatg gttgataagc tgctggaact ggcgaaactg gagttcaatt    4500
tgtttcactc gctgcaacag accgagctga acacgtttc ccgttggtgg aaggatagcg    4560
gctttagcca gctgaccttc acgcgtcatc gtcacgtgga gttttacacc ctggctagct    4620
gtattgcaat tgaaccgaaa cattctgcgt ttcgtttggg tttcgcgaag gtctgctacc    4680
tgggcattgt gctggacgat atctatgaca cgttcggtaa aatgaaagaa ctggagttat    4740
tcacggcggc aatcaagcgt tgggacccga gcacgaccga gtgcctgcct gagtatatga    4800 aggtgtcta catggcgttt tacaactgcg ttaatgaact ggcgctgcaa gccgagaaaa    4860
cccagggccg tgcatgttg aactatgcac gtaaggcgtg ggaagccctg ttcgatgcgt    4920
tcctggaaga agcgaagtgg attagctccg gctatctgcc gaccttttgag gaatacctgg    4980
```

| | |
|---|---|
| agaacggcaa agtgtccttc ggttatcgtg ctgccactct gcagccaatc ctgaccctgg | 5040 |
| acattccgtt gccgctgcac atcttgcagc agatcgattt cccgagccgc tttaatgacc | 5100 |
| tggccagctc aattttgcgt ctgcgcggtg atatctgcgg ttatcaagcc gagcgttctc | 5160 |
| gtggcgaaga ggcgagcagc attagctgct acatgaagga caatccgggt tccaccgagg | 5220 |
| aagatgcgct gagccacatt aacgcgatga tttcggacaa catcaacgaa ctgaattggg | 5280 |
| agctgctgaa gccgaacagc aatgttccaa tcagcagcaa aaagcacgct ttcgatatcc | 5340 |
| tgcgtgcgtt ttaccatctc tataagtacc gtgatggttt tagcattgcg aagattgaaa | 5400 |
| cgaagaacct ggtgatgcgc accgtcctgg agccggtccc gatgtaagaa ttc | 5453 |

<210> SEQ ID NO 91
<211> LENGTH: 5370
<212> TYPE: DNA
<213> ORGANISM: Artificial Sequence
<220> FEATURE:
<223> OTHER INFORMATION: SaCP10374-CPRm-ClTps2, synthetic operon
      encoding for SaCP10374, CPRm and an alpha-santalene synthase

<400> SEQUENCE: 91

| | |
|---|---|
| catatggcac tgctgctggc tgtcttttgg agcgcactga ttattctgac ccgcaaacgc | 60 |
| cgcaaaggtc cgggtctgcc accgggtccg cgtgcgtacc cgattattgg caatctgcac | 120 |
| atgatgggcc agctgccaca ccacaatttg cgtgagctgg cacgtgagta tggtccgatt | 180 |
| atgagcatgc gcctgggtct ggtgccggca atcgtggtta gctctcctga ggctgcgcag | 240 |
| ctgttcctca agacgcatga taccgttttc gcgagccgtc aaagaccgga gactgccaaa | 300 |
| tacttccatt acggtatcaa aggtctgatc ctgaccgagt atggcccgta ctggcgcaat | 360 |
| attcgtcgtt tgagcaccgt taagctgttg aatgccgcga aaatcgatag cttcgcggct | 420 |
| atgcgtagaa gcgaagttga acgcctggtc gcgtccgttc gtggttcggc ggttcgtcgt | 480 |
| gaggttgtgg acgtcagcag caaagtggcg gaagctatgg agaatatggt ctgccagatg | 540 |
| gttatcggcc gttcaggtga cgatcgtttt aagctgaaag aaacctttca agagggcacc | 600 |
| caactggcag gcgcgttcaa ttttggtgag tttgtgccgt ttctgctgcc gctggacttg | 660 |
| caaggtatta cccgtcgcat caaagaagtc agcactcgtt tcaataagat tttggaccctg | 720 |
| atcgttgacg agcacattcg cgatgccgct ggtaccaaaa acagcggcgg tcgtgatagc | 780 |
| gacaattttc tggatgttct gctgtccttg atgaacacct ctattagcga tagcaatgac | 840 |
| acgggtgaca caaccgtaa caacgtgatc gagcgtgata acattaaagc gatcctgacg | 900 |
| gacatgctgg tgcagcgat ggacacgagc gcgagcacgg tcgagtggac gatctccgaa | 960 |
| ctgtttcgcc acccgaaaac catgcagaag ctgcaagcag aaatccgtgg tgtcgtgggc | 1020 |
| ccgacccgca atgtgagcga agatgacttg ccgaagctga cctatctgga catggtcgtt | 1080 |
| aaggaaggca tgcgtttgca tccggccgtg ccgctgcttc tgccgcatga gtctctggaa | 1140 |
| gaagccacga tcgatggcta ctacattccg aagggttccc gcattctgat caacgtctgg | 1200 |
| gcgattggtc gcgacccgaa ggcctggccg gatcgtcctg aagagttcat cccggagcgt | 1260 |
| ttcgagaaaa gcaacgtgga tgtgctgggc cgtgacttcc agctgctgcc gtttggttcg | 1320 |
| ggtcgtcgcg gttgtgcagg cattcgcctg ggcctgatct tcgtacgtct ggttctggca | 1380 |
| cagttagttc actgtttcga ctgggaactg gcgcgcaaca tggcgagcag cccggagaag | 1440 |
| ttggatatgg aagagaagtt cggcctggcg gtgcatcgtg tcaaccacct gaaagccctg | 1500 |
| ccgacgtatc gtctggagtg ctaagtcgac taactttaag aaggagatat atccatgaaa | 1560 |

```
cctagctctc agaaactgtc tccgttggaa tttgttgctg ctatcctgaa gggcgactac    1620
agcagcggtc aggttgaagg tggtccaccg ccaggtctgg cagctatgtt gatggaaaat    1680
aaggatttgg tgatggttct gacgacgtcc gtggcagtcc tgatcggctg tgtcgtggtc    1740
ctggcatggc gtcgtgcggc aggtagcggt aagtacaagc aacctgaact gcctaaactg    1800
gtggtcccga aagcagccga accggaggag gcagaggatg ataaaaccaa gatcagcgtg    1860
tttttcggca cccaaaccgg tacgcagaaa ggtttcgcga aggcttttgt tgaagaggcc    1920
aaggcgcgtt atcagcaggc ccgttttcaaa gttatcgacc tggacgacta tgcggcagac    1980
gatgacgagt acgaagagaa actgaagaag gaaaacttgg cattcttctt cttggcgtcc    2040
tacggtgacg gcgagccgac ggacaacgcg gcacgctttt acaaatggtt tacggagggt    2100
aaggaccgtg gtgaatggct gaacaatctg cagtacggcg tttttggtct gggtaaccgt    2160
caatatgagc atttcaataa gatcgccatt gtcgtcgatg atctgatctt cgagcaaggt    2220
ggcaagaagc tggttccggt gggtctgggt gacgatgacc agtgcattga ggatgatttt    2280
gcggcgtggc gtgaactggt ctggccgaaa ctggataaac tgctgcgtaa cgaagacgac    2340
gctaccgtgg caaccccgta cagcgccgct gtgctgcaat accgcgtggt tttccacgat    2400
cacattgacg gcctgattag cgaaaacggt agcccgaacg gtcatgctaa tggcaatacc    2460
gtgtacgatg cgcaacaccc gtgccgtagc aacgtcgcgg tcaagaagga attgcatact    2520
ccggcgagcg atcgcagctg cacccacctg gaatttaaca ttagcggtac cggcctgatg    2580
tacgagacgg gtgaccacgt cggtgtgtat tgcgagaacc tgttggaaac cgtggaggag    2640
gccgagaagt tgttgaacct gagcccgcag acgtacttct ccgttcacac cgacaacgag    2700
gacggtacgc cgttgagcgg cagcagcctg ccgccaccgt ttccgccgtg caccttgcgc    2760
acggcattga ccaaatacgc agacttgact tctgcaccga aaaagtcggt gctggtggcg    2820
ctggccgagt acgcatctga ccagggtgaa gcggatcgtt tgcgtttctt ggcgagcccg    2880
agcggcaaag aggaatatgc acagtacatc ttggcaagcc agcgcacgct gctggaggtc    2940
atggcggagt tcccgtcggc gaaaccgccg ctgggtgtct ttttcgcggg tgtcgctccg    3000
cgcctgcagc gcgttttcta ttccattagc tctagcccga agatcgcacc gttccgtatt    3060
cacgtgacct gcgccctggt ttatgacaaa tcccctaccg gtcgcgttca agggcatc    3120 tgtagcacgt ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggcccct tttcgtggct ttttgcaaga gcgcttggcg    3300
ttgaaagaga gcggtgctga attgggtccg gcgatcttgt tctttggttg ccgtaaccgt    3360
aaaatggact ttatttacga ggatgaactg aatgatttcg tcaaagcggg cgttgtcagc    3420
gagctgatcg tcgcttttag ccgcgaaggc ccgatgaaag aatacgtgca acacaaaatg    3480
agccaacgtg cctccgatgt gtggaacatc attagcgacg tggttatgt ttatgtttgc    3540 ggtgacgcga agggtatggc tcgtgatgtt caccgtaccc tgcataccat cgcacaggag    3600
caaggtagca tgtccagctc ggaggccgaa ggtatggtca aaaacctgca aaccaccggt    3660
cgttacctgc gtgatgtgtg gtaataaaag cttgaaggag atatactaat gtctacccag    3720
caggttagct ccgagaatat cgttcgcaac gcggcgaact tccacccgaa tatctgggt    3780 aatcatttct tgacgtgtcc aagccagacg atcgattctt ggacgcaaca acaccataaa    3840
gagctgaaag aagaggtccg caagatgatg gtgagcgacg caaacaaacc ggcacaacgt    3900
ctgcgtctga ttgacaccgt tcaacgtttg ggcgtggcgt atcatttcga aaaagaaatc    3960
```

```
gatgacgctc tggaaaagat cggtcacgat ccgtttgacg ataaggatga cctgtatatc    4020
gttagcctgt gttttcgcct gctgcgtcag catggcatca agattagctg cgatgttttt    4080
gagaagttca agacgacga tggcaagttt aaggcttccc tgatgaatga tgtccaaggt    4140
atgctgtcgt tgtatgaagc ggcccacctg gcaattcatg cgaggacat cctggatgag    4200 gctattgtct ttacgaccac ccacctgaag agcaccgttt ctaactcccc ggtcaattcc    4260
acctttgcgg aacagattcg ccacagcctg cgtgtgccgc tgcgtaaggc agtcccgcgt    4320
ttggagagcc gctacttcct ggatatctat agccgtgacg acctgcacga caagactctg    4380
ctgaactttg ccaaactgga cttcaacatc ctgcaggcga tgcaccagaa agaggcaagc    4440
gagatgaccc gttggtggcg tgatttcgat ttcctgaaga agctgccgta cattcgtgat    4500
cgcgtggttg aactgtactt ttggattttg gtcggtgtga gctaccaacc gaaattcagc    4560
acgggtcgta tcttttgag caagattatc tgtctggaaa ccctggtgga cgacacgttt    4620
gatgcgtacg gtactttcga cgaactggcc attttcaccg aggccgttac gcgttgggac    4680
ctgggtcatc gcgacgcgct gcctgagtac atgaaattca ttttcaagac cctgattgat    4740
gtgtacagcg aggcggaaca agagctggca aagaggggcc gctcctatag cattcactat    4800
gcgatccgta gcttccagga gttggtcatg aagtactttt gcgaggcgaa atggctgaat    4860
aagggttatt ttccgagcct ggatgactac aagagcgtca gcctgcgcag catcggcttc    4920
ctgccgatcg ccgtggcttc ttttgttttc atgggcgaca ttgctacgaa agaggttttt    4980
gagtgggaaa tgaataaccc gaaaatcatc atcgcagccg aaaccatttt ccgctttctg    5040
gatgacattg caggtcatcg cttcgaacaa aaacgtgagc agagcccgag cgcaatcgag    5100
tgctacaaaa accaacatgg tgtctcggaa gaagaggcag tgaaagcgct gagcttggag    5160
gtcgccaatt cgtggaaaga cattaacgaa gagctgctgc tgaaccctat ggcaattcca    5220
ctgccgttgc tgcaggtgat cctggatttg agccgtagcg cggacttcat gtacggtaat    5280
gcgcaggacc gtttcacgca ctccaccatg atgaaagatc aagttgacct ggttctgaaa    5340
gatccggtga aactggacga ttaagaattc                                    5370
```

<210> SEQ ID NO 92
<211> LENGTH: 5423
<212> TYPE: DNA
<213> ORGANISM: Artificial Sequence
<220> FEATURE:
<223> OTHER INFORMATION: SaCP10374-CPRm-SaTps8201, synthetic operon encoding forSaCP10374, CPRm and an alpha-/beta-santalene synthase

<400> SEQUENCE: 92

```
catatggcac tgctgctggc tgtcttttgg agcgcactga ttattctgac ccgcaaacgc     60
cgcaaaggtc cgggtctgcc accgggtccg cgtgcgtacc cgattattgg caatctgcac    120
atgatgggcc agctgccaca ccacaatttg cgtgagctgg cacgtgagta tggtccgatt    180
atgagcatgc gcctgggtct ggtgccggca atcgtggtta gctctcctga ggctgcgcag    240
ctgttcctca agacgcatga taccgttttc gcgagccgtc caaagaccga gactgccaaa    300
tacttccatt acggtatcaa aggtctgatc ctgaccgagt atggcccgta ctggcgcaat    360
attcgtcgtt tgagcaccgt taagctgttg aatgccgcga aaatcgatag cttcgcggct    420
atgcgtagaa gcgaagttga acgcctggtc gcgtccgttc gtggttcggc ggttcgtcgt    480
gaggttgtgg acgtcagcag caaagtgcg gaagctatgg agaatatggt ctgccagatg    540
gttatcggcc gttcaggtga cgatcgtttt aagctgaaag aaacctttca agagggcacc    600
```

-continued

```
caactggcag gcgcgttcaa ttttggtgag tttgtgccgt ttctgctgcc gctggacttg       660
caaggtatta cccgtcgcat caaagaagtc agcactcgtt tcaataagat tttggacctg       720
atcgttgacg agcacattcg cgatgccgct ggtaccaaaa acagcggcgg tcgtgatagc       780
gacaattttc tggatgttct gctgtccttg atgaacacct ctattagcga tagcaatgac       840
acgggtgaca caaccgtaa caacgtgatc gagcgtgata acattaaagc gatcctgacg        900
gacatgctgg gtgcagcgat ggacacgagc gcgagcacgg tcgagtggac gatctccgaa       960
ctgtttcgcc acccgaaaac catgcagaag ctgcaagcag aaatccgtgg tgtcgtgggc      1020
ccgacccgca atgtgagcga agatgacttg ccgaagctga cctatctgga catggtcgtt      1080
aaggaaggca tgcgtttgca tccggccgtg ccgctgcttc tgccgcatga gtctctggaa      1140
gaagccacga tcgatggcta ctacattccg aagggttccc gcattctgat caacgtctgg      1200
gcgattggtc gcgacccgaa ggcctggccg gatcgtcctg aagagttcat cccggagcgt      1260
ttcgagaaaa gcaacgtgga tgtgctgggc cgtgacttcc agctgctgcc gtttggttcg      1320
ggtcgtcgcg gttgtgcagg cattcgcctg ggcctgatct tcgtacgtct ggttctggca      1380
cagttagttc actgtttcga ctgggaactg gcgcgcaaca tggcgagcag cccggagaag      1440
ttggatatgg aagagaagtt cggcctggcg gtgcatcgtg tcaaccacct gaaagccctg      1500
ccgacgtatc gtctggagtg ctaagtcgac taactttaag aaggagatat atccatggaa      1560
cctagctctc agaaactgtc tccgttggaa tttgttgctg ctatcctgaa gggcgactac      1620
agcagcggtc aggttgaagg tggtccaccg ccaggtctgg cagctatgtt gatggaaaat      1680
aaggatttgg tgatggttct gacgacgtcc gtggcagtcc tgatcggctg tgtcgtggtc      1740
ctggcatggc gtcgtgcggc aggtagcggt aagtacaagc aacctgaact gcctaaactg      1800
gtggtcccga aagcagccga accggaggag gcagaggatg ataaaaccaa gatcagcgtg      1860
tttttcggca cccaaaccgg tacggcagaa ggttttcgcg aggcttttgt tgaagaggcc      1920
aaggcgcgtt atcagcaggc ccgttttcaaa gttatcgacc tggacgacta tgcggcagac      1980
gatgacgagt acgaagagaa actgaagaag gaaaacttgg cattcttctt cttggcgtcc      2040
tacggtgacg gcgagccgac ggacaacgcg gcacgctttt acaaatggtt tacggagggt      2100
aaggaccgtg gtgaatggct gaacaatctg cagtacggcg ttttttggtct gggtaaccgt      2160 caatatgagc atttcaataa gatcgccatt gtcgtcgatg atctgatctt cgagcaaggt      2220
ggcaagaagc tggttccggt gggtctgggt gacgatgacc agtgcattga ggatgatttt      2280
gcggcgtggc gtgaactggt ctggccggaa ctggataaac tgctgcgtaa cgaagacgac      2340
gctaccgtgg caaccccgta cagcgccgct gtgctgcaat accgcgtggt tttccacgat      2400
cacattgacg gcctgattag cgaaaacggt agcccgaacg tcatgctaa tggcaatacc      2460 gtgtacgatg cgcaacaccc gtgccgtagc aacgtcgcgg tcaagaagga attgcatact      2520
ccggcgagcg atcgcagctg cacccacctg gaatttaaca ttagcggtac cggcctgatg      2580
tacgagacgg gtgaccacgt cggtgtgtat tgcgagaacc tgttggaaac cgtggaggag      2640
gccgagaagt tgttgaacct gagcccgcag acgtacttct ccgttcacac cgacaacgag      2700
gacggtacgc cgttgagcgg cagcagcctg ccgccaccgt ttccgccgtg caccttgcgc      2760
acggcattga ccaaatacgc agacttgact tctgcaccga aaagtcggt gctggtggcg      2820 ctggccgagt acgcatctga ccagggtgaa gcggatcgtt tgcgttttctt ggcgagcccg      2880 agcggcaaag aggaatatgc acagtacatc ttggcaagcc agcgcacgct gctggaggtc      2940
```

```
atggcggagt tcccgtcggc gaaaccgccg ctgggtgtct ttttcgcggg tgtcgctccg    3000
cgcctgcagc cgcgtttcta ttccattagc tctagcccga agatcgcacc gttccgtatt    3060
cacgtgacct gcgccctggt ttatgacaaa tcccctaccg gtcgcgttca aagggcatc     3120
tgtagcacgg ggatgaaaaa tgcggtcccg ctggaagaaa gcaacgattg ttcctgggct    3180
ccgatcttcg tccgcaacag caacttcaag ctgccgaccg acccgaaggt tccgattatc    3240
atgattggtc cgggtaccgg tctggcccct tttcgtggct ttttgcaaga gcgcttggcg    3300
ttgaaagaga gcggtgctga attgggtccg gcgatcttgt tctttggttg ccgtaaccgt    3360
aaaatggact tatttacga ggatgaactg aatgatttcg tcaaagcggg cgttgtcagc     3420
gagctgatcg tcgcttttag ccgcgaaggc ccgatgaaag aatacgtgca acacaaaatg    3480
agccaacgtg cctccgatgt gtggaacatc attagcgacg gtggttatgt ttatgtttgc    3540
ggtgacgcga agggtatggc tcgtgatgtt caccgtaccc tgcataccat cgcacaggag    3600
caaggtagca tgtccagctc ggaggccgaa ggtatggtca aaaacctgca aaccaccggt    3660
cgttacctgc gtgatgtgtg gtaataaaag cttaggaggg aaaacatatg gacagcagca    3720
ccgccaccgc aatgaccgca ccattcatcg acccgacgga tcatgtgaat ctgaaaaccg    3780
acacggatgc gagcgaaaat cgtcgtatgg gtaactacaa gccgagcatt tggaactacg    3840
attttctgca gtccctggcg acgcaccaca acattgttga agagcgtcac ctgaagctgg    3900
cagagaaact gaaaggtcaa gtgaaattca tgttcggtgc gccgatggag ccattggcta    3960
agttggagct ggttgatgtg gtgcaacgct gggtctgaa ccacctgttc gagactgaaa      4020
tcaaagaagc tctgttcagc atctacaaag atggcagcaa tggctggtgg tttggccatc    4080
tgcatgctac ctctttgcgc ttccgtctgt tgcgccaatg tggcctgttt atcccgcagg    4140
acgttttcaa aacctttcaa aacaagaccg gtgagtttga catgaagctg tgcgacaacg    4200
ttaagggcct gctgagcctg tacgaggcga gctacctggg ctggaagggc gagaacatct    4260
tggatgaagc aaaggcgttc acgaccaagt gcctgaagag cgcatgggag aacattagcg    4320
agaagtggct ggcgaagcgt gttaaacatg cgttggcgct gccgctgcac tggcgtgttc    4380
cgcgtattga agcacgctgg tttatcgagg cctacgaaca agaggccaat atgaatccga    4440
cgctgctgaa actggcgaaa ctggacttca acatggtcca aagcattcac cagaaagaaa    4500
tcggtgaact ggcccgctgg tgggttacta ccggcctgga caagctggcg ttcgcacgca    4560
acaatctgtt gcagtcttat atgtggagct gcgccatcgc gtccgacccg aaattcaaac    4620
tggcgcgtga aaccattgtc gagatcggtt ccgtgttgac ggttgtcgac gacggctatg    4680
atgtgtacgg ttctatcgat gagctggacc tgtacaccag ctcggtggag cgttggtcct    4740
gtgtcgagat tgacaagctg cctaatacgc tgaagctgat cttatgtct atgttcaaca     4800
aaaccaacga ggtgggtctg cgtgttcaac acgagcgtgg ttacaatagc atcccgacct    4860
tcattaaggc gtgggtggaa cagtgtaaga gctatcaaaa agaggcgcgt tggtttcatg    4920
gtggtcacac gcctccgctg gaagaataca gcctgaacgg tctggtcagc attggttttc    4980
cgctgttgct gatcaccggc tatgttgcga ttgctgagaa tgaagcagcc ctggataaag    5040
tccacccgct gccggacctg ctgcattatt ccagcttgct gagccgtctg attaatgata    5100
tcggcactag cccggatgaa atggcgcgtg gtgacaatct gaagagcatt cactgctata    5160
tgaatgaaac cggtgccagc gaagaggtcg cacgcgagca catcaaaggc gtcatcgaag    5220
agaattggaa aattctgaac cagtgttgct ttgaccagtc ccagttccag gagccgttca    5280
tcacgtttaa cctgaacagc gtgcgcggct cgcatttctt ctatgaattt ggtgatggtt    5340
```
ttggtgttac cgacagctgg accaaggtgg atatgaaaag cgtcctgatt gatccgattc    5400
cgctgggtga agagtaagaa ttc                                            5423

<210> SEQ ID NO 93
<211> LENGTH: 53
<212> TYPE: DNA
<213> ORGANISM: Artificial Sequence
<220> FEATURE:
<223> OTHER INFORMATION: mutagenesis reverse primer AV8-L358-rev
<220> FEATURE:
<221> NAME/KEY: misc_feature
<222> LOCATION: (22)..(22)
<223> OTHER INFORMATION: n is a, c, g, or t

<400> SEQUENCE: 93
cacgcggcat caccagcgga vncggcggat gcaggcgcag ggtttcttta atc          53

<210> SEQ ID NO 94
<211> LENGTH: 40
<212> TYPE: DNA
<213> ORGANISM: Artificial Sequence
<220> FEATURE:
<223> OTHER INFORMATION: primer AV8-pcw-fw

<400> SEQUENCE: 94
catcgatgct taggaggtca tatggctctg ttattagcag                          40

<210> SEQ ID NO 95
<211> LENGTH: 25
<212> TYPE: DNA
<213> ORGANISM: Artificial Sequence
<220> FEATURE:
<223> OTHER INFORMATION: primer AV8-L358-fw

<400> SEQUENCE: 95
tccgctggtg atgccgcgtg agtgc                                          25

<210> SEQ ID NO 96
<211> LENGTH: 38
<212> TYPE: DNA
<213> ORGANISM: Artificial Sequence
<220> FEATURE:
<223> OTHER INFORMATION: primer AV8-CPR-rev

<400> SEQUENCE: 96
atatatctcc ttcttaaagt tagtcgactc attaggtg                            38

<210> SEQ ID NO 97
<211> LENGTH: 65
<212> TYPE: DNA
<213> ORGANISM: Artificial Sequence
<220> FEATURE:
<223> OTHER INFORMATION: foward primer CPRm_aaBFS_Inf1

<400> SEQUENCE: 97
ttacctgcgt gatgtgtggt aataaaagct taggaggtaa aaatgtctac cctgccaatt    60
tcttc                                                                65

<210> SEQ ID NO 98
<211> LENGTH: 63
<212> TYPE: DNA
<213> ORGANISM: Artificial Sequence
<220> FEATURE:
<223> OTHER INFORMATION: reverse primer AaBFS_Inf2

-continued

<400> SEQUENCE: 98
atgtttgaca gcttatcatc gataagctga attcttacac aaccatcggg tgcacaaaga    60
atg    63

<210> SEQ ID NO 99
<211> LENGTH: 65
<212> TYPE: DNA
<213> ORGANISM: Artificial Sequence
<220> FEATURE:
<223> OTHER INFORMATION: foward primer CPRm_PaAFS_Inf1

<400> SEQUENCE: 99
ttacctgcgt gatgtgtggt aataaaagct taggaggtaa aaatggatct ggcagtggaa    60
atcgc    65

<210> SEQ ID NO 100
<211> LENGTH: 66
<212> TYPE: DNA
<213> ORGANISM: Artificial Sequence
<220> FEATURE:
<223> OTHER INFORMATION: reverse primer PaAFS_Inf2

<400> SEQUENCE: 100
ctcatgtttg acagcttatc atcgataagc tgaattctta catcgggacc ggctccagga    60
cggtgc    66

<210> SEQ ID NO 101
<211> LENGTH: 60
<212> TYPE: DNA
<213> ORGANISM: Artificial Sequence
<220> FEATURE:
<223> OTHER INFORMATION: primer foward CPRm_Tps647_inf1

<400> SEQUENCE: 101
gcgtgatgtg tggtaataaa agcttaggag gtaaaaatgg cgaccgttgt ggatgattct    60

<210> SEQ ID NO 102
<211> LENGTH: 53
<212> TYPE: DNA
<213> ORGANISM: Artificial Sequence
<220> FEATURE:
<223> OTHER INFORMATION: primer reverse Tps647_Inf2

<400> SEQUENCE: 102
gcttatcatc gataagctga attcttactc ttcatccagg gtaatcgggt gga    53

<210> SEQ ID NO 103
<211> LENGTH: 58
<212> TYPE: DNA
<213> ORGANISM: Artificial Sequence
<220> FEATURE:
<223> OTHER INFORMATION: primer foward CPRm_Tps30_Inf1

<400> SEQUENCE: 103
gcgtgatgtg tggtaataaa agcttaggag gtaaaaatgg acgcattcgc aacgagcc    58

<210> SEQ ID NO 104
<211> LENGTH: 59
<212> TYPE: DNA
<213> ORGANISM: Artificial Sequence

```
<220> FEATURE:
<223> OTHER INFORMATION: primer reverse Tps30_Inf2

<400> SEQUENCE: 104
gtgatgtgtg gtaataaaaa gctgaattct tagtcctctt cattcagcgg gatcgggtg       59
```

METHOD FOR PRODUCING FRAGRANT ALCOHOLS

RELATED APPLICATIONS

This application is a continuation of U.S. patent application Ser. No. 15/877,183 filed on Jan. 22, 2018, now U.S. patent Ser. No. 10/570,420, which was a divisional of U.S. patent application Ser. No. 15/023,640, now U.S. Pat. No. 9,909,145, filed Mar. 21, 2016, which is a national stage application under 35 U.S.C. § 371 of International Patent Application PCT/EP2014/070060 filed on Sep. 19, 2014, which claims the benefit of U.S. provisional application 61/880,149, filed on Sep. 19, 2013. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 9000US_DIV_SequenceListing. The size of the text file is 423 KB, and the text file was created on Jan. 16, 2018.

FIELD

The field relates to cytochrome P450s and uses to produce sesquiterpene alcohols.

BACKGROUND

Terpenes hydrocarbons such as alpha and beta santalenes have been produced via biochemical processes for example such as through genetically altered cells. These terpenes and the alcohol derived from them are major constituents of sandalwood oil and the alcohols are important perfumery ingredients typically obtained commercially through the distillation of the heartwood of *Santalum* species (e.g., Sandalwood). Examples of such alcohols include α-sinensol, β-sinensol, α-santalol, β-santalol, α-trans-bergamotol and epi-β-santalol. Although new biochemical pathways have been developed, including genetically engineered cells, to generate the terpene hydrocarbons, it is desirable to find a biochemical pathway to generate and produce the alcohols derived from the santalenes. It is further desirable to use a biochemical pathway to not only generate such alcohols but it is further desirable to selectively produce, via a biochemical pathway, cis-isomers of the alcohols such as iso-α-sinensol, iso-β-sinensol, (Z)-α-santalol, (Z)-β-santalol, (Z)-α-trans-bergamotol and (Z)-epi-β-santalol.

Cytochrome P450s represent a family of enzymes of oxidases. P450s commonly catalyze a monooxygenase reaction. Cytochrome P450 enzymes are classified into families and subfamilies based on the amino acid sequences homology. Members of a same subfamily share over 55% amino acid sequence identity and have usually similar enzymatic activities (substrate and/or product selectivity). CYP71AV1 (NCBI accession No ABB82944.1, SEQ ID No. 51 and 52) and CYP71AV8 (NCBI accession No ADM86719.1, SEQ ID No. 1 and 2) are two members of the CYP71AV subfamily and shares 78% sequence identity. CYP71AV1 has previously been shown to oxidize amorphadiene (Teoh et al, *FEBS letters* 580 (2006) 1411-1416). CYP71AV8 has previously been shown to oxidize (+)-valencene, germacrene A and amorphadiene (Cankar et al, *FEBS Lett.* 585(1), 178-182 (2011)).

Processes using engineered cells have been reported that use terpene synthases to catalyze the production of a diterpene or sesquiterpene. The diterpenes or sesquiterpenes were further processed using a cytochrome P450 polypeptide to catalyze the hydroxylation, oxidation, demethylation or methylation of the diterpene or sesquiterpene produced by the cell.

SUMMARY

Provided herein is a method of producing an sesquiterpene alcohol comprising:
i) contacting a terpene of Formula I:

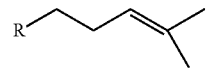

Formula I with a polypeptide having an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73, SEQ ID NO: 79, and SEQ ID NO: 81; and
ii) optionally isolating the alcohol wherein R is a saturated, mono-unsaturated or poly-unsaturated aliphatic group composed of 9 carbons and wherein R can be a branched chain or composed of one or more non-aromatic rings.

Further provided herein is a method of producing a sesquiterpene comprising α-sinensol, β-sinensol, α-santalol, β-santalol, α-trans-bergamotol, epi-β-santalol, lancelol and/or or mixtures thereof comprising:
i) contacting α-farnesene, β-farnesene, α-santalene, β-santalene, α-trans-bergamotene, epi-β-santalene, and/or β-bisabolene, with a polypeptide having an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73, SEQ ID NO: 79, and SEQ ID NO: 81 to produce the alcohol; and
ii) optionally isolating the alcohol.

Also provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide having a P450 monooxygenase activity wherein the sesquiterpene alcohol produced comprises at least, or at least about, 36% of a cis isomer.

Further provided herein is an isolated polypeptide having monooxygenase activity comprising an amino acid sequence that is at least, or at least about 45%, 50%, 55%, 50%, 65%, 70%, 80%, 90%, 95%, 98% or more identical to an amino acid sequence selected from the group consisting of SEQ ID NO: 71, and SEQ ID NO:73.

Further provided herein is an isolated polypeptide having monooxygenase activity comprising an amino acid sequence that is at least, or at least about 45%, 50%, 55%, 50%, 65%, 70%, 80%, 90%, 95%, 98% or more identical to an amino acid sequence selected from the group consisting of SEQ ID NO: 79, and SEQ ID NO: 81.

Also provided herein is an isolated polypeptide having monooxygenase activity comprising an amino acid sequence selected from the group consisting of SEQ ID NO: SEQ ID NO:28, SEQ ID NO:30, SEQ ID NO:32, SEQ ID NO: 34, SEQ ID NO:36, SEQ ID NO:71, SEQ ID NO:73 SEQ ID NO: 79, and SEQ ID NO: 81.

Further provided herein is method of producing a sesquiterpene alcohol selected from the group consisting of α-sinensol, β-sinensol, α-santalol, β-santalol, α-trans-bergamotol, epi-β-santalol, and lancelol or mixtures thereof:

i) cultivating a cell under conditions suitable to produce a p450 polypeptide having monooxygenase activity wherein the cell: a) produces a acylic pyrophosphate terpene precursor; b) expresses a P450 reductase, c) expresses a polypeptide that has α-farnesene, β-farnesene, α-santalene, β-santalene, α-trans-bergamotene and/or epi-β-santalene, synthase activity and produces α-farnesene, β-farnesene, α-santalene, β-santalene, α-trans-bergamotene and/or epi-β-santalene and d) expresses a polypeptide with an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73 SEQ ID NO: 79, and SEQ ID NO: 81; and ii) optionally isolating the alcohol from the cell.

DETAILED DESCRIPTION OF THE DRAWINGS

FIG. 1. Amino acid sequence alignment of the N-terminal region of the different CYP71AV8 variants: CYP71AV8_wt (SEQ ID NO: 2), cyp71AV8-65188 (SEQ ID NO: 4), CYP71AV8-P2 (SEQ ID NO: 6), CYP71AV8-P2O (SEQ ID NO: 8).

FIG. 2A-D. Alignment of DNA sequences of the different CYP71AV8 variants: CYP71AV8_wt (SEQ ID NO: 1), cyp71AV8-65188 (SEQ ID NO: 3), CYP71AV8-P2 (SEQ ID NO: 5), CYP71AV8-P20 (SEQ ID NO: 6). The encoded amino acid sequences are shown below each sequence using the one-letter code.

FIG. 3. GCMS analysis of the conversion of sesquiterpenes by E. coli cells expressing the CYP71AV8 and the CPRm proteins. A, Bioconversion of (+)-alpha-santalene. B, Bioconversion of a (+)-alpha-santalene/(−)-beta-santalene mixture.

FIG. 4. Organisation of the synthetic bi-cistronic operon containing a P450 and a CPR cDNA.

FIG. 5. Comparison of the bioconversion of (+)-α-santalene and the α/β-santalene mixture by E. coli cells transformed with different bi-cistronic operons composed of a P450 and a CPR cDNA. 1, CYP71AV8-65188 and aaCPR. 2, CYP71AV8-P2 and aaCPR. 3, CYP71AV8-P2O and aaCPR. 4, CYP71AV8-65188 and CPRm. 5, CYP71AV8-P2 and CPRm. 6, CYP71AV8-P2O and CPRm.

FIG. 6. GCMS analysis of the sesquiterpene molecules produced by E. coli cells expressing CYP71AV8, CPRm, an alpha-santalene synthase (A) or a alpha-santalene/beta-santalene synthase (B), and mevalonate pathway enzymes. 1, (+)-α-santalene; 2 (−)-α-trans-bergamotene; 3, (+)-epi-β-santalene; 4, (−)-β-santalene.

FIG. 7. Oxidation of (+)-α-santalene by CYP71AV8 wild type (A) and mutant L-358 (B). GC-MS profiles of the sesquiterpene products generated by E. coli KRX cells expressing CPRm, ClASS, the mevalonate pathway enzymes and CYP71AV8 (A) or CYP71AV8-L358F (B). The cultivations were performed in TB medium containing 3% glycerol as carbon source. The different products were identified as α-santalene (1), (E)-α-santalal (2), (Z)-α-santalol (4), and (E)-α-santalol (3).

FIG. 8. GC-MS profiles of the sesquiterpene products generated by E. coli KRX cells expressing CPRm, SaSAS, the mevalonate pathway enzymes and CYP71AV8-L358F. The cultivations were performed in TB medium containing 3% glycerol as carbon source. The different products identified by their mass spectra are indicated.

FIG. 9. GCMS analysis of the conversion of (+)-α-santalene by E. coli cells expressing the CYP71AV1 and the CPRm proteins.

FIG. 10: GC analysis of the in vivo conversion of (+)-α-santalene to (Z)-α-santalol by a P450-BM3 double-mutant (variant #17). Solvent extracts of cultures of recombinant E. coli cells co-expressing a Clausena lansium α-santalene synthase and either the wild-type P450-BM3 (A) or the P450-BM3 variant #17 (B) were analyzed as described in example 11.1, (+)-α-santalene; 2, (−)-α-trans-bergamotene; 3, (Z)-α-santalol; The chromatograms are shown in selected ion mode (M/Z 93).

FIG. 11: GC analysis of the in vivo conversion of (+)-α-santalene, (−)-β-santalene, (−)-α-trans-bergamotene and (+)-epi-β-santalene by a P450-BM3 double-mutant. Solvent extracts of cultures of recombinant E. coli cells co-expressing an alpha-santalene/beta-santalene synthase from Santalum album and either the wild-type P450-BM3 (A) or the P450-BM3 variant #17 (B) were analyzed as described in example 11.1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol. The chromatograms are shown in selected ion (M/Z 93).

FIG. 12: GCMS analysis of the conversion of (+)-α-santalene by the recombinant SaCP816 enzyme. A. Control without the recombinant P450 enzyme. B. Assay with E. coli crude protein extract containing the recombinant SaCP816 protein. C. Sandalwood oil for comparison of the retention times. All assays were performed in-vitro as described in example 4. 1, (+)-α-santalene; 5, (Z)-α-santalol; 6, (Z)-α-trans-bergamotol; 7, (Z)-epi-β-santalol; 8, (Z)-β-santalol. The identity of the sequiterpene molecules were confirmed by matching of the mass spectra with authentic standards.

FIG. 13: GCMS analysis of the conversion of (+)-α-santalene, (−)-β-santalene, (−)-α-trans-bergamotene and (+)-epi-β-santalene by the recombinant SaCP816 enzyme. A. Control without the recombinant P450 enzyme. B. Assay with E. coli crude protein extract containing the recombinant SaCP816 protein. C. Sandalwood oil for comparison of the retention times. All assays were performed in-vitro as described in example 4. 1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol. The identity of the sequiterpene molecules were confirmed by matching of the mass spectra with authentic standards.

FIG. 14: GCMS analysis of the molecules produced by *E. coli* engineered to produced sesquiterpenes and expressing SaCP816, CPRm, an alpha-santalene synthase (ClASS) (A) or a alpha-santalene/beta-santalene synthase (SaSAS) (B). 1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol (co-eluted with farnesol produced from an excess pool of farnesyl diphosphate). The identity of the sequiterpene molecules were confirmed by matching of the mass spectra with authentic standards.

FIG. 15: GCMS analysis of the conversion of (+)-α-santalene (21) by the recombinant SaCP10374 P450 enzyme. A. Control without the recombinant P450 enzyme. B. Assay with *E. coli* crude protein extract containing the recombinant SaCP10374 protein. The numbers indicated on the chromatograms refer to the structures presented in FIG. 27.

FIG. 16: GCMS analysis of the conversion of a mixture composed of (+)-α-santalene (21), (−)-α-trans-bergamotene (17); (+)-epi-β-santalene and (−)-β-santalene (25) (prepared using the SaTp8201 recombinant protein, example 4) by the recombinant SaCP10374 P450s enzymes. A. Control without the recombinant P450 enzyme. B. Assay with *E. coli* crude protein extract containing the recombinant SaCP10374 protein. The numbers indicated on the chromatograms refer to the structures presented in FIG. 27.

FIG. 17: GCMS analysis of the conversion of β-farnesene (1) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 18: GCMS analysis of the conversion of α-farnesene (5) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 19: GCMS analysis of the conversion of (−)-sesquisabinene B (9) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 20: GCMS analysis of the conversion of (−)-β-bisabolene (13) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 21: GCMS analysis of the conversion of (−)-α-bergamotene (17) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 22: GCMS analysis of the products generated in-vivo as described in example 23 by *E. coli* KRX cells transformed with the plasmids pACYC-29258-4506 and the plasmid pD444-SR-AaBFS (A), SaCP10374-CPRm-AaBFS-pCWori (B), or SaCP816-CPRm-AaBFS-pCWori (C). The chromatograms show the formation of (E)-β-farnesene (1) as well as oxidized derivatives (2-3) (see FIG. 27 for corresponding structures).

FIG. 23: GCMS analysis of the products generated in-vivo as described in example 23 by *E. coli* KRX cells transformed with the plasmids pACYC-29258-4506 and the plasmid pD444-SR-PaBAFS (A), SaCP10374-CPRm-PaAFS-pCWori (B), or SaCP816-CPRm-PaAFS-pCWori (C). The chromatograms show the formation of (E,E)-α-farnesene (5) as well as oxidized derivatives (6-8) (see FIG. 27 for corresponding structures). The peak of farnesol resulting from the hydrolysis of excess FPP is inducated on each chromatogram.

FIG. 24: GCMS analysis of the products generated in-vivo as described in example 23 by *E. coli* KRX cells transformed with the plasmids pACYC-29258-4506 and the plasmid pETDuet-SaTps647 (A), SaCP10374-CPRm-SaTps647-pCWori (B), or SaCP816-CPRm-SaTPS647-pCWori(C). The chromatograms show the formation of (−)-sesquisabinene B (9) as well as oxidized derivatives (10-12) (see FIG. 27 for corresponding structures).

FIG. 25: GCMS analysis of the products generated in-vivo as described in example 23 by *E. coli* KRX cells transformed with the plasmids pACYC-29258-4506 and the plasmid pETDuet-ClTps2 (A) or SaCP10374-CPRm-ClTps2-pCWori (B). The chromatograms show the formation of (+)-α-santalene (21) as well as oxidized derivatives (23-24) (see FIG. 27 for corresponding structures).

FIG. 26: GCMS analysis of the products generated in-vivo as described in example 23 by *E. coli* KRX cells transformed with the plasmids pACYC-29258-4506 and the plasmid pETDuet-SaTps8201 (A) or SaCP10374-CPRm-SaTps8201-pCWori (B). The chromatograms show the formation of (+)-α-santalene (21), (−)-β-santalene (25) and (−)-trans-α-Bergamotene (17) as well as oxidized derivatives (19, 20, 23, 24, 27 and 28) (see FIG. 27 for corresponding structures).

FIG. 27A-B: Structure of the enzymes substrates and products discussed in the text.

DETAILED DESCRIPTION

In some embodiments, provided herein is a method of producing a sesquiterpene comprising α-sinensol, β-sinensol, α-santalol, β-santalol, α-trans-bergamotol, epi-β-santalol, and lancelol and/or mixtures thereof comprising contacting α-farnesene, farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 2. In a particular embodiment, the method comprises a cell that expresses the polypeptide.

In some embodiments, provided herein is a method of producing a α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 4. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 6. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 8. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 28. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 30. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 32. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 34. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 36. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 38. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 40. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 42. In a particular embodiment, the method comprises a cell that expresses the polypeptide In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 44. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 50. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 52. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 54. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 58. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO:60. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 62. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 64. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 66. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 68. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 71. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 73. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 79. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% sequence identify to SEQ ID NO: 81. In a particular embodiment, the method comprises a cell that expresses the polypeptide.

The nucleotide sequences provided herein for producing a polypeptide for use in producing an alcohol have a nucleic acid sequence at least, or at least about 45%, 50%, 55%, 60%, 65%, 70%, 75%, 80%, 85%, 90%, 95% or 98% to a sequence selected from the group consisting of SEQ ID NO: 1, SEQ ID NO: 3, SEQ ID NO: 5, SEQ ID NO: 7, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 49, SEQ ID NO: 51, SEQ ID NO: 53, SEQ ID NO: 57, SEQ ID NO: 59, SEQ ID NO: 61, SEQ ID NO: 63, SEQ ID NO: 65, SEQ ID NO: 67, SEQ ID NO: 70 SEQ ID NO: 72, SEQ ID NO: 78 and SEQ ID NO: 80. The nucleotide sequences provided herein are heterologous in that they are not typically or normally produced by a cell in which it is expressed herein and is generally not endogenous to the cell into which it is introduced—it being typically obtained from another cell or could be made synthetically.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 36%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of SEQ ID NO: 28, SEQ ID NO: 30, SEQ ID NO: 58, SEQ ID NO: 60, SEQ ID NO: 62, SEQ ID NO: 64, SEQ ID NO: 66, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 46%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of SEQ ID NO: 30, SEQ ID NO: 58, SEQ ID NO: 60, SEQ ID NO: 62, SEQ ID NO: 66, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 50%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of SEQ ID NO: 58, SEQ ID NO: 60, SEQ ID NO: 62, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 72%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of 45%, 50%, 55%, 60%, 65%, 70%, 80%, 90%, 95%, or 98% sequence identify to a polypeptide having an amino acid sequence selected from the group consisting of SEQ ID NO: 58, SEQ ID NO: 60, SEQ ID NO: 62, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 96%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 100%, of a cis isomer and wherein the polpeptide e comprises an amino acid sequence having at least or at least about 45%, 50%, 55%, 60%, 65%, 70%, 80%, 90%, 95%, or 98% sequence identify to a polypeptide having an amino acid sequence selected from the group consisting of SEQ ID NO: 71, and 73.

Provided herein is also an isolated nucleic acid molecule selected from the group consisting of: i) a nucleic acid having an nucleic acid sequence selected from the group consisting SEQ ID. NO: 70 and 72; and ii) a nucleic acid molecule that encodes a polypeptide having p450 monooxygenase activity wherein the polypeptide comprises an amino acid sequence that is at least, or at least about 45%, 50%, 55%, 50%, 65%, 70%, 80%, 90%, 95%, or 98% or more identical to an amino acid sequence selected from the group consisting of SEQ ID NOs: 71, and SEQ ID NO: 73. More particularly the polypeptide encoded has the sequence selected from the group consisting of SEQ ID NOs: 71, and SEQ ID NO: 73.

Provided herein is also an isolated nucleic acid molecule selected from the group consisting of: i) a nucleic acid having an nucleic acid sequence selected from the group consisting SEQ ID. NO: 78 and 80; and ii) a nucleic acid molecule that encodes a polypeptide having p450 monooxygenase activity wherein the polypeptide comprises an amino acid sequence that is at least, or at least about 45%, 50%, 55%, 50%, 65%, 70%, 80%, 90%, 95%, or 98% or more identical to an amino acid sequence selected from the group consisting of SEQ ID NOs: 79, and SEQ ID NO: 82. More particularly the polypeptide encoded has the sequence selected from the group consisting of SEQ ID NOs: 79, and SEQ ID NO: 82.

Also provided herein is an isolated nucleic acid molecule selected from the group consisting of: i) a nucleic acid having an nucleic acid sequence selected from the group consisting SEQ ID. NO: 27, 29, 31, 33, and 35; and ii) a nucleic acid molecule that encodes a polypeptide having p450 monooxygenase activity wherein the polypeptide has the sequence selected from the group consisting of SEQ ID NO: 28, SEQ ID NO: 30, SEQ ID NO: 32, SEQ ID NO: 34, SEQ ID NO: 36.

In another embodiment provided herein is a method for producing a polypeptide having P450 monoxygenase activity comprising the steps of transforming a host cell or non-human organism with a nucleic acid encoding a polypeptide having at least, or at least about, 45%, 50%, 55%, 50%, 65%, 70%, 80%, 90%, 95%, or 98% sequence identity to a polypeptide selected from the group consisting of SEQ ID NO: 71, and SEQ ID NO: 73 and culturing the host cell or organism under conditions that allow for the production of the polypeptide.

In a further embodiment provided here is a method for producing a polypeptide having P450 monoxygenase activity comprising the steps of transforming a host cell or non-human organism with a nucleic acid encoding a polypeptide having the sequence selected from the group consisting of SEQ ID NO: 71, and SEQ ID NO: 73 and culturing the host cell or organism under conditions that allow for the production of the polypeptide.

In another embodiment provided herein is a method for producing a polypeptide having P450 monoxygenase activity comprising the steps of transforming a host cell or non-human organism with a nucleic acid encoding a polypeptide having at least, or at least about, 45%, 50%, 55%, 50%, 65%, 70%, 80%, 90%, 95%, or 98% sequence identity to a polypeptide selected from the group consisting of SEQ ID NO: 79, and SEQ ID NO: 81 and culturing the host cell or organism under conditions that allow for the production of the polypeptide.

In a further embodiment provided here is a method for producing a polypeptide having P450 monoxygenase activity comprising the steps of transforming a host cell or non-human organism with a nucleic acid encoding a polypeptide having the sequence selected from the group consisting of SEQ ID NO: 79, and SEQ ID NO: 81 and culturing the host cell or organism under conditions that allow for the production of the polypeptide.

The alcohols can be converted to aldehydes or acids such as but not limited to sinensals, santalals, bergamotenals, and lanceals. The alcohols, aldehydes or acids can be further converted to derivatives such as, but not limited to esters, amides, glycosides, ethers or acetals.

Nucleic acid and polypeptides described herein may be isolated for example from *Cichorium intybus* L., *Bacillus megaterium, Santalum album* and *Artemisia annua*. CYP71AV8, P450-BM3 (CYP102A1), and CYP71AV1 including variants are described herein.

CYP71AV8 from the plant *Cichorium intybus* L. was previously characterized as a P450 mono-oxygenase able to oxidize region-selectively (+)-valencene producing trans-nootkatol, cis-nootkatol and (+)-nootkatone. CYP71AV8 was also found to catalyse the oxidation of germacrene A and amorpha-4,11-diene in the C-12 position (Cankar et al, *FEBS Lett.* 585(1), 178-182 (2011)). The amino acid sequence of the wild type enzyme (NCBI accession No ADM86719.1, SEQ ID No 1 and 2) was used to design a cDNA sequence optimized for expression in *E. coli*.

In eukaryotes, the P450 monooxygenases are membrane-bound proteins and the N-terminal sequence of these proteins constitute a membrane anchor essential for the membrane localization of these enzymes. This part of the protein, usually delimited by a proline-rich domaine, is not essential for the control of the specificity of the enzymatic activity. This region can thus be modified by deletion, insertion or mutation without effect on the catalytic activity. However, specific modification of the N-terminal region of eukaryotic P450s, including plant P450s, have been shown to have a positive effect on the levels of functional recombinant proteins when expressed in microorganisms (Halkier et al (1995) *Arch. Biochem. Biophys.* 322, 369-377; Haudenschield et al (2000) *Arch. Biochem. Biophys.* 379, 127-136).

In P450 monooxygenases the recognition and binding of the substrate is controlled by several amino acid residues distributed in different regions along the protein amino acid sequences. These regions, defined as substrate recognition sites (SRS), can be localized in the amino acid sequence of any P450 by simple sequence alignment based for example on the work made by Gotoh (Gotoh O (1992) J. Biol. Chem. 267(1), 83-90). Thus residues in the CYP71AV8 protein that interact with the substrate and can influence the regioselectivity of the hydroxylation reaction are the amino acids Asn98 to Gly121, Thr198 to Leu205, Lys232 to Ile 240, Asn282 to Ala300, His355 to Arg367 and Thr469 to Val 476. The modification of one or more residues in these regions can potentially alter the substrate specificity, the stereochemistry of the reaction or its regioselectivity. One example of alteration of the regioselectivity of the reaction catalyzed by a P450 can be found in Schalk et al (2002) Proc. Natl. Acad. Sci. USA 97(22), 11948-11953. In this publication a single residue change in plant P450 enzymes led to a complete conversion to the regiospecificity of the enzymatique reaction.

A "sesquiterpene synthase" or a "polypeptide having a sesquiterpene synthase activity" is intended for the purpose of the present application as a polypeptide capable of catalyzing the synthesis of a sesquiterpene molecule or of a mixture of sesquiterpene molecules from a acyclic pyrophosphate terpene precursor selected from the group consisting of geranyl-pyrophosphate (GPP), farnesy-diphosphate (FPP) and geranylgeranyl-pyrophosphate (GGPP).

Alpha santalene, beta-santalene, alpha-trans-bergamotene, and/or epi-beta santalene may be prepared using the synthases described for example in U.S. Patent Publication No.: 2011-0008836, published Jan. 13, 20111 and in U.S. Patent Publication No.: 2011-0281257, published Nov. 27, 2011, both of which are incorporated herein in their entirety.

According to the present invention, polypeptides are also meant to include truncated polypeptides provided that they keep their P450 monooxygenase activity as defined in any of the above embodiments.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the world wide web. Particularly, the BLAST program (Tatiana et al, *FEMS Microbiol Lett.*, 1999, 174:247-250, 1999) set to the default parameters, available from the National Center for Biotechnology Information (NCBI) at their webpage ncbi.nlm.nih.gov/BLAST/bl2seq/wblast2.cgi, can be used to obtain an optimal alignment of peptidic or nucleotidic sequences and to calculate the percentage of sequence identity.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications: Martin, V. J., Pitera, D. J., Withers, S. T., Newman, J. D., and Keasling, J. D. Nat Biotechnol., 2003, 21(7), 796-802 (transformation of *E. coli*); Wu, S., Schalk, M., Clark, A., Miles, R. B., Coates, R., and Chappell, J., *Nat Biotechnol.*, 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering*, 2007, 97(1), 170-181 (transformation of yeast).

Non-human host organisms suitable to carry out the method described herein in vivo may be any non-human multicellular or unicellular organisms. In a particular embodiment, the non-human host organism used to carry out the invention in vivo is a plant, a prokaryote or a fungus. Any plant, prokaryote or fungus can be used. Particularly useful plants are those that naturally produce high amounts of terpenes. In a more particular embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Particularly, the plant belongs to the species of *Nicotiana tabacum*.

In a more particular embodiment the non-human host organism used to carry out the method of the invention in vivo is a microorganism. Any microorganism can be used but according to an even more particular embodiment said microorganism is a bacteria or yeast. Most particularly, said bacteria is *E. coli* and said yeast *is Saccharomyces cerevisiae*.

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are particularly plant or fungal cells.

As used herein, the polypeptide is intended as a polypeptide or peptide fragment that encompasses the amino acid sequences identified herein, as well as truncated or variant polypeptides, provided that they keep their P450 monooxygenaseactivity as defined above and that they share at least the defined percentage of identity with the corresponding polypeptide.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

As used herein, the polypeptide is intended as a polypeptide or peptide fragment that encompasses the amino acid sequence identified herein, as well as truncated or variant polypeptides, provided that they keep their activity as defined above. Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for making polypeptides having a P450 monooxygenase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a particular embodiment, the non-human host organism is a plant, a prokaryote or a fungus. Any plant, prokaryote or fungus is suitable to be transformed according to the present invention. Particularly useful plants are those that naturally produce high amounts of terpenes. In a more particular embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Particularly, the plant belongs to the species of *Nicotiana tabacum*.

In a more particular embodiment the non-human host organism is a microorganism. Any microorganism is suitable for the present invention, but according to an even more particular embodiment said microorganism is a bacteria or yeast. Most particularly, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

The term "transformed" refers to the fact that the host was subjected to genetic engineering to comprise one, two or more copies of each of the nucleic acids required in any of the above-described embodiment. Particularly the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual*, 1985, Elsevier, New York and Sambrook et al., *Molecular Cloning: A Laboratory Manual*, $2^{nd}$ edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

A "polypeptide variant" as referred to herein means a polypeptide having the above described activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry*, 1983, Addison-Wesley Pub. Co. The effects of such substitutions can be calculated using substitution score matrices such a PAM-120, PAM-200, and PAM-250 as discussed in Altschul, *J. Mol. Biol.*, 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acid from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, for examples plants from the *Santalum* species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptide encompassed by the invention also comprise fusion polypeptides resulting from a fusion of other functional proteins, such as other proteins from the terpene biosynthesis pathway.

The alcohols produced herein may be isolated by extraction for example using known methods to extract the alcohols generated in nature (e.g., extraction from Sandalwood). The alcohols produced herein have use as fragrant compounds that may be used in perfumery.

ABBREVIATIONS USED aaCPR *Arthemisia annua* Cytochrome P450 reductase
bp base pair
kb kilo base
DNA deoxyribonucleic acid
cDNA complementary DNA
ClASS *Clausena lansium* (+)-α-santalene synthase
CPRm *Mentha piperita* Cytochrome P450 reductase
DTT dithiothreitol
EDTA ethylene-diamine-tetraacetic acid
FPP farnesyl pyrophosphate
GC gaseous chromatograph
IPTG isopropyl-D-thiogalacto-pyranoside
LB lysogeny broth
MS mass spectrometer
MTBE methyl tert-buthyl ether
PCR polymerase chain reaction
RMCE recombinase-mediated cassette exchange
RNA ribonucleic acid
mRNA messenger ribonucleic acid
SaSAS *Santalum album* (+)-α-santalene/(⊕)-β-santalene synthase The following examples are illustrative only and are not meant to limit the scope of invention as set forth in the Summary, Description or in the Claims.

EXAMPLES

Example 1

Optimization of the CYP71AV8 cDNA Sequence for Expression in Bacteria

The membrane anchor region of CYP71AV8 was redesigned to introduce the modifications detailed bellow.

In the optimized CYP71AV8 sequences the 5'-end was modified to replace the first amino acids of the membrane anchor region with a peptide sequence shown to improve the heterologous expression of membrane-bound P450s in bacterial cells (Alkier, B. A. et al. *Arch. Biochem. Biophys.* 322, 369-377 (1995), Haudenschield, et al *Arch. Biochem. Biophys.* 379, 127-136 (2000)). In addition, for the entire cDNA, the codon usage was adapted to match the *E. coli* codon usage. Thus, several cDNA were designed for CYP71AV8 with different 3'-end modifications and optimizations:

CYP71AV8-65188: in this construct the 22 first codons were replaced by a sequence coding for the MALL-LAVFWSALIILV peptide (SEQ ID NO 3 and 4).

CYP71AV8-P2: the entire anchor-encoding sequence was replaced by the anchor sequence of an optimized limonene-hydroxylase from mint (PM2 in Haudenschield, et al *Arch. Biochem. Biophys.* 379, 127-136 (2000)) (SEQ ID NO 5 and 6).

CYP71AV8-P2O: this construct encodes for the same protein as the previous one but the membrane anchor region was further codon optimize (SEQ ID NO 7 and 8).

The FIG. 1 compares the amino acid sequences of the N-terminal regions of the different CYP71AV8 variants and FIG. 2 compares the DNA sequences of the 3 constructs. The three optimized CYP71AV8 cDNAs were synthesized in-vitro (DNA2.0, Menlo Park, Calif., USA) and cloned as NdeI-HindIII fragment into the pCWori+ expression plasmid (Barnes, H. J. *Method Enzymol.* 272, 3-14; (1996)).

Example 2

Functional Expression of CYP71AV8 in Bacterial Cells

For heterologous expression, the JM109 *E. coli* cells were transformed with the CYP71AV8 expression plasmids (example 1). Single colonies of transformants were used to inoculated cultures of 5 mL LB medium containing 50 µg/mL ampicillin. The cells are grown for 10 to 12 hours at 37° C. The cultures were then used to inoculate 250 mL TB Medium (Terrific Broth) supplemented with 50 µg/mL ampicillin and 1 mM Thiamine HCL. The cultures were incubated at 28° C. for 3-4 h with moderate shaking (200 rpm) before 75 mg/L δ-aminolevulinic acid (sigma) and 1 mM IPTG (Isopropyl β-D-1-thiogalactopyranoside) was added, and the cultures were maintained at 28° C. for 24-48 h with 200 rpm shaking.

The expression of the P450 enzymes can be evaluated qualitatively and quantitatively by measuring the CO-binding spectrum (Omura, T. & Sato, R. (1964) *J. Biol. Chem.* 239, 2379-2387) in the *E. coli* protein fractions. For protein extraction, the cells are centrifuged (10 min, 5000 g, 4° C.) and resuspended in 35 mL ice-cold buffer 1 (100 mM Tris-HCl pH 7.5, 20% glycerol, 0.5 mM EDTA). One volume of 0.3 mg/ml lysozyme (Sigma-Aldrich) in water was added and the suspension left 10-15 min at 4° C. with agitation. The suspension is centrifuged 10 min at 7000 g and 4° C. and the pellet is resuspended in 20 mL buffer 2 (25 mM KPO$_4$ pH 7.4, 0.1 mM EDTA, 0.1 mM DTT, 20% glycerol). The suspension is subject to one cycle of freeze-thaw at −80° C., 0.5 mM PMSF (phenylmethylsulfonyl fluoride, Sigma-Aldrich) is added and the suspension is sonicated 3 times for 20 sec. The suspension is centrifuged 10 min at 10000 g (to remove cell debris) and the supernatant is recovered and centrifuged 2 hours at 100,000 g. The pellet (membrane protein fraction) is resuspended in 2-3 ml of buffer 3 (50 mM Tris-HCl pH 7.4, 1 mM EDTA, 20% glycerol). To measure the CO-spectrum, the protein fraction is diluted (1/10) in buffer 3 to a final volume of 2 mL. Some crystals of sodium dithionite (Na$_2$S$_2$O$_4$) are added, the sample is divided into two cuvettes and the baseline recorded between 370 and 500 nm. The sample cuvette is then saturated with carbon monoxide and the difference spectrum is recorded. The concentration of P450 enzyme can be estimated from the amplitude of the peak at 450 nm using the extension coefficient for the reduced CO complex of 91 $mM^{-1} \cdot cm^{-1}$ (Omura, T. & Sato, R. (1964) *J. Biol. Chem.* 239, 2379-2387).

Following this procedure, typical CO-spectra with a maximum absorbance at 450 nm were measured for the recombinant CYP71AV8, attesting for a proper folding into functional P450 enzymes.

Example 3

Co-Expression of CYP71AV8 and a P450-Reductase in Bacteria

To reconstitute the activity of plant P450s, the presence of a second membrane protein is essential. This protein, the P450-reductase (CPR), is involved in the transfer of electrons from the cofactor NADPH (reduced Nicotinamide adenine dinucleotide phosphate) to the P450 active site. It has been shown that a CPR from one plant can complement the activity of P450 enzyme from another plant (Jensen and Moller (2010) *Phytochemsitry* 71, 132-141). Several CPR-encoding DNA sequences have been reported from different plant sources. We first selected a CPR previously isolated from *Mentha piperita* (CPRm, unpublished data, SEQ ID NO 10), optimized the codon usage of the full-length cDNA (SEQ ID No 9) and cloned it into the NcoI and HindIII restriction sites of the pACYCDuet-1 expression plasmid (Novagen) providing the plasmid pACYC-CPRm.

CYP71AV8 and CPRm were co-expressed in *E. coli* cells using the two plasmids pCWori-CYP71AV8-65188 and pACYCDuet-CPRm. BL21 Star™(DE3) *E. coli* cells (Invitrogen, Carlsbad, Calif.) were co-transformed with these two plasmids. Transformed cells were selected on carbenicillin (50 μg/ml) and chloramphenicol (34 μg/ml) LB-agarose plates. Single colonies were used to inoculate 5 mL liquid LB medium supplemented with the same antibiotics. The culture was incubated overnight at 37° C. The next day, 2 to 250 mL of TB medium supplemented with the same antibiotics were inoculated with 0.2 to 2 mL of the overnight culture. After 6 hours incubation at 37° C., the culture was cooled down to 28° C. and 1 mM IPTG and 75 mg/L δ-aminolevulinic acid were added. After 16 to 24 hours, the cells were harvested in exponential growing phase, centrifuged and resuspended in 0.5 volume of potassium phosphate buffer 50 mM pH 7.0 supplemented with 5% glycerol or 3% glucose. These cells were used for evaluation of the enzymatic activities of the P450 enzymes.

Example 4

Bioconversion of (+)-α-Santalene, (−)-β-Santalene, (−)-α-Trans-Bergamotene and (+)-Epi-β-Santalene Using *E. coli* Cells Expressing CYP71AV8

The different sequiterpene hydrocarbons used as substrates in the bioconversion assays were prepared as described previously using *E. coli* cells engineered to produced farnesyl diphosphate (FPP) from an heterologous mevalonate pathway and expressing a plant derived sesquiterpene synthase. The engineering and use of the *E. coli* host cells was described in patent WO2013064411 or in Schalk et al (2013) *J. Am. Chem. Soc.* 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of Streptococcus pneumoniae (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP. *E. coli* cells (BL21 Star™(DE3), Invitrogen) were co-transformed with the plasmid pACYC-29258-4506 and either the plasmid pET101-Cont2_1 (containing a cDNA encoding for the *Clausena lansium* (+)-α-santalene synthase (ClASS), WO2009109597) or the plasmid pETDuet-SCH10-Tps8201-opt (containing a cDNA encoding for a *Santalum album* (+)-α-santalene/(−)-β-santalene synthase (SaSAS), WO2010067309) and this cells were used to produce and purify (+)-α-santalene or a mixture of (+)-α-santalene, (−)-β-santalene, (−)-α-trans-bergamotene and (+)-epi-β-santalene.

The enzymatic activity of CYP71AV8 was evaluated by bioconversion in *E. coli* cells using the sesquiterpene molecules listed above as substrates. BL21 Star™(DE3) *E. coli* cells (Invitrogen) transformed with the plasmids pACYC-Duet-CPRm and pCWori-CYP71AV8-65188 were cultivated and harvested as described in example 3. The substrates (sesquiterpene hydrocarbons) were added to the cell suspension to a final concentration of 0.5 mg/ml as mixture composed of 10 mg Tween® 20 (sigma-Aldrich), 10 mg antifoam (Erol DF, PMC Ouvrie, Lesquin, France), 20 mg sesquiterpene and 1 ml water. The conversion was allowed to proceed for 24 hours at 20° C. with moderate shaking. The media were extracted with 2 volumes of MTBE (Methyl tert-buthyl ether, Sigma) and the extracts were analyzed by GCMS on an Agilent 6890 Series GC system connected to an Agilent 5975 mass detector. The GC was equipped with 0.25 mm inner diameter by 30 m SPB-1 capillary column (Supelco, Bellefonte, Pa.). The carrier gas was He at a constant flow of 1 mL/min. The initial oven temperature was 80° C. (1 min hold) followed by a gradient of 10° C./min to 300° C. The identification of the products was based on the comparison of the mass spectra and retention indices with authentic standards and internal databases.

In these conditions, oxidation of (+)-α-santalene was observed. The primary product of the conversion was (E)-α-santalol. Other products derived from the conversion of (E)-α-santalol by *E. coli* endogenous enzymes were detected: (E)-α-santalal (produced by an alcohol dehydrogenase) and (E)-α-dihydrosantalol (produced by an enoate reductase) (FIG. 3A). Similarly, using a mixture of (+)-α-santalene, (−)-β-santalene, (−)-α-trans-bergamotene and (+)-epi-β-santalene as substrate the formation of (E)-α-santalol, (E)-β-santalol, (E)-α-trans-bergamotol and (E)-epi-β-santalol was observed as well as further metabolized products were obtained (FIG. 3B). This example shows that CYP71AV8 can be used for the terminal oxidation of (+)-α-santalene, (−)-β-santalene, and structurally similar molecules.

Example 5

Construction of Synthetic Operons to Co-Express CYP71AV8 and a CPR from a Single Plasmid Several bicistronic operons were designed to express the P450 enzyme and a CPR from a single plasmid and under the control of a unique promoter. The three variants of optimized CYP71AV8 cDNAs (example 1) were combined with 2 CPR cDNAs: the codon optimized CPRm cDNA (example 2) and a codon optimized cDNA (Seq ID No 11) encoding for an *Artemisia annua* CPR (NCBI accession No. ABM88789.1, SEQ ID No 12). Thus, six constructs were designed (Seq ID No 13-18), each containing a P450 cDNA followed by a linker sequence including a ribosome binding site (RBS) and a CPR cDNA (FIG. 4). This constructs were prepared by PCR: the P450 and CPR cDNAs were amplified separately and with 5' and 3' overhangs suitable for the cloning using the In-Fusion® procedure (Clontech) in the NdeI-HindIII sites of the pCWori+ plasmid.

To evaluate the effect of the different N-terminal modification made on the P450s and the coupling with the CPRs, the 6 plasmids were transferred into *E. coli* BL21 Star™ (DE3) cells and the recombinant cells were used in bioconversion assays as described in example 4. The (+)-α-santalene and the (+)-α-santalene, (−)-β-santalene, (−)-α-trans-bergamotene and (+)-epi-β-santalene mixture were used as substrates and quantities of total oxygenated sesquiterpene products were evaluated. The results presented in FIG. 5 show that all recombinant bacterial cells transformed with one of the 6 plasmids described above can be used for the oxidation of (+)-α-santalene, (−)-β-santalene and the structurally similar molecules. The highest titer was obtained with the operon combining the CYP71AV8-P2O cDNA and the CPRm cDNA. This construct (plasmid pCWori-CYP71AV8-P2O-CPRm) was used for further experiments.

Example 6

In-Vivo Production of Oxygenated Sesquiterpenes in Engineered Cells

The oxidized products of (+)-α-santalene and the (+)-α-santalene, (−)-β-santalene, (−)-α-trans-bergamotene, (+)-epi-β-santalene or other structurally similar molecules can also be produced directly in *E. coli* cells engineered to produce sesquiterpenes from a carbon source such as glucose or glycerol. Plasmids were prepared consisting of the pCWori+ plasmid (Barnes H. J (1996) *Method Enzymol.* 272, 3-14) containing a synthetic operon composed of a P450, a CPR and the terpene synthase. For the P450, the CYP71AV8-P2 or CYP71AV8-P2O cDNA was used and for the terpene synthase, the *Clausena lansium* (+)-α-santalene synthase cDNA (ClASS) (WO2009109597) or a cDNA encoding for a *Santalum album* (+)-α-santalene/(−)-β-santalene synthase (SaSAS) (WO2010067309) was used. Four plasmids were thus constructed using the following procedure. A codon optimized version of the ClASS cDNA (SEQ ID NO 19-20) was designed and synthesized (DNA 2.0) and cloned in the NdeI-KpnI sites of the pETDUET-1 plasmid (Novagen) providing the plasmid pETDuet-Tps2opt. For SaSAS an optimized full-length cDNA was designed (SEQ ID NO 21-22), synthesized and cloned in the pJexpress414 plasmid (DNA2.0) providing the plasmid pJ414-SaTps8201-1-FLopt. For each constructs primer were designed for cloning using the In-Fusion® technique (Clontech, Takara Bio Europe). The optimized ClASS cDNA and the optimized SaSAS cDNA were amplified using these primers and the pETDuet-Tps2opt and pJ414-SaTps8201-1-FLopt plasmids as template, respectively. The two PCR products were ligated in the plasmids pCWori-CYP71AV8-P2-CPRm or pCWori-CYP71AV8-P2O-CPRm digested with the HindIII restriction enzyme and using the In-Fusion® Dry-Down PCR Cloning Kit (Clontech, Takara Bio Europe), providing four new plasmids: pCWori-CYP71AV8-P2-CPRm-ClASS, pCWori-CYP71AV8-P2-CPRm-SaSAS, pCWori-CYP71AV8-P2O-CPRm-ClASS, and pCWori-CYP71AV8-P2O-CPRm-SaSAS (SEQ ID NO 23-26).

The evaluation of the performance of these operons was performed in the *E. coli* BL21 Star™(DE3) (Invitrogen) cells co-transformed with either of the 4 plasmids and with the plasmid pACYC-29258-4506 carrying a complete mevalonate pathway (example 4). Transformed cells were selected on carbenicillin (50 µg/ml) and chloramphenicol (34 µg/ml) LB-agarose plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 µg/L carbenicilin and 17 µg/L chloramphenicol, were inoculated with 200 µl of the LB pre-culture and incubated at 37° C. and 250 rpm. After 6 hours of cultivation (or when the optical density at 600 nm of the culture reach a value of 3), the culture were cooled down to 20° C. and the expression of the proteins was induced with 0.1 mM IPTG (Isopropyl β-D-1-thiogalactopyranoside), and 75 µg/L δ-aminolevulinic acid (sigma) and 2% (v/v) of decane were added. After 48 h incubation with 250 rpm shaking, the whole culture broth was extracted with 1 volume of MTBE and analyzed by GCMS as described in example 4.

All resulting strains produced the sesquiterpene hydrocarbons as well as the corresponding oxygenated products also observed in the bioconversion experiments (FIG. 6). This experiment shows that using engineered cells expressing CYP71AV8, the sesquiterpenes (E)-α-santalol, (E)-β-santalol and other structurally similar molecules can be produced.

Example 7

Production of (E)-α-Santalol and (E)-β-Santalol Using CYP71AV8 Variants

In previous examples we showed that CYP71AV8 is highly selective for the 'terminal trans carbon' of (+)-α-santalene and (−)-β-santalene and produced exclusively (E)-α-santalol, (E)-β-santalol. In this example, we describe a site directed mutagenesis approach to modify the CYP71AV8 enzyme activity in order to produce (Z)-α-santalol and (Z)-β-santalol. L358 was first selected as an active site residue controlling the enzyme activity. A series of variant of CYP71AV8 were generated by replacing the codon encoding for L358 by codons encoding for other amino acids. The mutation was introduced in a two-step PCR procedure using a combination of degenerated oligonucleotide (containing the NBT (N=A,C,G,T; B=C,G,T) codon in place of L358 encoding codon) and specific oligonucleotides. This combination of oligonucleotides allow to change the L358 encoding codon with codons encoding for 12 other residues including all the amino acids with a hydrophobic side chain. A first PCR was performed to amplify the 5' portion of the cDNA using the mutagenesis reverse primer AV8-L358-rev (5'-CACGCGGCATCAC-CAGCGGAVNCGGCGGATGCAGGCGCAGGGTTTC-TTTAATC-3') (SEQ ID NO: 93) and the primer AV8-pcw-fw (5'-CATCGATGCTTAGGAGGTCATATGGCTCTGTT-ATTAGCAG-3') (SEQ ID NO: 94). A second PCR product was amplified using the primer AV8-L358-fw (5'-TCCGCTGGTGATGCCGCGTGAGTGC-3') (SEQ ID NO: 95) and AV8-CPR-rev (5'-ATATATCTCCTTCTTAAAGT-TAGTCGACTCATTAGGTG-3') (SEQ ID NO: 96). For both amplifications the pCWori-CYP71AV8-P2-CPRm-ClASS was use for the template. A second round of amplification was performed using the two above PCR products as template and the primers AV8-L358-fw+AV8-CPR-rev and allowed to amplify the full-length CYP71AV8 variant cDNAs. All the PCR reactions were performed using the PfuUltra II fusion HS DNA polymerase (Stratagene) following the manufacturer instruction. The modified cDNA were ligated into the NdeI-SalI digested pCWori-CYP71AV8-P2-CPRm-ClASS using the Gibson Assembly Master Mix (New England Biolabs). The final constructions were controlled by sequencing and one plasmid clone was selected for each desired CYP71AV8 variant. Twelve variants were thus generated by replacing Leu358 by Ala, Phe, Thr, Ser, Val, Gly, Ile, Met, Pro, Tyr, Trp, and Arg (SEQ ID NO 27 to 50).

The evaluation of each CYP71AV8 variant was performed using the in-vivo sesquiterpene production method described in example 6. Briefly, the pCWori+ plasmid containing one of the CYP71AV8 variant cDNA, the CPRm cDNA and the ClASS cDNA was co-transformed with the pACYC-29258 plasmid into KRX E. coli cells (Promega). The transformed cells were selected, cultivated and the production of sesquiterpenes was evaluated as described in example 6. As shown in FIG. 7, compared to the wild type P450 enzyme, with some of the variants (Z)-α-santalol was produced in addition to the trans oxidation products. For each variant, the ratio of cis to trans oxidation was calculated by dividing the total amount of (Z)-α-santalol produced by the total amount of oxygenated α-santalene derivatives. The results of these calculations for each variants is presented in Table 1 below:

TABLE 1

Regio-selectivity of the CYP71AV8 wild-type enzyme and active site variants for the oxidation of α-santalene.

| CYp71AV8 variants | Titer [mg/L] | | % (Z)-α-santalol of total santalol content |
|---|---|---|---|
| | sesquiterpenes | Oxygenated products | |
| CYP71AV8 wt | 97.7 ± 2.8 | 78.1 ± 3.5 | 0% |
| L358A | 28 ± 1.5 | 40.3 ± 2.8 | 36% |
| L358F | 88.4 ± 3.9 | 40.7 ± 0.4 | 46% |
| L358T | 90.9 ± 5.6 | 33.8 ± 1.5 | 5% |
| L358S | 43.4 ± 1.8 | 15.3 ± 0.8 | 17% |
| L358V | 56.1 ± 3.5 | 66.1 ± 1.1 | 1% |
| L358G | 84.3 ± 2.8 | 85 ± 2.2 | 0% |
| L358I | 71.2 ± 3.7 | 41 ± 0.3 | 0% |
| L358M | 84 ± 4.5 | 2.3 ± 0.3 | 0% |
| L358P | 71.6 ± 2.0 | 21 ± 1.1 | 0% |
| L358Y | 71.6 ± 2.9 | 0 ± 0 | 0% |
| L358W | 78.2 ± 0.6 | 0 ± 0 | 0% |
| L358R | 76 ± 1.1 | 2.3 ± 0.3 | 0% |

The data presented in Table 1 above show that CYP71AV8 can be engineered and used to produce the (Z)-α-santalol. Particularly, the L358T, L358S, L358A and L358F variants can be used for the terminal oxidation of (+)-α-santalene with a selectivity up to 46% for the cis terminal carbon.

In a similar approach the variants of CYP71AV8 were evaluated for the production of (Z)-β-santalol. New plasmids were prepared by replacing the ClASS cDNA in the above plasmid by the SaSAS cDNA. Thus the plasmid pCW-CYP71AV8-L358F-CPRm-ClASS was digested with the restriction enzymes HindIII and EcoRI to remove the ClASS cDNA. In parallel, the pCWori-CYP71AV8-P2-CPRm-SaSAS was digested with the same enzymes to recover the SaSAS cDNA with the compatible cohesive ends. The linearized vector and the digested insert were ligated using the T4 DNA ligase (New England Biolabs). The plasmid thus obtained was used for in-vivo production of oxygenated sesquiterpenes in E. coli cells in the same condition as described above. The FIG. 8 present the GCMS profile of the analysis of the products formed by CYP71AV8-L358F and shows that modified CYP71AV8 enzymes can also be used to produce (Z)-β-santalol.

Example 8

Evaluation of Other Members of CYP71AV Family

CYP71AV1 (NCBI accession No ABB82944.1) was evaluated for the oxidation of sesquiterpenes with the santalene skeleton. A plasmid was prepared with a configuration similar to the plasmids described in example 5: a bi-cistronic operon containing an optimized cDNA encoding for an N-terminal modified CYP71AV1 protein (SEQ ID NO 53 and 54) and the aaCPR cDNA (example 5) was designed, synthesized in-vitro (DNA2.0) and cloned as a bi-cistronic operon into the pCWori+ plasmid. The plasmid was used to transform KRX E. coli cells (Promega). The transformed cells were cultivated and protein expression was induced as described in example 3. A bioconversion experiment using (+)-α-santalene as substrate was conducted as described in example 4. As shown in FIG. 9 the same products as with CYP71AV8 were obtained (i.e. (E)-α-santalol and (E)-α-santalal) showing that other members of the CYP71AV P450 family can be use for the terminal oxidation of santalenes.

Using CYP71AV1, a synthetic operon containing the CYP71AV1 cDNA, the aaCPR and the (+)-α-santalene synthase cDNA (ClASS) was prepared. The pCWori+ plasmid containing the CYP71AV8-P2-CPRm-ClASS operon (example 6) was digested with NdeI and HindIII to cut out the P450 encoding cDNA. In parallel, the CYP71AV1 cDNA was recovered from the bi-cistronic operon described in the previous paragraph by digestion with the same enzymes and ligated, using the T4 DNA ligase (New England Biolabs), into the digested pCWori plasmid described above yielding the plasmid pCWori-CYP71AV1-CPRm-ClASS. This plasmid together with the plasmid pACYC-29258-4506 were used to co-transform E. coli BL21 Star™ (DE3) (Invitrogen) cells. The recombinant cells were cultivated in conditions allowing the production of sesquiterpene molecules as described in example 6. The GCMS analysis of the sesquiterpene produced revealed the formation of the same product as in the bio-conversion experiments. This experiment shows that CYP71AV1 can also be used oxidize santalene molecules and to produce santalols (FIG. 9).

Example 9

Construction of a P450-BM3 (CYP102A1) Mutant Library

A P450-BM3 mutant library of 24 variants was constructed by systematically combining five hydrophobic amino-acids (alanine, valine, phenylalanine, leucine and isoleucine) in two positions located close to the centre of the heme group of P450-BM3. Altering the side chain size of these two amino acids has been shown to drastically change the shape of the substrate binding cavity in close proximity of the heme group (*Appl Microbiol Biotechnol* 2006, 70:53; *Adv Synth Catal* 2006, 348:763). The first hot spot (Phe 87) is known to alter substrate specificity and regioselectivity while the second position (Ala 328) has been predicted to interact with all substrates during oxidation (*ChemBiochem* 2009, 10:853). The P450-BM3 variants were either generated using the QuickChange™ site-directed mutagenesis kit (Invitrogen, Carlsbad, Calif.) or were chemically synthetized by DNA2.0 (Menlo Park, Calif.). The P450-BM3 variants and wild-type were subcloned into the bacteria expression plasmids pET22b, pET28+, pETDuet-1 and pCDFDuet-1 (Novagen, Madison, Wis.) and were transformed in *Escherichia coli* BL21(DE3) or BL21Star™ (DE3) (Invitrogen, Carlsbad, Calif.).

Example 10

Alpha-Santalene: In Vitro Screening of the P450-BM3 Library

The 24 P450-BM3 mutants and the wild-type version of the enzyme were heterologously expressed in *E. coli* BL21 (DE3) cells as reported previously (*Adv. Synth. Catal.* 2003, 345:802). In brief, a single colony of transformed cells was used to inoculate 2 ml of Luria-Bertani (LB) medium supplemented with 30 µg/ml kanamycin and grown at 37° C. with orbital shaking (150 rpm) until $OD_{578}$ reaches a value of 0.6 to 1.0. This pre-culture was used to inoculate 200 ml of LB medium containing 30 µg/ml kanamycin. The cells were grown at 37° C. with orbital shaking at 160 rpm to an $OD_{578}$ of 0.8. Expression of the protein was then induced by the addition of 0.35 mM isopropyl β-D-1-thiogalactopyranoside (IPTG). After 6 hours of growth at 30° C. under agitation, the cells were harvested by centrifugation and lysed by sonication.

The alpha-santalene used as substrate in the bioconversion assays was prepared as described in Example 4. The conversions were carried out in 1 ml of 50 mM potassium phosphate buffer containing ~0.5 µM CYP enzyme, 2% (v/v) DMSO, and 0.2 mM µ-santalene substrate. Reaction was started by adding 0.1 mM NADPH and was carried out for 22 h at room temperature with moderate shaking.

Samples were then analyzed on a GC/MS QP-2010 instrument (Shimadzu, Japan) equipped with a FS-Supreme-5 column (30 m×0.25 mm×0.25 µm), helium as carrier gas (flow rate: 0.68 ml/min; linear velocity: 30 cm/s). Mass spectra were collected using electrospray ionization. The injector temperature was set at 250° C. The column oven was set at 50° C. for 1 min, then raised to 170° C. at 30° C./min, then raised to 185° C. at 5° C./min, held isotherm for 3 min, then raised to 200° C. at 5° C./min, then raised to 300° C. at 30° C./min, and finally held isotherm for 1 min.

Example 11

Alpha-Santalene In Vivo Screening of the P450-BM3 Library

The P450-BM3 mutant library was also screened in vivo using a bacteria strain engineered to produce (+)-α-santalene from a simple carbon source. To this end, the FPP-overproducing strain described in Example 4 was transformed with a pETDuet-1 plasmid containing a codon-optimized version of a (+)-α-santalene synthase from *Clausena lansium* (ClASS) (WO2009109597) (SEQ ID No 19 and 20) and each of the P450-BM3 variants cloned into the first and second multiple cloning sites (MCS) of the vector, respectively. Alternatively, the (+)-α-santalene synthase cDNA was cloned into the pET101expression plasmid (Novagen) and each of the P450-BM3 mutants from the library into the pCDFDuet-1 vector (Novagen). The resulting recombinant vectors were co-transformed in the FPP-overproducing strain.

Single colonies of transformed cells were used to inoculate 5 mL of LB medium supplemented with the appropriate antibiotics. Cultures were then incubated overnight at 37° C. and 250 rpm. The following day, 2 mL of Terrific Broth (TB) medium supplemented with 3% glycerol, 1 mM thiamine-HCl (Sigma-Aldrich, St Louis, Mich.) and 75 µg/L δ-aminolevulinic acid (Sigma-Aldrich) were inoculated with 200 µl of the overnight culture and incubated at 37° C. and 250 rpm. After 4 to 6 hours of cultivation (or when the optical density at 600 nm of the culture reach a value of 2 to 3), the cultures were cooled down to 28° C. and the protein expression was induced with 0.1 mM IPTG.

At that time, 10% (v/v) of dodecane were added to the growth media. After 48 h incubation with orbital shaking (250 rpm), the cell culture was extracted twice with one volume of methyl tert-butyl ether (MTBE) and the solvent extract analyzed by GC/MS. GC/MS was performed on an Agilent 6890 series GC system equipped with a DB1 column (30 m×0.25 mm×0.25 mm film thickness; Agilent) and coupled with a 5975 series mass spectrometer. The carrier gas was helium at a constant flow of 1 ml/min. Injection was in split-less mode with the injector temperature set at 250° C. and the oven temperature was programmed from 50° C. to 225° C. at 10° C./min and to 320° C. at 20° C./min. The identities of the products were confirmed based on the concordance of the retention indices and mass spectra of authentic standards.

The in vitro (Example 10) and in vivo screening of the P450-BM3 mutant library gave comparable results that are summarized in Table 2. While P450-BM3 wild-type (SEQ ID No 55 and 56) did not show any detectable activity on (+)-α-santalene, 6 P450-BM3 variants were able to convert α-santalene to the desired α-santalol(s). These variants revealed between 45% to 96% preference for oxidation of the cis-terminal carbon of (+)-α-santalene. The single mutant #23 (A328V) (SEQ ID No 67 and 68) and the double mutants #7 (F87I/A328I) (SEQ ID No 57 and 58), #17 (F87V/A328I) (SEQ ID No 59 and 60) and #18 (F87V/A328L) (SEQ ID No 61 and 62) showed the highest regioselectivity ranging from 72% to 96% (Table 2 and FIG. 10). Two additional variants #19 (F87V/A328V) (SEQ ID No 63 and 64) and #20 (F87V/A328F) (SEQ ID No 65 and 66) were less selective for the cis-hydroxylation (in the range of 45%-50%) and generated additional oxidation products.

TABLE 2

Alpha-santalene conversion to alpha-santalol(s) by P450-BM3 variants

| P450-BM3 | | cis-α-santalol (%) | trans-α-santalol (%) | Additional oxydation products (%) | Conversion (%) |
|---|---|---|---|---|---|
| Wild-type | F87/A328 | | | | |
| Variant #7 | F87 I/A328 I | 87 | | 13 | 6 |
| Variant #17 | F87 V/A328 I | 78 | 11 | 11 | 16 |
| Variant #18 | F87 V/A328 L | 72 | 13 | 15 | 9 |

TABLE 2-continued

Alpha-santalene conversion to alpha-santalol(s) by P450-BM3 variants

| P450-BM3 | | cis-α-santalol (%) | trans-α-santalol (%) | Additional oxydation products (%) | Conversion (%) |
|---|---|---|---|---|---|
| Variant #19 | F87 V/A328 V | 45.5 | 4 | 50.5 | 8 |
| Variant #20 | F87 V/A328 F | 49 | 8 | 43 | 3 |
| Variant #23 | F87/A328 V | 96 | | 4 | 5 |

These results indicate that P450-BM3 active site mutations enable binding of the non-native substrate (+)-α-santalene. Selected P450-BM3 variants incorporating these mutations were shown to selectively hydroxylate the cis-terminal carbon of (+)-α-santalene to generate the olfactively important compound (Z)-α-santalol (FIG. 10).

Example 12

In Vivo Production of (Z)-α-Santalol, (Z)-β-Santalol, (Z)-α-Trans-Bergamotol and (Z)-Epi-β-Santalol Using a P450-BM3 Double Mutant One of the P450-BM3 variants identified in the α-santalene screen (variant #17; Table 2) was tested for its ability to oxidize a sandalwood oil-like mixture of sesquiterpene hydrocarbons consisting of (+)-α-santalene, (−)-β-santalene, (−)-α-trans-bergamotene and (+)-epi-β-santalene. To this end, the FPP-overproducing bacteria strain described in Example 4 was transformed with a recombinant pETDuet-1 expression vector containing a codon-optimized cDNA encoding for a *Santalum album* (+)-α-santalene/(−)-β-santalene synthase (WO2010067309) (SEQ ID No 21 and 22) into the first MCS and the P450-BM3 variant #17 in the second MCS. Cell growth, induction conditions, culture extraction and product analysis were performed essentially as described in Example 11.

As shown in FIG. 11, (+)-α-santalene, (−)-β-santalene, (−)-α-trans-bergamotene and (+)-epi-β-santalene were efficiently oxidized by the P450-BM3 double-mutant to yield (Z)-α-santalol, (Z)-β-santalol, (Z)-α-trans-bergamotol and (Z)-epi-β-santalol. Remarkably, only the desired cis-isomers of the sesquiterpene alcohols were detected under these experimental conditions. These data show that the *Bacillus megaterium* CYP102A1 (P450-BM3) can be efficiently engineer to selectively hydroxylate the cis-terminal carbon of (+)-α-santalene, (−)-β-santalene and structurally related terpenes such as bergamotane sesquiterpenes and to generate the key sesquiterpene alcohols found in Sandalwood oil.

Example 13

Isolation of a cDNA Encoding for SaCP816, a Cytochrome P450 from *Santalum album*

The seeds of *S. album* were obtained from B&T World Seeds (Aigues-Vives, France) and from Sandeman Seeds (Lalongue, France). The seeds were first surface sterilised in 2.5% Hypochlorous acid (HClO) for 120 min, and rinsed 3 times in sterile ultrapure water. The seeds were then shelled and placed on MS basal medium (Murashige & Skoog, 1962, Physiologia Plantarum 15, 473-497) supplemented with 15 g/L sucrose and 7.8 g/L agar, pH 5.7. Germination was typically observed after 9 to 18 days with a yield of approximately 40%. Seedlings of *Santalum album* obtained from the aseptically germinated seeds were transferred to soil 5 to 10 weeks after germination. Since *Santalum* species are root hemiparasites, the soil adaptation was made in close contact with 6-months to 1-year old citrus (*Citrus sinensis*) plants. The roots of the *Santalum* plants were harvested, 2-3 years after the transfer to the soils and separated from the host plant roots. GC-MS analysis of an extract of these roots showed the presence of the sandalwood oil characteristic sesquiterpenes. Total RNA was extracted from the roots using the Concert™ Plant RNA Reagent (Invitrogen). From 12 grams of tissue, 640 micrograms of total RNA were isolated.

The whole transcriptome was sequenced using the Illumina Total RNA-Seq technique and the Illumina HiSeq 2000 sequencer. A total of 108.7 millions of paired-reads of 2×100 bp were generated. The reads were assembled using the De Novo Assembly application of CLC-Bio Genomic Workbench (CLCBo, Denmark). A total 82'479 of contigs with an average size of 683 bp were assembled. The contigs were search using the tBlastn algorithm (Altschul et al, J. Mol. Biol. 215, 403-410, 1990) and using as query sequence known P450 amino acid sequences such as the sequence of CYP71AV1 (NCBI accession No ABB82944.1). This approach allowed identifying several contigs encoding for proteins with characteristic cytochrome P450 motifs. One selected contig, SCH37-Ct816 (SEQ ID NO 69), contained a 1503 bp length open reading frame (ORF) (SEQ ID NO 70) encoding for a 500 amino acid protein, SaCP816 (SEQ ID NO 71). This amino acid showed homology with know cytochrome P450 sequences the closest sequence being a P450 from *Vitis vinifera*, CYP71D10 (NCBI accession No AAB94588.1) sharing 62% amino acid sequence identity.

Example 14

Heterologous Expression of SaCP816 in Bacterial Cells

For functional characterization of the protein encoded by SCH37-Ct816, the protein was heterologously expressed in *E. coli* cells. The ORF sequence was modified for improved expression in *E. coli*: the first 17 codons were replaced by the codons encoding for the MALLLAVFWSALIILV peptide (first 17 amino acids of SEQ ID NO: 73) and the codon usage of the whole ORF sequence was modified to match the *E. coli* codon usage. This cDNA (SaCP120293 (SEQ ID NO: 72) encoding for the modified SaCP816 (SEQ ID NO: 73) was synthesized in-vitro (DNA2.0) and cloned in the pJExpress404 plasmid (DNA2.0). The heterologous expression was performed as described in example 2.

Example 15

Co-Expression of SaCP816 and a P450-Reductase in Bacteria

A bicistronic operons was designed to express the P450 enzyme and a CPR from a single plasmid and under the control of a unique promoter. The optimized SaCP120293 cDNA was combined with the CPRm cDNA (SEQ ID No 9, Example 3) to prepare a bicistronic construct (SEQ ID NO 74) containing successively the P450 cDNA a linker sequence including a ribosome binding site (RBS) and the CPRm cDNA. This construct was prepared by PCR by amplifying the P450 and CPR cDNAs separately and with 5' and 3' overhangs suitable for the cloning using the In-Fusion® procedure (Clotech) in the NdeI-HindIII sites of the pCWori+ plasmid (Barnes H. J (1996) *Method Enzymol.* 272, 3-14) providing the plasmid SaCP816-CPRm-pCWori (SEQ ID NO 74).

The JM109 *E. coli* cells were transformed with the SaCP816-CPRm-pCWori expression plasmid. The transformed cells were grown and the cell-free extract containing the recombinant proteins were prepared as described in example 2. This protein fraction was used for the evaluation the enzymatique conversion of sesquiterpene molecules (example 16).

Example 16

In-Vitro Conversion of (+)-α-Santalene, (−)-β-Santalene, (−)-α-Trans-Bergamotene and (+)-Epi-β-Santalene Using the Recombinant SaCP816 P450 Enzyme The different sequiterpene hydrocarbons used as substrates in the bioconversion assays were prepared as described in example 4.

The crude protein extract from *E. coli* cells expressing the recombinant SaCP816 and CPRm proteins (example 15) was used for the in-vitro oxidation of these sesquiterpene molecules. The assays were performed in 1 mL of 100 mM Tris-HCL pH 7.4 buffer containing 20 to 50 microL protein extract, 500 microM NADPH (reduced Nicotinamide adenine dinucleotide phosphate), 5 microM FAD (Flavine adenine dinucleotide), 5 microM FMN (flavine mononucleotide), and 300 microM of sesquiterpenes (either (α)-santalene or a mixture of (+)-α-santalene, (−)-β-santalene, (−)-α-trans-bergamotene and (+)-epi-β-santalene). After 2 hours of incubation in Teflon sealed glass tubes with gentle agitation, the reaction was stopped on ice and extraction with 1 volume of MTBE (Methyl tert-buthyl ether, Sigma). The extracts were analyzed by GCMS as described in example 4.

In these conditions, oxidation of (+)-α-santalene, (−)-β-santalene, (−)-α-trans-bergamotene and (+)-epi-β-santalene was observed. FIG. 12 shows that the oxidation of (+)-α-santalene by SaCP816 provides (Z)-α-santalol. FIG. 13 shows that (+)-α-santalene, (−)-β-santalene, (−)-α-trans-bergamotene and (+)-epi-β-santalene were oxidized by SaCP816 to forme (Z)-α-santalol, (Z)-β-santalol, (Z)-α-trans-bergamotol and (Z)-epi-β-santalol. In all assays, no detectable amounts of the corresponding trans-isomers of the sesquiterpene alcohols was observed (the trans and cis isomers of each sesquiterpene alcohol are easily separated in the chromatographic conditions used in these assays).

This experiments show that the cytochrome P450 enzymes, SaCP816, isolated from *Santalum album* can be used for the selective hydroxylates the cis-terminal carbon of (+)-α-santalene, (−)-β-santalene and similar sesquiterpene structures.

Example 17

In-Vivo Production of Oxygenated Sesquiterpenes in Engineered Cells Using the Recombinant SaCP816 P450 Enzyme The oxidized products of (+)-α-santalene and the (+)-α-santalene, (−)-β-santalene, (−)-α-trans-bergamotene, (+)-epi-β-santalene or other structurally similar molecules can also be produced directly in *E. coli* cells engineered to produce sesquiterpenes from a carbon source such as glucose or glycerol. Plasmids were prepared consisting of the pCWori+ plasmid containing a synthetic operon composed of the SaCP120293 cDNA (SEQ ID No 72), the CPRm cDNA (SEQ ID No 9) and a terpene synthase encoding cDNA. For the terpene synthase, the *Clausena lansium* (+)-α-santalene synthase cDNA (ClASS) (WO2009109597) or a cDNA encoding for a *Santalum album* (+)-α-santalene/(−)-β-santalene synthase (SaSAS) (WO2010067309) was used.

Two plasmids were thus constructed using a procedure similar to the procedure described in example 6. The codon optimized (+)-α-santalene synthase cDNA (SEQ ID NO 19) and the (+)-α-santalene/(−)-β-santalene synthase cDNA (SEQ ID NO 21) were amplified as described in example 6 and ligated using the In-Fusion® Dry-Down PCR Cloning Kit (Clontech, Takara Bio Europe) in the plasmids SaCP816-CPRm-pCWori digested with the HindIII restriction enzyme providing the two new plasmids SaCP816-CPRm-ClASS-pCWori (SEQ ID NO 75) and SaCP816-CPRm-SaSAS-pCWori (SEQ ID NO 76).

The evaluation of the performance of these operons was performed in the *E. coli* XRX cells (Promega) co-transformed with either of these 2 plasmids and with the plasmid pACYC-29258-4506 carrying a complete mevalonate pathway (example 4). Transformed cells were selected on carbenicillin (50 µg/ml) and chloramphenicol (34 µg/ml) LB-agarose plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 µg/L carbenicilin and 17 µg/L chloramphenicol, were inoculated with 200 µl of the LB pre-culture and incubated at 37° C. and 250 rpm. After 6 hours of cultivation (or when the optical density at 600 nm of the culture reach a value of 3), the culture were cooled down to 20° C. and the expression of the proteins was induced with 0.1 mM IPTG (Isopropyl β-D-1-thiogalactopyranoside) and 0.1% Rhamnose, and 75 µg/L δ-aminolevulinic acid (sigma) and 2% (v/v) of decane were added. After 48 h incubation with 250 rpm shaking, the whole culture broth was extracted with 1 volume of MTBE and analyzed by GCMS as described in example 4.

All resulting strains produced the sesquiterpene hydrocarbons as well as the corresponding oxygenated products also observed in the in-vitro experiments (FIG. 14). This experiment shows that using engineered cells expressing SaCP816, the sesquiterpenes (Z)-α-santalol, (Z)-β-santalol and other structurally similar molecules can be produced.

Example 18

Isolation of a cDNA Encoding SaCP10374, a Cytochrome P450 from *Santalum album*

As described in example 13, several P450-encoding contig sequences were identified in the transcriptome from *Santalum album* roots. Beside SCH37-Ct816, another contig was selected: SCH37-Ct10374 (SEQ ID NO 77), contained a 1533 bp length ORF (SEQ ID NO 78) encoding for a protein composed of 510 amino acids, SaCP10374 (SEQ ID NO 79), showing homology with know cytochrome P450 sequences and 58% identity with CYP71D10 from *Vitis vinifera*, CYP71D10.

Example 19

Heterologous Expression of SaCP10374 in Bacterial Cells and Co-Expression with a P450-Reductase in Bacteria For functional characterization of the enzymes encoded by SCH37-Ct10374, the protein was heterologously expressed in *E. coli* cells. The ORFs sequence were modified to improve the expression in *E. coli*: the 18 first codons were replaced by the codons encoding for the MALLLAVFWSA-LII peptide and the codon usage of the whole ORF sequence was optimized. The new cDNA, SaCP120292 (SEQ ID NO 80), encoding for the modified SaCP10374 (SEQ ID NO 81) was synthesized in-vitro (DNA2.0) and cloned in the pJExpress404 plasmid (DNA2.0).

The heterologous expression was performed as described in example 2. Following this procedure, typical CO-spectra with a maximum absorbance at 450 nm was measured for this new recombinant *S. album* P450, attesting for a proper folding into functional P450 enzymes.

To reconstitute the activity of this P450 enzyme, a P450 reductase (CPR) was coexpressed. For this purpose, a bicistronic operons was designed similarly as described in example 15 to express SaCP10374 and CPRm (a mint P450 reductase) from a single plasmid and under the control of a unique promoter. The optimized SaCP12092 cDNA was combined with the CPRm cDNA to prepare the bicistronic constructs (SEQ ID NO 82) containing successively the P450 cDNA a linker sequence including a ribosome binding site (RBS) and the CPRm cDNA. This construct was prepared by PCR as described in example 15. and cloned in the pCWori+ plasmid (Barnes H. J (1996) *Method Enzymol*. 272, 3-14) providing the plasmid SaCP10374-CPRm-pCWori.

The JM109 *E. coli* cells were transformed with these bicistronic expression plasmid. The transformed cells were grown and the cell-free extract containing the recombinant proteins were prepared as described in example 2. The membrane protein fractions were used for the evaluation the enzymatique conversion of sesquiterpene molecules (example 21)

Example 21

In-Vitro Conversion of (+)-α-Santalene, (−)-β-Santalene and (−)-α-Trans-Bergamotene Using the Recombinant SaCP10374 P450 Enzyme The different sequiterpene hydrocarbons (either (α)-santalene or a mixture of (+)-α-santalene, (−)-β-santalene, (−)-α-trans-bergamotene and (+)-epi-β-santalene) used as substrates in this example of bioconversion assays were prepared as described in example 4.

The crude protein extract from *E. coli* cells expressing the recombinant SaCP10374 and CPRm proteins (example 20) was used for the in-vitro oxidation of these sesquiterpene molecules and the assays were performed as described in example 16. After 2 hours of incubation in Teflon sealed glass tubes with gentle agitation, the reaction was stopped on ice and extraction with 1 volume of MTBE (Methyl tert-buthyl ether, Sigma). The extracts were analyzed by GCMS as described in example 4.

In these conditions, oxidation of (+)-α-santalene, (−)-β-santalene, (−)-α-trans-bergamotene and (+)-epi-β-santalene by SaCP10374 was observed. FIGS. 15 and 16 show that (+)-α-santalene, (−)-β-santalene, (−)-α-trans-bergamotene and (+)-epi-β-santalene were oxidized by SaCP10374 to form (E)-α-santalol, (E)-β-santalol, (E)-α-trans-bergamotol and (E)-epi-β-santalol. In all assays, no detectable amounts of the corresponding cis-isomers of the sesquiterpene alcohols was observed (the trans and cis isomers of each sesquiterpene alcohol are easily separated in the chromatographic conditions used in these assays).

This experiments show that the cytochrome P450 enzyme SaCP10374, isolated from *Santalum album*, can be used for the selective hydroxylation of the trans-terminal carbon of (+)-α-santalene, (−)-β-santalene and structurally similar sesquiterpene molecules.

Example 22

In-Vitro Conversion of (E)-β-Farnesene, (E)-α-Farnesene, (−)-Sesquisabinene B, (−)-β-Bisabolene and (−)-α-Trans-Bergamotene Using the Recombinant SaCP816 and SaCP10374 P450s Enzyme Using the method described in example 4, several sequiterpene hydrocarbons structurally similar to the santalenes were prepared. The (−)-sesquisabinene B and (−)-β-bisabolene were produced using the pETDuet expression plasmid containing either a cDNA encoding for SaTps647, a *Santalum album* (−)-sesquisabinene B synthase (NCBI accession No. ADP37190.1) or a cDNA encoding for SaTps30, a *Santalum album* (−)-β-bisabolene synthase (NCBI accession No. ADP37189.1), in combination with the pACYC-29258-4506 plasmid described in example 4. The β-farnesene was obtained from Bedoukian (Danbury, Conn., USA), α-farnesene was from Treatt (Suffolk, UK) and (−)-α-trans-bergamotene was purified from citrus oil.

The crude protein extracts from *E. coli* cells expressing the recombinant SaCP816 or SaCP10374 together with CPRm proteins (example 15 and 20) were used for the in-vitro oxidation of these sesquiterpene molecules. The assays and product identification by GCMS analysis was performed as described in example 16.

In these conditions oxidation of (E)-β-farnesene, (E)-α-farnesene, (−)-sesquisabinene B, (−)-β-bisabolene and (−)-α-trans-bergamotene, was observed (FIGS. 17 to 21). For all these compounds, the two *S. album* P450s are regioselective for one of the two carbons of the terminal gem-dimethyl group (R1 or R2 in FIG. 27): SaCP816 catalyzes the selective oxidation of the carbon atom of the methyl in cis position relative to the terminal double bond (R1 in FIG. 27), whereas SaCP10374 catalyzes the oxidation of the same substrates exclusively on the carbon atom of the methyl group in trans relative to the terminal double bond (R2 in FIG. 27). The trans and cis isomers of each sesquiterpene alcohol are easily separated in the chromatographic conditions used in these assays. The formation of the corresponding aldehyde when the trans-methyl group is oxidyzes is attributed to *E. coli* endogenous alcohol dehydrogenase activity.

This experiments show that the cytochrome P450 enzymes, SaCP816 and SaCP10374, isolated from *Santalum album* can be used for the selective hydroxylation of the cis-terminal and trans-terminal carbon, respectively, of various sesquiterpene molecules have structure similarities with β-farnesene, α-farnesene, (+)-α-santalene, (−)-β-santalene, (−)-α-trans-bergamotene, (−)-sesquisabinene B or (−)-β-bisabolene.

Example 23

In-Vivo Production of Various Oxygenated Sesquiterpenes in Engineered Cells Using the Recombinant SaCP816 or SaCP10374 P450s Enzyme The oxidized sesquiterpene molecules described in example 21 and 22 can also be produced directly using whole cells, such as for example *E. coli* cells engineered to produce sesquiterpenes from a carbon source such as glucose or glycerol. Plasmids were prepared consisting of the pCWori+ plasmid containing a synthetic operon composed of the SaCP120293 cDNA (SEQ ID No 72), or the SaCP120292 (SEQ ID No 80), the CPRm cDNA (SEQ ID No 9) and a terpene synthase encoding cDNA (encoding either for an *Artemisia annua* β-farnesene synthase cDNA (NCBI accession No AAX39387.1.1), a *Picea abies* α-farnesene synthase (NCBI accession No AAS47697.1), a *S. album* (−)-Sesquisabinene B (NCBI accession No ADP37190.1), a *S. album* (−)-β-Bisabolene synthase (NCBI accession No ADP37189.1), a *Clausena lansium* α-santalene synthase (NCBI accession No ADR71055.1) or a *S. album* α-/β-santalene synthase (NCBI accession No ADP30867.1)).

The plasmids carrying the different combinations of synthetic operons were prepared using the following procedure. The plasmid pD444-SR-AaBFS (containing an optimized cDNA encoding for AaBFS, an *Artemisia annua* (E)-β-farnesene synthase (NCBI accession No AAX39387.1), the plasmid pD444-SR-PaAFS (containing an optimized cDNA encoding for PaAFS, a *Picea abies* (E)-α-farnesene synthase (NCBI accession No. AAS47697.1) were used to amplify by PCR the (E)-β-farnesene synthase and (E)-α-farnesene synthase cDNAs, respectively. The plasmids pETDuet-SaTps647 and pETDuet-SaTps30 (example 22) were used as template to amplify by PCR the sesquisabinene B synthase and the bisabolene synthase cDNAs, respectively. For each constructs primer were designed for the cloning using the In-Fusion® technique (Clontech, Takara Bio Europe). The AaBFS cDNA was amplified using the forward primer CPRm_aaBFS_Inf1 (TTACCTGCGTGATGTGTGGTAATAAAAGCTTAGGAGGTAAAAATGTCTACCCTGCCAATTTCTTC) (SEQ ID NO: 97) and the reverse primer AaBFS_Inf2 (ATGTTTGACAGCTTATCATCGATAAGCTGAATTCTTACACAACCATCGGGTGCACAAAGAATG) (SEQ ID NO: 98). The PaAFS cDNA was amplified using the forward primer CPRm_PaAFS_Inf1 (TTACCTGCGTGATGTGTGGTAATAAAAGCTTAGGAGGTAAAAATGGATCTGGCAGTGGAAATCGC) (SEQ ID NO: 99) and the reverse primer PaAFS_Inf2 (CTCATGTTTGACAGCTTATCATCGATAAGCTGAATTCTTACATCGGGACCGGCTCCAGGACGGTGC) (SEQ ID NO: 100). The SaTps647 cDNA was amplified using the primer forward CPRm_Tps_647_inf1 (5'GCGTGATGTGTGGTAATAAAAGCTTAGGAGGTAAAAATGGCGACCGTTGTGGATGATTCT-3') (SEQ ID NO: 101) and the primer reverse Tps647_Inf2 (GCTTATCATCGATAAGCTGAATTCTTACTCTTCATCCAGGGTAATCGGGTGG) (SEQ ID NO: 102). The SaTps30 cDNA was amplified using the primer forward CPRm_Tps30_Inf1-(GCGTGATGTGTGGTAATAAAAGCTTAGGAGGTAAAAATGGACGCATTCGCAACGAGCC) (SEQ ID NO: 103) and the primer reverse Tps30_Inf2 (GTGATGTGTGGTAATAAAAAGCTGAATTCTTAGTCCTCTTCATTCAGCGGGATCGGGTG) (SEQ ID NO: 104).

The PCR products were ligated in the plasmids SaCP816-CPRm-pCWori (SEQ ID No 74) or SaCP10374-CPRm-pCWOri (SEQ ID NO 82) digested with the HindIII restriction enzyme and using the In-Fusion Dry-Down PCR Cloning Kit (Clontech, Takara Bio Europe), providing the new plasmids SaCP816-CPRm-SaTPS647-pCWori (SEQ ID NO 83), SaCP10374-CPRm-SaTPS647-pCWori (SEQ ID NO 84), SaCP816-CPRm-SaTPS30-pCWori (SEQ ID NO 85), SaCP10374-CPRm-SaTPS30-pCWori (SEQ ID NO 86), SaCP816-CPRm-AaBFS-pCWori (SEQ ID NO 87), SaCP10374-CPRm-AaBFS-pCWori (SEQ ID NO 88), SaCP816-CPRm-PaAFS-pCWori (SEQ ID NO 89), SaCP10374-CPRm-PaAFS-pCWori (SEQ ID NO 90), SaCP10374-CPRm-ClTps2-pCWori (SEQ ID NO 91), and SaCP10374-CPRm-SaTps8201-pCWori (SEQ ID NO 92).

The in-vivo production of oxygenated sesquiterpenes in *E. coli* cells using the above plasmids was performed as described in example 17. All recombinant bacteria cells transformed with these plasmids produced the expected sesquiterpene hydrocarbons as well as the corresponding oxygenated products also observed in the in-vitro experiments (FIGS. 22 to 26).

What is claimed is:

1. An isolated nucleic acid molecule comprising the nucleic acid sequence of SEQ ID NO: 72.

2. A method for producing a polypeptide having P450 monoxygenase activity comprising transforming a host cell or non-human organism with the nucleic acid of claim 1; and culturing the host cell or organism under conditions that allow for the production of the polypeptide.

3. A vector comprising the nucleic acid molecule of claim 1.

4. The vector of claim 3, wherein the vector is a prokaryotic vector, viral vector or a eukaryotic vector.

5. The vector of claim 3, wherein the vector is an expression vector.

6. A host cell or non-human organism comprising the nucleic acid molecule of claim 1, or a vector comprising said nucleic acid molecule.

7. An isolated host cell or single celled organism comprising the nucleic acid molecule of claim 1, or a vector comprising said nucleic acid molecule.

* * * * *